(12) United States Patent
Do et al.

(10) Patent No.: US 12,414,985 B2
(45) Date of Patent: *Sep. 16, 2025

(54) AUGMENTED ACID ALPHA-GLUCOSIDASE FOR THE TREATMENT OF POMPE DISEASE

(71) Applicant: Amicus Therapeutics, Inc., Philadelphia, PA (US)

(72) Inventors: Hung V. Do, New Hope, PA (US); Richie Khanna, Somerset, NJ (US); Russell Gotschall, Doylestown, PA (US)

(73) Assignee: Amicus Therapeutics, Inc., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/699,927

(22) Filed: Mar. 21, 2022

(65) Prior Publication Data

US 2022/0370571 A1    Nov. 24, 2022

Related U.S. Application Data

(63) Continuation of application No. 17/061,691, filed on Oct. 2, 2020, now Pat. No. 11,278,601, which is a continuation of application No. 15/950,347, filed on Apr. 11, 2018, now Pat. No. 10,857,212, which is a continuation of application No. 15/394,135, filed on Dec. 29, 2016, now abandoned.

(60) Provisional application No. 62/431,791, filed on Dec. 8, 2016, provisional application No. 62/428,867, filed on Dec. 1, 2016, provisional application No. 62/402,454, filed on Sep. 30, 2016, provisional application No. 62/315,412, filed on Mar. 30, 2016, provisional application No. 62/300,479, filed on Feb. 26, 2016, provisional application No. 62/272,890, filed on Dec. 30, 2015.

(51) Int. Cl.
| | | |
|---|---|---|
| *A61P 21/00* | (2006.01) | |
| *A61K 31/445* | (2006.01) | |
| *A61K 38/47* | (2006.01) | |
| *A61P 3/00* | (2006.01) | |
| *C07H 15/00* | (2006.01) | |
| *C07H 17/00* | (2006.01) | |

(52) U.S. Cl.
CPC ............ *A61K 38/47* (2013.01); *A61K 31/445* (2013.01); *A61P 3/00* (2018.01); *A61P 21/00* (2018.01); *C12Y 302/0102* (2013.01)

(58) Field of Classification Search
CPC . A61P 3/00; A61P 21/00; A61K 38/47; A61K 31/445; C12N 9/26
See application file for complete search history.

(56) References Cited

U.S. PATENT DOCUMENTS

| | | |
|---|---|---|
| 4,837,237 A | 6/1989 | Rohrschneider |
| 4,985,445 A | 1/1991 | Tsuruoka et al. |
| 5,011,829 A | 4/1991 | Hirsch et al. |
| 5,103,008 A | 4/1992 | Scudder et al. |
| 5,236,838 A | 8/1993 | Rasmussen et al. |
| 5,399,567 A | 3/1995 | Platt et al. |
| 5,472,969 A | 12/1995 | Platt et al. |
| 5,580,757 A | 12/1996 | Desnick et al. |
| 5,786,369 A | 7/1998 | Platt et al. |
| 5,801,185 A | 9/1998 | Platt et al. |
| 5,879,680 A | 3/1999 | Ginns et al. |
| 6,083,725 A | 7/2000 | Selden et al. |
| 6,118,045 A | 9/2000 | Reuser et al. |
| 6,210,666 B1 | 4/2001 | Miyamura |
| 6,225,325 B1 | 5/2001 | Jacob et al. |
| 6,274,597 B1 | 8/2001 | Fan et al. |
| 6,395,884 B1 | 5/2002 | Selden et al. |
| 6,451,600 B1 | 9/2002 | Rasmussen et al. |
| 6,458,574 B1 | 10/2002 | Selden et al. |
| 6,461,609 B1 | 10/2002 | Calhoun et al. |
| 6,465,488 B1 | 10/2002 | Butters et al. |
| 6,534,300 B1 | 3/2003 | Canfield |
| 6,537,785 B1 | 3/2003 | Canfield |
| 6,545,021 B1 | 4/2003 | Mueller et al. |
| 6,583,158 B1 | 6/2003 | Fan et al. |
| 6,589,964 B2 | 7/2003 | Fan et al. |
| 6,599,919 B2 | 7/2003 | Fan et al. |
| 6,696,059 B2 | 2/2004 | Jacob et al. |
| 6,916,829 B2 | 7/2005 | Fan et al. |
| 7,141,582 B2 | 11/2006 | Fan et al. |

(Continued)

FOREIGN PATENT DOCUMENTS

| | | |
|---|---|---|
| CN | 104164412 A | 11/2014 |
| CN | 104379162 A | 2/2015 |

(Continued)

OTHER PUBLICATIONS

Roberts, M , et al., "First-in-Human Study of ATB200/AT2221 in Patients With Pompe Disease: Interim Results from the ATB200-02 Trial", The 22nd International Congress of the World Muscle Society, Oct. 3-7, 2017, St. Malo, France, 7 pages.

(Continued)

*Primary Examiner* — Maryam Monshipouri

(74) *Attorney, Agent, or Firm* — Servilla Whitney LLC

(57) ABSTRACT

A method for treating Pompe disease including administration of recombinant human acid α-glucosidase having optimal glycosylation with mannose-6-phosphate residues in combination with an amount of miglustat effective to maximize tissue uptake of recombinant human acid α-glucosidase while minimizing inhibition of the enzymatic activity of the recombinant human acid α-glucosidase is provided.

33 Claims, 51 Drawing Sheets

Specification includes a Sequence Listing.

(56) References Cited

U.S. PATENT DOCUMENTS

| | | |
|---|---|---|
| 7,351,410 B2 | 4/2008 | Van Bree et al. |
| 7,371,366 B2 | 5/2008 | Canfield |
| 7,396,811 B2 | 7/2008 | Lebowitz et al. |
| 7,560,424 B2 | 7/2009 | Lebowitz et al. |
| 7,655,226 B2 | 2/2010 | Van Bree et al. |
| 7,658,916 B2 | 2/2010 | Zhu et al. |
| 7,723,296 B2 | 5/2010 | Zhu |
| 7,785,856 B2 | 8/2010 | Lebowitz et al. |
| 7,858,576 B2 | 12/2010 | Lebowitz et al. |
| 7,910,545 B2 | 3/2011 | Meeker et al. |
| 7,981,864 B2 | 7/2011 | Lebowitz |
| 8,759,501 B2 | 6/2014 | Zhu et al. |
| 8,785,168 B2 | 7/2014 | Lebowitz et al. |
| 8,900,552 B2 | 12/2014 | Chen |
| 8,940,766 B2 | 1/2015 | Boyd et al. |
| 9,056,101 B2 | 6/2015 | Lockhart |
| 9,181,184 B2 | 11/2015 | Mugrage et al. |
| 9,186,420 B2 | 11/2015 | Koeberl |
| 9,303,249 B2 | 4/2016 | Valenzano et al. |
| 9,404,100 B2 | 8/2016 | Valenzano et al. |
| 9,598,682 B2 | 3/2017 | Callewaert et al. |
| 10,046,033 B2 | 8/2018 | Valenzano et al. |
| 10,208,299 B2 | 2/2019 | Gotschall et al. |
| 10,227,577 B2 | 3/2019 | Do et al. |
| 10,464,962 B2 | 11/2019 | Avila et al. |
| 10,512,676 B2 | 12/2019 | Char et al. |
| 10,512,677 B2 | 12/2019 | Valenzano et al. |
| 10,857,212 B2 | 12/2020 | Do et al. |
| 10,961,522 B2 | 3/2021 | Gotschall et al. |
| 11,278,601 B2 | 3/2022 | Do et al. |
| 2002/0049233 A1 | 4/2002 | Kararli et al. |
| 2002/0073438 A1 | 6/2002 | Reuser et al. |
| 2002/0095135 A1 | 7/2002 | Meeker et al. |
| 2002/0137125 A1 | 9/2002 | Zhu |
| 2002/0157123 A1 | 10/2002 | Reuser et al. |
| 2004/0180419 A1 | 9/2004 | Fan |
| 2004/0204379 A1 | 10/2004 | Cheng et al. |
| 2005/0058634 A1 | 3/2005 | Zhu |
| 2005/0244400 A1 | 11/2005 | Lebowitz et al. |
| 2006/0121018 A1 | 6/2006 | Lebowitz |
| 2006/0264467 A1 | 11/2006 | Mugrage et al. |
| 2007/0178081 A1 | 8/2007 | Fan |
| 2009/0117091 A1 | 5/2009 | Lebowitz et al. |
| 2009/0191178 A1 | 7/2009 | Zankel et al. |
| 2009/0203575 A1 | 8/2009 | Lebowitz et al. |
| 2010/0119502 A1 | 5/2010 | Do et al. |
| 2010/0260740 A1 | 10/2010 | Boyd et al. |
| 2010/0266571 A1 | 10/2010 | Lockhart et al. |
| 2011/0136151 A1 | 6/2011 | Wustman et al. |
| 2011/0189710 A1 | 8/2011 | Wustman et al. |
| 2011/0223147 A1 | 9/2011 | Lebowitz |
| 2011/0268721 A1 | 11/2011 | Do et al. |
| 2011/0300120 A1 | 12/2011 | Avila et al. |
| 2012/0064545 A1 | 3/2012 | Khanna et al. |
| 2012/0148556 A1 | 6/2012 | Lebowitz et al. |
| 2013/0158239 A1 | 6/2013 | Callewaert et al. |
| 2014/0186326 A1 | 7/2014 | Canfield et al. |
| 2014/0193390 A1 | 7/2014 | Valenzano et al. |
| 2014/0249054 A1 | 9/2014 | Gelb et al. |
| 2015/0044194 A1 | 2/2015 | Valenzano et al. |
| 2015/0086530 A1 | 3/2015 | Greene et al. |
| 2015/0147309 A1 | 5/2015 | Parenti et al. |
| 2015/0258081 A1 | 9/2015 | Lukas et al. |
| 2015/0352042 A1 | 12/2015 | Char et al. |
| 2016/0051528 A1 | 2/2016 | Mugrage et al. |
| 2016/0184410 A1 | 6/2016 | Chen |
| 2016/0243203 A1 | 8/2016 | Van Bree et al. |
| 2017/0056483 A1 | 3/2017 | Valenzano et al. |
| 2017/0298335 A1 | 10/2017 | Gotschall et al. |
| 2017/0335301 A1 | 11/2017 | Do et al. |
| 2018/0221357 A1 | 8/2018 | Mugrage et al. |
| 2018/0360928 A1 | 12/2018 | Valenzano et al. |
| 2019/0382742 A1 | 12/2019 | Do et al. |

FOREIGN PATENT DOCUMENTS

| | | |
|---|---|---|
| CN | 107075468 A | 8/2017 |
| EP | 1820862 A2 | 8/2007 |
| EP | 1137762 B1 | 10/2008 |
| EP | 2020438 A1 | 2/2009 |
| FR | 2861991 A1 | 5/2005 |
| JP | 2005523882 A | 8/2005 |
| JP | 2007523648 A | 8/2007 |
| JP | 2008525457 A | 7/2008 |
| JP | 2008545657 A | 12/2008 |
| JP | 2010525084 A | 7/2010 |
| JP | 2011512876 A | 4/2011 |
| WO | 00034451 A1 | 6/2000 |
| WO | 01019955 A2 | 3/2001 |
| WO | 0197829 A2 | 12/2001 |
| WO | 03032907 A2 | 4/2003 |
| WO | 2004069190 A2 | 8/2004 |
| WO | 2005077093 A2 | 8/2005 |
| WO | 2006071613 A2 | 7/2006 |
| WO | 2006125141 A2 | 11/2006 |
| WO | 2008112525 A2 | 9/2008 |
| WO | 2008/134628 A2 | 11/2008 |
| WO | 2009066069 A1 | 5/2009 |
| WO | 2009102895 A2 | 8/2009 |
| WO | 2009114679 A2 | 9/2009 |
| WO | 2010015816 A2 | 2/2010 |
| WO | 2010075010 A2 | 7/2010 |
| WO | 2010148253 A2 | 12/2010 |
| WO | 2011039634 A2 | 4/2011 |
| WO | 2011109600 A1 | 9/2011 |
| WO | 2012042386 A2 | 4/2012 |
| WO | 2012145644 A1 | 10/2012 |
| WO | 2013013017 A2 | 1/2013 |
| WO | 2013091897 | 6/2013 |
| WO | 2013136189 A2 | 9/2013 |
| WO | 2013166249 A1 | 11/2013 |
| WO | 2015097088 | 7/2015 |
| WO | 2016054231 A1 | 4/2016 |
| WO | 2017049161 A1 | 3/2017 |
| WO | 2017117407 A1 | 7/2017 |
| WO | 2017173059 A1 | 10/2017 |

OTHER PUBLICATIONS

Ruvinov, S.B., et al., "Monovalent cations partially repair a conformational defect in a mutant tryptophan synthase alpha 2 beta 2 complex (beta-E109A)", J. Biol. Chem. 1995; 270: 17333-38, Jul. 1995.

Sathe, S., et al., "Preliminary Pharmacokinetic and Safety Data in Patients With Pompe Disease in Firstin-Human Study Receiving ATB200/AT2221", Amicus Therapeutics: Poster from the 2017 Muscular Dystrophy Association Scientific Conference, Mar. 19-11, 2017, Arlington, Virginia; 1 page.

Sathe, S., et al., "Preliminary Safety, Pharmacokinetic, Pharmacodynamic, and Efficacy Data in Patients With Pompe Disease Receiving ATB200/AT2221 in First-in-Human Study", Amicus Therapeutics: Poster from the 4th International Glycogen Storage Disease (GSD) Conference, Jun. 15-17, 2017, University Medical Center, Groningen, The Netherlands; 1 page.

Tajima, et al., "Structural and biochemical studies on Pompe disease and a pseudodeficiency of acid aglucosidase", J Hum Genet., 2007, 52:898-906.

Valenzano, K. J., et al., "Identification and characterization of pharmacological chaperones to correct enzyme deficiencies in lysosomal storage disorders", Assay and Drug Development Technologies, 9(3):213-235. (Jun. 2011).

Van Hove, J.L.K., et al., "High-level production of recombinant human lysosomal acid a-glucosidase in Chinese hamster ovary cells which targets to heart muscle and corrects glycogen accumulation in fibroblasts from patients with Pompe disease", Proc Natl Acad Sci USA, 93:65-70. (1996).

Van Hove, J.L.K., et al., "Purification of recombinant human precursor acid a-glucosidase", Biochem Mo/Biol Int, 43(3) :613-623. (1997).

(56) References Cited

OTHER PUBLICATIONS

Vanderploeg, A. T., et al., "Receptor-Mediated Uptake of Acid a-Glucosidase Corrects Lysosomal Glycogen Storage in Cultured Skeletal Muscle", Pediatric Research, 24(1):90-94. (1988).
Wilson, B.A., et al., "Prentice Hall Nurse's Drug Guide 2003, Companion Website", http://wps.prenhall.com/chet_wilson_drugguides_1/6/1576/403472.cw/index.html; accessed Sep. 30, 2014.
Database Score. Seq ID No. 1 sequence in WO 2012145644A1. Retrieved from: http://score.uspto.gov/ScoreAccessWeb/viewSeqIdResult.htm, pp. 1-3; accessed Jan. 22, 2018, 3 pages.
Duke University Medical Center (1997) "Duke Obtains FDA Designation for Pompe Disease Therapy" Press Release, dated Sep. 2, 1997, 2 pages.
Genzyme Corporation (2010) Myozyme®. Highlights of Prescribing Information. Cambridge, MA: Genzyme Corporation, Jun. 2010, 3 pages.
Legler, G. and S. Pohl (1986) "Synthesis of 5-amino-5-deoxy-D-galactopyranose and 1,5-dideoxy-1,5-imino-D-galactitol, and their inhibition of alpha- and beta-D galactosidases" Carbohydrate Res, 155:119-129.
National Institutes of Heal TH Clinical Center (2002) Patient Education Materials: Giving a subcutaneous injection. Bethesda, MD: NIH Clinical Center, 3 pages.
PCT International Search Report and Written Opinion mailed Jan. 6, 2016, in PCT/US2015/053252, 9 pages.
PCT International Search Report and Written Opinion mailed Mar. 7, 2017, in PCT/US2016/069243, 10 pages.
PCT International Search Report and Written Opinion mailed May 8, 2013, in PCT/US2013/029660, 8 pages.
PCT International Search Report and Written Opinion mailed Oct. 1, 2013, in PCT/US2013/039215, 9 pages.
U.S. Appl. No. 14/379,131: Non-Final Office Action, dated Sep. 15, 2015, 13 pages.
Nilsson MI et al., lysosomal alpha-glucosidase preproprotein [*Homo sapiens*], Accession No. NP_000143.2, dated Jun. 26, 2021, 4 pages.
Amalfitano, et al., "Recombinant human acid a-glucosidase enzyme therapy for infantile glycogen storage disease type II: Results of a phase I/II clinical trial", Genetics in Medicine 3(2): 132-138 (2001).
Asano, N, et al., "Nitrogen-in-the-ring pyranoses and furanoses: structural basis of inhibition of mammalian glycosidases", J Med Chem, 37:3701-3706. (1994).
Banati, M, et al., "Enzyme replacement therapy induces T-cell responses in late-onset Pompe disease", Muscle Nerve, 44(5):720-726. (2011).
Barton, N. W., et al., "Replacement Therapy for Inherited Enzyme Deficiency-Macrophage-Targeted Glucocerebrosidase for Gaucher's Disease", N Eng J Med, 324:1464-1470. (1991).
Beck, M., "Alglucosidase alfa: Long term use in the treatment of patients with Pompe disease", Therapeutics and Clinical Risk Management, 5:767-772. (Sep. 2009).
Berge, Stephen M, et al., "Pharmaceutical Salts", Journal of Pharmaceutical Sciences, vol. 66 No. 1, Jan. 1977, 1-19.
Butters, T. D., et al., "Imino Sugar Inhibitors for Treating the Lysosomal Glycosphingolipidoses", Glycobiology, 15 (10):43E-52R. (2005).
Courageot, et al., "a-Glucosidase inhibitors reduce dengue virus production by affecting the initial steps of virion morphogenesis in the endoplasmic reticulum", Journal of Virology vol. 74, 2000, 564-572.
Cox, et al., "Novel oral treatment of Gaucher's disease with N-butyldeoxynojirimycin (OGT 918) to decrease substrate biosynthesis", The Lancet, vol. 355, Apr. 29, 2000, 1481-1485.
Dale, M. P., "Reversible inhibitors of 6-glucosidase", Biochemistry, 24:3530-3539, (1985).
Do, H., et al., "ATB200/AT2221 Cleared Accumulated Glycogen and Reversed Cellular Dysfunction to Increase Functional Muscle Strength in Mouse Model of Pompe Disease", Amicus Technologies: Poster from the 13th Annual Lysosomal Disease Network WORLDSymposium, San Diego, CA, Feb. 13-17, 2017; Poster #74, Abstract A-348, 1 page.
Do, H, et al., "Chemical Conjugation of Targeting Peptide to ERTs Improve Receptor Binding and Substrate Clearance in Mouse Models of Disease", Amicus Technologies: Poster from the 1 Oth Annual Lysosomal Disease Network WORLDSymposium, San Diego, CA, Feb. 10-13, 2014, Abstract #277; 1 page. (Feb. 13, 2014).
Fryar, C. D., et al., "Anthropometric Reference Data for Children and Adults: United States 2007-201 O", National Center for Health Statistics. Vital Health Stat, Series 11, No. 252, 48 pages. (Oct. 2012).
Gotschall, R., et al., "ATB200/AT2221 Reverses Cellular Dysfunction and Increases Muscle Strength in a Pompe Disease Mouse Model", Amicus Therapeutics: Poster from the 4th International Glycogen Storage Disease (GSD) Conference, Jun. 15-17, 2017, University Medical Center, Groningen, The Netherlands; Abstract 48, 1 page.
Gotschall, R., "Novel rhGAA with Optimal Glycosylation Is Significantly Better than Alglucosidase Alfa for Glycogen Clearance in Skeletal Muscles of Gaa KO Mice", Amicus Technologies: Poster from the ACMG Annual Clinical Genetics Meeting, Mar. 25-27, 2015, Salt Lake City, Utah; Abstract #739, 1 page. (2015).
Gotschall, R., "Novel rhGAA with Optimal Glycosylation Is Significantly Better than Alglucosidase Alfa for Glycogen Clearance in Skeletal Muscles of Gaa KO Mice", Amicus Technologies: Presentation from the 11th Lysosomal Disease Network WorldSymposium, Feb. 9-13, 2015, Orlando, Florida; 12 pages. (2015).
Gotschall, R., et al., "Novel rhGAA with Optimal Glycosylation Is Significantly Better than Alglucosidase Alfa for Glycogen Clearance in Skeletal Muscles of Gaa KO Mice", Amicus Technologies: Abstract from the 11th Lysosomal Disease Network WORLDSymposium, Feb. 9-13, 2015, Orlando, Florida. Abstract 94, 1 page. (2015).
Jeyakumar, et al., "Delayed symptom onset and increased life expectancy in Sandhoff disease mice treated with N-butyldeoxynojirimycin", Proc. Acad. Sci. USA, Medical Sciences, vol. 96, May 1999, 6388-6393.
Johnson, F. K., et al., "First-in-Human Preliminary Pharmacokinetic and Safety Data on a Novel Recombinant Acid a-Glucosidase, ATB200, Co-administered With the Pharmacological Chaperone AT2221 in ERT-Experienced Patients With Pompe Disease", Amicus Technologies: Poster from the 13th Annual Lysosomal Disease Network WORLDSymposium, San Diego, CA, Feb. 13-17, 2017; Poster #LB-26, 1 page.
Khanna, R., et al., "Co-Administration of the Pharmacological Chaperone AT2221 with A Proprietary Recombinant Human Acid a-Glucosidase Leads to Greater Plasma Exposure and Substrate Reduction Compared to Alglucosidase Alfa", Amicus Therapeutics: Poster from the 12th Annual Lysosomal Disease Network WORLDSymposium Meeting, Feb. 29-Mar. 4, 2016, San Diego, California; 1 page.
Khanna, R., et al., "The pharmacological chaperone AT2220 increases recombinant human acid aglucosidase uptake and glycogen reduction in a mouse model of Pompe disease", PLoS ONE, 7(7):e40776, 14 pages. (2012).
Khanna, R., et al., "The pharmacological chaperone AT2220 increases the specific activity and lysosomal delivery of mutant acid alpha-glucosidase, and promotes glycogen reduction in a transgenic mouse model of Pompe disease", PLoS One, 9(7) : e102092, 16 pages. (2014).
Kishnani, P., et al., "Duvoglustat HCI Increases Systemic and Tissue Exposure of Active Acid a-Glucosidase in Pompe Patients Co-administered with Alglucosidase a", Molecular Therapy, 25(5):1199-1208. (2017).
Klinge, L., et al., "Enzyme replacement therapy in classical infantile Pompe disease: results of a tenmonth follow-up study", Neuropediatrics, 36(1):6-11. (2005).
Lembcke, B., et al., "Lysosomal storage of glycogen as a sequel of alpha-glucosidase inhibition by the absorbed deoxynojirimycin derivative emiglitate (BAYo1248). A drug-induced pattern of hepatic

(56) References Cited

OTHER PUBLICATIONS glycogen storage mimicking Pompe's disease (glycogenesis type II)", Res Exp Med, 191 (6): 389-404. (1991).

Lun, Y., et al., "A Novel Recombinant Human Acid Alpha-Glucosidase, ATB200, Leads to Greater Substrate Reduction and Improvement in Pompe Disease-Relevant Markers Compared to Alglucosidase Alfa in Gaa KO Mice", Amicus Technologies: Poster from the 13th Annual Lysosomal Disease Network WORLDSymposium, San Diego, CA, Feb. 13-17, 2017; 1 page.

Lun, Y., et al., "Histological examination of the effect of a highly phosphorylated proprietary recombinant human acid alpha-glucosidase on glycogen reduction in disease-relevant muscles of Pompe mice", Amicus Technologies: Poster from the Lysosomal Disease Network 11th WORLD Symposium, Feb. 9-13, 2015, Orlando, Florida; 1 page. (2015).

Lun, Y., et al., "Stabilized Next-Generation Recombinant Human Acid Alpha-Glucosidase ATB200 Clears Accumulated Glycogen and Reverses Cellular Dysfunction to Increase Muscle Strength in A Mouse Model of Pompe Disease", Amicus Therapeutics: Poster from the 2017 Muscular Dystrophy Association Scientific Conference, Mar. 19-11, 2017, Arlington, Virginia; 1 page.

Martiniuk, et al., "Correction of Glycogen Storage Disease Type II by Enzyme Replacement with a Recombinant Human Acid Maltase Produced by Over-Expression in a CHO-HDFR"e9 Cell Line", Biochemical and Biophysical Research Communications, 276(3):917-923 (2000).

McVie-Wylie, et al., "Biochemical and pharmacological characterization of different recombinant acid aglucosidase preparations evaluated for the treatment of Pompe disease", Molecular Genetics and Metabolism, 94: 448-455 (2008).

Mellor, Howard R., et al., "Cellular effects of deoxynojirimycin analogues; uptake, retention and inhibition of glycosphingolipid biosynthesis", Biochem J. vol. 381, 2004, 861-866.

Nagase, T., et al., "Synthetic construct DNA, clone: pF1KB4173, *Homo sapiens* GAA gene for lysosomal alpha-glucosidase precursor, complete cds, without stop codon, in Flexi system", Accession: AB384912.1.

Okumiya, et al., "Chemical chaperones improve transport and enhance stability of mutant a-glucosidases in glycogen storage disease type II", Mol. Genet. Metab. 90: 49-57 (2007).

Parenti, et al., "A Chaperone Enhances Blood a-Glucosidase Activity in Pompe Disease Patients Treated with Enzyme Replacement Therapy", Mol. Th er. 22(11) :2004-2012 (2014).

Parenti, G., et al., "Alpha-Glusosidase Enhancement in Fibroblasts from Patients with Pompe Disease", J. Inherit. Metab. Dis. vol. 28 Suppl. I, 2005, 193.

Parenti, et al., "Lysosomal Storage Diseases: From Pathophysiology to Therapy", Annu. Rev. Med., 2015, 66 (1 ):471-486.

Platt, et al., "Prevention of Lysosomal Storage in Tay-Sachs Mice Treated with N-butyldeoxynojirimycin", Science vol. 276 18, Apr. 1997, pp. 428-431.

Porto, Caterina, et al., "The Pharmacological Chaperone N-butyldeoxynokirimycin Enhances Enzyme Replacement Therapy in Pompe Disease Fibroblasts", Molecular Therapy (www.moleculartherapy.org), vol. 17 No. 6, Jun. 2009, 964-971.

Raben, N., et al., "Replacing acid alpha-glucosidase in Pompe disease: recombinant and transgenic enzymes are equipotent, but neither completely clears glycogen from type II muscle fibers", Mo/ Ther, 11 (1 ):48-56. (2005).

"World Symposium Investor Dinner Slides, Perspectives on Pompe: Progress, Persistence and Passion", Feb. 12, 2020, 41 pages.

Kalia, Jeet, et al., "Hydrolytic Stability of Hydrazones and Oximes", Angew Chem Int Ed Engl. 2008 ; 47(39): 7523-7526.

Kalia, Jeet, et al., "Hydrolytic Stability of Hydrazones and Oximes", Supporting Information, Anal. Chem. 1968, 40, 700-706.

Zhu, Yunxiang, et al., "Glycoengineered Acid α-Glucosidase With Improved Efficacy at Correcting the Metabolic Aberrations and Motor Function Deficits in a Mouse Model of Pompe Disease", The American Society of Gene Therapy, Molecular Therapy, vol. 17 No. 6, 954-963 Jun. 2009.

Xu, et al., "Improved efficacy of a next-generation ERT in murine Pompe disease", JCI Insight, 2019, 4(5):e125358, 20 pages.

Zhou, Qun, et al., "Glycan Structure Determinants for Cation-Independent Mannose 6-Phosphate Receptor Binding and Cellular Uptake of a Recombinant Protein", Bioconjugate Chemistry, vol. 24, No. 12, Nov. 12, 2013, pp. 2025-2035.

Zhou, S., et al., "LC-MS/MS Analysis of Permethylated N-Glycans Facilitating Characterization", Anal Bioanal Chem. Vol. 409(2), 2017, pp. 453-466.

Zhou, et al., "The Mechanistic Impact of N-Glycosylation on Stability, Pharmacokinetics, and Immunogenicity of Therapeutic Proteins", Journal of Pharmaceutical Sciences, 2019, 108:1366-1377.

Zhu, Yunxiang, et al., "Conjugation of Mannose 6-Phosphate-containing Oligosaccharides to Acid [alpha]- Glucosidase Improves the Clearance of Glycogen in Pompe Mice", Journal of Biological Chemistry, vol. 279, No. 48, Nov. 26, 2004, p. 50336-50341.

European Application No. 15845664.0, filed Apr. 6, 2017, by Amicus Therapeutics, Inc .: Supplementary European Search Report, mailed Feb. 12, 2018, 12 pages.

Moreland et al., Lysosomal Acid alpha-Glucosidase Consists of Four Different Peptides Processed from a Single Chain Precursor, The Journal of Biological Chemistry, 2005, 280:6780-6791.

Nippon Rinsho, vol. 68, Suppl 8, pp. 665-669.

"Amicus' AT-GAA Shows Clinically Meaningful & Significant Improvements in Both Musculoskeletal and Respiratory Measures in Late-Onset Pompe Disease Compared to Standard of Care in Pivotal Phase 3 PROPEL Study", Amicus Therapeutics. 2021, Study on the web at: ir.amicusrx.com/news-releases/news-release-details/amicus-gaa-shows- clinically-meaningful-significant-improvements. Pages 1-5.

"Amicus Therapeutics Announces Additional Positive Data in Pompe Disease Phase 1/2 Study at World Muscle Society", Amicus Therapeutics, Oct. 4, 2017, 4 pages,.

Center For Disease Control and Prevention (Data Table of Weight-for-age Charts. 2001, pp. 1-15).

EMEA (2006, Scientific Discussion. pages 1-30).

Extended European Search Report for Application No. 20207542.0, mailed on Jul. 29, 2021, 11 pages.

Extended European Search Report issued by the European Patent Office for Application No. 18802722.1, dated Jan. 20, 2021, 8 pages.

Final Office Action in U.S. Appl. No. 11/440,473, dated Jan. 5, 2015, 8 pages.

Final Office Action in U.S. Appl. No. 11/440,473, dated May 15, 2009, 8 pages.

Final Office Action in U.S. Appl. No. 11/440,473, dated May 19, 2010, 7 pages.

Final Office Action in U.S. Appl. No. 11/440,473, dated May 9, 2011, 8 pages.

"Guidance for Industry: Estimating the Maximum Safe Starting Dose in Initial Clinical Trials for Therapeutics in Adult Healthy Volunteers", U.S. Department of Health and Human Services, Food and Drug Administration, Center for Drug Evaluation and Research (CDER), Jul. 2005, 30 pages.

Non-Final Office Action in U.S. Appl. No. 11/440,473, dated Dec. 5, 2008, 8 pages.

Non-Final Office Action in U.S. Appl. No. 11/440,473, dated Mar. 28, 2014, 9 pages.

Non-Final Office Action in U.S. Appl. No. 11/440,473, dated May 7, 2008, 8 pages.

Non-Final Office Action in U.S. Appl. No. 11/440,473, dated Sep. 14, 2009, 6 pages.

Non-Final Office Action in U.S. Appl. No. 11/440,473, dated Sep. 30, 2010 , 8 pages.

Non-Final Office Action in U.S. Appl. No. 17/665,179, dated Jul. 11, 2022, 15 pages.

Non-Final Office Action in U.S. Appl. No. 14/379,131, dated Sep. 15, 2015, 9 pages.

"Opfolda—SmPC", Jun. 2023, 25 pgs.

"Opfolda US Label", 2 pgs.

"Pombiliti—SmPC", 37 pgs.

"Pombiliti US Label", 24 pgs.

(56) References Cited

OTHER PUBLICATIONS

"Pompe Phase 1/2 Study (ATB200-02) Preliminary Data", Amicus Therapeutics, Dec. 8, 2016, pp. 1-13.

The extended European search report dated Jan. 27, 2021, issued in European Application No. 201774 73.4, 10 pages.

Anding, Allyson, et al., "Increasing Enzyme Mannose-6-Phosphate Levels but Not Miglustat Coadministration Enhances the Efficacy of Enzyme Replacement Therapy in Pompe Mice", Journal of Pharmacology and Experimental Therapeutics, vol. 387, No. 2, Sep. 7, 2023, pp. 188-203.

Andra, et al., "(Ask Dr, Andra: What Are Human Equivalent Doses (HED) and How Do I Calculate Them? 2011 pp. 1-4).".

Block, et al., "Immobilized-metal affinity chromatography (IMAC): a review", Methods Enzymol. 2009; 463: 439-73.

Chavez, et al., "Domain 5 of the Cation-Independent Man nose 6-Phosphate Receptor Preferentially Binds Phosphodiesters (Man nose 6-Phosphate N-Acetylglucosamine Ester).", Biochemistry (2007), 46: 12604-12617.

Chien, et al., "Pompe Disease: Early Diagnosis and Early Treatment Make a Difference", Pediatrics and Neonatology, 2013, 54, pp. 219-227.

Do, et al., "Stabilized next generation recombinant human acid alphaglucosidase ATB200 clears accumulated glycogen and reverses cellular dysfunction to increase functional muscle strength in a mouse model of Pompe disease", Molecular Genetics and Metabolism 120(12); page S42 (2017).

Hermans, et al., "Human lysosomal a-glucosidase: functional characterization of the glycosylation sites", Biochem J. 289:681-686 (1993).

Hoja-Lukowicz, Dorota, et al., "Characterization of the oligosaccharide component of microsomal [beta]- glucuronidase from rat liver", Biochimie, Fr, (20040601), vol. 86, No. 6, pp. 363-372.

Khanna, R., et al., "Molecular Genetics and Metabolism", vol. 117, Issue 2, Feb. 2016, Pages S66-867. doi: 10.1016/j.ymgme.2015.12.318).

Kuperus, et al., "Long-term benefit of enzyme replacement therapy in Pompe disease A 5-year prospective study", Neurology 89:2365-2373 (2017).

Liu, et al., "The Impact of Sialic Acids on the Pharmacokinetics of a PEGylated Erythropoietin", Journal of Pharmaceutical Sciences, 2012, 101 :4414-4418.

Nair, A., et al., "A Simple Practice Guide for Dose Conversion Between Animals and Human", Journal of Basic and Clinical Pharmacy, vol. 7, No. 2, 2016, 5 pages, XP055407475.

Overkleeft, Herman S., et al., "Generation of Specific Deoxynojirimycin-type Inhibitors of the Non-lysosomal Glucosylceramidase", The Journal of Biological Chemistry, 1998, vol. 273, No. 41, p. 26522-26527.

Platt, Frances M., et al., "N-Butyldeoxygalactonojirimycin Inhibits Glycolipid Biosynthesis but Does Not Affect N- Linked Oligosaccharide Processing", The Journal of Biological Chemistry, 1994, vol. 269, No. 43, p. 27108-27114.

Raben, et al., "Deconstructing Pompe Disease by Analyzing Single Muscle Fibers", Autophagy, 2007, 3, pp. 546-552.

Schoser, et al., "A systemic review of the health economics of Pompe Disease", PharmacoEconomics. 3: 479-493. 2019.

Shin-Buehring, Y.S., et al., "Separation of acid and neutral a-glucosidase isoenzymes from fetal and adult tissues, cultivated fibroblasts and amniotic fluid cells by DEAE-cellulose and Sephadex G-100 column chromatography", Clinica Chimica Acta 89(3):393-404, 12 pages (1978).

Sola, et al., "Glycosylation of Therapeutic Proteins: An Effective Strategy to Optimize Efficacy", BioDrugs., 2010, 24 (1 ):9-21.

Stanley, et al., "Essentials of Glycobiology", 2nd edition, Cold Spring Harbor (NY): Cold Spring Harbor Laboratory Press, Chapter 8, NCBI Bookshelf, 10 pages.

Sugawara, Kanako, et al., "Structural modeling of mutant rt-glucosidases resulting in a processing/transport defect in Pompe disease", Journal of Human Genetics (2009) 54, 624-330.

Tarnopolsky, et al., "Pompe Disease: Diagnosis and Management. Evidence Based Guidelines from a Canadian Expert Panel", Canadian Journal of Neurological Sciences 43(4):472-485 (2016).

Toonkool, P, et al., "(2006) Expression and purification of dalcochinase, a beta-glucosidase from Dalbergia cochinchinensis Pierre, in yeast and bacterial hosts", Protein Expression and Purification, 48(2): 195-204.

Winkel, et al., "Enzyme replacement therapy in late-onset Pompe's disease: a three-year follow-up", Ann. Neural. Apr. 2004;55(4): 495-502. PMID: 15048888. (Year: 2004).

Distribution of N-Glycans on rhGAA Preparations

| | Lumizyme | BP-rhGAA* | ATB200 1 | ATB200 2 |
|---|---|---|---|---|
| Complex Type N-Glycans | 70.7% | 48.9% | 51.0% | 47.5% |
| Hybrid Type N-Glycans | 6.7% | 9.7% | 4.4% | 3.7% |
| High Mannose Type N-Glycans: | | | | |
| Non-phosphorylated | 15.8% | 23.7% | 14.0% | 9.9% |
| Mono-M6P | 5.2% | 10.4% | 13.4% | 14.2% |
| Bis-M6P | 1.6% | 6.8% | 17.2% | 24.7% |

FIG. 7

| Cell Line | $K_{uptake}$ (nM) | |
|---|---|---|
| | AT200 | Lumizyme |
| normal | 2 | 56 |
| Pompe | 3 | 57 |

AUGMENTED ACID ALPHA-GLUCOSIDASE FOR THE TREATMENT OF POMPE DISEASE

CROSS-REFERENCE TO RELATED APPLICATIONS

This application is a continuation of U.S. patent application Ser. No. 17/061,691, filed Oct. 2, 2020, which is a continuation of U.S. patent application Ser. No. 15/950,347, filed Apr. 11, 2018 and issued as U.S. Pat. No. 10,857,212, which is a continuation of U.S. patent application Ser. No. 15/394,135, filed Dec. 29, 2016 (now abandoned), which claims the benefit under 35 U.S.C. § 119(e) to U.S. Provisional Application No. 62/272,890, filed Dec. 30, 2015, U.S. Provisional Application No. 62/300,479, filed Feb. 26, 2016, U.S. Provisional Application No. 62/315,412, filed Mar. 30, 2016, U.S. Provisional Application No. 62/402,454, filed Sep. 30, 2016, U.S. Provisional Application No. 62/428,867, filed Dec. 1, 2016 and U.S. Provisional Application No. 62/431,791, filed Dec. 8, 2016, the entire contents of each of which are incorporated herein by reference in their entirety.

The contents of the text file submitted electronically herewith are incorporated herein by reference in their entirety: A computer readable format copy of the Sequence Listing (filename: AMCS_006_09US_SeqList.txt, date recorded: Mar. 21, 2022, file size ~55,568 bytes).

FIELD

The present invention provides a method for treating Pompe disease comprising administering to an individual a combination of an acid α-glucosidase and a pharmacological chaperone thereof. More specifically, the present invention provides a method for treating Pompe disease comprising administering to an individual a combination of recombinant human acid α-glucosidase and miglustat.

BACKGROUND

Pompe disease, also known as acid maltase deficiency or glycogen storage disease type II, is one of several lysosomal storage disorders. Lysosomal storage disorders are a group of autosomal recessive genetic diseases characterized by the accumulation of cellular glycosphingolipids, glycogen, or mucopolysaccharides within intracellular compartments called lysosomes. Individuals with these diseases carry mutant genes coding for enzymes which are defective in catalyzing the hydrolysis of one or more of these substances, which then build up in the lysosomes. Other examples of lysosomal disorders include Gaucher disease, $G_{M1}$-gangliosidosis, fucosidosis, mucopolysaccharidoses, Hurler-Scheie disease, Niemann-Pick A and B diseases, and Fabry disease. Pompe disease is also classified as a neuromuscular disease or a metabolic myopathy.

Pompe disease is estimated to occur in about 1 in 40,000 births, and is caused by a mutation in the GAA gene, which codes for the enzyme lysosomal α-glucosidase (EC: 3.2.1.20), also commonly known as acid α-glucosidase. Acid α-glucosidase is involved in the metabolism of glycogen, a branched polysaccharide which is the major storage form of glucose in animals, by catalyzing its hydrolysis into glucose within the lysosomes. Because individuals with Pompe disease produce mutant, defective acid α-glucosidase which is inactive or has reduced activity, glycogen breakdown occurs slowly or not at all, and glycogen accumulates in the lysosomes of various tissues, particularly in striated muscles, leading to a broad spectrum of clinical manifestations, including progressive muscle weakness and respiratory insufficiency. Tissues such as the heart and skeletal muscles are particularly affected.

Pompe disease can vary widely in the degree of enzyme deficiency, severity and age of onset, and over 500 different mutations in the GAA gene have been identified, many of which cause disease symptoms of varying severity. The disease has been classified into broad types: early onset or infantile and late onset. Earlier onset of disease and lower enzymatic activity are generally associated with a more severe clinical course. Infantile Pompe disease is the most severe, resulting from complete or near complete acid α-glucosidase deficiency, and presents with symptoms that include severe lack of muscle tone, weakness, enlarged liver and heart, and cardiomyopathy. The tongue may become enlarged and protrude, and swallowing may become difficult. Most affected children die from respiratory or cardiac complications before the age of two. Late onset Pompe disease can present at any age older than 12 months and is characterized by a lack of cardiac involvement and better short-term prognosis. Symptoms are related to progressive skeletal muscle dysfunction, and involve generalized muscle weakness and wasting of respiratory muscles in the trunk, proximal lower limbs, and diaphragm. Some adult patients are devoid of major symptoms or motor limitations. Prognosis generally depends on the extent of respiratory muscle involvement. Most subjects with Pompe disease eventually progress to physical debilitation requiring the use of a wheelchair and assisted ventilation, with premature death often occurring due to respiratory failure.

Recent treatment options for Pompe disease include enzyme replacement therapy (ERT) with recombinant human acid α-glucosidase (rhGAA). Conventional rhGAA products are known under the names alglucosidase alfa, Myozyme® or Lumizyme®; Genzyme, Inc. ERT is a chronic treatment required throughout the lifetime of the patient, and involves administering the replacement enzyme by intravenous infusion. The replacement enzyme is then transported in the circulation and enters lysosomes within cells, where it acts to break down the accumulated glycogen, compensating for the deficient activity of the endogenous defective mutant enzyme, and thus relieving the disease symptoms. In subjects with infantile onset Pompe disease, treatment with alglucosidase alfa has been shown to significantly improve survival compared to historical controls, and in late onset Pompe disease, alglucosidase alfa has been shown to have a statistically significant, if modest, effect on the 6-Minute Walk Test (6MWT) and forced vital capacity (FVC) compared to placebo.

However, the majority of subjects either remain stable or continue to deteriorate while undergoing treatment with alglucosidase alfa. The reason for the apparent sub-optimal effect of ERT with alglucosidase alfa is unclear, but could be partly due to the progressive nature of underlying muscle pathology, or the poor tissue targeting of the current ERT. For example, the infused enzyme is not stable at neutral pH, including at the pH of plasma (about pH 7.4), and can be irreversibly inactivated within the circulation. Furthermore, infused alglucosidase alfa shows insufficient uptake in key disease-relevant muscles, possibly due to inadequate glycosylation with mannose-6-phosphate (M6P) residues. Such residues bind cation-independent mannose-6-phosphate receptors (CIMPR) at the cell surface, allowing the enzyme to enter the cell and the lysosomes within. Therefore, high doses of the enzyme may be required for effective treatment so that an adequate amount of active enzyme can reach the lysosomes, making the therapy costly and time-consuming.

In addition, development of anti-recombinant human acid α-glucosidase neutralizing antibodies often develop in Pompe disease patients, due to repeated exposure to the treatment. Such immune responses can severely reduce the tolerance of patients to the treatment. The US product label for alglucosidase alfa includes a black box warning with information on the potential risk of hypersensitivity reaction. Life-threatening anaphylactic reactions, including anaphylactic shock, have been observed in subjects treated with alglucosidase alfa.

Next-generation ERT is being developed to address these shortcomings. In one strategy, recombinant enzymes can be co-administered with pharmacological chaperones which can induce or stabilize a proper conformation of the enzyme, to prevent or reduce degradation of the enzyme and/or its unfolding into an inactive form, either in vitro (for example, in storage prior to administration) or in vivo. Such a strategy is described in International Patent Application Publications No. WO 2004/069190, WO 2006/125141, WO 2013/166249 and WO 2014/014938.

The results of clinical trials of co-administration of alglucosidase alfa with miglustat to patients with Pompe disease have been described. In a clinical trial conducted in 13 subjects with Pompe disease (3 early onset (infantile) and 10 late onset) at 4 treatment centers in Italy, 20 to 40 mg/kg alglucosidase alfa was administered alone and then co-administered with 4 doses of 80 mg miglustat. The results of the study showed a mean 6.8-fold increase in acid α-glucosidase activity exposure (measured in terms of the pharmacokinetic parameter AUC (area under the concentration v. time curve)) for co-administration compared to alglucosidase alfa alone (Parenti, G., G. Andria, et al. (2015). "Lysosomal Storage Diseases: From Pathophysiology to Therapy." Annu. Rev. Med. 66(1): 471-486). In addition, a study conducted at the University of Florida evaluated the pharmacokinetics (PK) of plasma miglustat when co-administered with intravenous infusion of alglucosidase alfa to subjects with Pompe disease (Doerfler, P. A., J. S. Kelley, et al. (2014). "Pharmacological chaperones prevent the precipitation of rhGAA by anti-GAA antibodies during enzyme replacement therapy." Mol. Genet. Metab. 111(2): S38).

However, there remains a need for further improvements to enzyme replacement therapy for treatment of Pompe disease. For example, new recombinant human acid α-glucosidase enzymes are desirable which can have one or more advantages over presently used enzymes, including but not limited to improved tissue uptake, improved enzymatic activity, improved stability or reduced immunogenicity.

SUMMARY

The present invention provides a method of treating Pompe disease in a patient in need thereof, the method including administering miglustat to the patient in combination with a recombinant human acid α-glucosidase (rhGAA), wherein the recombinant human acid α-glucosidase is expressed in Chinese hamster ovary (CHO) cells and comprises an increased content of N-glycan units bearing one or two mannose-6-phosphate residues when compared to a content of N-glycan units bearing one or two mannose-6-phosphate residues of alglucosidase alfa. In at least one embodiment, the recombinant human acid α-glucosidase is administered intravenously at a dose of about 20 mg/kg and the miglustat is administered orally at a dose of about 260 mg.

In another aspect, the present invention provides a combination of miglustat and a recombinant human acid α-glucosidase as defined herein for the treatment of Pompe disease in a patient in need thereof.

In another aspect, the present invention provides the use of a combination of miglustat and a recombinant human acid α-glucosidase as defined herein in the preparation of an agent for the treatment of Pompe disease in a patient in need thereof Another aspect of the present invention provides a kit for combination therapy of Pompe disease in a patient in need thereof, the kit including a pharmaceutically acceptable dosage form comprising miglustat, a pharmaceutically acceptable dosage form comprising a recombinant human acid α-glucosidase as defined herein, and instructions for administering the pharmaceutically acceptable dosage form comprising miglustat and the pharmaceutically acceptable dosage form comprising the recombinant acid α-glucosidase to a patient in need thereof.

BRIEF DESCRIPTION OF THE DRAWINGS

Further features of the present invention will become apparent from the following written description and the accompanying figures, in which:

As shown in FIG. 2A, 78% of the GAA activity in Lumizyme® eluted prior to addition of M6P. FIG. 2B shows that 73% of the GAA Myozyme® activity eluted prior to addition of M6P. Only 22% or 27% of the rhGAA in Lumizyme® or Myozyme®, respectively, was eluted with M6P. These figures show that most of the rhGAA in these two conventional rhGAA products lack glycans having M6P needed for cellular uptake and lysosomal targeting.

FIG. 7 shows a summary of N-glycan structures of Lumizyme® compared to three different preparations of ATB200 rhGAA, identified as BP-rhGAA, ATB200-1 and ATB200-2.

DEFINITIONS

Figure 1:
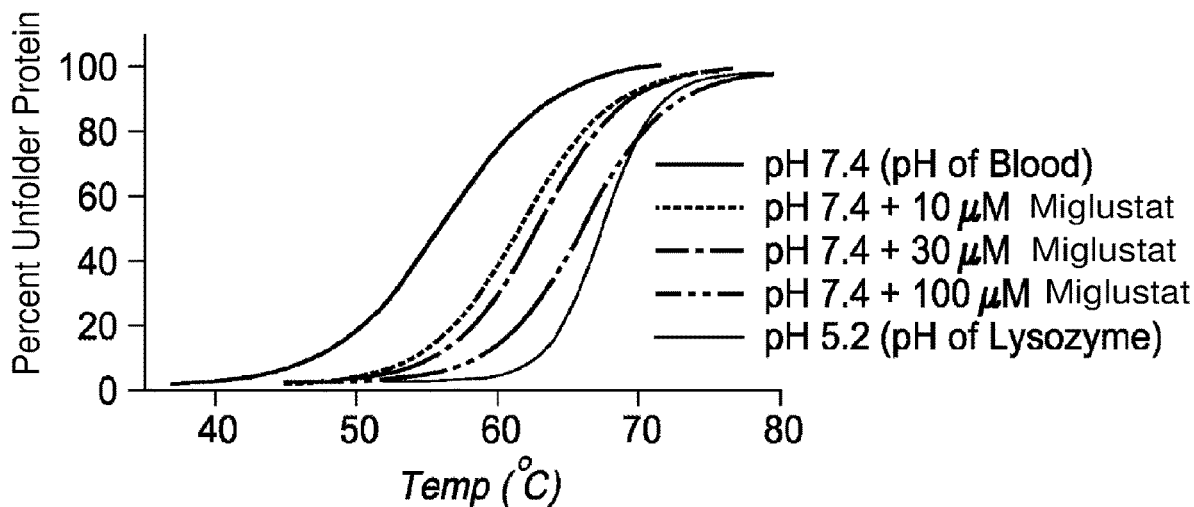
FIG. 1 is a graph showing the percentage of unfolded ATB200 protein at various pH values and in the presence and absence of miglustat vs. temperature.

The terms used in this specification generally have their ordinary meanings in the art, within the context of this invention and in the specific context where each term is used. Certain terms are discussed below, or elsewhere in the specification, to provide additional guidance to the practitioner.

In the present specification, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

As used herein, the term "Pompe disease," also referred to as acid maltase deficiency, glycogen storage disease type II (GSDII), and glycogenosis type II, is intended to refer to a genetic lysosomal storage disorder characterized by mutations in the GAA gene, which codes for the human acid α-glucosidase enzyme. The term includes but is not limited to early and late onset forms of the disease, including but not limited to infantile, juvenile and adult-onset Pompe disease.

As used herein, the term "acid α-glucosidase" is intended to refer to a lysosomal enzyme which hydrolyzes α-1,4 linkages between the D-glucose units of glycogen, maltose, and isomaltose. Alternative names include but are not limited to lysosomal α-glucosidase (EC:3.2.1.20); glucoamylase; 1,4-α-D-glucan glucohydrolase; amyloglucosidase; gamma-amylase and exo-1,4-α-glucosidase. Human acid α-glucosidase is encoded by the GAA gene (National Centre for Biotechnology Information (NCBI) Gene ID 2548), which has been mapped to the long arm of chromosome 17 (location 17q25.2-q25.3). More than 500 mutations have currently been identified in the human GAA gene, many of which are associated with Pompe disease. Mutations resulting in misfolding or misprocessing of the acid α-glucosidase enzyme include T1064C (Leu355Pro) and C2104T (Arg702Cys). In addition, GAA mutations which affect maturation and processing of the enzyme include Leu405Pro and Met519Thr. The conserved hexapeptide WIDMNE at amino acid residues 516-521 is required for activity of the acid α-glucosidase protein. As used herein, the abbreviation "GAA" is intended to refer to the acid α-glucosidase enzyme, while the italicized abbreviation "GAA" is intended to refer to the human gene coding for the human acid α-glucosidase enzyme The italicized abbreviation "Gaa" is intended to refer to non-human genes coding for non-human acid α-glucosidase enzymes, including but not limited to rat or mouse genes, and the abbreviation "Gaa" is intended to refer to non-human acid α-glucosidase enzymes. Thus, the abbreviation "rhGAA" is intended to refer to the recombinant human acid α-glucosidase enzyme.

As used herein, the term "alglucosidase alfa" is intended to refer to a recombinant human acid α-glucosidase identified as [199-arginine,223-histidine]prepro-α-glucosidase (human); Chemical Abstracts Registry Number 420794-05-0. Alglucosidase alfa is approved for marketing in the United States by Genzyme, as of Oct. 1, 2014, as the products Lumizyme® and Myozyme®.

As used herein, the term "ATB200" is intended to refer to a recombinant human acid α-glucosidase described in co-pending patent application PCT/US2015/053252, the disclosure of which is herein incorporated by reference.

As used herein, the term "glycan" is intended to refer to a polysaccharide chain covalently bound to an amino acid residue on a protein or polypeptide. As used herein, the term "N-glycan" or "N-linked glycan" is intended to refer to a polysaccharide chain attached to an amino acid residue on a protein or polypeptide through covalent binding to a nitrogen atom of the amino acid residue. For example, an N-glycan can be covalently bound to the side chain nitrogen atom of an asparagine residue. Glycans can contain one or several monosaccharide units, and the monosaccharide units can be covalently linked to form a straight chain or a branched chain. In at least one embodiment, N-glycan units attached to ATB200 can comprise one or more monosaccharide units each independently selected from N-acetylglucosamine, mannose, galactose or sialic acid. The N-glycan units on the protein can be determined by any appropriate analytical technique, such as mass spectrometry. In some embodiments, the N-glycan units can be determined by liquid chromatography-tandem mass spectrometry (LC-MS/MS) utilizing an instrument such as the Thermo Scientific Orbitrap Velos Pro™ Mass Spectrometer, Thermo Scientific Orbitrap Fusion Lumos Tribid™ Mass Spectrometer or Waters Xevo® G2-XS QT of Mass Spectrometer.

As used herein, the term "high-mannose N-glycan" is intended to refer to an N-glycan having one to six or more mannose units. In at least one embodiment, a high mannose N-glycan unit can contain a bis(N-acetylglucosamine) chain bonded to an asparagine residue and further bonded to a branched polymannose chain. As used herein interchangeably, the term "M6P" or "mannose-6-phosphate" is intended to refer to a mannose unit phosphorylated at the 6 position; i.e. having a phosphate group bonded to the hydroxyl group at the 6 position. In at least one embodiment, one or more mannose units of one or more N-glycan units are phosphorylated at the 6 position to form mannose-6-phosphate units. In at least one embodiment, the term "M6P" or "mannose-6-phosphate" refers to both a mannose phosphodiester having N-acetylglucosamine (GlcNAc) as a "cap" on the phosphate group, as well as a mannose unit having an exposed phosphate group lacking the GlcNAc cap. In at least one embodiment, the N-glycans of a protein can have multiple M6P groups, with at least one M6P group having a GlcNAc cap and at least one other M6P group lacking a GlcNAc cap.

As used herein, the term "complex N-glycan" is intended to refer to an N-glycan containing one or more galactose and/or sialic acid units. In at least one embodiment, a complex N-glycan can be a high-mannose N-glycan in which one or mannose units are further bonded to one or more monosaccharide units each independently selected from N-acetylglucosamine, galactose and sialic acid.

As used herein, the compound miglustat, also known as N-butyl-1-deoxynojirimycin or NB-DNJ or (2R,3R,4R,5S)-1-butyl-2-(hydroxymethyl)piperidine-3,4,5-triol, is a compound having the following chemical formula:

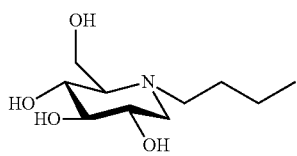

One formulation of miglustat is marketed commercially under the trade name Zavesca® as monotherapy for type 1 Gaucher disease.

As discussed below, pharmaceutically acceptable salts of miglustat may also be used in the present invention. When a salt of miglustat is used, the dosage of the salt will be adjusted so that the dose of miglustat received by the patient is equivalent to the amount which would have been received had the miglustat free base been used.

As used herein, the compound duvoglustat, also known as 1-deoxynojirimycin or DNJ or (2R,3R,4R,5S)-2-(hydroxymethyl)piperidine-3,4,5-triol, is a compound having the following chemical formula:

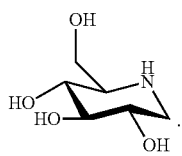

As used herein, the term "pharmacological chaperone" or sometimes simply the term "chaperone" is intended to refer to a molecule that specifically binds to acid α-glucosidase and has one or more of the following effects:

enhances the formation of a stable molecular conformation of the protein;

enhances proper trafficking of the protein from the endoplasmic reticulum to another cellular location, preferably a native cellular location, so as to prevent endoplasmic reticulum-associated degradation of the protein;

prevents aggregation of conformationally unstable or misfolded proteins;

restores and/or enhances at least partial wild-type function, stability, and/or activity of the protein; and/or improves the phenotype or function of the cell harboring acid α-glucosidase.

Thus, a pharmacological chaperone for acid α-glucosidase is a molecule that binds to acid α-glucosidase, resulting in proper folding, trafficking, non-aggregation, and activity of acid α-glucosidase. As used herein, this term includes but is not limited to active site-specific chaperones (ASSCs) which bind in the active site of the enzyme, inhibitors or antagonists, and agonists. In at least one embodiment, the pharmacological chaperone can be an inhibitor or antagonist of acid α-glucosidase. As used herein, the term "antagonist" is intended to refer to any molecule that binds to acid α-glucosidase and either partially or completely blocks, inhibits, reduces, or neutralizes an activity of acid α-glucosidase. In at least one embodiment, the pharmacological chaperone is miglustat. Another non-limiting example of a pharmacological chaperone for acid α-glucosidase is duvoglustat.

As used herein, the term "active site" is intended to refer to a region of a protein that is associated with and necessary for a specific biological activity of the protein. In at least one embodiment, the active site can be a site that binds a substrate or other binding partner and contributes the amino acid residues that directly participate in the making and breaking of chemical bonds. Active sites in this invention can encompass catalytic sites of enzymes, antigen binding sites of antibodies, ligand binding domains of receptors, binding domains of regulators, or receptor binding domains of secreted proteins. The active sites can also encompass transactivation, protein-protein interaction, or DNA binding domains of transcription factors and regulators.

As used herein, the term "AUC" is intended to refer to a mathematical calculation to evaluate the body's total exposure over time to a given drug. In a graph plotting how concentration in the blood of a drug administered to a subject changes with time after dosing, the drug concentration variable lies on the y-axis and time lies on the x-axis. The area between the drug concentration curve and the x-axis for a designated time interval is the AUC ("area under the curve"). AUCs are used as a guide for dosing schedules and to compare the bioavailability of different drugs' availability in the body.

As used herein, the term "$C_{max}$" is intended to refer to the maximum plasma concentration of a drug achieved after administration to a subject.

As used herein, the term "volume of distribution" or "V" is intended to refer to the theoretical volume that would be necessary to contain the total amount of an administered drug at the same concentration that it is observed in the blood plasma, and represents the degree to which a drug is distributed in body tissue rather than the plasma. Higher values of V indicate a greater degree of tissue distribution. "Central volume of distribution" or "$V_c$" is intended to refer to the volume of distribution within the blood and tissues highly perfused by blood. "Peripheral volume of distribution" or "V2" is intended to refer to the volume of distribution within the peripheral tissue.

As used interchangeably herein, the terms "clearance", "systemic clearance" or "CL" are intended to refer to the volume of plasma that is completely cleared of an administered drug per unit time. "Peripheral clearance" is intended to refer to the volume of peripheral tissue that is cleared of an administered drug per unit time.

As used herein, the "therapeutically effective dose" and "effective amount" are intended to refer to an amount of acid α-glucosidase and/or of miglustat and/or of a combination thereof, which is sufficient to result in a therapeutic response in a subject. A therapeutic response may be any response that a user (for example, a clinician) will recognize as an effective response to the therapy, including any surrogate clinical markers or symptoms described herein and known in the art. Thus, in at least one embodiment, a therapeutic response can be an amelioration or inhibition of one or more symptoms or markers of Pompe disease such as those known in the art. Symptoms or markers of Pompe disease include but are not limited to decreased acid α-glucosidase tissue activity; cardiomyopathy; cardiomegaly; progressive muscle weakness, especially in the trunk or lower limbs; profound hypotonia; macroglossia (and in some cases, protrusion of the tongue); difficulty swallowing, sucking, and/or feeding; respiratory insufficiency; hepatomegaly (moderate); laxity of facial muscles; areflexia; exercise intolerance; exertional dyspnea; orthopnea; sleep apnea; morning headaches; somnolence; lordosis and/or scoliosis; decreased deep tendon reflexes; lower back pain; and failure to meet developmental motor milestones. It should be noted that a concentration of miglustat that has an inhibitory effect on acid α-glucosidase may constitute an "effective amount" for purposes of this invention because of dilution (and consequent shift in binding due to the change in equilibrium), bioavailability and metabolism of miglustat upon administration in vivo.

As used herein, the term "enzyme replacement therapy" or "ERT" is intended to refer to the introduction of a non-native, purified enzyme into an individual having a deficiency in such enzyme. The administered protein can be obtained from natural sources or by recombinant expression. The term also refers to the introduction of a purified enzyme in an individual otherwise requiring or benefiting from administration of a purified enzyme. In at least one embodiment, such an individual suffers from enzyme insufficiency. The introduced enzyme may be a purified, recombinant enzyme produced in vitro, or a protein purified from isolated tissue or fluid, such as, for example, placenta or animal milk, or from plants.

As used herein, the term "combination therapy" is intended to refer to any therapy wherein two or more individual therapies are administered concurrently or consecutively. In at least one embodiment, the results of the combination therapy are enhanced as compared to the effect of each therapy when it is performed individually. Enhancement may include any improvement of the effect of the various therapies that may result in an advantageous result as compared to the results achieved by the therapies when performed alone. Enhanced effect or results can include a synergistic enhancement, wherein the enhanced effect is more than the additive effects of each therapy when performed by itself; an additive enhancement, wherein the enhanced effect is substantially equal to the additive effect of each therapy when performed by itself; or less than a synergistic effect, wherein the enhanced effect is lower than the additive effect of each therapy when performed by itself, but still better than the effect of each therapy when performed by itself. Enhanced effect may be measured by any means known in the art by which treatment efficacy or outcome can be measured.

As used herein, the term "pharmaceutically acceptable" is intended to refer to molecular entities and compositions that are physiologically tolerable and do not typically produce untoward reactions when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans.

As used herein, the term "carrier" is intended to refer to a diluent, adjuvant, excipient, or vehicle with which a compound is administered. Suitable pharmaceutical carriers are known in the art and, in at least one embodiment, are described in "Remington's Pharmaceutical Sciences" by E. W. Martin, 18th Edition, or other editions.

As used herein, the terms "subject" or "patient" are intended to refer to a human or non-human animal. In at least one embodiment, the subject is a mammal. In at least one embodiment, the subject is a human.

As used herein, the term "anti-drug antibody" is intended to refer to an antibody specifically binding to a drug administered to a subject and generated by the subject as at least part of a humoral immune response to administration of the drug to the subject. In at least one embodiment the drug is a therapeutic protein drug product. The presence of the anti-drug antibody in the subject can cause immune responses ranging from mild to severe, including but not limited to life-threatening immune responses which include but are not limited to anaphylaxis, cytokine release syndrome and cross-reactive neutralization of endogenous proteins mediating critical functions. In addition or alternatively, the presence of the anti-drug antibody in the subject can decrease the efficacy of the drug.

As used herein, the term "neutralizing antibody" is intended to refer to an anti-drug antibody acting to neutralize the function of the drug. In at least one embodiment, the therapeutic protein drug product is a counterpart of an endogenous protein for which expression is reduced or absent in the subject. In at least one embodiment, the neutralizing antibody can act to neutralize the function of the endogenous protein.

As used herein, the terms "about" and "approximately" are intended to refer to an acceptable degree of error for the quantity measured given the nature or precision of the measurements. For example, the degree of error can be indicated by the number of significant figures provided for the measurement, as is understood in the art, and includes but is not limited to a variation of ±1 in the most precise significant figure reported for the measurement. Typical exemplary degrees of error are within 20 percent (%), preferably within 10%, and more preferably within 5% of a given value or range of values. Alternatively, and particularly in biological systems, the terms "about" and "approximately" can mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "concurrently" as used herein is intended to mean at the same time as or within a reasonably short period of time before or after, as will be understood by those skilled in the art. For example, if two treatments are administered concurrently with each other, one treatment can be administered before or after the other treatment, to allow for time needed to prepare for the later of the two treatments. Therefore "concurrent administration" of two treatments includes but is not limited to one treatment following the other by 20 minutes or less, about 20 minutes, about 15 minutes, about 10 minutes, about 5 minutes, about 2 minutes, about 1 minute or less than 1 minute.

The term "pharmaceutically acceptable salt" as used herein is intended to mean a salt which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, for example, S. M. Birge et al., J. Pharm. Sci., 1977, 66, pp. 1-19, herein incorporated by reference.

The term "pharmaceutically-acceptable acid addition salt" as used herein is intended to mean those salts which retain the biological effectiveness and properties of the free bases and which are not biologically or otherwise undesirable, formed with inorganic acids including but not limited to hydrochloric acid, hydrobromic acid, sulfuric acid, sulfamic acid, nitric acid, phosphoric acid and the like, and organic acids including but not limited to acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid and the like.

The term "pharmaceutically-acceptable base addition salt" as used herein is intended to mean those salts which retain the biological effectiveness and properties of the free acids and which are not biologically or otherwise undesirable, formed with inorganic bases including but not limited to ammonia or the hydroxide, carbonate, or bicarbonate of ammonium or a metal cation such as sodium, potassium, lithium, calcium, magnesium, iron, zinc, copper, manganese, aluminum and the like. Salts derived from pharmaceutically-acceptable organic nontoxic bases include but are not limited to salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins and the like.

DETAILED DESCRIPTION

The present invention provides a method of treating Pompe disease in a patient in need thereof, the method including administering miglustat, or a pharmaceutically acceptable salt thereof, to the patient in combination with a recombinant human acid α-glucosidase, wherein the recombinant human acid α-glucosidase is expressed in Chinese hamster ovary (CHO) cells and comprises an increased content of N-glycan units bearing one or two mannose-6-phosphate residues when compared to a content of N-glycan units bearing one or two mannose-6-phosphate residues of alglucosidase alfa. In at least one embodiment, the recombinant human acid α-glucosidase has low levels of complex glycans with terminal galactose. In another aspect, the present invention provides the use of miglustat and the recombinant human acid α-glucosidase in combination for the treatment of Pompe disease in a patient in need thereof.

In at least one embodiment, the miglustat is administered orally. In at least one embodiment, the miglustat is administered at an oral dose of about 200 mg to about 600 mg, or at an oral dose of about 200 mg, about 250 mg, about 300 mg, about 350 mg, about 400 mg, about 450 mg, about 500 mg, about 550 mg or about 600 mg. In at least one embodiment, the miglustat is administered at an oral dose of about 233 mg to about 400 mg. In at least one embodiment, the miglustat is administered at an oral dose of about 250 to about 270 mg, or at an oral dose of about 250 mg, about 255 mg, about 260 mg, about 265 mg or about 270 mg. In at least one embodiment, the miglustat is administered as an oral dose of about 260 mg.

It will be understood by those skilled in the art that an oral dose of miglustat in the range of about 200 mg to 600 mg or any smaller range therewithin can be suitable for an adult patient with an average body weight of about 70 kg. For patients having a significantly lower body weight than about 70 kg, including but not limited to infants, children or underweight adults, a smaller dose may be considered suitable by a physician. Therefore, in at least one embodiment, the miglustat is administered as an oral dose of from about 50 mg to about 200 mg, or as an oral dose of about 50 mg, about 75 mg, about 100 mg, 125 mg, about 150 mg, about 175 mg or about 200 mg. In at least one embodiment, the miglustat is administered as an oral dose of from about 65 mg to about 195 mg, or as an oral dose of about 65 mg, about 130 mg or about 195 mg.

In at least one embodiment, the miglustat is administered as a pharmaceutically acceptable dosage form suitable for oral administration, and includes but is not limited to tablets, capsules, ovules, elixirs, solutions or suspensions, gels, syrups, mouth washes, or a dry powder for reconstitution with water or other suitable vehicle before use, optionally with flavoring and coloring agents for immediate-, delayed-, modified-, sustained-, pulsed- or controlled-release applications. Solid compositions such as tablets, capsules, lozenges, pastilles, pills, boluses, powder, pastes, granules, bullets, dragées or premix preparations can also be used. In at least one embodiment, the miglustat is administered as a tablet. In at least one embodiment, the miglustat is administered as a capsule. In at least one embodiment, the dosage form contains from about 50 mg to about 300 mg of miglustat. In at least one embodiment, the dosage form contains about 65 mg of miglustat. In at least one embodiment, the dosage form contains about 130 mg of miglustat. In at least one embodiment, the dosage form contains about 260 mg of miglustat. It is contemplated that when the dosage form contains about 65 mg of miglustat, the miglustat can be administered as a dosage of four dosage forms, or a total dose of 260 mg of miglustat. However, for patients who have a significantly lower weight than an average adult weight of 70 kg, including but not limited to infants, children or underweight adults, the miglustat can be administered as a dosage of one dosage form (a total dose of 65 mg of miglustat), two dosage forms (a total dose of 130 mg of miglustat), or three dosage forms (a total dose of 195 mg of miglustat).

Solid and liquid compositions for oral use can be prepared according to methods well known in the art. Such compositions can also contain one or more pharmaceutically acceptable carriers and excipients which can be in solid or liquid form. Tablets or capsules can be prepared by conventional means with pharmaceutically acceptable excipients, including but not limited to binding agents, fillers, lubricants, disintegrants or wetting agents. Suitable pharmaceutically acceptable excipients are known in the art and include but are not limited to pregelatinized starch, polyvinylpyrrolidone, povidone, hydroxypropyl methylcellulose (HPMC), hydroxypropyl ethylcellulose (HPEC), hydroxypropyl cellulose (HPC), sucrose, gelatin, acacia, lactose, microcrystalline cellulose, calcium hydrogen phosphate, magnesium stearate, stearic acid, glyceryl behenate, talc, silica, corn, potato or tapioca starch, sodium starch glycolate, sodium lauryl sulfate, sodium citrate, calcium carbonate, dibasic calcium phosphate, glycine croscarmellose sodium and complex silicates. Tablets can be coated by methods well known in the art. In at least one embodiment, the miglustat is administered as a formulation available commercially as Zavesca® (Actelion Pharmaceuticals).

In at least one embodiment, the recombinant human acid α-glucosidase is expressed in Chinese hamster ovary (CHO) cells and comprises an increased content of N-glycan units bearing one or more mannose-6-phosphate residues when compared to a content of N-glycan units bearing one or more mannose-6-phosphate residues of alglucosidase alfa. In at least one embodiment, the acid α-glucosidase is a recombinant human acid α-glucosidase referred to herein as ATB200, as described in co-pending international patent application PCT/US2015/053252. ATB200 has been shown to bind cation-independent mannose-6-phosphate receptors (CIMPR) with high affinity ($K_D$~2-4 nM) and to be efficiently internalized by Pompe fibroblasts and skeletal muscle myoblasts ($K_{uptake}$~7-14 nM). ATB200 was characterized in vivo and shown to have a shorter apparent plasma half-life ($t_{1/2}$~45 min) than alglucosidase alfa ($t_{1/2}$~60 min).

In at least one embodiment, the recombinant human acid α-glucosidase is an enzyme having an amino acid sequence as set forth in SEQ ID NO: 1, SEQ ID NO: 2 (or as encoded by SEQ ID NO: 2), SEQ ID NO: 3, SEQ ID NO: 4 or SEQ ID NO: 5.

```
                                                    SEQ ID NO: 1
Met Gly Val Arg His Pro Pro Cys Ser His Arg

Leu Leu Ala Val Cys Ala Leu Val Ser Leu Ala

Thr Ala Ala Leu Leu Gly His Ile Leu Leu His

Asp Phe Leu Leu Val Pro Arg Glu Leu Ser Gly

Ser Ser Pro Val Leu Glu Glu Thr His Pro Ala

His Gln Gln Gly Ala Ser Arg Pro Gly Pro Arg

Asp Ala Gln Ala His Pro Gly Arg Pro Arg Ala

Val Pro Thr Gln Cys Asp Val Pro Pro Asn Ser

Arg Phe Asp Cys Ala Pro Asp Lys Ala Ile Thr

Gln Glu Gln Cys Glu Ala Arg Gly Cys Cys Tyr

Ile Pro Ala Lys Gln Gly Leu Gln Gly Ala Gln

Met Gly Gln Pro Trp Cys Phe Phe Pro Pro Ser

Tyr Pro Ser Tyr Lys Leu Glu Asn Leu Ser Ser

Ser Glu Met Gly Tyr Thr Ala Thr Leu Thr Arg

Thr Thr Pro Thr Phe Phe Pro Lys Asp Ile Leu

Thr Leu Arg Leu Asp Val Met Met Glu Thr Glu

Asn Arg Leu His Phe Thr Ile Lys Asp Pro Ala

Asn Arg Arg Tyr Glu Val Pro Leu Glu Thr Pro

Arg Val His Ser Arg Ala Pro Ser Pro Leu Tyr

Ser Val Glu Phe Ser Glu Glu Pro Phe Gly Val

Ile Val His Arg Gln Leu Asp Gly Arg Val Leu
```

```
                    -continued
Leu Asn Thr Thr Val Ala Pro Leu Phe Phe Ala

Asp Gln Phe Leu Gln Leu Ser Thr Ser Leu Pro

Ser Gln Tyr Ile Thr Gly Leu Ala Glu His Leu

Ser Pro Leu Met Leu Ser Thr Ser Trp Thr Arg

Ile Thr Leu Trp Asn Arg Asp Leu Ala Pro Thr

Pro Gly Ala Asn Leu Tyr Gly Ser His Pro Phe

Tyr Leu Ala Leu Glu Asp Gly Gly Ser Ala His

Gly Val Phe Leu Leu Asn Ser Asn Ala Met Asp

Val Val Leu Gln Pro Ser Pro Ala Leu Ser Trp

Arg Ser Thr Gly Gly Ile Leu Asp Val Tyr Ile

Phe Leu Gly Pro Glu Pro Lys Ser Val Val Gln

Gln Tyr Leu Asp Val Val Gly Tyr Pro Phe Met

Pro Pro Tyr Trp Gly Leu Gly Phe His Leu Cys

Arg Trp Gly Tyr Ser Ser Thr Ala Ile Thr Arg

Gln Val Val Glu Asn Met Thr Arg Ala His Phe

Pro Leu Asp Val Gln Trp Asn Asp Leu Asp Tyr

Met Asp Ser Arg Arg Asp Phe Thr Phe Asn Lys

Asp Gly Phe Arg Asp Phe Pro Ala Met Val Gln

Glu Leu His Gln Gly Gly Arg Arg Tyr Met Met

Ile Val Asp Pro Ala Ile Ser Ser Ser Gly Pro

Ala Gly Ser Tyr Arg Pro Tyr Asp Glu Gly Leu

Arg Arg Gly Val Phe Ile Thr Asn Glu Thr Gly

Gln Pro Leu Ile Gly Lys Val Trp Pro Gly Ser

Thr Ala Phe Pro Asp Phe Thr Asn Pro Thr Ala

Leu Ala Trp Trp Glu Asp Met Val Ala Glu Phe

His Asp Gln Val Pro Phe Asp Gly Met Trp Ile

Asp Met Asn Glu Pro Ser Asn Phe Ile Arg Gly

Ser Glu Asp Gly Cys Pro Asn Asn Glu Leu Glu

Asn Pro Pro Tyr Val Pro Gly Val Val Gly Gly

Thr Leu Gln Ala Ala Thr Ile Cys Ala Ser Ser

His Gln Phe Leu Ser Thr His Tyr Asn Leu His

Asn Leu Tyr Gly Leu Thr Glu Ala Ile Ala Ser

His Arg Ala Leu Val Lys Ala Arg Gly Thr Arg

Pro Phe Val Ile Ser Arg Ser Thr Phe Ala Gly

His Gly Arg Tyr Ala Gly His Trp Thr Gly Asp

Val Trp Ser Ser Trp Glu Gln Leu Ala Ser Ser

Val Pro Glu Ile Leu Gln Phe Asn Leu Leu Gly

Val Pro Leu Val Gly Ala Asp Val Cys Gly Phe

Leu Gly Asn Thr Ser Glu Glu Leu Cys Val Arg

Trp Thr Gln Leu Gly Ala Phe Tyr Pro Phe Met
```

-continued

Arg Asn His Asn Ser Leu Leu Ser Leu Pro Gln
Glu Pro Tyr Ser Phe Ser Glu Pro Ala Gln Gln
Ala Met Arg Lys Ala Leu Thr Leu Arg Tyr Ala
Leu Leu Pro His Leu Tyr Thr Leu Phe His Gln
Ala His Val Ala Gly Glu Thr Val Ala Arg Pro
Leu Phe Leu Glu Phe Pro Lys Asp Ser Ser Thr
Trp Thr Val Asp His Gln Leu Leu Trp Gly Glu
Ala Leu Leu Ile Thr Pro Val Leu Gln Ala Gly
Lys Ala Glu Val Thr Gly Tyr Phe Pro Leu Gly
Thr Trp Tyr Asp Leu Gln Thr Val Pro Ile Glu
Ala Leu Gly Ser Leu Pro Pro Pro Ala Ala
Pro Arg Glu Pro Ala Ile His Ser Glu Gly Gln
Trp Val Thr Leu Pro Ala Pro Leu Asp Thr Ile
Asn Val His Leu Arg Ala Gly Tyr Ile Ile Pro
Leu Gln Gly Pro Gly Leu Thr Thr Thr Glu Ser
Arg Gln Gln Pro Met Ala Leu Ala Val Ala Leu
Thr Lys Gly Gly Glu Ala Arg Gly Glu Leu Phe
Trp Asp Asp Gly Glu Ser Leu Glu Val Leu Glu
Arg Gly Ala Tyr Thr Gln Val Ile Phe Leu Ala
Arg Asn Asn Thr Ile Val Asn Glu Leu Val Arg
Val Thr Ser Glu Gly Ala Gly Leu Gln Leu Gln
Lys Val Thr Val Leu Gly Val Ala Thr Ala Pro
Gln Gln Val Leu Ser Asn Gly Val Pro Val Ser
Asn Phe Thr Tyr Ser Pro Asp Thr Lys Val Leu
Asp Ile Cys Val Ser Leu Leu Met Gly Glu Gln
Phe Leu Val Ser Trp Cys

SEQ ID NO: 2
cagttgggaaagctgaggttgtcgccggggccgcgggtggaggtc
ggggatgaggcagcaggtaggacagtgacctcggtgacgcgaag
gaccccggccacctctaggttctcctcgtccgcccgttgttcag
cgagggaggctctgggcctgccgcagctgacggggaaactgagg
cacggagcgggcctgtaggagctgtccaggccatctccaaccat
gggagtgaggcacccgccctgctcccaccggctcctggccgtct
gcgccctcgtgtccttggcaaccgctgcactcctggggcacatc
ctactccatgatttcctgctggttccccgagagctgagtggctc
ctccccagtcctggaggagactcacccagctcaccagcagggag
ccagcagaccagggccccgggatgcccaggcacaccccggccgt
cccagagcagtgcccacacagtgcgacgtccccccccaacagccg
cttcgattgcgcccctgacaaggccatcacccaggaacagtgcg
aggcccgcggctgctgctacatccctgcaaagcaggggctgcag
ggagcccagatggggcagcccggtgcttcttcccacccagcta -continued ccccagctacaagctggagaacctgagctcctctgaaatgggct
acacggccaccctgaccgtaccaccccaccttcttccccaag
gacatcctgaccctgcggctggacgtgatgatggagactgagaa
ccgcctccacttcacgatcaaagatccagctaacaggcgctacg
aggtgcccttggagaccccgcgtgtccacagccgggcaccgtcc
ccactctacagcgtggagttctccgaggagcccttcggggtgat
cgtgcaccggcagctggacggccgcgtgctgctgaacacgacgg
tggcgcccctgttctttgcggaccagttccttcagctgtccacc
tcgctgccctcgcagtatatcacaggcctcgccgagcacctcag
tccctgatgctcagcaccagctggaccaggatcaccctgtgga
accgggaccttgcgcccacgcccggtgcgaacctctacgggtct
caccctttctacctggcgctggaggacggcgggtcggcacacgg
ggtgttcctgctaaacagcaatgccatggatgtggtcctgcagc
cgagccctgcccttagctggaggtcgacaggtgggatcctggat
gtctacatcttcctgggcccagagcccaagagcgtggtgcagca
gtacctggacgttgtgggatacccgttcatgccgccatactggg
gcctgggcttccacctgtgccgctgggctactcctccaccgct
atcacccgccaggtggtggagaacatgaccagggcccacttccc
cctggacgtccaatgaacgacctggactacatggactcccga
gggacttcacgttcaacaaggatggcttccgggacttcccggcc
atggtgcaggagctgcaccagggcggccggcgctacatgatgat
cgtggatcctgccatcagcagctcgggccctgccgggagctaca
ggccctacgacgagggtctgcggaggggggttttcatcaccaac
gagaccggccagccgctgattgggaaggtatggcccgggtccac
tgccttccccgacttcaccaaccccacagccctggcctggtggg
aggacatggtggctgagttccatgaccaggtgcccttcgacggc
atgtggattgacatgaacgagccttccaacttcatcagaggctc
tgaggacggctgccccaacaatgagctggagaacccaccctacg
tgcctggggtggttgggggggaccctccaggcggccaccatctgt
gcctccagccaccagtttctctccacacactacaacctgcacaa
cctctacggcctgaccgaagccatcgcctcccacagggcgctgg
tgaaggctcgggggacacgcccatttgtgatctcccgctcgacc
tttgctggcacggccgatacgccggccactggacgggggacgt
gtggagctcctgggagcagctcgcctcctccgtgccagaaatcc
tgcagtttaacctgctggggtgcctctggtcggggccgacgtc
tgcggcttcctgggcaacacctcagaggagctgtgtgtgcgctg
gacccagctgggggccttctaccccttcatgcggaaccacaaca
gcctgctcagtctgccccaggagccgtacagcttcagcgagccg
gcccagcaggccatgaggaaggccctcacccctgcgctacgcact
cctccccacctctacacactgttccaccaggcccacgtcgcgg
gggagaccgtggcccggcccctcttcctggagttccccaaggac -continued tctagcacctggactgtggaccaccagctcctgtgggggaggc
cctgctcatcaccccagtgctccaggccgggaaggccgaagtga
ctggctacttccccttgggcacatggtacgacctgcagacggtg
ccaatagaggcccttggcagcctccaccccacctgcagctcc
ccgtgagccagccatccacagcgaggggcagtgggtgacgctgc
cggccccctggacaccatcaacgtccacctccgggctgggtac
atcatcccctgcagggccctggcctcacaaccacagagtcccg
ccagcagcccatggccctggctgtggccctgaccaaggggtggag
aggcccgaggggagctgttctgggacgatggagagagcctggaa
gtgctggagcgaggggcctacacacaggtcatcttcctggccag
gaataacacgatcgtgaatgagctggtacgtgtgaccagtgagg
gagctggcctgcagctgcagaaggtgactgtcctgggcgtggcc
acggcgcccagcaggtcctctccaacggtgtccctgtctccaa
cttcacctacagccccgacaccaaggtcctggacatctgtgtct
cgctgttgatgggagagcagtttctcgtcagctggtgttagccg
ggcggagtgtgttagtctctccagagggaggctggttccccagg
gaagcagagcctgtgtgcgggcagcagctgtgtgcgggcctggg
ggttgcatgtgtcacctggagctgggcactaaccattccaagcc
gccgcatcgcttgtttccacctcctgggccggggctctggcccc
caacgtgtctaggagagctttctccctagatcgcactgtgggcc
ggggcctggagggctgctctgtgttaataagattgtaaggtttg
ccctcctcacctgttgccggcatgcgggtagtattagccacccc
cctccatctgttcccagcaccggagaagggggtgctcaggtgga
ggtgtggggtatgcacctgagctcctgcttcgcgcctgctgctc
tgccccaacgcgaccgcttcccggctgcccagagggctggatgc
ctgccggtccccgagcaagcctgggaactcaggaaaattcacag
gacttgggagattctaaatcttaagtgcaattatttttaataaaa
ggggcatttggaatc SEQ ID NO: 3
Met Gly Val Arg His Pro Pro Cys Ser His Arg
Leu Leu Ala Val Cys Ala Leu Val Ser Leu Ala
Thr Ala Ala Leu Leu Gly His Ile Leu Leu His
Asp Phe Leu Leu Val Pro Arg Glu Leu Ser Gly
Ser Ser Pro Val Leu Glu Glu Thr His Pro Ala
His Gln Gln Gly Ala Ser Arg Pro Gly Pro Arg
Asp Ala Gln Ala His Pro Gly Arg Pro Arg Ala
Val Pro Thr Gln Cys Asp Val Pro Pro Asn Ser
Arg Phe Asp Cys Ala Pro Asp Lys Ala Ile Thr
Gln Glu Gln Cys Glu Ala Arg Gly Cys Cys Tyr
Ile Pro Ala Lys Gln Gly Leu Gln Gly Ala Gln
Met Gly Gln Pro Trp Cys Phe Phe Pro Pro Ser
Tyr Pro Ser Tyr Lys Leu Glu Asn Leu Ser Ser
Ser Glu Met Gly Tyr Thr Ala Thr Leu Thr Arg
Thr Thr Pro Thr Phe Phe Pro Lys Asp Ile Leu
Thr Leu Arg Leu Asp Val Met Met Glu Thr Glu
Asn Arg Leu His Phe Thr Ile Lys Asp Pro Ala
Asn Arg Arg Tyr Glu Val Pro Leu Glu Thr Pro
Arg Val His Ser Arg Ala Pro Ser Pro Leu Tyr
Ser Val Glu Phe Ser Glu Glu Pro Phe Gly Val
Ile Val His Arg Gln Leu Asp Gly Arg Val Leu
Leu Asn Thr Thr Val Ala Pro Leu Phe Phe Ala
Asp Gln Phe Leu Gln Leu Ser Thr Ser Leu Pro
Ser Gln Tyr Ile Thr Gly Leu Ala Glu His Leu
Ser Pro Leu Met Leu Ser Thr Ser Trp Thr Arg
Ile Thr Leu Trp Asn Arg Asp Leu Ala Pro Thr
Pro Gly Ala Asn Leu Tyr Gly Ser His Pro Phe
Tyr Leu Ala Leu Glu Asp Gly Gly Ser Ala His
Gly Val Phe Leu Leu Asn Ser Asn Ala Met Asp
Val Val Leu Gln Pro Ser Pro Ala Leu Ser Trp
Arg Ser Thr Gly Gly Ile Leu Asp Val Tyr Ile
Phe Leu Gly Pro Glu Pro Lys Ser Val Val Gln
Gln Tyr Leu Asp Val Val Gly Tyr Pro Phe Met
Pro Pro Tyr Trp Gly Leu Gly Phe His Leu Cys
Arg Trp Gly Tyr Ser Ser Thr Ala Ile Thr Arg
Gln Val Val Glu Asn Met Thr Arg Ala His Phe
Pro Leu Asp Val Gln Trp Asn Asp Leu Asp Tyr
Met Asp Ser Arg Arg Asp Phe Thr Phe Asn Lys
Asp Gly Phe Arg Asp Phe Pro Ala Met Val Gln
Glu Leu His Gln Gly Gly Arg Arg Tyr Met Met
Ile Val Asp Pro Ala Ile Ser Ser Ser Gly Pro
Ala Gly Ser Tyr Arg Pro Tyr Asp Glu Gly Leu
Arg Arg Gly Val Phe Ile Thr Asn Glu Thr Gly
Gln Pro Leu Ile Gly Lys Val Trp Pro Gly Ser
Thr Ala Phe Pro Asp Phe Thr Asn Pro Thr Ala
Leu Ala Trp Trp Glu Asp Met Val Ala Glu Phe
His Asp Gln Val Pro Phe Asp Gly Met Trp Ile
Asp Met Asn Glu Pro Ser Asn Phe Ile Arg Gly
Ser Glu Asp Gly Cys Pro Asn Asn Glu Leu Glu
Asn Pro Pro Tyr Val Pro Gly Val Val Gly Gly
Thr Leu Gln Ala Ala Thr Ile Cys Ala Ser Ser
His Gln Phe Leu Ser Thr His Tyr Asn Leu His -continued Asn Leu Tyr Gly Leu Thr Glu Ala Ile Ala Ser
His Arg Ala Leu Val Lys Ala Arg Gly Thr Arg
Pro Phe Val Ile Ser Arg Ser Thr Phe Ala Gly
His Gly Arg Tyr Ala Gly His Trp Thr Gly Asp
Val Trp Ser Ser Trp Glu Gln Leu Ala Ser Ser
Val Pro Glu Ile Leu Gln Phe Asn Leu Leu Gly
Val Pro Leu Val Gly Ala Asp Val Cys Gly Phe
Leu Gly Asn Thr Ser Glu Glu Leu Cys Val Arg
Trp Thr Gln Leu Gly Ala Phe Tyr Pro Phe Met
Arg Asn His Asn Ser Leu Leu Ser Leu Pro Gln
Glu Pro Tyr Ser Phe Ser Glu Pro Ala Gln Gln
Ala Met Arg Lys Ala Leu Thr Leu Arg Tyr Ala
Leu Leu Pro His Leu Tyr Thr Leu Phe His Gln
Ala His Val Ala Gly Glu Thr Val Ala Arg Pro
Leu Phe Leu Glu Phe Pro Lys Asp Ser Ser Thr
Trp Thr Val Asp His Gln Leu Leu Trp Gly Glu
Ala Leu Leu Ile Thr Pro Val Leu Gln Ala Gly
Lys Ala Glu Val Thr Gly Tyr Phe Pro Leu Gly
Thr Trp Tyr Asp Leu Gln Thr Val Pro Ile Glu
Ala Leu Gly Ser Leu Pro Pro Pro Ala Ala
Pro Arg Glu Pro Ala Ile His Ser Glu Gly Gln
Trp Val Thr Leu Pro Ala Pro Leu Asp Thr Ile
Asn Val His Leu Arg Ala Gly Tyr Ile Ile Pro
Leu Gln Gly Pro Gly Leu Thr Thr Thr Glu Ser
Arg Gln Gln Pro Met Ala Leu Ala Val Ala Leu
Thr Lys Gly Gly Glu Ala Arg Gly Glu Leu Phe
Trp Asp Asp Gly Glu Ser Leu Glu Val Leu Glu
Arg Gly Ala Tyr Thr Gln Val Ile Phe Leu Ala
Arg Asn Asn Thr Ile Val Asn Glu Leu Val Arg
Val Thr Ser Glu Gly Ala Gly Leu Gln Leu Gln
Lys Val Thr Val Leu Gly Val Ala Thr Ala Pro
Gln Gln Val Leu Ser Asn Gly Val Pro Val Ser
Asn Phe Thr Tyr Ser Pro Asp Thr Lys Val Leu
Asp Ile Cys Val Ser Leu Leu Met Gly Glu Gln
Phe Leu Val Ser Trp Cys Met Gly Val Arg His
Pro Pro Cys Ser His Arg Leu Leu Ala Val Cys SEQ ID NO: 4
Ala Leu Val Ser Leu Ala Thr Ala Ala Leu Leu
Gly His Ile Leu Leu His Asp Phe Leu Leu Val
Pro Arg Glu Leu Ser Gly Ser Ser Pro Val Leu
Glu Glu Thr His Pro Ala His Gln Gln Gly Ala Ser Arg Pro Gly Pro Arg Asp Ala Gln Ala His
Pro Gly Arg Pro Arg Ala Val Pro Thr Gln Cys
Asp Val Pro Pro Asn Ser Arg Phe Asp Cys Ala
Pro Asp Lys Ala Ile Thr Gln Glu Gln Cys Glu
Ala Arg Gly Cys Cys Tyr Ile Pro Ala Lys Gln
Gly Leu Gln Gly Ala Gln Met Gly Gln Pro Trp
Cys Phe Phe Pro Pro Ser Tyr Pro Ser Tyr Lys
Leu Glu Asn Leu Ser Ser Ser Glu Met Gly Tyr
Thr Ala Thr Leu Thr Arg Thr Thr Pro Thr Phe
Phe Pro Lys Asp Ile Leu Thr Leu Arg Leu Asp
Val Met Met Glu Thr Glu Asn Arg Leu His Phe
Thr Ile Lys Asp Pro Ala Asn Arg Arg Tyr Glu
Val Pro Leu Glu Thr Pro His Val His Ser Arg
Ala Pro Ser Pro Leu Tyr Ser Val Glu Phe Ser
Glu Glu Pro Phe Gly Val Ile Val Arg Arg Gln
Leu Asp Gly Arg Val Leu Leu Asn Thr Thr Val
Ala Pro Leu Phe Phe Ala Asp Gln Phe Leu Gln
Leu Ser Thr Ser Leu Pro Ser Gln Tyr Ile Thr
Gly Leu Ala Glu His Leu Ser Pro Leu Met Leu
Ser Thr Ser Trp Thr Arg Ile Thr Leu Trp Asn
Arg Asp Leu Ala Pro Thr Pro Gly Ala Asn Leu
Tyr Gly Ser His Pro Phe Tyr Leu Ala Leu Glu
Asp Gly Gly Ser Ala His Gly Val Phe Leu Leu
Asn Ser Asn Ala Met Asp Val Val Leu Gln Pro
Ser Pro Ala Leu Ser Trp Arg Ser Thr Gly Gly
Ile Leu Asp Val Tyr Ile Phe Leu Gly Pro Glu
Pro Lys Ser Val Val Gln Gln Tyr Leu Asp Val
Val Gly Tyr Pro Phe Met Pro Pro Tyr Trp Gly
Leu Gly Phe His Leu Cys Arg Trp Gly Tyr Ser
Ser Thr Ala Ile Thr Arg Gln Val Val Glu Asn
Met Thr Arg Ala His Phe Pro Leu Asp Val Gln
Trp Asn Asp Leu Asp Tyr Met Asp Ser Arg Arg
Asp Phe Thr Phe Asn Lys Asp Gly Phe Arg Asp
Phe Pro Ala Met Val Gln Glu Leu His Gln Gly
Gly Arg Arg Tyr Met Met Ile Val Asp Pro Ala
Ile Ser Ser Ser Gly Pro Ala Gly Ser Tyr Arg
Pro Tyr Asp Glu Gly Leu Arg Arg Gly Val Phe
Ile Thr Asn Glu Thr Gly Gln Pro Leu Ile Gly
Lys Val Trp Pro Gly Ser Thr Ala Phe Pro Asp
Phe Thr Asn Pro Thr Ala Leu Ala Trp Trp Glu
Asp Met Val Ala Glu Phe His Asp Gln Val Pro Phe Asp Gly Met Trp Ile Asp Met Asn Glu Pro Ser Asn Phe Ile Arg Gly Ser Glu Asp Gly Cys Pro Asn Asn Glu Leu Glu Asn Pro Pro Tyr Val Pro Gly Val Val Gly Gly Thr Leu Gln Ala Ala Thr Ile Cys Ala Ser Ser His Gln Phe Leu Ser Thr His Tyr Asn Leu His Asn Leu Tyr Gly Leu Thr Glu Ala Ile Ala Ser His Arg Ala Leu Val Lys Ala Arg Gly Thr Arg Pro Phe Val Ile Ser Arg Ser Thr Phe Ala Gly His Gly Arg Tyr Ala Gly His Trp Thr Gly Asp Val Trp Ser Ser Trp Glu Gln Leu Ala Ser Ser Val Pro Glu Ile Leu Gln Phe Asn Leu Leu Gly Val Pro Leu Val Gly Ala Asp Val Cys Gly Phe Leu Gly Asn Thr Ser Glu Glu Leu Cys Val Arg Trp Thr Gln Leu Gly Ala Phe Tyr Pro Phe Met Arg Asn His Asn Ser Leu Leu Ser Leu Pro Gln Glu Pro Tyr Ser Phe Ser Glu Pro Ala Gln Gln Ala Met Arg Lys Ala Leu Thr Leu Arg Tyr Ala Leu Leu Pro His Leu Tyr Thr Leu Phe His Gln Ala His Val Ala Gly Glu Thr Val Ala Arg Pro Leu Phe Leu Glu Phe Pro Lys Asp Ser Ser Thr Trp Thr Val Asp His Gln Leu Leu Trp Gly Glu Ala Leu Leu Ile Thr Pro Val Leu Gln Ala Gly Lys Ala Glu Val Thr Gly Tyr Phe Pro Leu Gly Thr Trp Tyr Asp Leu Gln Thr Val Pro Val Glu Ala Leu Gly Ser Leu Pro Pro Pro Pro Ala Ala Pro Arg Glu Pro Ala Ile His Ser Glu Gly Gln Trp Val Thr Leu Pro Ala Pro Leu Asp Thr Ile Asn Val His Leu Arg Ala Gly Tyr Ile Ile Pro Leu Gln Gly Pro Gly Leu Thr Thr Thr Glu Ser Arg Gln Gln Pro Met Ala Leu Ala Val Ala Leu Thr Lys Gly Gly Glu Ala Arg Gly Glu Leu Phe Trp Asp Asp Gly Glu Ser Leu Glu Val Leu Glu Arg Gly Ala Tyr Thr Gln Val Ile Phe Leu Ala Arg Asn Asn Thr Ile Val Asn Glu Leu Val Arg Val Thr Ser Glu Gly Ala Gly Leu Gln Leu Gln Lys Val Thr Val Leu Gly Val Ala Thr Ala Pro Gln Gln Val Leu Ser Asn Gly Val Pro Val Ser Asn Phe Thr Tyr Ser Pro Asp Thr Lys Val Leu Asp Ile Cys Val Ser Leu Leu Met Gly Glu Gln Phe Leu Val Ser Trp Cys

SEQ ID NO: 5

Gln Gln Gly Ala Ser Arg Pro Gly Pro Arg Asp

Ala Gln Ala His Pro Gly Arg Pro Arg Ala Val

Pro Thr Gln Cys Asp Val Pro Pro Asn Ser Arg

Phe Asp Cys Ala Pro Asp Lys Ala Ile Thr Gln

Glu Gln Cys Glu Ala Arg Gly Cys Cys Tyr Ile

Pro Ala Lys Gln Gly Leu Gln Gly Ala Gln Met

Gly Gln Pro Trp Cys Phe Phe Pro Pro Ser Tyr

Pro Ser Tyr Lys Leu Glu Asn Leu Ser Ser Ser

Glu Met Gly Tyr Thr Ala Thr Leu Thr Arg Thr

Thr Pro Thr Phe Phe Pro Lys Asp Ile Leu Thr

Leu Arg Leu Asp Val Met Met Glu Thr Glu Asn

Arg Leu His Phe Thr Ile Lys Asp Pro Ala Asn

Arg Arg Tyr Glu Val Pro Leu Glu Thr Pro Arg

Val His Ser Arg Ala Pro Ser Pro Leu Tyr Ser

Val Glu Phe Ser Glu Pro Phe Gly Val Ile

Val His Arg Gln Leu Asp Gly Arg Val Leu Leu

Asn Thr Thr Val Ala Pro Leu Phe Phe Ala Asp

Gln Phe Leu Gln Leu Ser Thr Ser Leu Pro Ser

Gln Tyr Ile Thr Gly Leu Ala Glu His Leu Ser

Pro Leu Met Leu Ser Thr Ser Trp Thr Arg Ile

Thr Leu Trp Asn Arg Asp Leu Ala Pro Thr Pro

Gly Ala Asn Leu Tyr Gly Ser His Pro Phe Tyr

Leu Ala Leu Glu Asp Gly Gly Ser Ala His Gly

Val Phe Leu Leu Asn Ser Asn Ala Met Asp Val

Val Leu Gln Pro Ser Pro Ala Leu Ser Trp Arg

Ser Thr Gly Gly Ile Leu Asp Val Tyr Ile Phe

Leu Gly Pro Glu Pro Lys Ser Val Val Gln Gln

Tyr Leu Asp Val Val Gly Tyr Pro Phe Met Pro

Pro Tyr Trp Gly Leu Gly Phe His Leu Cys Arg

Trp Gly Tyr Ser Ser Thr Ala Ile Thr Arg Gln

Val Val Glu Asn Met Thr Arg Ala His Phe Pro

Leu Asp Val Gln Trp Asn Asp Leu Asp Tyr Met

Asp Ser Arg Arg Asp Phe Thr Phe Asn Lys Asp

Gly Phe Arg Asp Phe Pro Ala Met Val Gln Glu

Leu His Gln Gly Gly Arg Arg Tyr Met Met Ile

Val Asp Pro Ala Ile Ser Ser Ser Gly Pro Ala

Gly Ser Tyr Arg Pro Tyr Asp Glu Gly Leu Arg

Arg Gly Val Phe Ile Thr Asn Glu Thr Gly Gln

```
Pro Leu Ile Gly Lys Val Trp Pro Gly Ser Thr

Ala Phe Pro Asp Phe Thr Asn Pro Thr Ala Leu

Ala Trp Trp Glu Asp Met Val Ala Glu Phe His

Asp Gln Val Pro Phe Asp Gly Met Trp Ile Asp

Met Asn Glu Pro Ser Asn Phe Ile Arg Gly Ser

Glu Asp Gly Cys Pro Asn Asn Glu Leu Glu Asn

Pro Pro Tyr Val Pro Gly Val Val Gly Gly Thr

Leu Gln Ala Ala Thr Ile Cys Ala Ser Ser His

Gln Phe Leu Ser Thr His Tyr Asn Leu His Asn

Leu Tyr Gly Leu Thr Glu Ala Ile Ala Ser His

Arg Ala Leu Val Lys Ala Arg Gly Thr Arg Pro

Phe Val Ile Ser Arg Ser Thr Phe Ala Gly His

Gly Arg Tyr Ala Gly His Trp Thr Gly Asp Val

Trp Ser Ser Trp Glu Gln Leu Ala Ser Ser Val

Pro Glu Ile Leu Gln Phe Asn Leu Leu Gly Val

Pro Leu Val Gly Ala Asp Val Cys Gly Phe Leu

Gly Asn Thr Ser Glu Glu Leu Cys Val Arg Trp

Thr Gln Leu Gly Ala Phe Tyr Pro Phe Met Arg

Asn His Asn Ser Leu Leu Ser Leu Pro Gln Glu

Pro Tyr Ser Phe Ser Glu Pro Ala Gln Gln Ala

Met Arg Lys Ala Leu Thr Leu Arg Tyr Ala Leu

Leu Pro His Leu Tyr Thr Leu Phe His Gln Ala

His Val Ala Gly Glu Thr Val Ala Arg Pro Leu

Phe Leu Glu Phe Pro Lys Asp Ser Ser Thr Trp

Thr Val Asp His Gln Leu Leu Trp Gly Glu Ala

Leu Leu Ile Thr Pro Val Leu Gln Ala Gly Lys

Ala Glu Val Thr Gly Tyr Phe Pro Leu Gly Thr

Trp Tyr Asp Leu Gln Thr Val Pro Ile Glu Ala

Leu Gly Ser Leu Pro Pro Pro Ala Ala Pro

Arg Glu Pro Ala Ile His Ser Glu Gly Gln Trp

Val Thr Leu Pro Ala Pro Leu Asp Thr Ile Asn

Val His Leu Arg Ala Gly Tyr Ile Ile Pro Leu

Gln Gly Pro Gly Leu Thr Thr Thr Glu Ser Arg

Gln Gln Pro Met Ala Leu Ala Val Ala Leu Thr

Lys Gly Gly Glu Ala Arg Gly Glu Leu Phe Trp

Asp Asp Gly Glu Ser Leu Glu Val Leu Glu Arg

Gly Ala Tyr Thr Gln Val Ile Phe Leu Ala Arg sAn Asn Thr Ile Val Asn Glu Leu Val Arg Val

Thr Ser Glu Gly Ala Gly Leu Gln Leu Gln Lys

Val Thr Val Leu Gly Val Ala Thr Ala Pro Gln

Gln Val Leu Ser Asn Gly Val Pro Val Ser Asn

Phe Thr Tyr Ser Pro Asp Thr Lys Val Leu Asp

Ile Cys Val Ser Leu Leu Met Gly Glu Gln Phe

Leu Val Ser Trp Cys
```

In at least one embodiment, the recombinant human acid α-glucosidase has a wild-type GAA amino acid sequence as set forth in SEQ ID NO: 1, as described in U.S. Pat. No. 8,592,362 and has GenBank accession number AHE24104.1 (GI:568760974). In at least one embodiment, the recombinant human acid α-glucosidase has a wild-type GAA amino acid sequence as encoded in SEQ ID NO: 2, the mRNA sequence having GenBank accession number Y00839.1. In at least one embodiment, the recombinant human acid α-glucosidase has a wild-type GAA amino acid sequence as set forth in SEQ ID NO: 3. In at least one embodiment, the recombinant human acid α-glucosidase has a GAA amino acid sequence as set forth in SEQ ID NO: 4, and has National Center for Biotechnology Information (NCBI) accession number NP_000143.2. In at least one embodiment, the recombinant human acid α-glucosidase is glucosidase alfa, the human acid α-glucosidase enzyme encoded by the most predominant of nine observed haplotypes of the GAA gene.

In at least one embodiment, the recombinant human acid α-glucosidase is initially expressed as having the full-length 952 amino acid sequence of wild-type GAA as set forth in SEQ ID NO: 1, and the recombinant human acid α-glucosidase undergoes intracellular processing that removes a portion of the amino acids, e.g. the first 56 amino acids. Accordingly, the recombinant human acid α-glucosidase that is secreted by the host cell can have a shorter amino acid sequence than the recombinant human acid α-glucosidase that is initially expressed within the cell. In at least one embodiment, the shorter protein can have the amino acid sequence set forth in SEQ ID NO: 5, which only differs from SEQ ID NO: 1 in that the first 56 amino acids comprising the signal peptide and precursor peptide have been removed, thus resulting in a protein having 896 amino acids. Other variations in the number of amino acids is also possible, such as having 1, 2, 3, 4, 5, 6, 7, 8, 9, 10, 11, 12, 13, 14, 15 or more deletions, substitutions and/or insertions relative to the amino acid sequence described by SEQ ID NO: 1 or SEQ ID NO: 5. In some embodiments, the rhGAA product includes a mixture of recombinant human acid α-glucosidase molecules having different amino acid lengths.

In at least one embodiment, the recombinant human acid α-glucosidase undergoes post-translational and/or chemical modifications at one or more amino acid residues in the protein. For example, methionine and tryptophan residues can undergo oxidation. As another example, the N-terminal glutamine can form pyro-glutamate. As another example, asparagine residues can undergo deamidation to aspartic acid. As yet another example, aspartic acid residues can undergo isomerization to iso-aspartic acid. As yet another example, unpaired cysteine residues in the protein can form disulfide bonds with free glutathione and/or cysteine. Accordingly, in some embodiments the enzyme is initially expressed as having an amino acid sequence as set forth in SEQ ID NO: 1, SEQ ID NO: 2 (or as encoded by SEQ ID NO: 2), SEQ ID NO: 3, SEQ ID NO: 4 or SEQ ID NO: 5, and the enzyme undergoes one or more of these post-translational and/or chemical modifications. Such modifications are also within the scope of the present disclosure.

Polynucleotide sequences encoding GAA and such variant human GAAs are also contemplated and may be used to recombinantly express rhGAAs according to the invention.

Preferably, no more than 70, 65, 60, 55, 45, 40, 35, 30, 25, 20, 15, 10, or 5% of the total recombinant human acid α-glucosidase molecules lack an N-glycan unit bearing one or more mannose-6-phosphate residues or lacks a capacity to bind to the cation independent mannose-6-phosphate receptor (CIMPR). Alternatively, 30, 35, 40, 45, 50, 55, 60, 65, 70, 75, 80, 85, 90, 95, 99%, <100% or more of the recombinant human acid α-glucosidase molecules comprise at least one N-glycan unit bearing one or more mannose-6-phosphate residues or has the capacity to bind to CIMPR.

The recombinant human acid α-glucosidase molecules may have 1, 2, 3 or 4 mannose-6-phosphate (M6P) groups on their glycans. For example, only one N-glycan on a recombinant human acid α-glucosidase molecule may bear M6P (mono-phosphorylated), a single N-glycan may bear two M6P groups (bis-phosphorylated), or two different N-glycans on the same recombinant human acid α-glucosidase molecule may each bear single M6P groups. Recombinant human acid α-glucosidase molecules may also have N-glycans bearing no M6P groups. In another embodiment, on average the N-glycans contain greater than 2.5 mol/mol of M6P and greater than 4 mol/mol sialic acid, such that the recombinant human acid α-glucosidase comprises on average at least 2.5 moles of mannose-6-phosphate residues per mole of recombinant human acid α-glucosidase and at least 4 moles of sialic acid per mole of recombinant human acid α-glucosidase. On average at least about 3, 4, 5, 6, 7, 8, 9, or 10% of the total glycans on the recombinant human acid α-glucosidase may be in the form of a mono-M6P glycan, for example, about 6.25% of the total glycans may carry a single M6P group and on average, at least about 0.5, 1, 1.5, 2.0, 2.5, 3.0% of the total glycans on the recombinant human acid α-glucosidase are in the form of a bis-M6P glycan and on average less than 25% of total recombinant human acid α-glucosidase contains no phosphorylated glycan binding to CIMPR.

The recombinant human acid α-glucosidase may have an average content of N-glycans carrying M6P ranging from 0.5 to 7.0 mol/mol recombinant human acid α-glucosidase or any intermediate value of subrange including 0.5, 1.0, 1.5, 2.0, 2.5, 3.0, 3.5, 4.0, 4.5, 5.0, 5.5, 6.0, 6.5, or 7.0 mol/mol recombinant human acid α-glucosidase. The recombinant human acid α-glucosidase can be fractionated to provide recombinant human acid α-glucosidase preparations with different average numbers of M6P-bearing or bis-M6P-bearing glycans thus permitting further customization of recombinant human acid α-glucosidase targeting to the lysosomes in target tissues by selecting a particular fraction or by selectively combining different fractions.

Up to 60% of the N-glycans on the recombinant human acid α-glucosidase may be fully sialylated, for example, up to 10%, 20%, 30%, 40%, 50% or 60% of the N-glycans may be fully sialylated. In some embodiments from 4 to 20% of the total N-glycans are fully sialylated. In other embodiments no more than 5%, 10%, 20% or 30% of N-glycans on the recombinant human acid α-glucosidase carry sialic acid and a terminal galactose residue (Gal). This range includes all intermediate values and subranges, for example, 7 to 30% of the total N-glycans on the recombinant human acid α-glucosidase can carry sialic acid and terminal galactose. In yet other embodiments, no more than 5, 10, 15, 16, 17, 18, 19 or 20% of the N-glycans on the recombinant human acid α-glucosidase have a terminal galactose only and do not contain sialic acid. This range includes all intermediate values and subranges, for example, from 8 to 19% of the total N-glycans on the recombinant human acid α-glucosidase in the composition may have terminal galactose only and do not contain sialic acid.

In other embodiments of the invention, 40, 45, 50, 55 to 60% of the total N-glycans on the recombinant human acid α-glucosidase are complex type N-glycans; or no more than 1, 2, 3, 4, 5, 6, 7% of total N-glycans on the recombinant human acid α-glucosidase are hybrid-type N-glycans; no more than 5, 10, or 15% of the high mannose-type N-glycans on the recombinant human acid α-glucosidase are non-phosphorylated; at least 5% or 10% of the high mannose-type N-glycans on the recombinant human acid α-glucosidase are mono-M6P phosphorylated; and/or at least 1 or 2% of the high mannose-type N-glycans on the recombinant human acid α-glucosidase are bis-M6P phosphorylated. These values include all intermediate values and subranges. A recombinant human acid α-glucosidase may meet one or more of the content ranges described above.

In some embodiments, the recombinant human acid α-glucosidase will bear, on average, 2.0 to 8.0 moles of sialic acid residues per mole of recombinant human acid α-glucosidase. This range includes all intermediate values and subranges including 2.0, 2.5, 3.0, 3.5, 4.0, 4.5, 5.0, 5.5, 6.0, 6.5, 7.0, 7.5 and 8.0 mol residues/mol recombinant human acid α-glucosidase. Without being bound by theory, it is believed that the presence of N-glycan units bearing sialic acid residues may prevent non-productive clearance of the recombinant human acid α-glucosidase by asialoglycoprotein receptors. In one or more embodiments, the rhGAA has M6P and/or sialic acid units at certain N-glycosylation sites of the recombinant human lysosomal protein. For example, there are seven potential N-linked glycosylation sites on rhGAA. These potential glycosylation sites are at the following positions of SEQ ID NO: 5: N84, N177, N334, N414, N596, N826 and N869. Similarly, for the full-length amino acid sequence of SEQ ID NO: 1, these potential glycosylation sites are at the following positions: N140, N233, N390, N470, N652, N882 and N925. Other variants of rhGAA can have similar glycosylation sites, depending on the location of asparagine residues. Generally, sequences of ASN-X-SER or ASN-X-THR in the protein amino acid sequence indicate potential glycosylation sites, with the exception that X cannot be HIS or PRO.

In various embodiments, the rhGAA has a certain N-glycosylation profile. In one or more embodiments, at least 20% of the rhGAA is phosphorylated at the first N-glycosylation site (e.g. N84 for SEQ ID NO: 5 and N140 for SEQ ID NO: 1). For example, at least 20%, 25%, 30%, 35%, 40%, 50%, 55%, 60%, 65%, 70%, 75%, 80%, 85%, 90% or 95% of the rhGAA can be phosphorylated at the first N-glycosylation site. This phosphorylation can be the result of mono-M6P and/or bis-M6P units. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a mono-M6P unit at the first N-glycosylation site. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a bis-M6P unit at the first N-glycosylation site.

In one or more embodiments, at least 20% of the rhGAA is phosphorylated at the second N-glycosylation site (e.g. N177 for SEQ ID NO: 5 and N223 for SEQ ID NO: 1). For example, at least 20%, 25%, 30%, 35%, 40%, 45%, 50%, 55%, 60%, 65%, 70%, 75%, 80%, 85%, 90% or 95% of the rhGAA can be phosphorylated at the second N-glycosylation site. This phosphorylation can be the result of mono-M6P and/or bis-M6P units. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a mono-M6P unit at the second N-glycosylation site. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a bis-M6P unit at the second N-glycosylation site. In one or more embodiments, at least 5% of the rhGAA is phosphorylated at the third N-glycosylation site (e.g. N334 for SEQ ID NO: 5 and N390 for SEQ ID NO: 1). In other embodiments, less than 5%, 10%, 15%, 20% or 25% of the rhGAA is phosphorylated at the third N-glycosylation site. For example, the third N-glycosylation site can have a mixture of non-phosphorylated high mannose glycans, di-, tri-, and tetra-antennary complex glycans, and hybrid glycans as the major species. In some embodiments, at least 3%, 5%, 8%, 10%, 15%, 20%, 25%, 30%, 35%, 40%, 45% or 50% of the rhGAA is sialylated at the third N-glycosylation site.

In one or more embodiments, at least 20% of the rhGAA is phosphorylated at the fourth N-glycosylation site (e.g. N414 for SEQ ID NO: 5 and N470 for SEQ ID NO: 1). For example, at least 20%, 25%, 30%, 35%, 40%, 45%, 50%, 55%, 60%, 65%, 70%, 75%, 80%, 85%, 90% or 95% of the rhGAA can be phosphorylated at the fourth N-glycosylation site. This phosphorylation can be the result of mono-M6P and/or bis-M6P units. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a mono-M6P unit at the fourth N-glycosylation site. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a bis-M6P unit at the fourth N-glycosylation site. In some embodiments, at least 3%, 5%, 8%, 10%, 15%, 20% or 25% of the rhGAA is sialylated at the fourth N-glycosylation site.

In one or more embodiments, at least 5% of the rhGAA is phosphorylated at the fifth N-glycosylation site (e.g. N596 for SEQ ID NO: 5 and N692 for SEQ ID NO: 1). In other embodiments, less than 5%, 10%, 15%, 20% or 25% of the rhGAA is phosphorylated at the fifth N-glycosylation site. For example, the fifth N-glycosylation site can have fucosylated di-antennary complex glycans as the major species. In some embodiments, at least 3%, 5%, 8%, 10%, 15%, 20%, 25%, 30%, 35%, 40%, 45%, 50%, 55%, 60%, 65%, 70%, 75%, 80%, 85%, 90% or 95% of the rhGAA is sialylated at the fifth N-glycosylation site.

In one or more embodiments, at least 5% of the rhGAA is phosphorylated at the sixth N-glycosylation site (e.g. N826 for SEQ ID NO: 5 and N882 for SEQ ID NO: 1). In other embodiments, less than 5%, 10%, 15%, 20% or 25% of the rhGAA is phosphorylated at the sixth N-glycosylation site. For example, the sixth N-glycosylation site can have a mixture of di-, tri-, and tetra-antennary complex glycans as the major species. In some embodiments, at least 3%, 5%, 8%, 10%, 15%, 20%, 25%, 30%, 35%, 40%, 45%, 50%, 55%, 60%, 65%, 70%, 75%, 80%, 85%, 90% or 95% of the rhGAA is sialylated at the sixth N-glycosylation site.

In one or more embodiments, at least 5% of the rhGAA is phosphorylated at the seventh N-glycosylation site (e.g. N869 for SEQ ID NO: 5 and N925 for SEQ ID NO: 1). In other embodiments, less than 5%, 10%, 15%, 20% or 25% of the rhGAA is phosphorylated at the seventh N-glycosylation site. In some embodiments, less than 40%, 45%, 50%, 55%, 60% or 65% % of the rhGAA has any glycan at the seventh N-glycosylation site. In some embodiments, at least 30%, 35% or 40% of the rhGAA has a glycan at the seventh N-glycosylation site.

The recombinant human acid α-glucosidase is preferably produced by Chinese hamster ovary (CHO) cells, such as CHO cell line GA-ATB-200 or ATB-200-001-X5-14, or by a subculture or derivative of such a CHO cell culture. DNA constructs, which express allelic variants of acid α-glucosidase or other variant acid α-glucosidase amino acid sequences such as those that are at least 90%, 95%, 98% or 99% identical to SEQ ID NO: 1 or SEQ ID NO: 5, may be constructed and expressed in CHO cells. These variant acid α-glucosidase amino acid sequences may contain deletions, substitutions and/or insertions relative to SEQ ID NO: 1 or SEQ ID NO: 5, such as having 1, 2, 3, 4, 5, 6, 7, 8, 9, 10, 11, 12, 13, 14, 15 or more deletions, substitutions and/or insertions relative to the amino acid sequence described by SEQ ID NO: 1 or SEQ ID NO: 5. Those of skill in the art can select alternative vectors suitable for transforming CHO cells for production of such DNA constructs.

Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

The inventors have found that recombinant human acid α-glucosidase having superior ability to target cation-independent mannose-6-phosphate receptors (CIMPR) and cellular lysosomes as well as glycosylation patterns that reduce its non-productive clearance in vivo can be produced using Chinese hamster ovary (CHO) cells. These cells can be induced to express recombinant human acid α-glucosidase with significantly higher levels of N-glycan units bearing one or more mannose-6-phosphate residues than conventional recombinant human acid α-glucosidase products such as alglucosidase alfa. The recombinant human acid α-glucosidase produced by these cells, for example, as exemplified by ATB200, has significantly more muscle cell-targeting mannose-6-phosphate (mono-M6P) and bis-mannose-6-phosphate (bis-M6P) N-glycan residues than conventional acid α-glucosidase, such as Lumizyme®. Without being bound by theory, it is believed that this extensive glycosylation allows the ATB200 enzyme to be taken up more effectively into target cells, and therefore to be cleared from the circulation more efficiently than other recombinant human acid α-glucosidases, such as for example, alglucosidase alfa, which has a much lower M6P and bis-M6P content. ATB200 has been shown to efficiently bind to CIMPR and be efficiently taken up by skeletal muscle and cardiac muscle and to have a glycosylation pattern that provides a favorable pharmacokinetic profile and reduces non-productive clearance in vivo.

It is also contemplated that the unique glycosylation of ATB200 can contribute to a reduction of the immunogenicity of ATB200 compared to, for example, alglucosidase alfa. As will be appreciated by those skilled in the art, glycosylation of proteins with conserved mammalian sugars generally enhances product solubility and diminishes product aggregation and immunogenicity. Glycosylation indirectly alters protein immunogenicity by minimizing protein aggregation as well as by shielding immunogenic protein epitopes from the immune system (*Guidance for Industry—Immunogenicity Assessment for Therapeutic Protein Products*, US Department of Health and Human Services, Food and Drug Administration, Center for Drug Evaluation and Research, Center for Biologics Evaluation and Research, August 2014). Therefore, in at least one embodiment, administration of the recombinant human acid α-glucosidase does not induce anti-drug antibodies. In at least one embodiment, administration of the recombinant human acid α-glucosidase induces a lower incidence of anti-drug antibodies in a subject than the level of anti-drug antibodies induced by administration of alglucosidase alfa.

As described in co-pending international patent application PCT/US2015/053252, cells such as CHO cells can be used to produce the rhGAA described therein, and this rhGAA can be used in the present invention. Examples of such a CHO cell line are GA-ATB-200 or ATB-200-001-X5-14, or a subculture thereof that produces a rhGAA composition as described therein. Such CHO cell lines may contain multiple copies of a gene, such as 5, 10, 15, or 20 or more copies, of a polynucleotide encoding GAA.

The high M6P and bis-M6P rhGAA, such as ATB200 rhGAA, can be produced by transforming CHO cells with a DNA construct that encodes GAA. While CHO cells have been previously used to make rhGAA, it was not appreciated that transformed CHO cells could be cultured and selected in a way that would produce rhGAA having a high content of M6P and bis-M6P glycans which target the CIMPR.

Surprisingly, it was found that it was possible to transform CHO cell lines, select transformants that produce rhGAA containing a high content of glycans bearing M6P or bis-M6P that target the CIMPR, and to stably express this high-M6P rhGAA. Thus, methods for making these CHO cell lines are also described in co-pending international patent application PCT/US2015/053252. This method involves transforming a CHO cell with DNA encoding GAA or a GAA variant, selecting a CHO cell that stably integrates the DNA encoding GAA into its chromosome(s) and that stably expresses GAA, and selecting a CHO cell that expresses GAA having a high content of glycans bearing M6P or bis-M6P, and, optionally, selecting a CHO cell having N-glycans with high sialic acid content and/or having N-glycans with a low non-phosphorylated high-mannose content.

In at least one embodiment, the GAA has low levels of complex glycans with terminal galactose.

These CHO cell lines may be used to produce rhGAA and rhGAA compositions by culturing the CHO cell line and recovering said composition from the culture of CHO cells.

The recombinant human acid α-glucosidase, or a pharmaceutically acceptable salt thereof, can be formulated in accordance with the routine procedures as a pharmaceutical composition adapted for administration to human beings. For example, in a preferred embodiment, a composition for intravenous administration is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

Recombinant human acid α-glucosidase (or a composition or medicament containing recombinant human acid α-glucosidase) is administered by an appropriate route. In one embodiment, the recombinant human acid α-glucosidase is administered intravenously. In other embodiments, recombinant human acid α-glucosidase is administered by direct administration to a target tissue, such as to heart or skeletal muscle (e.g., intramuscular), or nervous system (e.g., direct injection into the brain; intraventricularly; intrathecally). More than one route can be used concurrently, if desired.

The recombinant human acid α-glucosidase (or a composition or medicament containing recombinant human acid α-glucosidase) is administered in a therapeutically effective amount (e.g., a dosage amount that, when administered at regular intervals, is sufficient to treat the disease, such as by ameliorating symptoms associated with the disease, preventing or delaying the onset of the disease, and/or lessening the severity or frequency of symptoms of the disease). The amount which will be therapeutically effective in the treatment of the disease will depend on the nature and extent of the disease's effects, and can be determined by standard clinical techniques. In addition, in vitro or in vivo assays may optionally be employed to help identify optimal dosage ranges. The precise dose to be employed will also depend on the route of administration, and the seriousness of the disease, and should be decided according to the judgment of a practitioner and each patient's circumstances. Effective doses may be extrapolated from dose-response curves derived from in vitro or animal model test systems. In at least one embodiment, the recombinant human acid α-glucosidase is administered by intravenous infusion at a dose of about 5 mg/kg to about 30 mg/kg, typically about 5 mg/kg to about 20 mg/kg. In at least one embodiment, the recombinant human acid α-glucosidase is administered by intravenous infusion at a dose of about 5 mg/kg, about 10 mg/kg, about 15 mg/kg or about 20 mg/kg. In at least one embodiment, the recombinant human acid α-glucosidase is administered by intravenous infusion at a dose of about 20 mg/kg. The effective dose for a particular individual can be varied (e.g., increased or decreased) over time, depending on the needs of the individual. For example, in times of physical illness or stress, or if anti-acid α-glucosidase antibodies become present or increase, or if disease symptoms worsen, the amount can be increased.

The therapeutically effective amount of recombinant human acid α-glucosidase (or composition or medicament containing recombinant human acid α-glucosidase) is administered at regular intervals, depending on the nature and extent of the disease's effects, and on an ongoing basis.

Administration at a "regular interval," as used herein, indicates that the therapeutically effective amount is administered periodically (as distinguished from a one-time dose). The interval can be determined by standard clinical techniques. In preferred embodiments, recombinant human acid α-glucosidase is administered monthly, bimonthly; weekly; twice weekly; or daily. The administration interval for a single individual need not be a fixed interval, but can be varied over time, depending on the needs of the individual. For example, in times of physical illness or stress, if anti-recombinant human acid α-glucosidase antibodies become present or increase, or if disease symptoms worsen, the interval between doses can be decreased. In some embodiments, a therapeutically effective amount of 5, 10, 20, 50, 100, or 200 mg enzyme/kg body weight is administered twice a week, weekly or every other week with or without a chaperone.

The recombinant human acid α-glucosidase of the invention may be prepared for later use, such as in a unit dose vial or syringe, or in a bottle or bag for intravenous administration. Kits containing the recombinant human acid α-glucosidase, as well as optional excipients or other active ingredients, such as chaperones or other drugs, may be enclosed in packaging material and accompanied by instructions for reconstitution, dilution or dosing for treating a subject in need of treatment, such as a patient having Pompe disease.

In at least one embodiment, the miglustat and the recombinant human acid α-glucosidase are administered simultaneously. In at least one embodiment, the miglustat and the recombinant human acid α-glucosidase are administered sequentially. In at least one embodiment, the miglustat is administered prior to administration of the recombinant human acid α-glucosidase. In at least one embodiment, the miglustat is administered less than three hours prior to administration of the recombinant human acid α-glucosidase. In at least one embodiment, the miglustat is administered about two hours prior to administration of the recombinant human acid α-glucosidase. In at least one embodiment, the miglustat is administered less than two hours prior to administration of the recombinant human acid α-glucosidase. In at least one embodiment, the miglustat is administered about 1.5 hours prior to administration of the recombinant human acid α-glucosidase. In at least one embodiment, the miglustat is administered about one hour prior to administration of the recombinant human acid α-glucosidase. In at least one embodiment, the miglustat is administered from about 50 minutes to about 70 minutes prior to administration of the recombinant human acid α-glucosidase. In at least one embodiment, the miglustat is administered from about 55 minutes to about 65 minutes prior to administration of the recombinant human acid α-glucosidase. In at least one embodiment, the miglustat is administered about 30 minutes prior to administration of the recombinant human acid α-glucosidase. In at least one embodiment, the miglustat is administered from about 25 minutes to about 35 minutes prior to administration of the recombinant human acid α-glucosidase. In at least one embodiment, the miglustat is administered from about 27 minutes to about 33 minutes prior to administration of the recombinant human acid α-glucosidase.

In at least one embodiment, the miglustat is administered concurrently with administration of the recombinant human acid α-glucosidase. In at least one embodiment, the miglustat is administered within 20 minutes before or after administration of the recombinant human acid α-glucosidase. In at least one embodiment, the miglustat is administered within 15 minutes before or after administration of the recombinant human acid α-glucosidase. In at least one embodiment, the miglustat is administered within 10 minutes before or after administration of the recombinant human acid α-glucosidase. In at least one embodiment, the miglustat is administered within 5 minutes before or after administration of the recombinant human acid α-glucosidase.

In at least one embodiment, the miglustat is administered after administration of the recombinant human acid α-glucosidase. In at least one embodiment, the miglustat is administered up to 2 hours after administration of the recombinant human acid α-glucosidase. In at least one embodiment, the miglustat is administered about 30 minutes after administration of the recombinant human acid α-glucosidase. In at least one embodiment, the miglustat is administered about one hour after administration of the recombinant human acid α-glucosidase. In at least one embodiment, the miglustat is administered about 1.5 hours after administration of the recombinant human acid α-glucosidase. In at least one embodiment, the miglustat is administered about 2 hours after administration of the recombinant human acid α-glucosidase.

Another aspect of the invention provides a kit for combination therapy of Pompe disease in a patient in need thereof. The kit includes a pharmaceutically acceptable dosage form comprising miglustat, a pharmaceutically acceptable dosage form comprising a recombinant human acid α-glucosidase as defined herein, and instructions for administering the pharmaceutically acceptable dosage form comprising miglustat and the pharmaceutically acceptable dosage form comprising the recombinant acid α-glucosidase to a patient in need thereof. In at least one embodiment, the pharmaceutically acceptable dosage form comprising miglustat is an oral dosage form as described herein, including but not limited to a tablet or a capsule. In at least one embodiment, the pharmaceutically acceptable dosage form comprising a recombinant human acid α-glucosidase is a sterile solution suitable for injection as described herein. In at least one embodiment, the instructions for administering the dosage forms include instructions to administer the pharmaceutically acceptable dosage form comprising miglustat orally prior to administering the pharmaceutically acceptable dosage form comprising the recombinant human acid α-glucosidase by intravenous infusion, as described herein.

Without being bound by theory, it is believed that miglustat acts as a pharmacological chaperone for the recombinant human acid α-glucosidase ATB200 and binds to its active site. Thus, as seen in FIG. 1, miglustat has been found to decrease the percentage of unfolded ATB200 protein and stabilize the active conformation of ATB200, preventing denaturation and irreversible inactivation at the neutral pH of plasma and allowing it to survive conditions in the circulation long enough to reach and be taken up by tissues. However, the binding of miglustat to the active site of ATB200 also can result in inhibition of the enzymatic activity of ATB200 by preventing the natural substrate, glycogen, from accessing the active site. It is believed that when miglustat and the recombinant human acid α-glucosidase are administered to a patient under the conditions described herein, the concentrations of miglustat and ATB200 within the plasma and tissues are such that ATB200 is stabilized until it can be taken up into the tissues and targeted to lysosomes, but, because of the rapid clearance of miglustat, hydrolysis of glycogen by ATB200 within lysosomes is not overly inhibited by the presence of miglustat, and the enzyme retains sufficient activity to be therapeutically useful.

All the embodiments described above may be combined. This includes in particular embodiments relating to:

the nature of the pharmacological chaperone, for example miglustat; and the active site for which it is specific;

the dosage, route of administration of the pharmacological chaperone (miglustat) and the type of pharmaceutical composition including the nature of the carrier and the use of commercially available compositions;

the nature of the drug, e.g. therapeutic protein drug product, which may be a counterpart of an endogenous protein for which expression is reduced or absent in the subject, suitably recombinant human acid α-glucosidase, for example the recombinant human acid α-glucosidase expressed in Chinese hamster ovary (CHO) cells and comprising an increased content of N-glycan units bearing one or more mannose-6-phosphate residues when compared to a content of N-glycan units bearing one or more mannose-6-phosphate residues of alglucosidase alfa; and suitably having an amino acid sequence as set forth in SEQ ID NO: 1, SEQ ID NO: 2 (or as encoded by SEQ ID NO: 2), SEQ ID NO: 3, SEQ ID NO: 4 or SEQ ID NO: 5;

the number and type of N-glycan units on the recombinant human acid α-glucosidase, e.g. N-acetylglucosamine, galactose, sialic acid or complex N-glycans formed from combinations of these) attached to the recombinant human acid α-glucosidase;

the degree of phosphorylation of mannose units on the recombinant human acid α-glucosidase to form mannose-6-phosphate and/or bis-mannose-6-phosphate;

the dosage and route of administration (e.g. intravenous administration, especially intravenous infusion, or direct administration to the target tissue) of the replacement enzyme (recombinant human acid α-glucosidase) and the type of formulation including carriers and therapeutically effective amount;

the dosage interval of the pharmacological chaperone (miglustat) and the recombinant human acid α-glucosidase;

the nature of the therapeutic response and the results of the combination therapy (e.g. enhanced results as compared to the effect of each therapy performed individually);

the timing of the administration of the combination therapy, e.g. simultaneous administration of miglustat and the recombinant human acid α-glucosidase or sequential administration, for example wherein the miglustat is administered prior to the recombinant human acid α-glucosidase or after the recombinant human acid α-glucosidase or within a certain time before or after administration of the recombinant human acid α-glucosidase; and the nature of the patient treated (e.g. mammal such as human) and the condition suffered by the individual (e.g. enzyme insufficiency).

Any of the embodiments in the list above may be combined with one or more of the other embodiments in the list.

EXAMPLES

Other features of the present invention will become apparent from the following non-limiting examples which illustrate, by way of example, the principles of the invention.

Example 1: Limitations of Existing Myozyme® and Lumizyme® rhGAA Products

To evaluate the ability of the rhGAA in Myozyme® and Lumizyme®, the only currently approved treatments for Pompe disease, these rhGAA preparations were injected onto a CIMPR column (which binds rhGAA having M6P groups) and subsequently eluted with a free M6 gradient. Fractions were collected in 96-well plate and GAA activity assayed by 4MU-α-glucose substrate. The relative amounts of bound and unbound rhGAA were determined based on GAA activity and reported as the fraction of total enzyme.

Figure 2A:
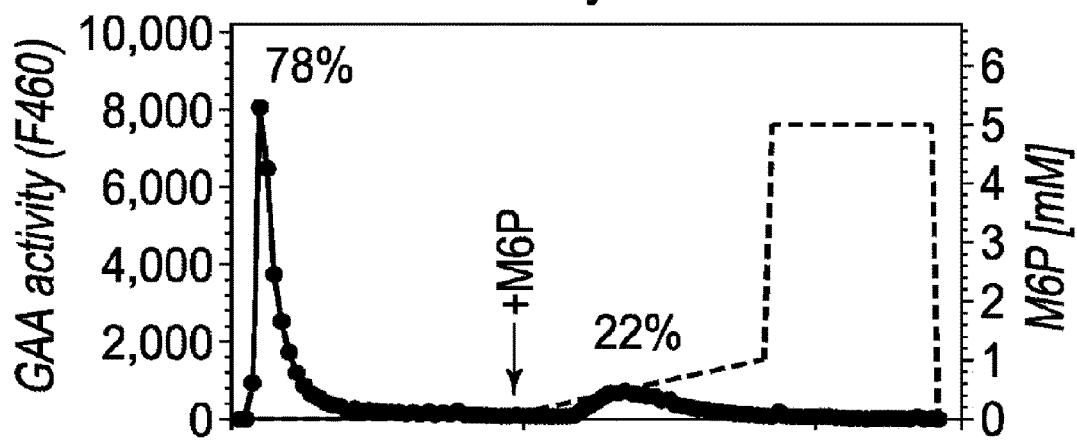
FIGS. 2A and 2B, respectively, show the results of CIMPR affinity chromatography of Lumizyme® and Myozyme®. The dashed lines refer to the M6P elution gradient. Elution with M6P displaces GAA molecules bound via an M6P containing glycan to CIMPR.
Figure 2B:
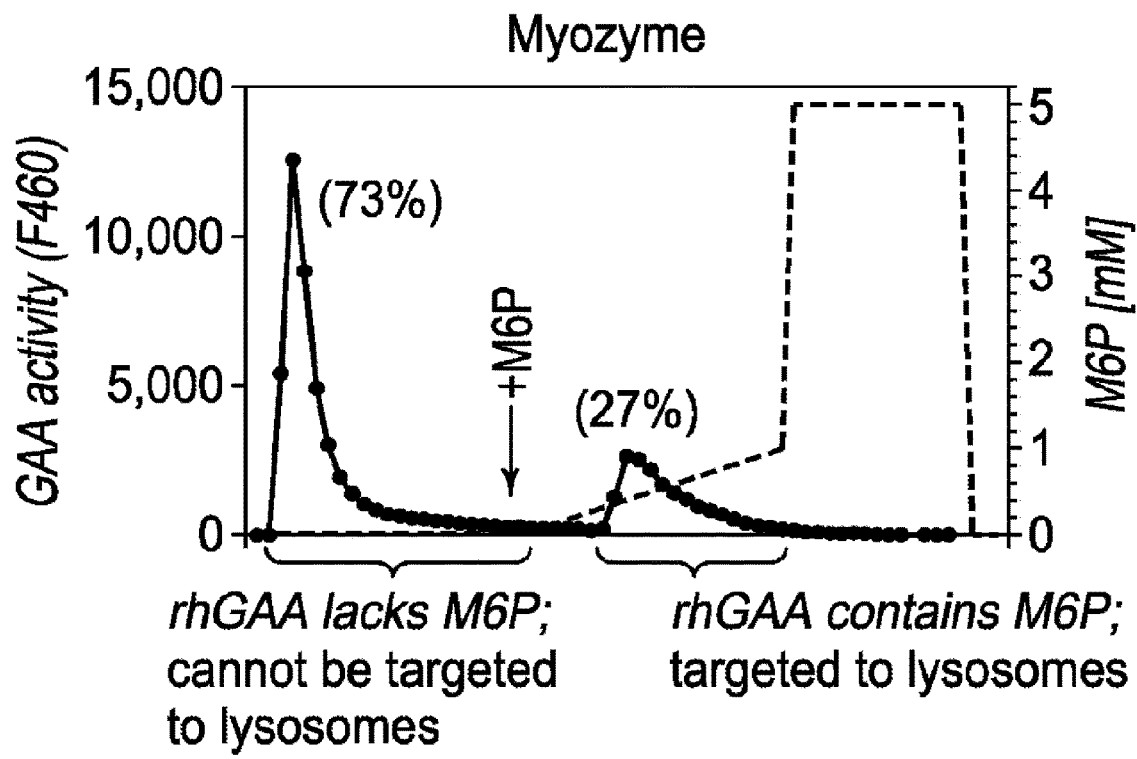

FIGS. 2A-B describe the problems associated with conventional ERTs (Myozyme® and Lumizyme®): 73% of the rhGAA in Myozyme® (FIG. 2B) and 78% of the rhGAA in Lumizyme® (FIG. 2A) did not bind to the CIMPR, see the left-most peaks in each figure. Only 27% of the rhGAA in Myozyme® and 22% of the rhGAA in Lumizyme® contained M6P that can productive to target it to the CIMPR on muscle cells.

An effective dose of Myozyme® and Lumizyme® corresponds to the amount of rhGAA containing M6P which targets the CIMPR on muscle cells. However, most of the rhGAA in these two conventional products does not target the CIMPR receptor on target muscle cells. The administration of a conventional rhGAA where most of the rhGAA is not targeted to muscle cells increases the risk of allergic reaction or induction of immunity to the non-targeted rhGAA.

Figure 3:
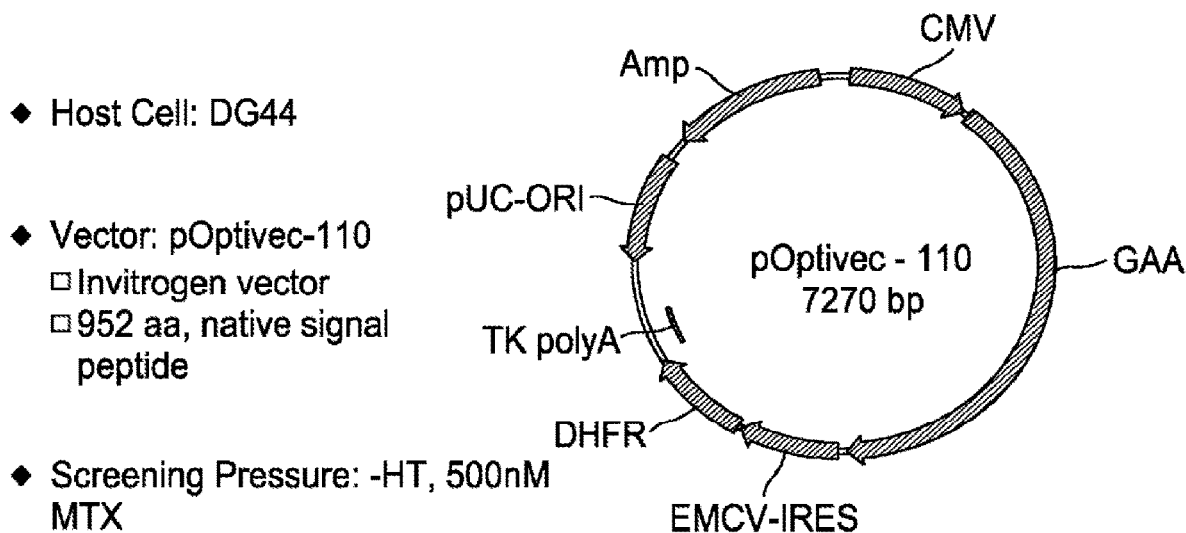
FIG. 3 shows a DNA construct for transforming CHO cells with DNA encoding rhGAA. CHO cells were transformed with a DNA construct encoding rhGAA.
Figure 4A:
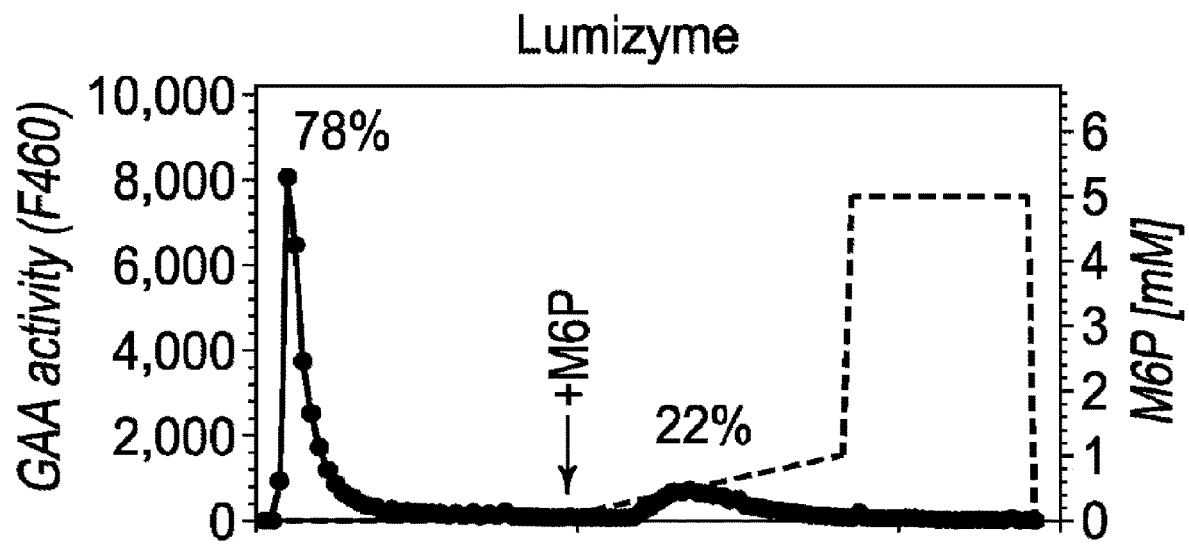
FIGS. 4A and 4B, respectively show the results of CIMPR affinity chromatography of Myozyme® and ATB200 rhGAA. As apparent from FIG. 4B, about 70% of the rhGAA in ATB200 rhGAA contained M6P.
Figure 4B:
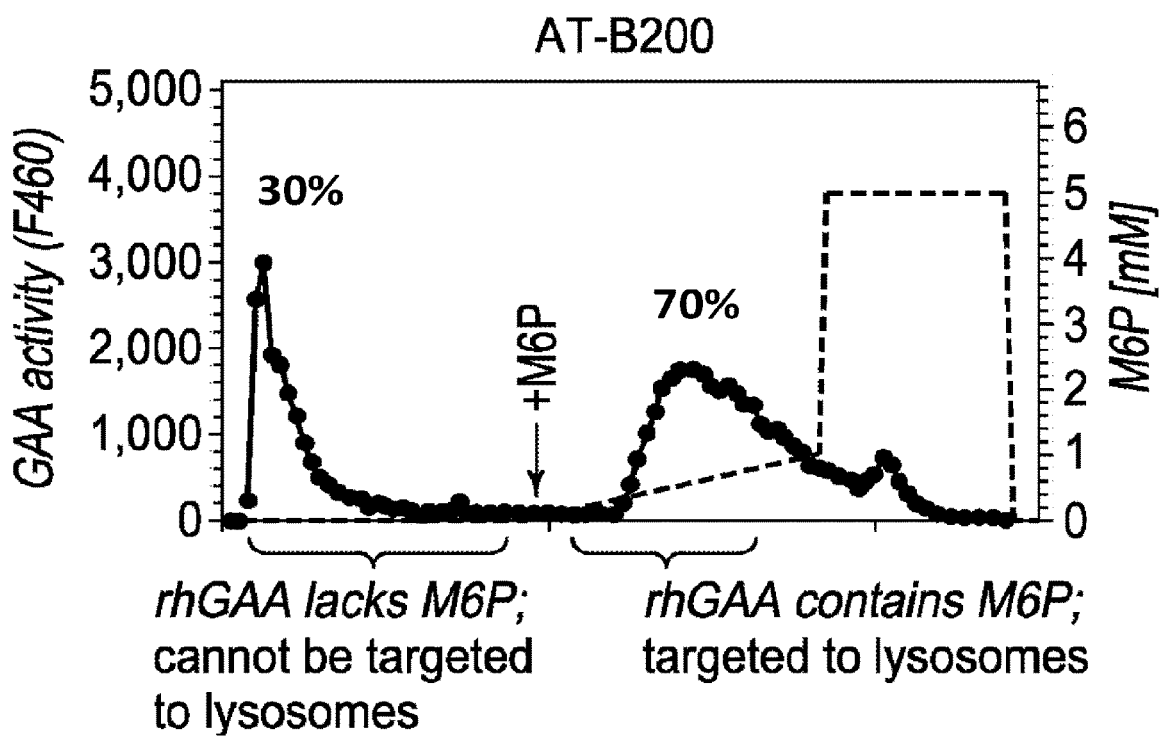

Example 2: Preparation of CHO Cells Producing ATB200 rhGAA Having a High Content of Mono- or Bis-M6P-bearing N-glycans CHO cells were transfected with DNA that expresses rhGAA followed by selection of transformants producing rhGAA. A DNA construct for transforming CHO cells with DNA encoding rhGAA is shown in FIG. 3. CHO cells were transfected with DNA that expresses rhGAA followed by selection of transformants producing rhGAA.

After transfection, DG44 CHO (DHFR–) cells containing a stably integrated GAA gene were selected with hypoxanthine/thymidine deficient (–HT) medium. Amplification of GAA expression in these cells was induced by methotrexate treatment (MTX, 500 nM). Cell pools that expressed high amounts of GAA were identified by GAA enzyme activity assays and were used to establish individual clones producing rhGAA. Individual clones were generated on semisolid media plates, picked by ClonePix system, and were transferred to 24-deep well plates. The individual clones were assayed for GAA enzyme activity to identify clones expressing a high level of GAA. Conditioned media for determining GAA activity used a 4-MU-α-glucopyranoside α-glucosidase substrate. Clones producing higher levels of GAA as measured by GAA enzyme assays were further evaluated for viability, ability to grow, GAA productivity, N-glycan structure and stable protein expression. CHO cell lines, including CHO cell line GA-ATB-200, expressing rhGAA with enhanced mono-M6P or bis-M6P N-glycans were isolated using this procedure.

Example 3: Capturing and Purification of ATB200 rhGAA

Figure 5A:
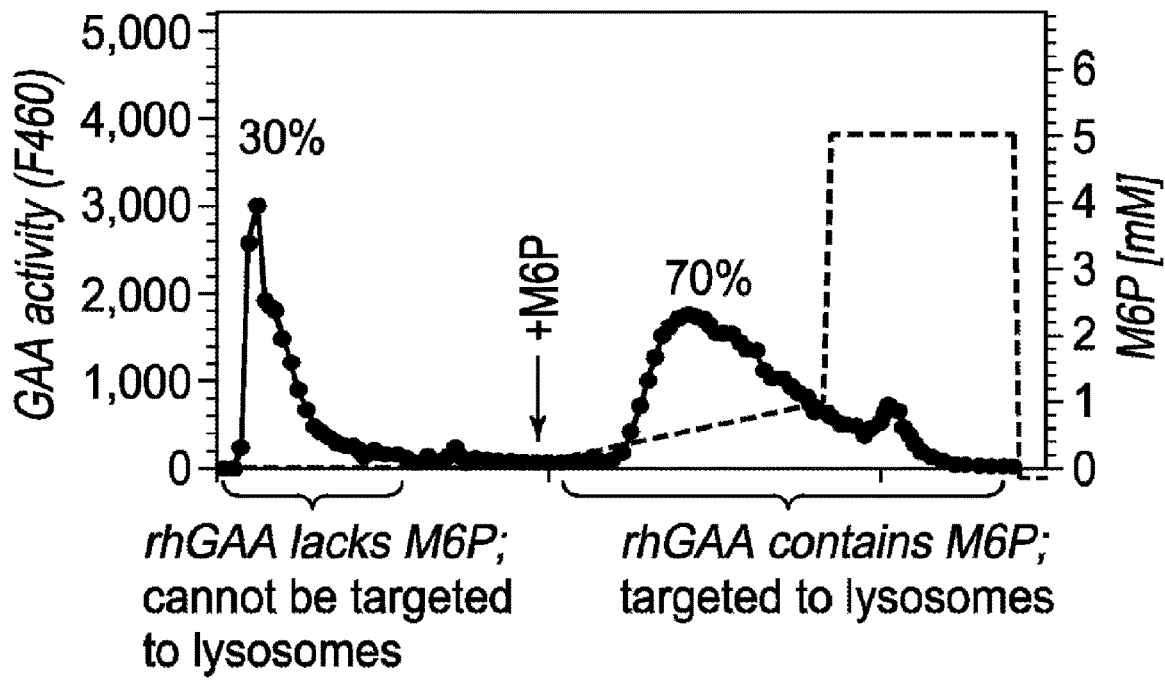
FIGS. 5A and 5B show the results of CIMPR affinity chromatography of ATB200 rhGAA with and without capture on an anion exchange (AEX) column.
Figure 5B:
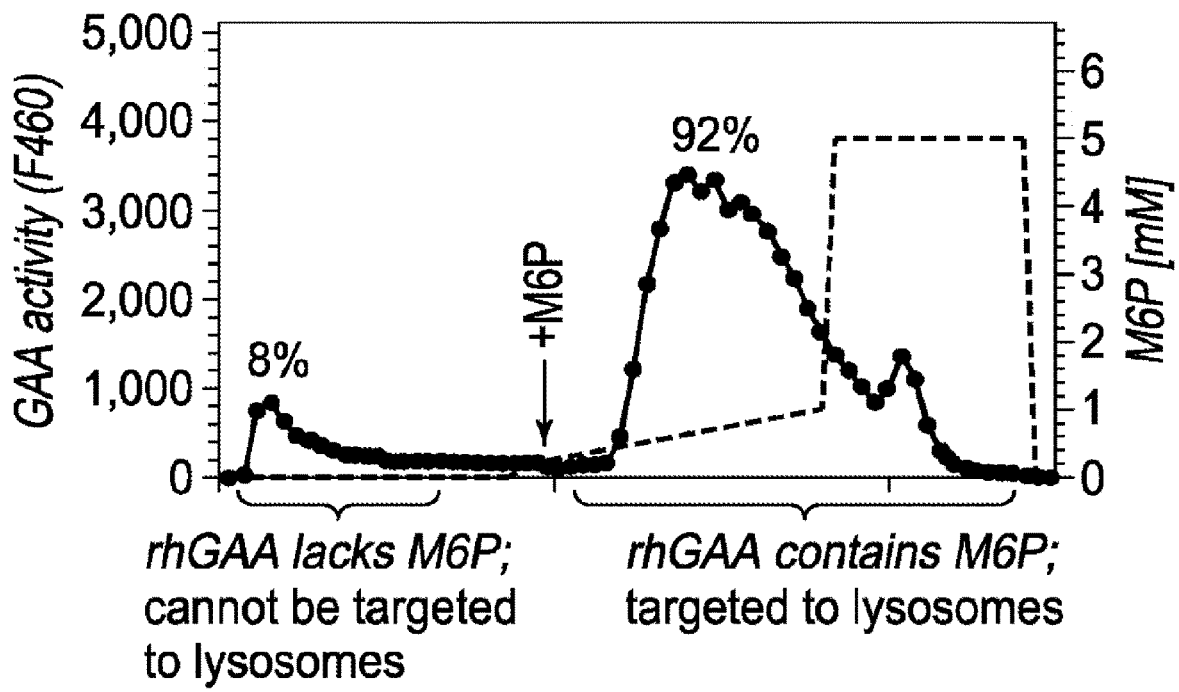

Multiple batches of the rhGAA according to the invention were produced in shake flasks and in perfusion bioreactors using CHO cell line GA-ATB-200 and CIMPR binding was measured. Similar CIMPR receptor binding (~70%) to that shown in FIG. 4B and FIG. 5A was observed for purified ATB200 rhGAA from different production batches indicating that ATB200 rhGAA can be consistently produced. As shown by FIGS. 2A, 2B, 4A and 4B, Myozyme® and Lumizyme® rhGAAs exhibited significantly less CIMPR binding than ATB200 rhGAA.

Example 4: Analytical Comparison of ATB200 to Lumizyme®

Figure 6:
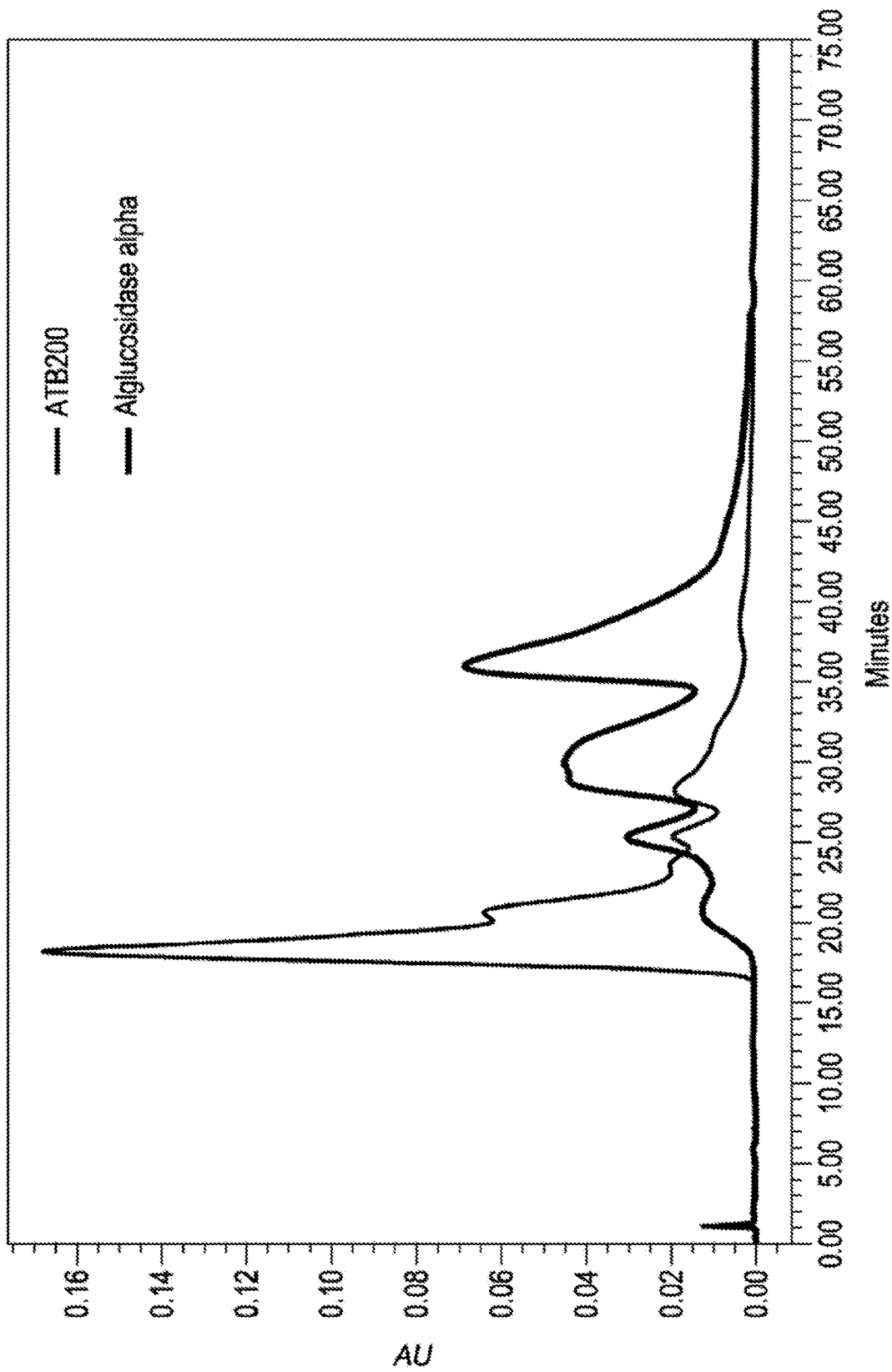
FIG. 6 shows Polywax elution profiles of Lumizyme® and ATB200 rhGAAs.

Weak anion exchange ("WAX") liquid chromatography was used to fractionate ATB200 rhGAA according to terminal phosphate. Elution profiles were generated by eluting the ERT with increasing amount of salt. The profiles were monitored by UV (A280 nm). ATB200 rhGAA was obtained from CHO cells and purified. Lumizyme® was obtained from a commercial source. Lumizyme® exhibited a high peak on the left of its elution profile. ATB200 rhGAA exhibited four prominent peaks eluting to the right of Lumizyme® (FIG. 6). This confirms that ATB200 rhGAA was phosphorylated to a greater extent than Lumizyme® since this evaluation is by terminal charge rather than CIMPR affinity.

Example 5: Oligosaccharide Characterization of ATB200 rhGAA

Purified ATB200 rhGAA and Lumizyme® glycans were evaluated by MALDI-TOF to determine the individual glycan structures found on each ERT (FIG. 7). ATB200 samples were found to contain lower amounts of non-phosphorylated high-mannose type N-glycans than Lumizyme®. The higher content of M6P glycans in ATB200 than in Lumizyme®, targets ATB200 rhGAA to muscle cells more effectively. The high percentage of mono-phosphorylated and bis-phosphorylated structures determined by MALDI agree with the CIMPR profiles which illustrated significantly greater binding of ATB200 to the CIMPR receptor. N-glycan analysis via MALDI-TOF mass spectrometry confirmed that on average each ATB200 molecule contains at least one natural bis-M6P N-glycan structure. This higher bis-M6P N-glycan content on ATB200 rhGAA directly correlated with high-affinity binding to CIMPR in M6P receptor plate binding assays (KD about 2-4 nM) FIG. 9A.

ATB200 rhGAA was also analyzed for site-specific N-glycan profiles using two different LC-MS/MS analytical techniques. In the first analysis, the protein was denatured, reduced, alkylated and digested prior to LC-MS/MS analysis. During protein denaturation and reduction, 200 µg of protein sample, 5 µL 1 mol/L tris-HCl (final concentration 50 mM), 75 µL 8 mol/L guanidine HCl (final concentration 6 M), 1 µL 0.5 mol/L EDTA (final concentration 5 mM), 2 µL 1 mol/L DTT (final concentration 20 mM) and Milli-Q® water were added to a 1.5 mL tube to provide a total volume of 100 µL. The sample was mixed and incubated at 56° C. for 30 minutes in a dry bath. During alkylation, the denatured and reduced protein sample was mixed with 5 µL 1 mol/L iodoacetamide (IAM, final concentration 50 mM), then incubated at 10-30° C. in the dark for 30 minutes. After alkylation, 400 µL of precooled acetone was added to the sample and the mixture was frozen at −80° C. refrigeration for 4 hours. The sample was then centrifuged for 5 min at 13000 rpm at 4° C. and the supernatant was removed. 400 µL of precooled acetone was added to the pellets, which was then centrifuged for 5 min at 13000 rpm at 4° C. and the supernatant was removed. The sample was then air dried on ice in the dark to remove acetone residue. 40 µL of 8M urea and 160 µL of 100 mM NH₄HCO₃ were added to the sample to dissolve the protein. During trypsin digestion, 50 µg of the protein was then added with trypsin digestion buffer to a final volume of 100 µL, and 5 µL 0.5 mg/mL trypsin (protein to enzyme ratio of 20/1 w/w) was added. The solution was mixed well and incubated overnight (16±2 hours) at 37° C. 2.5 µL 20% TFA (final concentration 0.5%) was added to quench the reaction. The sample was then analyzed using the Thermo Scientific Orbitrap Velos Pro™ Mass Spectrometer.

In the second LC-MS/MS analysis, the ATB200 sample was prepared according to a similar denaturation, reduction, alkylation and digestion procedure, except that iodoacetic acid (IAA) was used as the alkylation reagent instead of IAM, and then analyzed using the Thermo Scientific Orbitrap Fusion Lumos Tribid™ Mass Spectrometer.

In a third LC-MS/MS analysis, the ATB200 sample was prepared according to a similar denaturation, reduction, alkylation and digestion procedure using iodoacetamide (IAM) as the alkylation reagent, and then analyzed using the Thermo Scientific Orbitrap Fusion Mass Spectrometer.

Figure 8A:
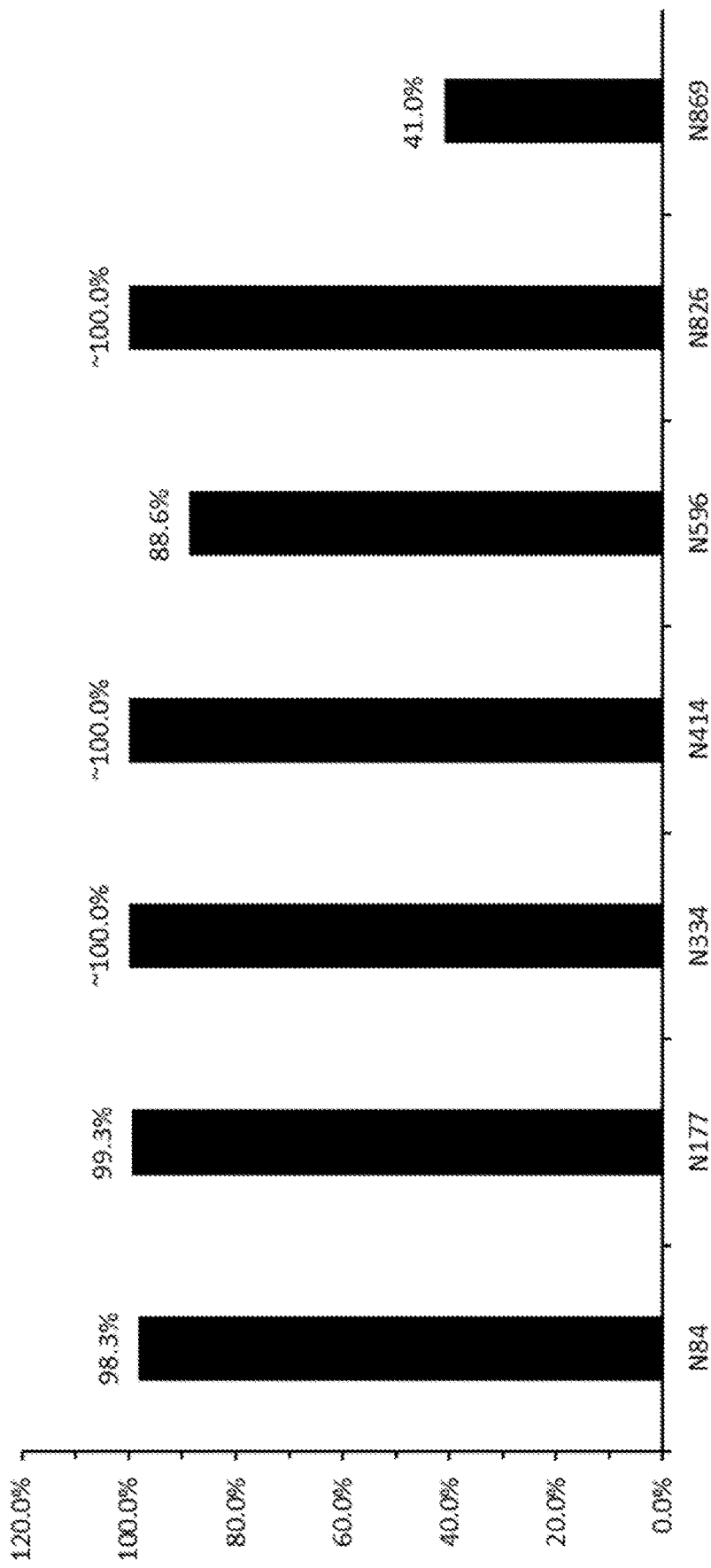
FIGS. 8A-8H show the results of a site-specific N-glycosylation analysis of ATB200 rhGAA.

The results of the first and second analyses are shown in FIGS. 8B-8H and the result of the third analysis is shown in FIG. 8A. In FIGS. 8B-8H, the results of the first analysis are represented by left bar (dark grey) and the results from the second analysis are represented by the right bar (light grey). In FIGS. 8B-8H, the symbol nomenclature for glycan representation is in accordance with Varki, A., Cummings, R. D., Esko J. D., et al., *Essentials of Glycobiology*, 2nd edition (2009). In FIGS. 8A-8H, the glycosylation sites are given relative to SEQ ID NO: 5: N84, N177, N334, N414, N596, N826 and N869. For the full-length amino acid sequence of SEQ ID NO: 1, these potential glycosylation sites are at the following positions: N140, N233, N390, N470, N652, N882 and N925.

As can be seen from FIGS. 8B-8H, the first two analyses provided similar results, although there was some variation between the results. This variation can be due to a number of factors, including the instrument used and the completeness of N-glycan analysis. For example, if some species of phosphorylated glycans were not identified and/or not quantified, then the total number of phosphorylated glycans may be underrepresented, and the percentage of rhGAA bearing the phosphorylated glycans at that site may be underrepresented. As another example, if some species of non-phosphorylated glycans were not identified and/or not quantified, then the total number of non-phosphorylated glycans may be underrepresented, and the percentage of rhGAA bearing the phosphorylated glycans at that site may be overrepresented.

FIG. 8A shows the N-glycosylation site occupancy of ATB200. As can be seen from FIG. 8A, the first, second, third, fourth, fifth and sixth N-glycosylation sites are mostly occupied, with approximately 90% and up to about 100% of the ATB200 enzyme having a glycan detected at each potential site. However, the seventh potential N-glycosylation site is glycosylated about half of the time.

Figure 8B:
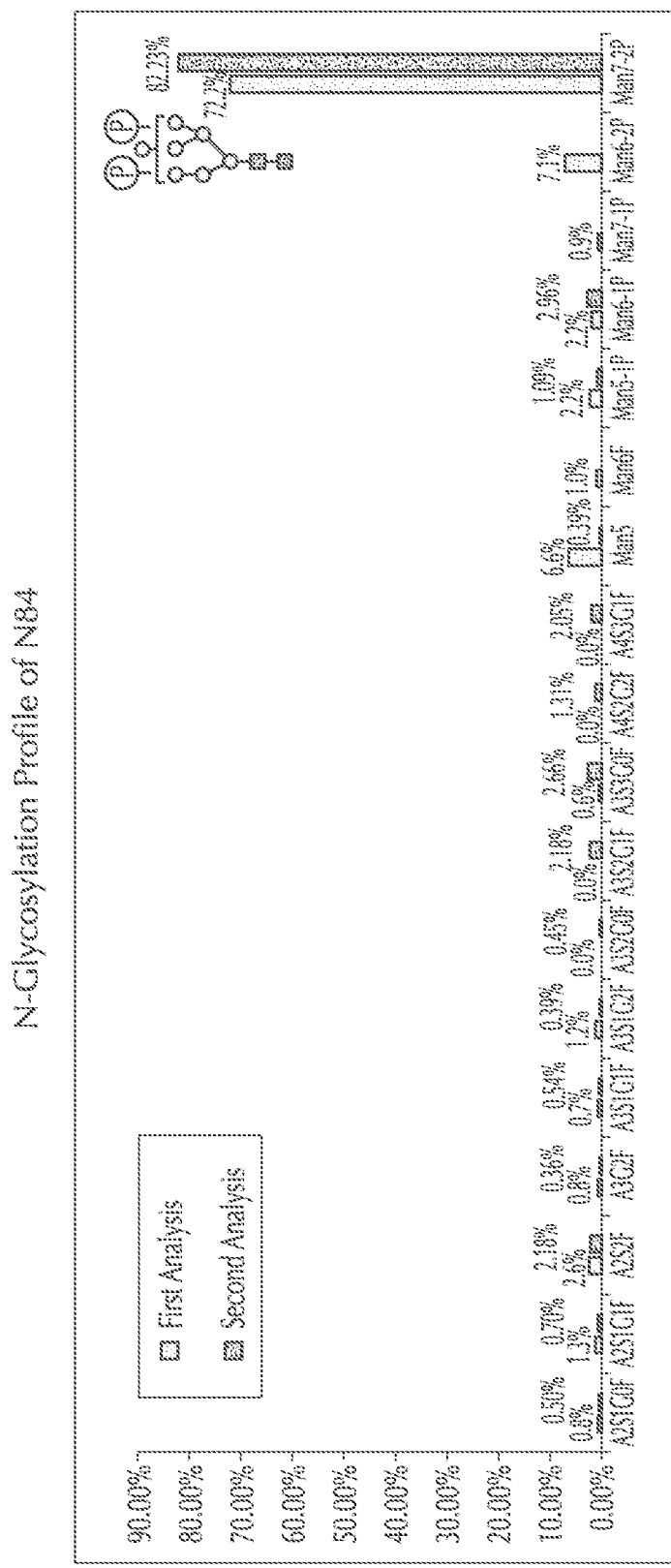

FIG. 8B shows the N-glycosylation profile of the first site, N84. As can be seen from FIG. 8B, the major glycan species is bis-M6P glycans. Both the first and second analyses detected over 75% of the ATB200 had a bis-M6P glycan at the first site.

Figure 8C:
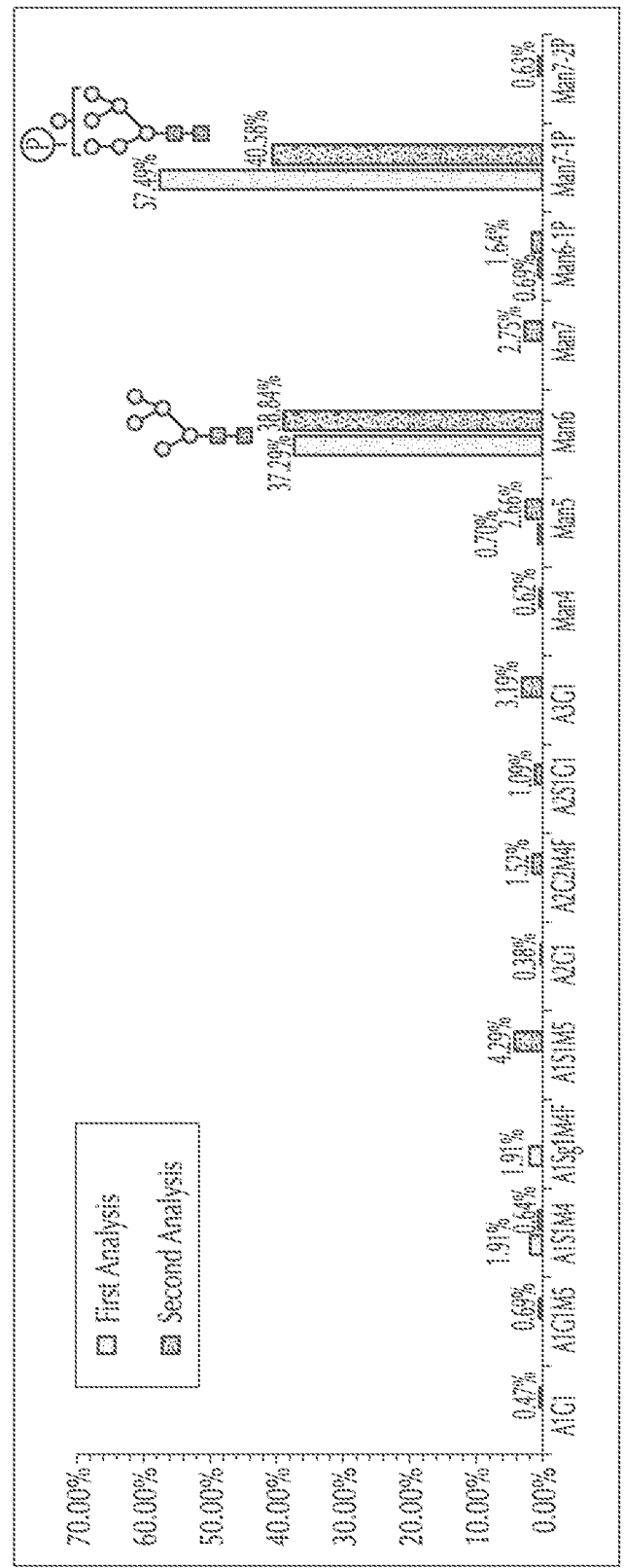

FIG. 8C shows the N-glycosylation profile of the second site, N177. As can be seen from FIG. 8C, the major glycan species are mono-M6P glycans and non-phosphorylated high mannose glycans. Both the first and second analyses detected over 40% of the ATB200 had a mono-M6P glycan at the second site.

Figure 8D:
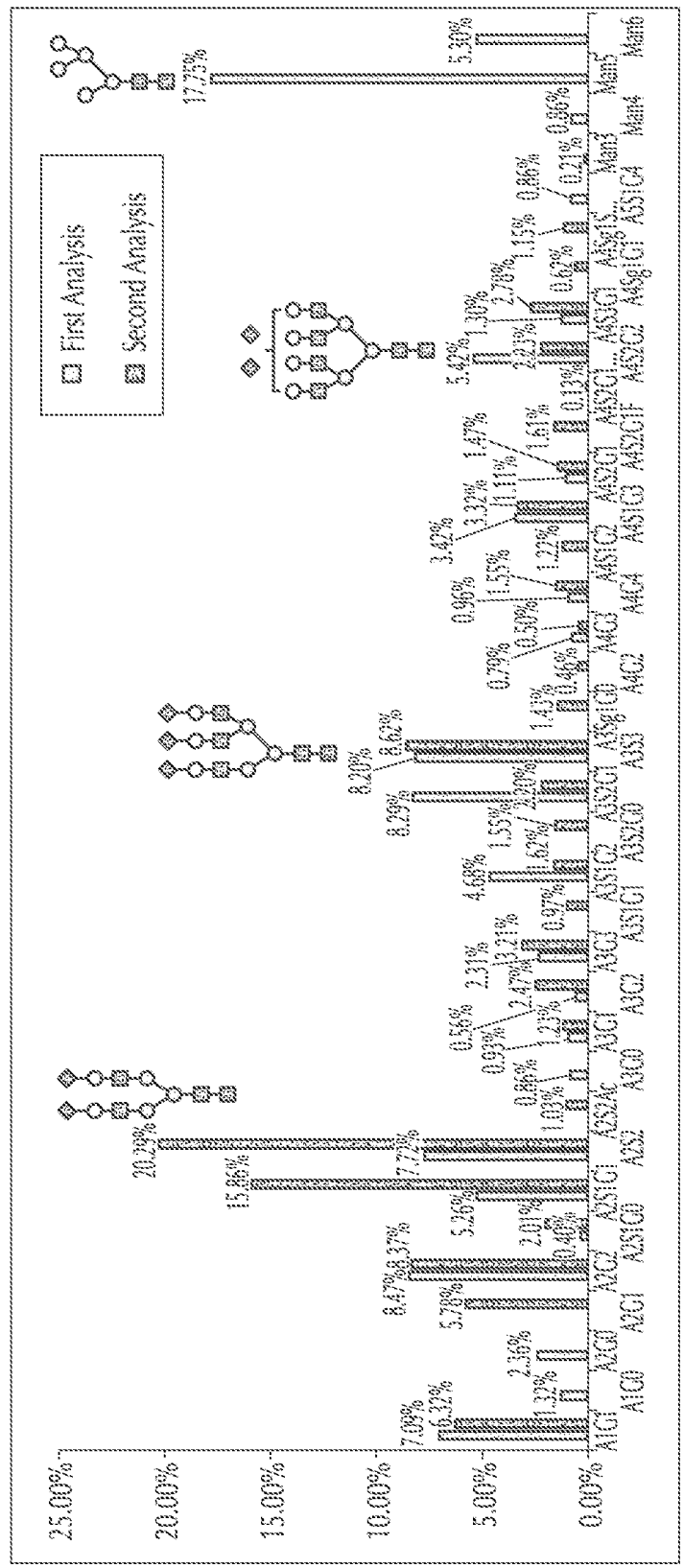

FIG. 8D shows the N-glycosylation profile of the third site, N334. As can be seen from FIG. 8D, the major glycan species are non-phosphorylated high mannose glycans, di-, tri-, and tetra-antennary complex glycans, and hybrid glycans. Both the first and second analyses detected over 20% of the ATB200 had a sialic acid residue at the third site.

Figure 8E:
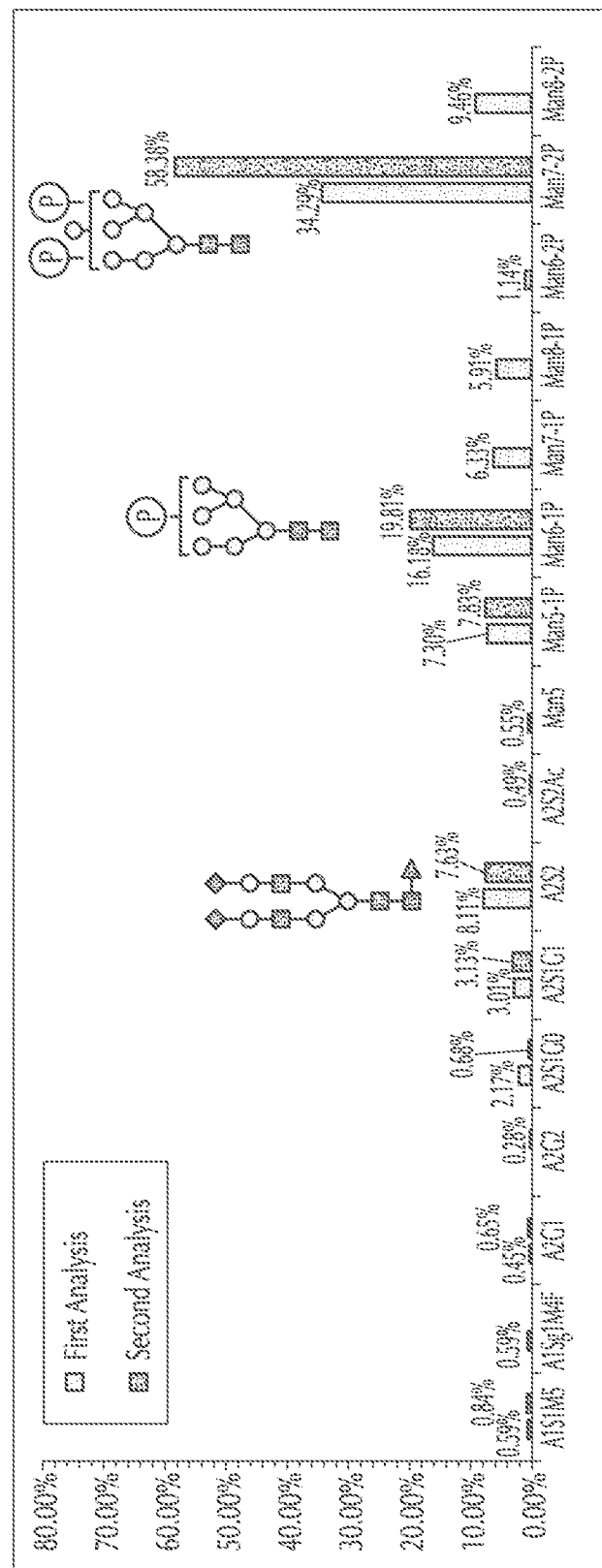

FIG. 8E shows the N-glycosylation profile of the fourth site, N414. As can be seen from FIG. 8E, the major glycan species are bis-M6P and mono-M6P glycans. Both the first and second analyses detected over 40% of the ATB200 had a bis-M6P glycan at the fourth site. Both the first and second analyses also detected over 25% of the ATB200 had a mono-M6P glycan at the fourth site.

Figure 8F:
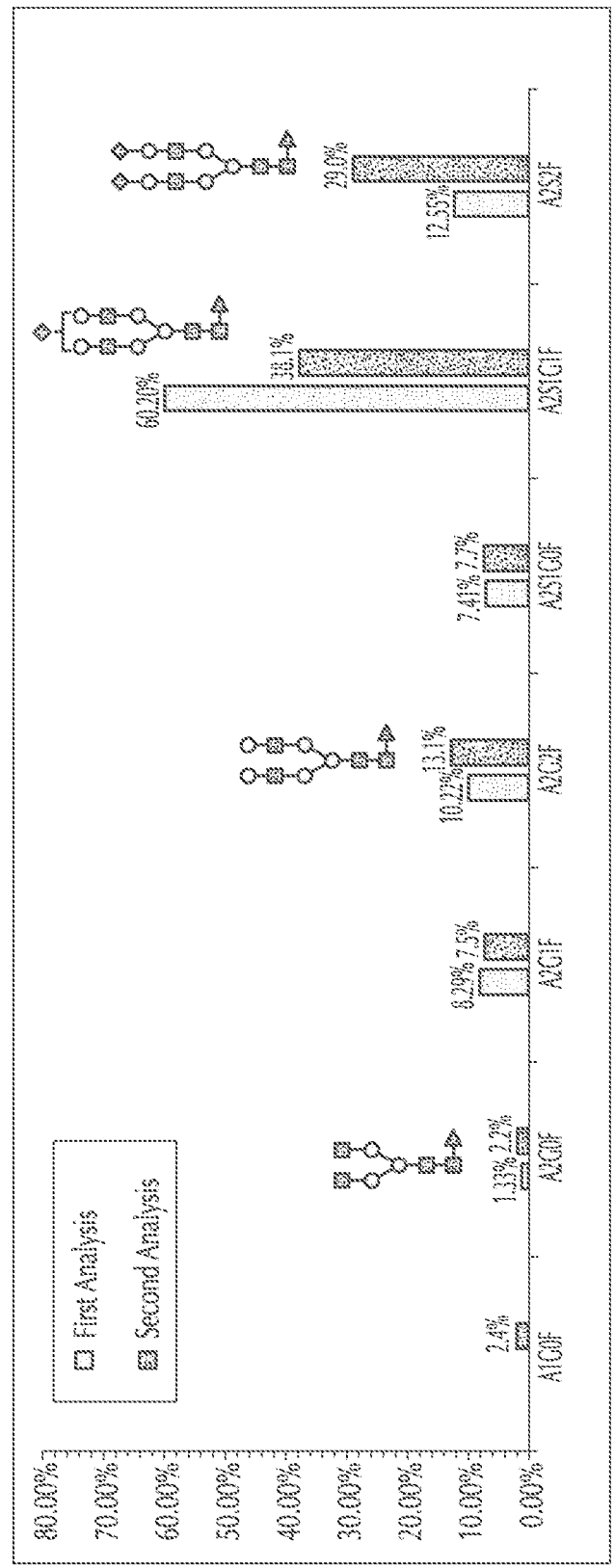

FIG. 8F shows the N-glycosylation profile of the fifth site, N596. As can be seen from FIG. 8F, the major glycan species are fucosylated di-antennary complex glycans. Both the first and second analyses detected over 70% of the ATB200 had a sialic acid residue at the fifth site.

Figure 8G:
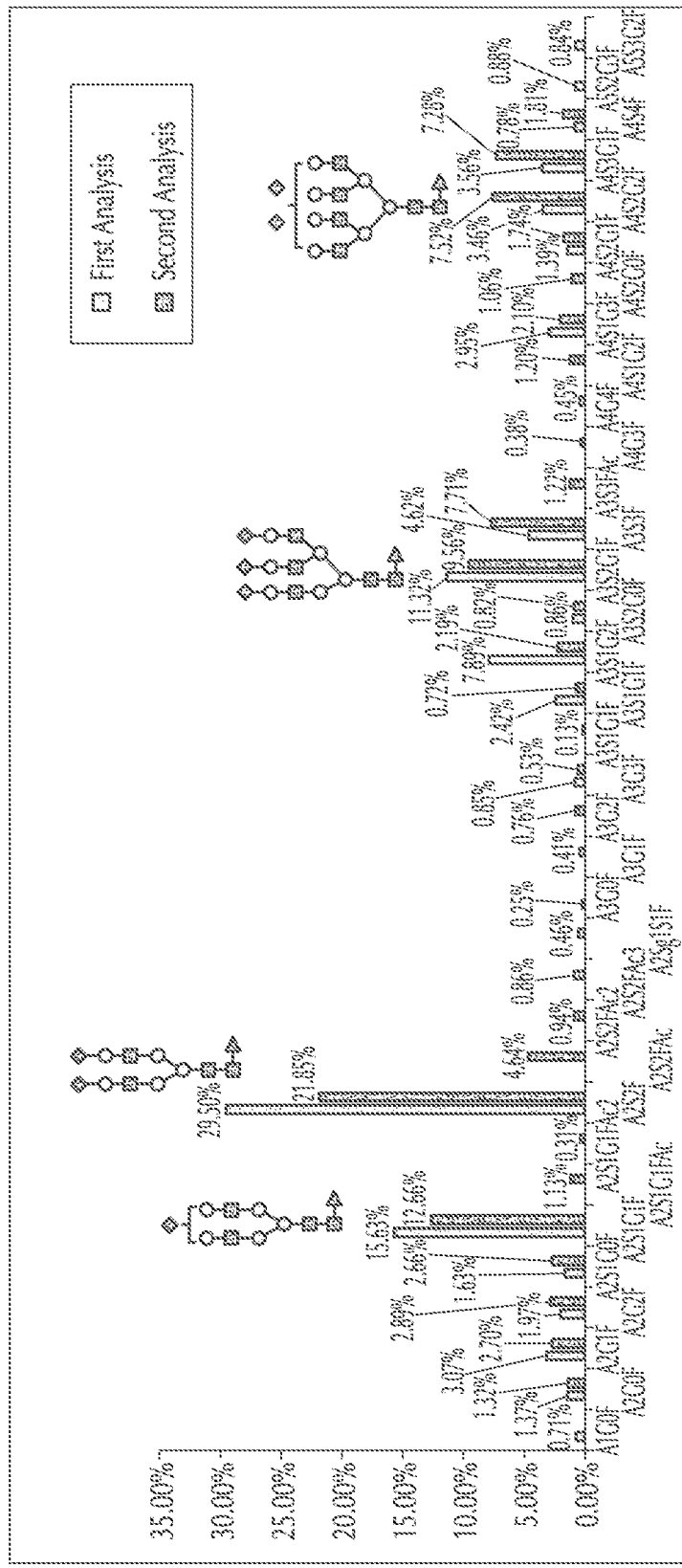

FIG. 8G shows the N-glycosylation profile of the sixth site, N826. As can be seen from FIG. 8G, the major glycan species are di-, tri-, and tetra-antennary complex glycans. Both the first and second analyses detected over 80% of the ATB200 had a sialic acid residue at the sixth site.

Figure 8H:
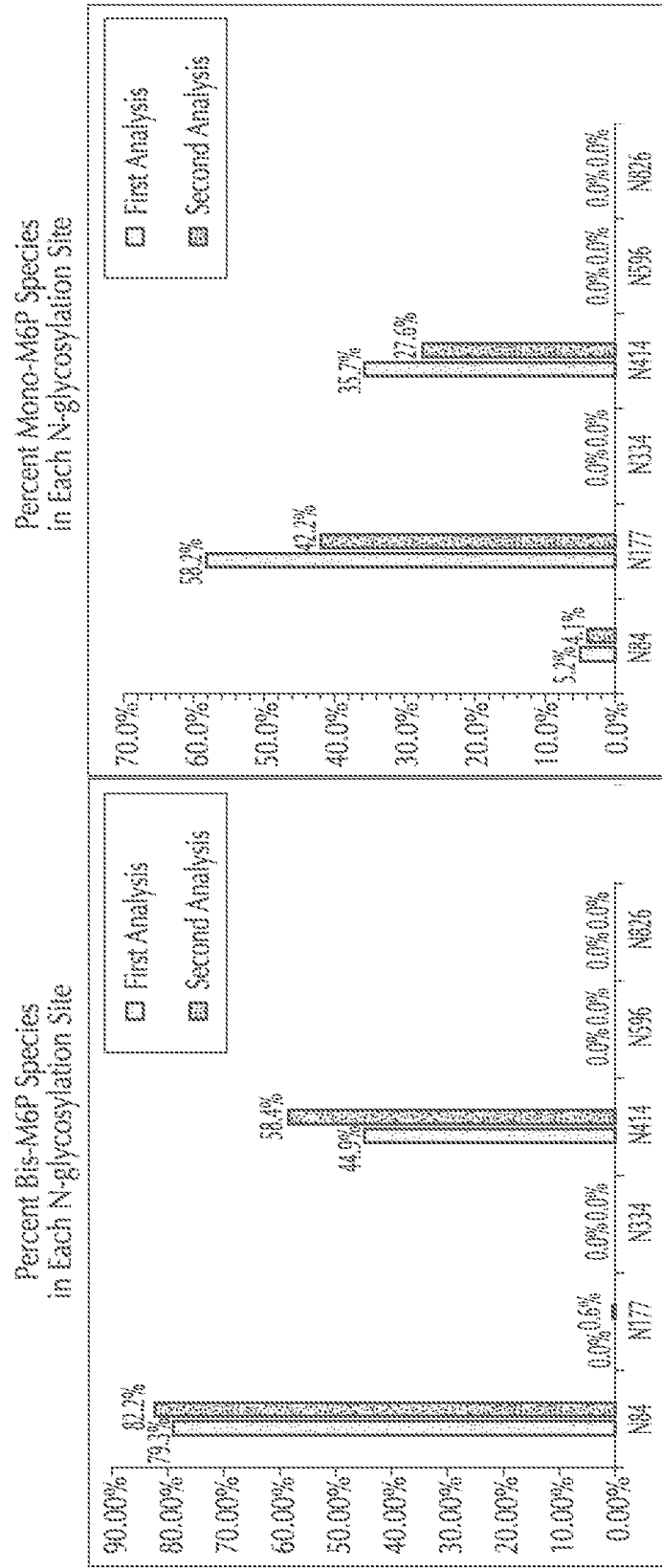

FIG. 8H shows a summary of the phosphorylation at each of the first six potential N-glycosylation sites. As can be seen from FIG. 8H, both the first and second analyses detected high phosphorylation levels at the first, second and fourth sites. Both analyses detected over 80% of the ATB200 was mono- or di-phosphorylated at the first site, over 40% of the ATB200 was mono-phosphorylated at the second site, and over 80% of the ATB200 was mono- or di-phosphorylated at the fourth site.

Example 6: Characterization of CIMPR Affinity of ATB200

Figures 9A, 9B:
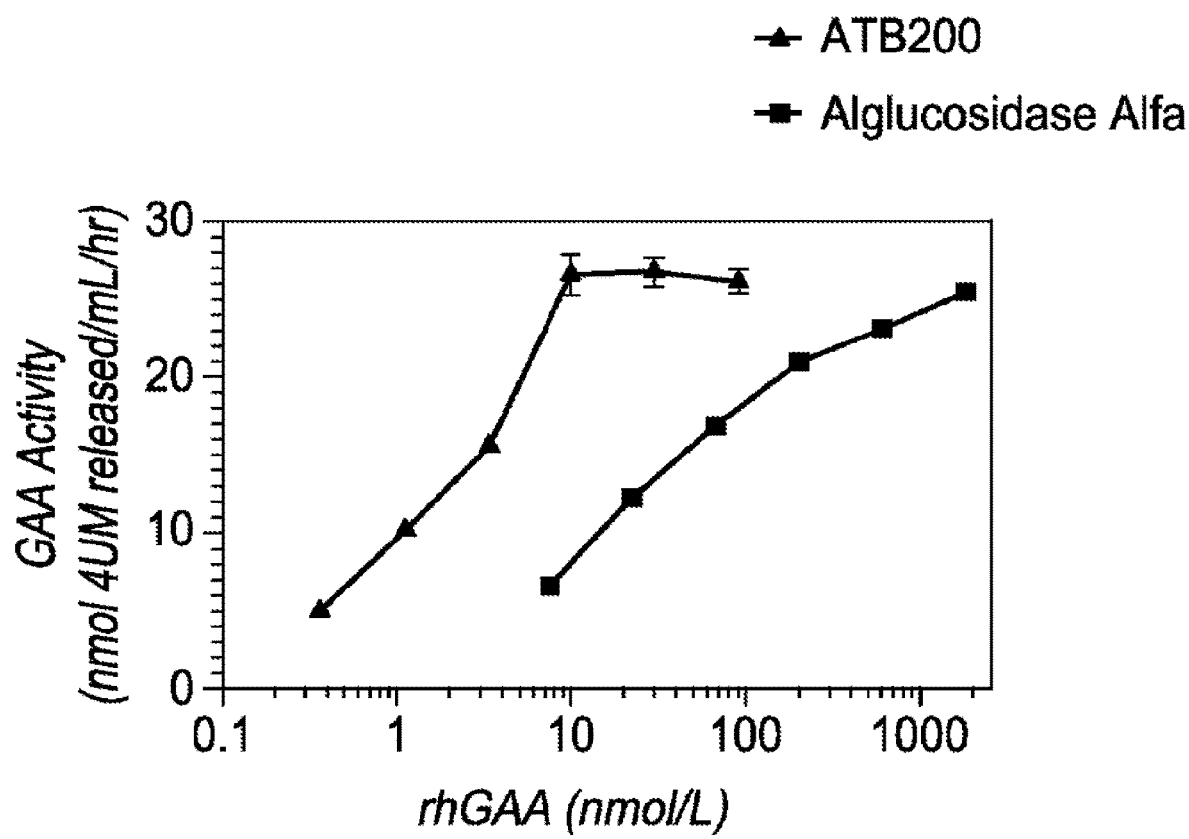
FIG. 9A compares the CIMPR binding affinity of ATB200 rhGAA (left trace) with that of Lumizyme® (right trace).
FIG. 9B compares the Bis-M6P content of Lumizyme® and ATB200 rhGAA.

In addition to having a greater percentage of rhGAA that can bind to the CIMPR, it is important to understand the quality of that interaction. Lumizyme® and ATB200 rhGAA receptor binding was determined using a CIMPR plate binding assay. Briefly, CIMPR-coated plates were used to capture GAA. Varying concentrations of rhGAA were applied to the immobilized receptor and unbound rhGAA was washed off. The amount of remaining rhGAA was determined by GAA activity. As shown by FIG. 9A, ATB200 rhGAA bound to CIMPR significantly better than Lumizyme®.

FIG. 9B shows the relative content of bis-M6P glycans in Lumizyme®, a conventional rhGAA, and ATB200 according to the invention. For Lumizyme® there is on average only 10% of molecules have a bis-phosphorylated glycan. Contrast this with ATB200 where on average every rhGAA molecule has at least one bis-phosphorylated glycan.

Example 7: ATB200 rhGAA was More Efficiently Internalized by Fibroblast than Lumizyme®

Figure 10A:
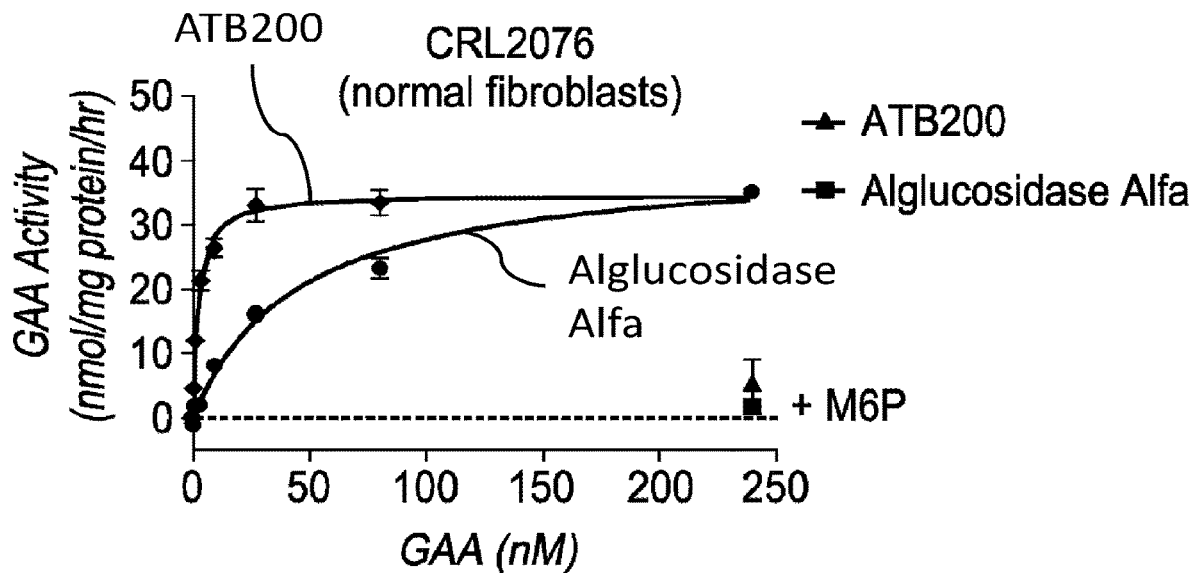
FIG. 10A compares ATB200 rhGAA activity (left trace) with Lumizyme® rhGAA activity (right trace) inside normal fibroblasts at various GAA concentrations.
Figure 10B:
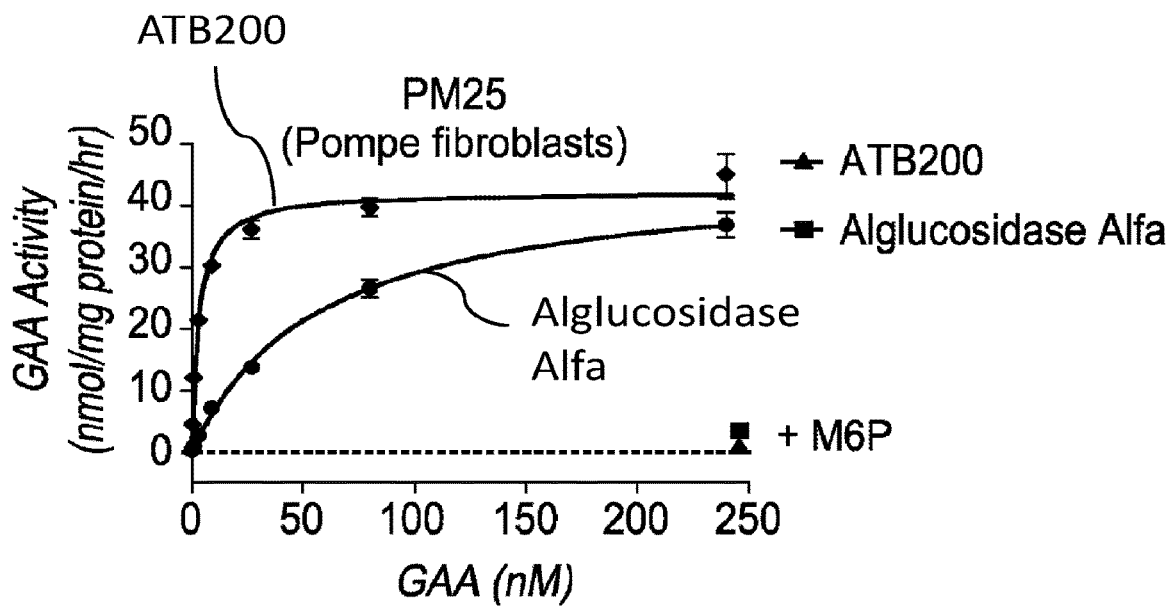
FIG. 10B compares ATB200 rhGAA activity (left trace) with Lumizyme® rhGAA activity (right trace) inside fibroblasts from a subject having Pompe Disease at various GAA concentrations.

The relative cellular uptake of ATB200 and Lumizyme® rhGAA were compared using normal and Pompe fibroblast cell lines. Comparisons involved 5-100 nM of ATB200 rhGAA according to the invention with 10-500 nM conventional rhGAA Lumizyme®. After 16-hr incubation, external rhGAA was inactivated with TRIS base and cells were washed 3-times with PBS prior to harvest. Internalized GAA measured by 4MU-α-Glucoside hydrolysis and was graphed relative to total cellular protein and the results appear in FIGS. 10A-B.

Figures 10C, 11:
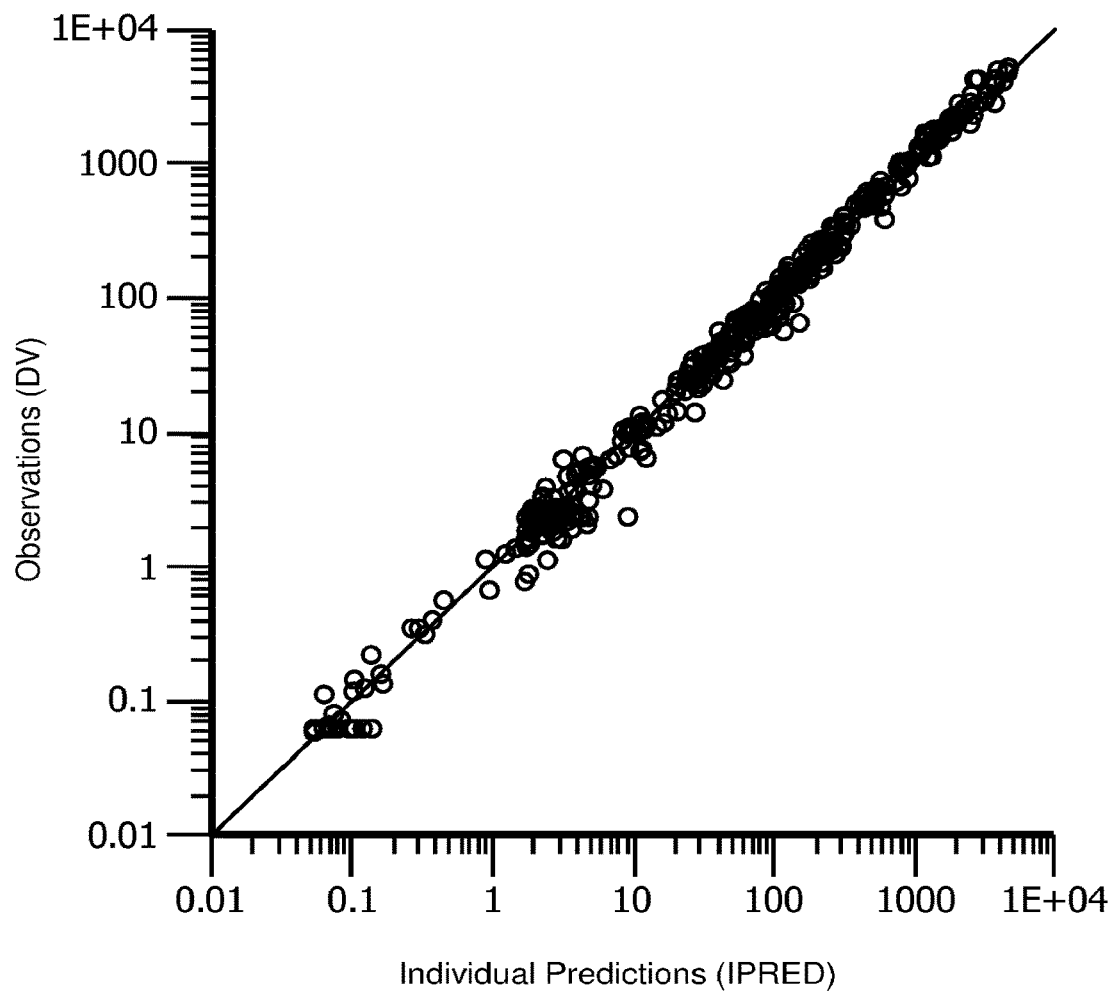
FIG. 10C compares ($K_{uptake}$) of fibroblasts from normal subjects and subjects with Pompe Disease.
FIG. 11 is a graph showing goodness of fit of a population pharmacokinetic (PK) model for ATB200.

ATB200 rhGAA was also shown to be efficiently internalized into cells (FIGS. 10A and 10B), respectively, show that ATB200 rhGAA is internalized into both normal and Pompe fibroblast cells and that it is internalized to a greater degree than conventional Lumizyme® rhGAA. ATB200 rhGAA saturates cellular receptors at about 20 nM, while about 250 nM of Lumizyme® is needed. The uptake efficiency constant (Kuptake) extrapolated from these results is 2-3 nm for ATB200 and 56 nM for Lumizyme® as shown by FIG. 10C. These results suggest that ATB200 rhGAA is a well-targeted treatment for Pompe disease.

Example 8: Population Pharmacokinetic (PK) Modeling for ATB200 and Miglustat Pharmacokinetic data for acid α-glucosidase (ATB200), including sampling times, dosing history and plasma concentrations of acid α-glucosidase, is obtained from mice, rats and monkeys administered ATB200 by intravenous injection. Pharmacokinetic data for miglustat and duvoglustat in plasma and tissue is collected from humans or from mice. Modeling and simulations are performed using Phoenix® NLME™ v1.3. Compartmental PK models are constructed to assess the PK of ATB200 in plasma. The models include:

Description of the relationships between plasma concentration and time;

A variance component characterizing between- and within-animal variability in model parameters; and A component describing uncertainty in the state of knowledge about critical model components.

Non-linear mixed effects (NLME) models have the form:

$$C_{P_{ij}} = C(D_i, t_j, \theta_i) + \varepsilon_{ij}$$

$$\theta_i = (\theta_{i1}, \ldots, \theta_{im})$$

where $C_{p_{ij}}$ is concentration at $j^{th}$ collection time ($t_j$) for animal i, $D_i$ represents the dosing history for animal i, $\theta_i$ is the vector of PK parameters for animal i, and $\varepsilon_{ij}$ is the random error associated with $j^{th}$ concentration for animal i.

Between-subject variability (BSV) in parameters are modeled as a log-normal distribution:

$$\theta_{in} = \theta_{TVn} \exp(\eta_{in})$$

$$(\eta_1, \ldots, \eta_m) \sim MVN(0, \Omega)$$

where $\theta_{TVn}$ is the population typical value for the $n^{th}$ PK parameter (e.g. clearance) and $\eta_{in}$ is the random inter-animal effect on the $n^{th}$ parameter for animal i. Random effects $(\eta_1, \ldots, \eta_m)$ were normally distributed with mean 0 and estimated variance $\omega^2$ included in the OMEGA ($\Omega$) matrix.

PK is assumed to be species independent and is scaled according to a generalized Dedrick approach that scales the disposition according to the power of an animal's body weight:

$$CL_{(p)i} = a_{(p)} BW_i^b$$

$$V_{(p)i} = c_{(p)} BW_i^d$$

where CL=systemic clearance, V=volume of distribution, BW=body weight, p=peripheral, b and d=allometric exponents, and a and c=typical values for a BW=1. In this scenario, the exponent b and d can be compared to more generalized values accepted in the literature (b=0.75 and d=1.0). Nominal BW (0.025, 0.25 and 2.5 kg) are used in the analyses.

Baseline acid α-glucosidase concentration is modeled as $C_{baseline}$=Rate of acid α-glucosidase synthesis/CL and can be extrapolated to humans, since $C_{baseline}$ is species specific, independent of the concentration of ATB200 and known in humans with Pompe disease. A base model is determined using Phoenix® FOCE-ELS, to evaluate whether a 1 or 2 compartment model is best to fit the data. Sources of variability in PK of acid α-glucosidase are also explored visually and by searching the effect of the various wild type/species/dose related effects on PK.

For ATB200, a two-compartment model with linear elimination adequately characterizes the concentration-time profiles of acid α-glucosidase activity for all dose levels across animal species. The model includes a theoretical allometric component accounting for difference in body weight across animal species on clearance (CL) and volume of distribution (Vc). The goodness of fit of the population PK model for ATB200 is shown in FIG. 11. Population PK parameters of ATB200 in nonclinical studies are presented in Table 1.

TABLE 1

| PK Parameter | Typical Values (Relative standard error (%)) | Between-subject variability (%) |
|---|---|---|
| Systemic clearance (CL; L/h) | $0.00957 \times (BW/0.25)^{0.78}$ (5.1) (3.2) | 21.0 |
| Central volume of distribution ($V_c$; L) | $0.0101 \times (BW/0.25)^{0.83}$ (4.3) (1.7) | 5.3 |
| Peripheral clearance ($CL_d$; L/h) | $0.000290 \times (BW/0.25)^{0.78}$ (43.2) | NA |
| Peripheral volume of distribution (V2; L) | $0.000653 \times (BW/0.25)^{0.83}$ (35.6) | NA |
| Endogenous rate of acid α-glucosidase synthesis (SYNT; mg/h) | Mouse: 0.00401 (8.1) Rat: 0.0203 (13.3) Monkey: 0.00518 (16.9) | NA |

BW: body weight

Figure 12:
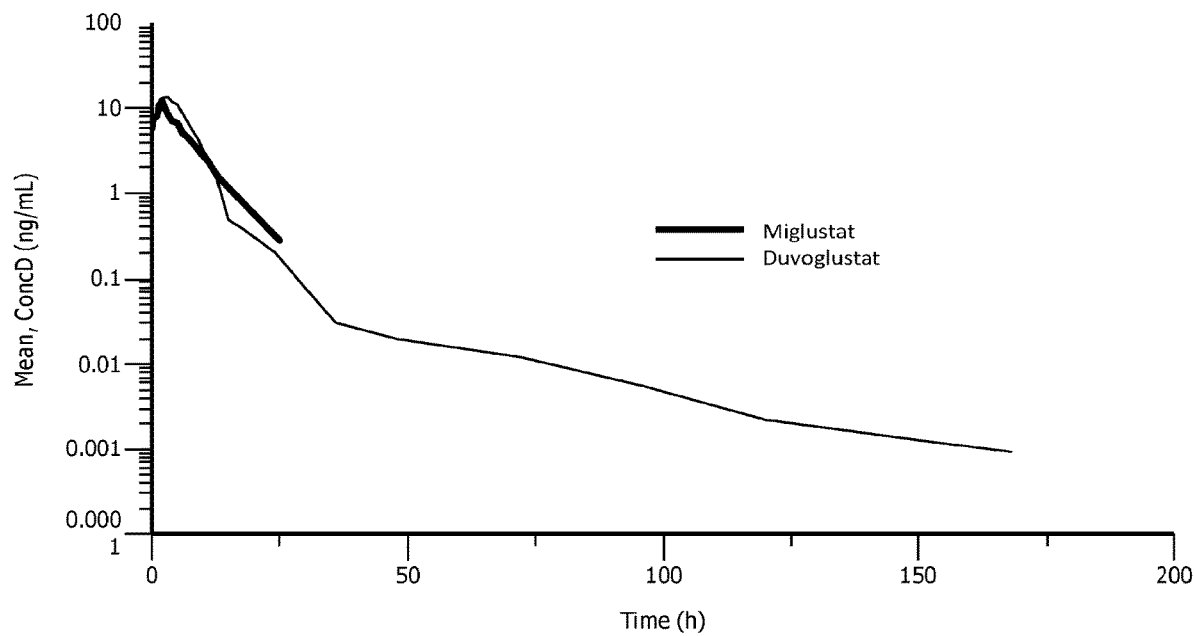
FIG. 12 is a graph showing dose-normalized plasma concentration-time profiles of miglustat and duvoglustat.

Concentration-time profiles of miglustat (200 mg) in Pompe disease patients are compared to those obtained following administration of duvoglustat in normal healthy volunteers (dose range: 50, 100, 250, 600, and 1000 mg). Dose-normalized plasma concentration-time profiles of miglustat and duvoglustat are shown in FIG. 12.

Because concentration-time profiles of miglustat in patients with Pompe disease are similar to those observed following dosing of duvoglustat in healthy subjects over 24 h, PK data collected for duvoglustat in peripheral tissues were used as a surrogate to model exposure to miglustat. A two-compartment model with linear elimination is used to characterize the concentration-time profiles of duvoglustat in tissues.

Figure 13A:
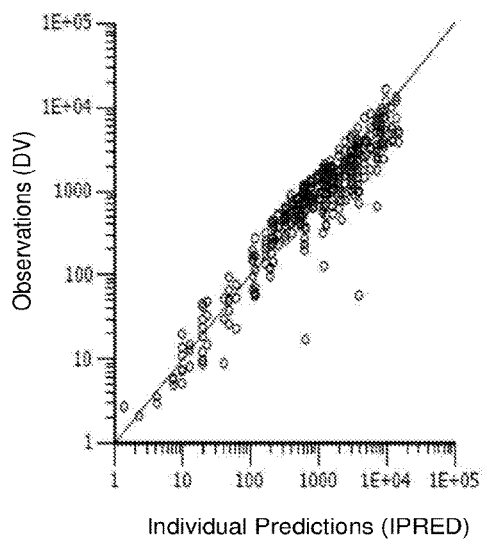
FIG. 13A is a graph showing goodness of fit of a population PK model for duvoglustat in plasma.
Figure 13B:
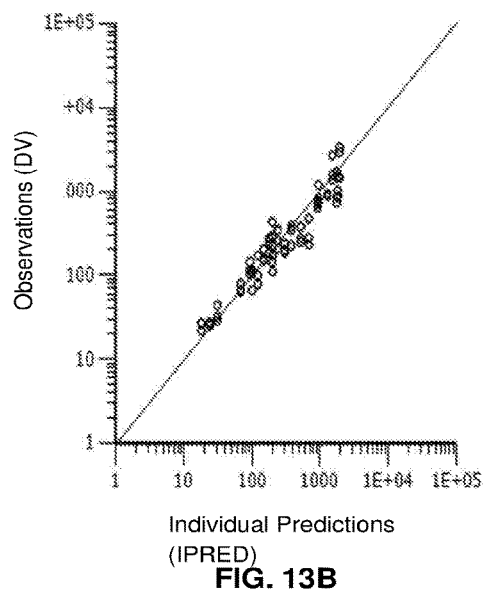
FIG. 13B is a graph showing goodness of fit of a population PK model for duvoglustat in muscle tissue.

Goodness of fit of the PK model of duvoglustat is shown in FIGS. 13A and 13B. Final model PK parameters of duvoglustat in plasma and tissue are shown in Table 2.

TABLE 2

| PK Parameter | Typical Values (CV %) |
|---|---|
| Volume of distribution (V; L) | 44.5 (7.41) |
| Systemic clearance (CL; L/h) | 9.44 (6.99) |
| Rate constant of absorption ($K_a$; 1/h)) | 1.10 (14.0) |
| Peripheral volume of distribution (V2; L) | 8.68 (19.39) |
| Central compartment clearance (CL2; L/h) | 0.205 (23.7) |
| Intercompartment volume of distribution (VQ; L) | 61.8 (21.2) |
| Elimination rate constant (Keo) | 0.378 (11.1) |
| Intercompartment volume of distribution within central compartment (VQ2; L) | 3390 |
| Peripheral compartment clearance (CL3; L/h) | 88.0 (7.72) |
| Apparent intercompartment clearance (CLQ; L/h) | 40.6 (10.6) |
| Lag time (h) | 0.176 (30.7) |
| Relative standard error of central compartment | 0.477 (6.56) |
| Relative standard error of peripheral compartment | 0.368 (8.19) |

CV: coefficient of variability

Figure 14:
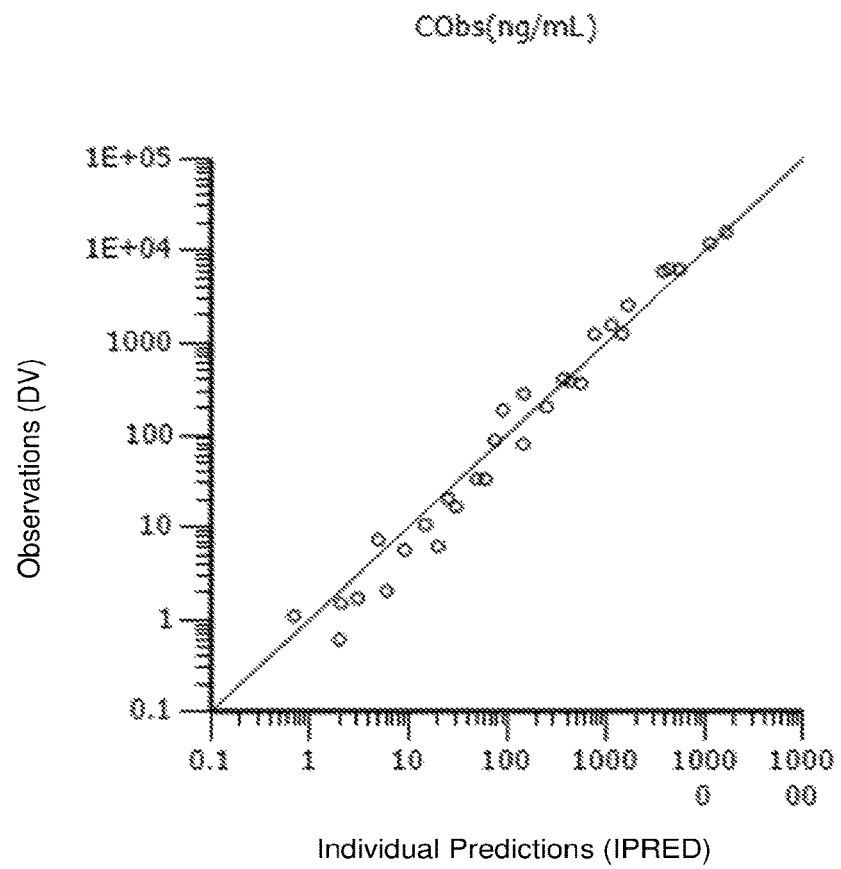
FIG. 14 is a graph showing goodness of fit of a population PK model for miglustat.

A population PK model of miglustat is constructed based on oral dosing in Gaa knockout (KO) mice. Population PK parameters of miglustat in Gaa KO mice are presented in Table 3. Goodness of fit is shown in FIG. 14. The model has a residual additive error of 0.475 ng/mL.

TABLE 3

| PK Parameter | Typical Values (BSV %) |
|---|---|
| Rate constant of absorption ($K_a$; $h^{-1}$) | 2.09 (4.56) |
| Systemic clearance (CL; mL/h) | 43.3 (9.61) |
| Central volume of distribution ($V_c$; mL) | 4.55 (45.1) |
| Peripheral clearance ($CL_d$; mL/h) | 4.57 (32.1) |
| Peripheral volume of distribution (V2; mL) | 19.6 (23.3) |

BSV: between-subject variability

Example 9: Modeling of Recombinant Acid α-glucosidase (ATB200) Pharmacokinetic (PK) Parameters in Humans Pharmacokinetic models (Example 8) were used to perform simulations and to predict concentration-time profiles of acid α-glucosidase in human subjects with late stage Pompe disease following dosing of ATB200. The allometric function allowed the linkage of body weight to clearance and volume of distribution, and therefore allowed the prediction of PK parameters in a typical human subjects with a body weight of 70 kg. The model is customized by including an endogenous rate of synthesis of acid α-glucosidase in humans (Umapathysivam K, Hopwood J J, Meikle P J. Determination of acid alpha-glucosidase activity in blood spots as a diagnostic test for Pompe disease. *Clin Chem.* (2001) August; 47(8): 1378-83).

Figure 15:
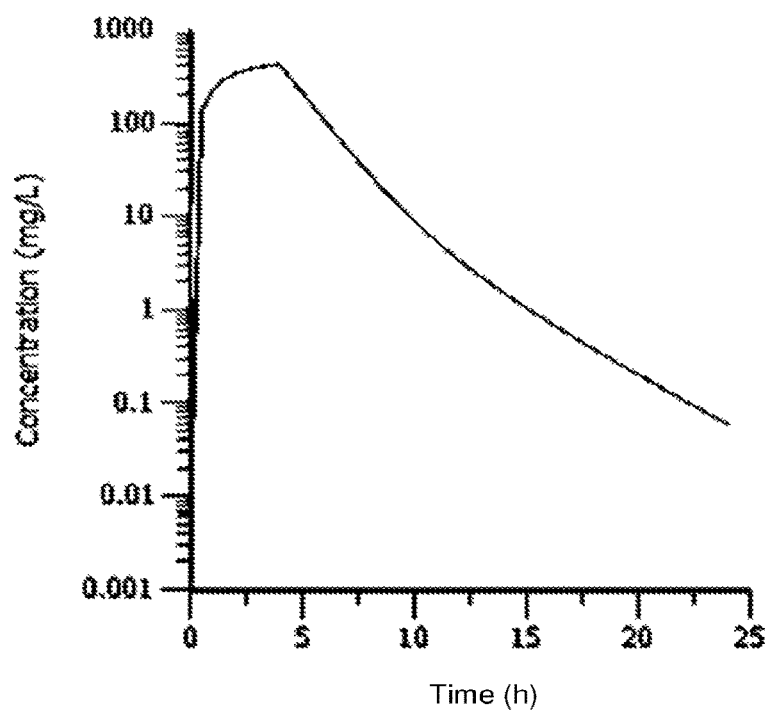
FIG. 15 is a graph showing the predicted concentration-time profile resulting from infusion of a single 20 mg/kg intravenous (IV) dose of ATB200 in humans over a 4 h period.
Figure 16A:
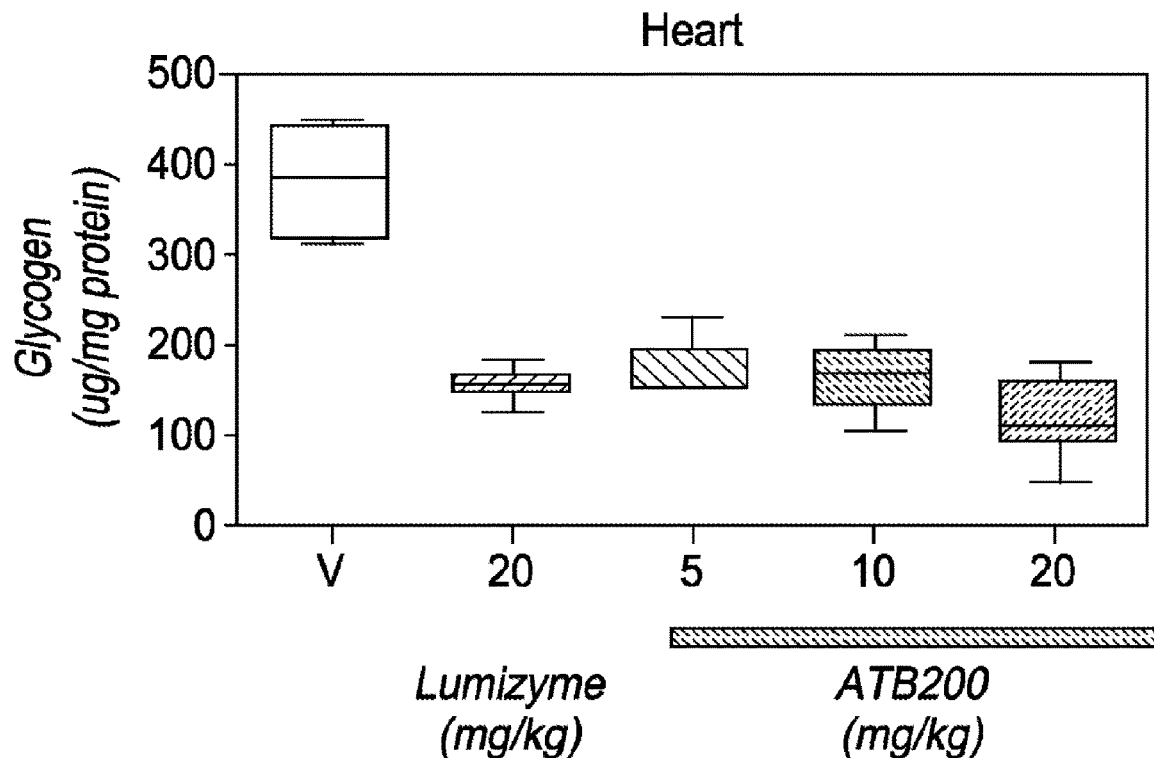
FIG. 16A is a graph showing the amount of glycogen relative to dose of recombinant human acid α-glucosidase in mouse heart muscle after contact with vehicle (negative control), with 20 mg/kg alglucosidase alfa (Lumizyme®), or with 5, 10 or 20 mg/kg ATB200.
Figure 16B:
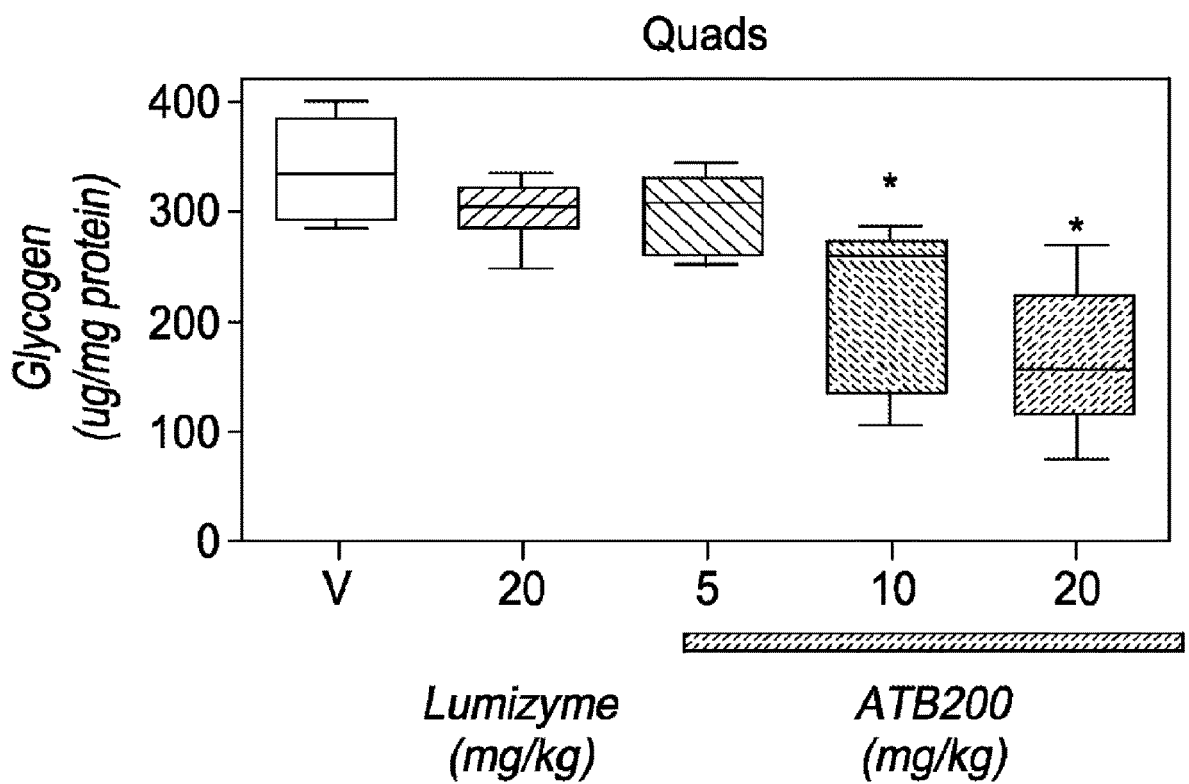
FIG. 16B is a graph showing the amount of glycogen relative to dose of recombinant human acid α-glucosidase in mouse quadriceps muscle after contact with vehicle (negative control), with 20 mg/kg alglucosidase alfa (Lumizyme®), or with 5, 10 or 20 mg/kg ATB200.
Figure 16C:
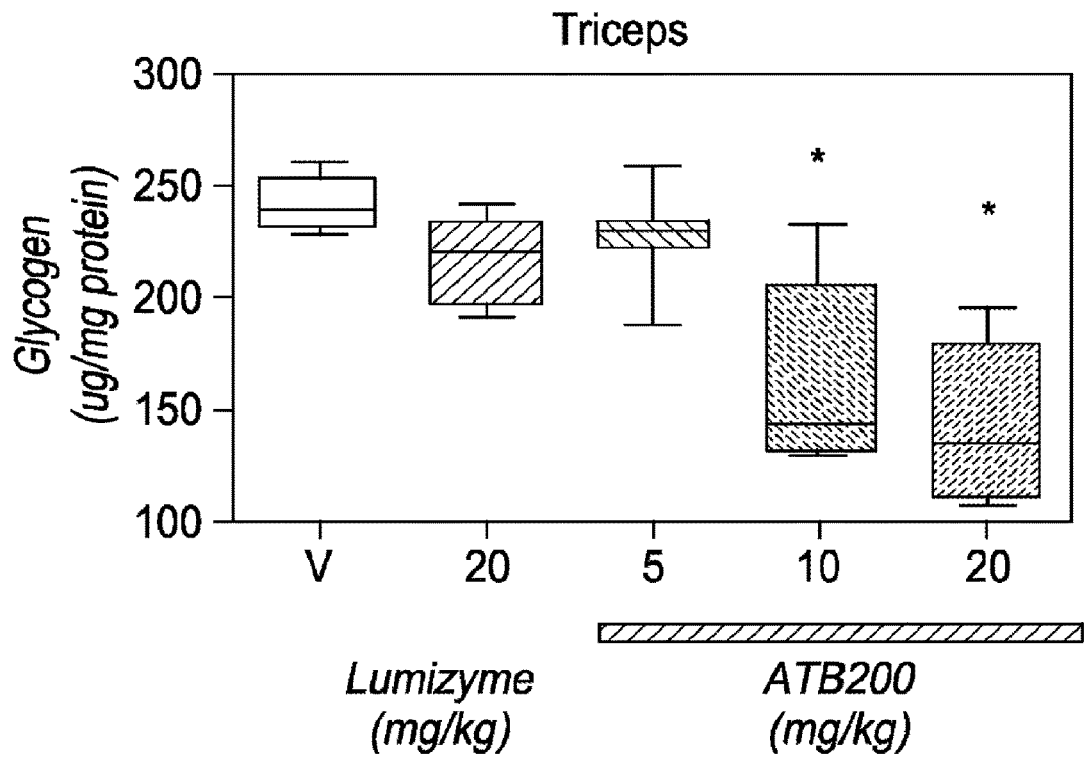
FIG. 16C is a graph showing the amount of glycogen relative to dose of recombinant human acid α-glucosidase in mouse triceps muscle after contact with vehicle (negative control), with 20 mg/kg alglucosidase alfa (Lumizyme®), or with 5, 10 or 20 mg/kg ATB200.

A single 20 mg/kg IV dose of ATB200 in humans over a 4-h infusion is predicted to result in the concentration-time profile presented in FIG. 15. PK parameters in a typical 70-kg human and the resulting exposure parameters following a 20 mg/kg IV infusion of ATB200 over 4 h are presented in Table 4.

TABLE 4

| Pharmacokinetic parameter | Predicted value |
|---|---|
| Systemic clearance (CL; L/h) | 0.768 |
| Central volume of distribution ($V_c$; L) | 1.09 |
| Area under the curve, extrapolated to infinity ($AUC_{0-inf}$; mg · h/L) | 1822 |
| Maximum concentration ($C_{max}$; mg/L) | 423 |
| Time at which maximum concentration is achieved ($T_{max}$; h) | 4 |
| Half-life ($T_{1/2}$; h) | 2.17 |

The predicted systemic clearance (CL) and volume of distribution (V) of ATB200 in a typical 70-kg patient are 0.768 L/h and 2.41 L, respectively.

According to the product label for Lumizyme® (alglucosidase alfa), the systemic clearance of acid α-glucosidase at Week 52 following repeated dosing of Lumizyme® in patients with late-stage Pompe disease is 601 mL/h (0.601 L/h) and the half-life of Lumizyme® is 2.4 h. Based on the above model, the systemic clearance of ATB200 in adult subjects with Pompe disease is expected to be approximately 28% faster than that reported for Lumizyme®. In addition, the predicted AUC in humans following a 20 mg/kg dose of ATB200 is expected to be about 25% lower ($AUC_{0\text{-}inf}$: 1822 mg·h/L) than the AUC reported following a 20 mg/kg dose of Lumizyme® (~2700 µg·h/mL).

Example 10: Exposure-Response Models for Glycogen Reduction

Gaa knockout mice are administered acid α-glucosidase (ATB200) intravenously at doses of 5, 10 and 20 mg/kg, rising oral doses of miglustat (1, 3 and 10 mg/kg) concomitantly with intravenous doses of 5 or 10 mg/kg of ATB200 or rising oral doses of miglustat (1, 3, 5, 10, 20, and 30 mg/kg) concomitantly with intravenous doses of 20 mg/kg of ATB200. Glycogen levels are measured as previously described (Khanna, R, Flanagan, J J, Feng, J, Soska, R, Frascella, M, Pellegrino, L J et al. (2012). "The pharmacological chaperone AT2220 increases recombinant human acid α-glucosidase uptake and glycogen reduction in a mouse model of Pompe disease. PLoS One 7(7): e40776). The ratios of glycogen levels observed after each combination therapy treatment to the glycogen level observed after monotherapy (glycogen ratio) are calculated. Results are provided in Table 5.

In addition, FIGS. 15A to 15C show the effects of administering alglucosidase alfa (Lumizyme®) and ATB200 on glycogen clearance in Gaa knockout mice. Animals are given two IV bolus administrations (every other week); tissues are harvested two weeks after the last dose and analyzed for acid α-glucosidase activity and glycogen content.

As seen from the results in Table 5, ATB200 was found to deplete tissue glycogen in acid α-glucosidase (Gaa) knockout mice in a dose-dependent fashion. The 20 mg/kg dose of ATB200 consistently removed a greater proportion of stored glycogen in Gaa knockout mice than the 5 and 10 mg/kg dose levels. However, as seen in FIGS. 15A to 15C, ATB200 administered at 5 mg/kg showed a similar reduction of glycogen in mouse heart and skeletal muscles (quadriceps and triceps) to Lumizyme® administered at 20 mg/kg, while ATB200 dosed at 10 and 20 mg/kg showed significantly better reduction of glycogen levels in skeletal muscles than Lumizyme®.

Furthermore, 10 and 20 mg/kg doses of miglustat co-administered with ATB200 at 20 mg/kg resulted in reduction of glycogen levels in Gaa knockout mice to 118 and 122 µg/mg protein, respectively. Dosing of miglustat at 30 mg/kg caused less reduction of glycogen. Without being bound by theory, it is believed that at higher concentrations of miglustat, inhibition of acid α-glucosidase in lysosomes may exceed the beneficial chaperone effect, thus reducing degradation of glycogen in the lysosome.

TABLE 5

| Treatments | | Monotherapy | Combination Therapy | | | Ratio |
|---|---|---|---|---|---|---|
| ATB200 (mg/kg) | Miglustat (mg/kg) | Median (N) | Study #1 Median (N) | Study #2 Median (N) | Study #3 Median (N) | (Combination/ Monotherapy) |
| 5 | NA | 307 (N = 7) | NA | NA | 307 (N = 7) | NA |
| 10 | NA | 259 (N = 7) | NA | NA | 259 (N = 7) | NA |
| 20 | NA | 157 (N = 7) | NA | 195 (N = 14) | 181 (N = 21) | NA |
| 5 | 1 | NA | 323 (N = 7) | NA | 323 (N = 7) | 1.05 |
|  | 3 | NA | 359 (N = 6) | NA | 359 (N = 6) | 1.17 |
|  | 10 | NA | 352 (N = 7) | NA | 352 (N = 7) | 1.15 |
| 10 | 1 | NA | 273 (N = 7) | NA | 273 (N = 7) | 1.05 |
|  | 3 | NA | 252 (N = 7) | NA | 252 (N = 7) | 0.973 |
|  | 10 | NA | 278 (N = 7) | NA | 278 (N = 7) | 1.07 |
| 20 | 1 | NA | 154 (N = 7) | NA | 154 (N = 7) | 0.851 |
|  | 3 | NA | 175 (N = 7) | NA | 175 (N = 7) | 0.967 |
|  | 5 | NA | NA | 163 (N = 14) | 163 (N = 14) | 0.900 |
|  | 10 | NA | 97 (N = 6) | 145 (N = 13) | 118 (N = 19) | 0.652 |
|  | 20 | NA | NA | 122 (N = 13) | 122 (N = 13) | 0.674 |
|  | 30 | NA | 167 (N = 6) | 175 (N = 14) | 170 (N = 20) | 0.939 |

Pharmacokinetic models (Example 8) are used to predict exposure to acid α-glucosidase and miglustat, time-matched to the values for tissue lysosomal glycogen levels in Table 5. Steady state exposure (AUC) ratios (average exposure over 24 hours) of miglustat/ATB200 are derived for each treatment combination tested, plotted against the corresponding glycogen ratio (Table 5) and fitted to a mathematical function. The exposure-response curve is shown in FIG. 17.

Figure 17:
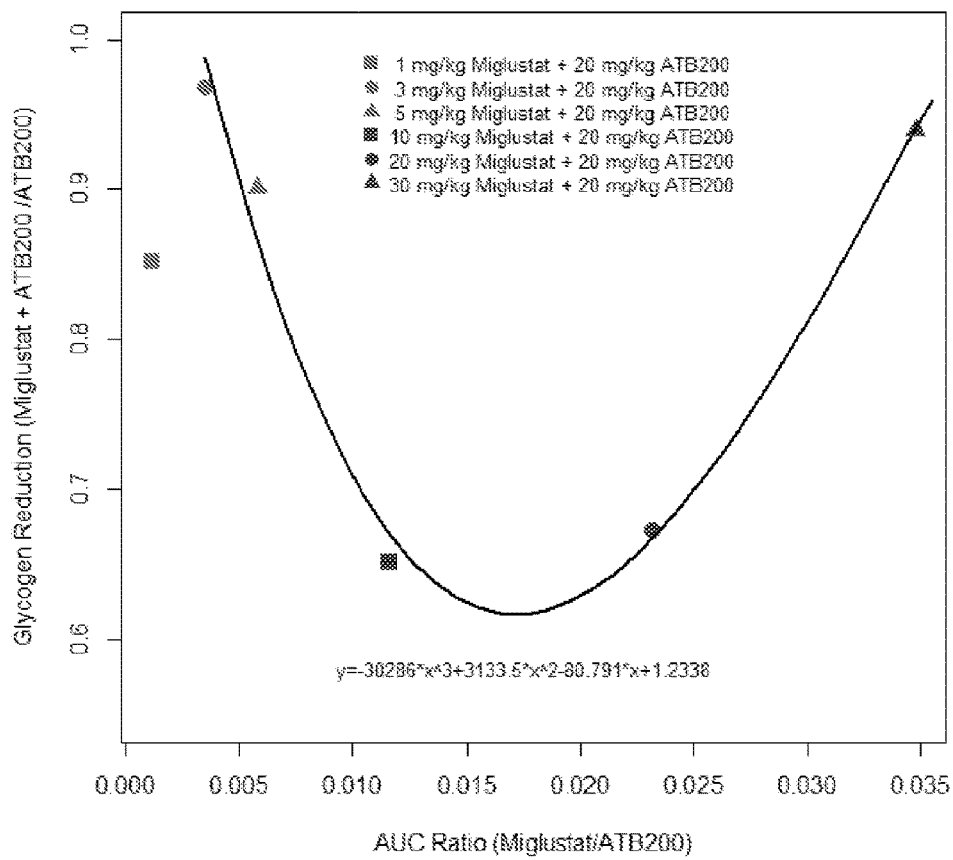
FIG. 17 is a graph plotting the ratio of glycogen levels in mice treated with varying doses of miglustat in the presence of ATB200 to glycogen levels in mice treated with ATB200 alone against the ratio of the AUC value of miglustat to the AUC value of ATB200.

As seen from the results in FIG. 17, co-administration of 10 and 20 mg/kg doses of miglustat with a 20 mg/kg dose of ATB200 provides good stability of acid α-glucosidase activity in plasma, while maximizing glycogen reduction. Lower doses of miglustat (1, 3, and 5 mg/kg) are believed to result in sub-optimal stabilization of acid α-glucosidase activity, whereas the highest dose of miglustat (30 mg/kg) is believed to result in excessive inhibition of α-glucosidase activity within lysosomes.

Based on pharmacokinetic models (Example 8), the observed miglustat/ATB200 AUC ratio of 0.01159 (10 mg/kg miglustat co-administered with 20 mg/kg ATB200) is expected to correspond to a miglustat dose of about 270 mg co-administered with 20 mg/kg ATB200 in a typical 70-kg human. AUC ratios of 0.01 and 0.02 would correspond to miglustat doses of 233 and 466 mg, respectively, co-administered with 20 mg/kg ATB200, in a typical 70-kg subject.

Example 11: Modeling of Miglustat/Duvoglustat Concentrations in Humans

Pharmacokinetic models (Example 8) were used to predict the length of time that the plasma or tissue concentrations of duvoglustat (a surrogate of miglustat) would remain above the $IC_{50}$ (the concentration giving 50% of maximum inhibition of acid α-glucosidase activity) of miglustat in plasma and lysosome. Inhibition of acid α-glucosidase activity is determined by methods described previously (Flanagan J J, Rossi B, Tang K, Wu X, Mascioli K, et al. (2009) "The pharmacological chaperone 1-deoxynojirimycin increases the activity and lysosomal trafficking of multiple mutant forms of acid alpha-glucosidase." Hum Mutat 30: 1683-1692). The $IC_{50}$ value of miglustat at the pH of plasma (pH 7.0) was determined to be 170 μg/L, while the $IC_{50}$ value at the pH of the lysosomal compartment (pH 5.2) was determined to be 377 μg/L.

Results of the model prediction are presented in Table 6. Predicted concentration-time profiles of miglustat in plasma and lysosomes following repeated dosing are shown in FIGS. 17 and 18, respectively.

TABLE 6

| Miglustat Dose | Time > $IC_{50}$ (h) | |
| --- | --- | --- |
| (mg) | Plasma (pH 7.0) | Lysosome (pH 5.2) |
| 100 | 13.1 | 0 |
| 150 | 15.0 | 0 |
| 200 | 16.4 | 1.19 |
| 233 | 17.2 | 2.96 |
| 250 | 17.5 | 3.58 |
| 270 | 17.9 | 4.15 |
| 300 | 18.4 | 4.92 |
| 466 | 20.7 | 8.04 |
| 600 | 22.0 | 9.96 |
| 699 | 22.8 | 11.2 |

Figure 18:
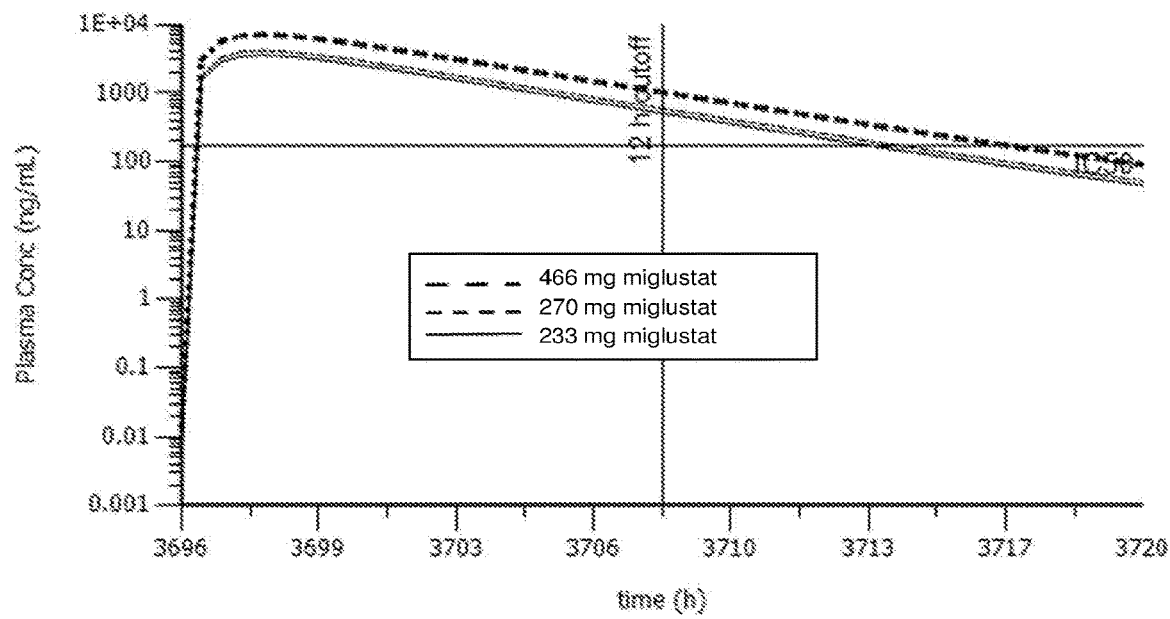
FIG. 18 is a graph showing the predicted concentration-time profile of miglustat in plasma following repeated dosing of doses of 466 mg, 270 mg and 233 mg of miglustat.
Figure 19:
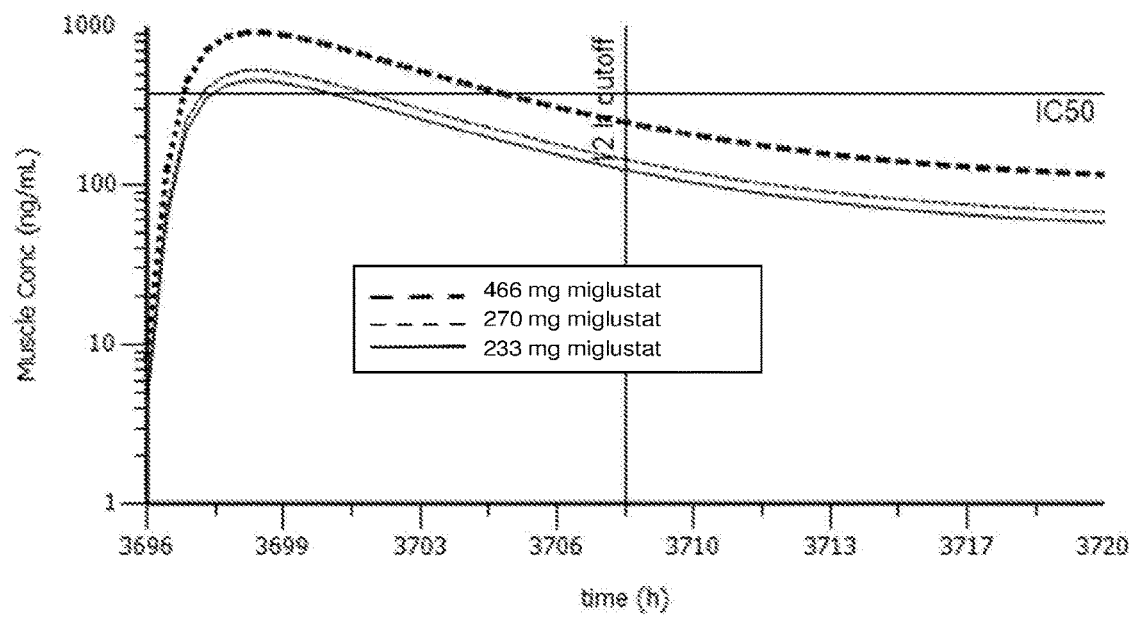
FIG. 19 is a graph showing the predicted concentration-time profile of miglustat in tissue lysosomes following repeated dosing of doses of 466 mg, 270 mg and 233 mg of miglustat.

Based on the results presented in Table 6 and FIGS. 17 and 18, a 260 mg dose of miglustat is expected to bind to and stabilize ATB200 in plasma up to 18 hours whereas inhibition of acid α-glucosidase activity in the lysosome is expected to last only 4 hours.

Example 12: Muscle Physiology and Morphology in Gaa-Knockout Mice

Gaa knockout mice are given two IV bolus administrations of recombinant human acid α-glucosidase (alglucosidase alfa or ATB200) at 20 mg/kg every other week. Miglustat is orally administered at dosages of 10 mg/kg to a subset of animals treated with ATB200 30 mins prior to administration of ATB200. Control mice are treated with vehicle alone. Soleus, quadriceps and diaphragm tissue is harvested two weeks after the last dose of recombinant human acid α-glucosidase. Soleus and diaphragm tissue are analyzed for glycogen levels, by staining with periodic acid—Schiff reagent (PAS), and for lysosome proliferation, by measuring levels of the lysosome-associated membrane protein (LAMP1) marker, which is upregulated in Pompe disease. Semi-thin sections of quadriceps muscle embedded in epoxy resin (Epon) are stained with methylene blue and observed by electron microscopy (1000×) to determine the extent of the presence of vacuoles. Quadriceps muscle samples are analyzed immunohistochemically to determine levels of the autophagy markers microtubule-associated protein 1A/1B-light chain 3 phosphatidylethanolamine conjugate (LC3A II) and p62, the insulin-dependent glucose transporter GLUT4 and the insulin-independent glucose transporter GLUT1.

In a similar study, Gaa knockout mice are given four IV bolus administrations of recombinant human acid α-glucosidase (alglucosidase alfa or ATB200) at 20 mg/kg every other week. Miglustat is orally administered at dosages of 10 mg/kg to a subset of animals treated with ATB200 30 mins prior to administration of ATB200. Control mice are treated with vehicle alone. Cardiac muscle tissue is harvested two weeks after the last dose of recombinant human acid α-glucosidase and analyzed for glycogen levels, by staining with periodic acid—Schiff reagent (PAS), and for lysosome proliferation, by measuring levels of LAMP1.

Figure 20:
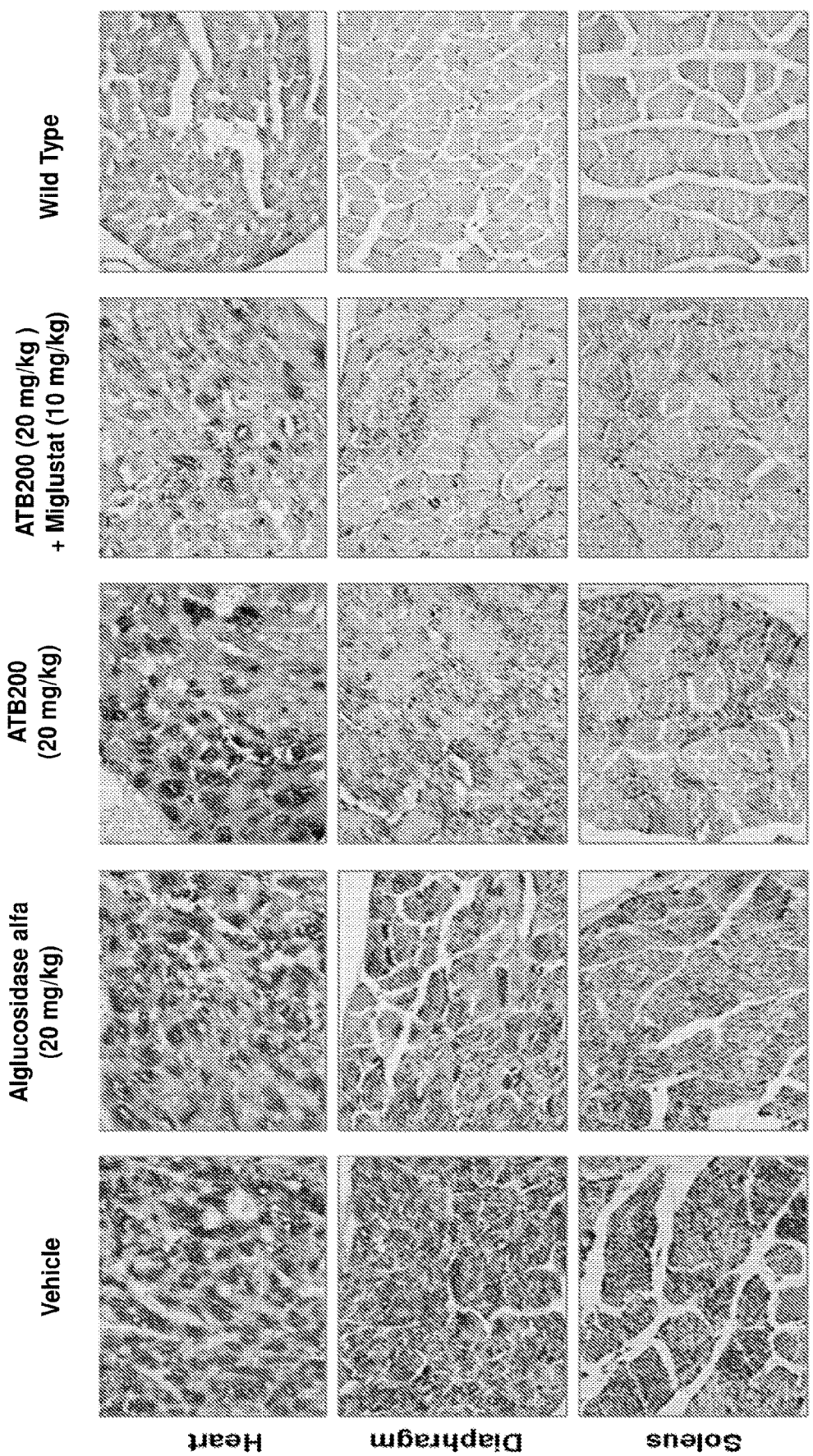
FIG. 20 is a series of photomicrographs of heart, diaphragm and soleus muscle from wild-type and Gaa-knockout mice treated with vehicle, alglucosidase alfa and ATB200 in the presence and absence of miglustat, showing levels of lysosome associated membrane protein (LAMP1)
Figure 21:
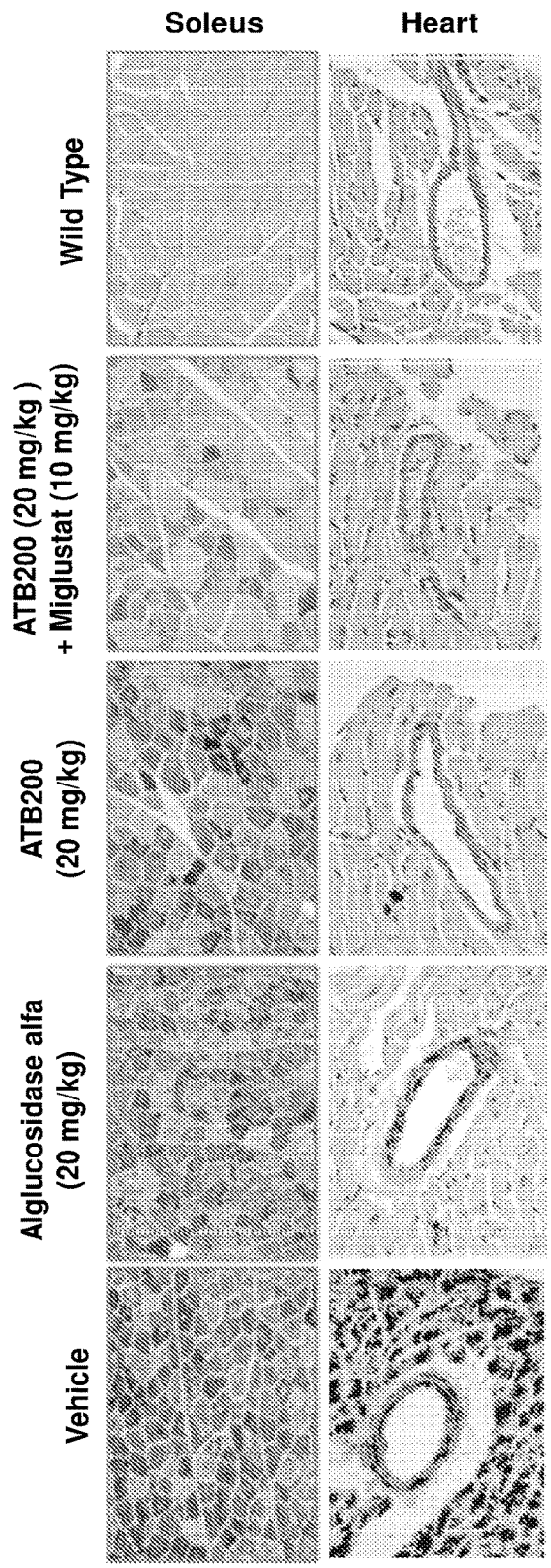
FIG. 21 is a series of photomicrographs of heart and soleus muscle from wild-type and Gaa-knockout mice treated with vehicle, alglucosidase alfa and ATB200 in the presence and absence of miglustat, showing glycogen levels by staining with periodic acid—Schiff reagent (PAS)

As seen in FIG. 20, administration of ATB200 showed a reduction in lysosome proliferation in heart, diaphragm and skeletal muscle (soleus) tissue compared to conventional treatment with alglucosidase alfa, and co-administration of miglustat with ATB200 showed a significant further reduction in lysosomal proliferation, approaching the levels seen in wild type (WT) mice. In addition, as seen in FIG. 21, administration of ATB200 showed a reduction in punctate glycogen levels in heart and skeletal muscle (soleus) tissue compared to conventional treatment with alglucosidase alfa, and co-administration of miglustat with ATB200 showed a significant further reduction, again approaching the levels seen in wild type (WT) mice.

Figure 22:
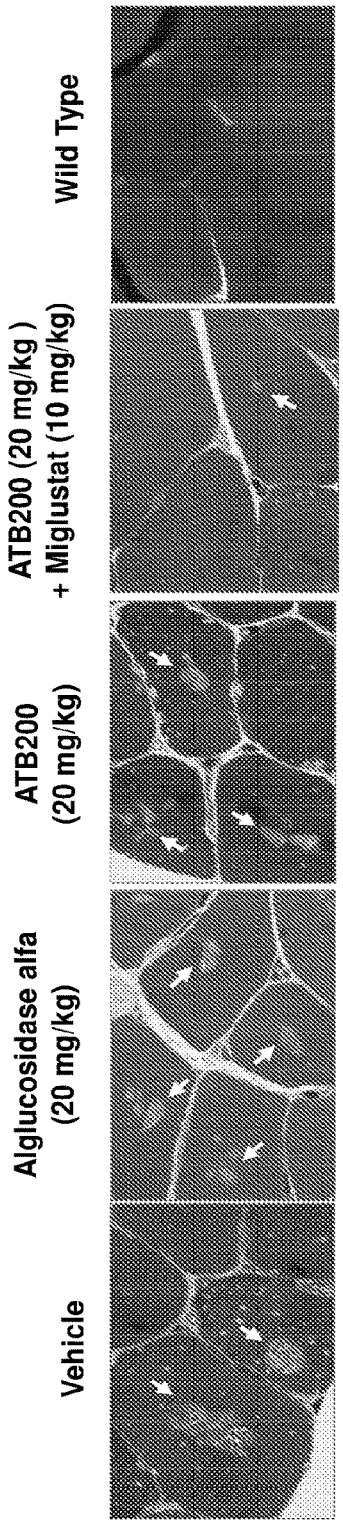
FIG. 22 is a series of photomicrographs (1000×) of quadriceps muscle from wild-type and Gaa-knockout mice treated with vehicle, alglucosidase alfa and ATB200 in the presence and absence of miglustat, stained with methylene blue to show vacuoles (indicated by arrows)
Figure 23:
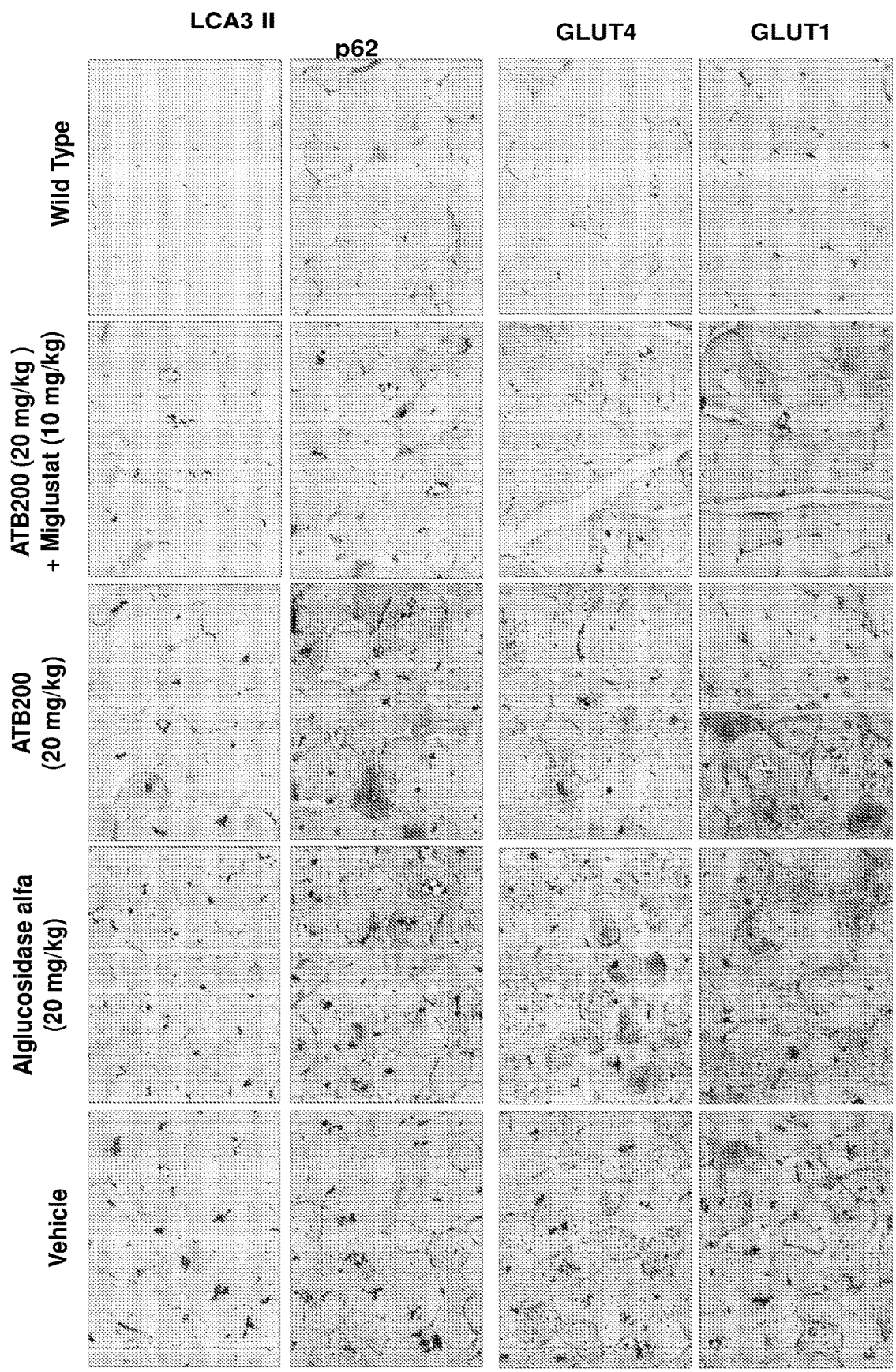
FIG. 23 is a series of photomicrographs (400×) of quadriceps muscle from wild-type and Gaa-knockout mice treated with vehicle, alglucosidase alfa and ATB200 in the presence and absence of miglustat, showing levels of the autophagy markers microtubule-associated protein 1A/1B-light chain 3 phosphatidylethanolamine conjugate (LC3A II) and p62, the insulin-dependent glucose transporter GLUT4 and the insulin-independent glucose transporter GLUT1.

As well, as seen in FIG. 22, co-administration of miglustat with ATB200 significantly reduced the number of vacuoles in muscle fiber in the quadriceps of Gaa knockout mice compared to untreated mice and mice treated with alglucosidase alfa. As seen in FIG. 23, levels of both LC3 II and p62 are increased in Gaa knockout mice compared to wild type mice, but are reduced significantly upon treatment with ATB200 and miglustat, indicating that the increase in autophagy associated with acid α-glucosidase deficiency is reduced upon co-administration of ATB200 and miglustat. In addition, levels of the insulin-dependent glucose transporter GLUT4 and the insulin-independent glucose transporter GLUT1 are increased in Gaa knockout mice compared to wild type mice, but again, are reduced significantly upon treatment with ATB200 and miglustat. The elevated GLUT4 and GLUT1 levels associated with acid α-glucosidase deficiency can contribute to increased glucose uptake into muscle fibers and increased glycogen synthesis both basally and after food intake. Thus, combination treatment with ATB200 and miglustat has been found to improve skeletal muscle morphology and physiology in a mouse model of Pompe disease.

Example 13: Toxicity of ATB200 Co-Administered with Miglustat in Cynomolgus Monkeys Naïve cynomolgus monkeys of Cambodian origin were assigned to dose groups as indicated in Table 7. Animals were acclimated to the study room for 18 (females) to 19 (males) days. On the final day of acclimation, animals weighed between 2.243 kg and 5.413 kg and were 2 to 3 years of age.

TABLE 7

| Group | Test Article | Route | Dose Level (mg/kg) | Dose Conc. (mg/mL) | Number of Animals (Male/Female) | Day 99 Necropsy (Male/Female) |
|---|---|---|---|---|---|---|
| 1 | Control (Formulation Buffer) | IV Infusion | 0 | 0 | 4/4 | 4/4 |
| 2 | Miglustat | NG | 25 | 2.5 | 4/4 | 4/4 |
|   | ATB200 | IV Infusion | 50 | 5 |  |  |
| 3 | Miglustat | NG | 175 | 17.5 | 4/4 | 4/4 |
|   | ATB200 | IV Infusion | 100 | 10 |  |  |
| 4 | Miglustat | NG | 175 | 17.5 | 4/4 | 4/4 |
| 5 | ATB200 | IV Infusion | 100 | 10 | 4/4 | 4/4 |

NG: nasogastric

Test dose levels were selected, based on previous studies in non-human primates, to provide exposures (AUC) comparable to or slightly above (for the 25 mg/kg miglustat and 50 mg/kg ATB200 group) or approximately 10- and 3-fold higher than (for the 175 mg/kg miglustat and/or 100 mg/kg ATB200 groups) the expected clinical AUCs in humans administered a dose of 260 mg miglustat and 20 mg/kg ATB200 as predicted from the pharmacokinetic models of Example 8 (approximately 20.9 hr·μg/mL and approximately 1822 hr·μg/mL, respectively). In previous studies in non-human primates, an IV dose of 100 mg/kg ATB200 was found to result in an AUC of 5330 hr·μg/mL, and an oral dose of 175 mg/kg of miglustat was extrapolated to result in an AUC of 196 hr·μg/mL.

ATB200 is formulated in 25 mM sodium phosphate buffer, pH 6 containing 2.92 mg/mL sodium chloride, 20 mg/mL mannitol, and 0.5 mg/mL polysorbate 80 (formulation buffer). Test article (ATB200 or miglustat) and control article/vehicle (formulation buffer) were administered once every other week for 13 weeks, starting on Day 1 and ending on Day 85. ATB200 and the control article/vehicle were administered by 2 hour (±10 minute) intravenous (IV) infusion at 0 mg/kg (Group 1, control article), 50 mg/kg (Group 2), or 100 mg/kg (Groups 3 and 5). Miglustat was administered nasogastrically in sterile water for injection, USP, at 25 mg/kg (Group 2) or 175 mg/kg (Groups 3 and 4), 30 minutes (±2 minutes) prior to the start of the infusion for ATB200, when given in combination. The dosing volume across all groups was 10 mL/kg.

Parameters assessed during the in-life phase of the study included body weights, food consumption, clinical observations, detailed clinical observations, physical examinations, electrocardiography, ophthalmic assessments, clinical pathology (hematology, coagulation, serum chemistry), anti-drug antibody (ADA) assessment, neutralizing ADA assessment, urinalysis, and plasma toxicokinetics (TK) for miglustat and ATB200 activity and total protein. Terminal necropsy of animals was performed on Day 99 (14 days after the last dose administration). At necropsy, gross observations and organ weights were recorded, and tissues were collected for microscopic examination.

All animals survived to the scheduled euthanasia and there were no changes attributable to administration of ATB200, miglustat or to the co-administration of ATB200 and miglustat during the physical examinations or during assessment of food consumption, clinical observations, detailed clinical observations, body weights, ophthalmology, or ECG parameters. In addition, there was no ATB200, miglustat, or ATB200/miglustat-related changes in the urinalysis, serum chemistry, hematology, or coagulation parameters, or during assessment of gross observations, organ weights, or histopathology.

Total Anti-Drug Antibody (ADA) and Neutralizing Antibody (NAb)

Total anti-drug antibody (ADA) and neutralizing antibody (NAb) levels are measured in plasma. Blood samples (approximately 1.6 mL) were collected in $K_2$EDTA tubes from all animals once during acclimation, predose (prior to administration of miglustat) and on Days 1, 85 and 99. Samples were maintained on wet ice until processed. Plasma was obtained by centrifugation at 2° C. to 8° C. and aliquots (approximately 0.2 mL) were transferred to polypropylene vials, and stored frozen at −60° C. to −86° C. within one hour from blood collection. Analysis of samples for ADA was conducted on samples collected from animals in Groups 1, 2, 3, and 5 (miglustat only samples were not analyzed). Analysis for neutralizing antibodies was conducted using an enzyme assay with the fluorogenic substrate 4-methylumbelliferyl-α-D-glucopyranoside (4MU-Glc).

All animals in the ATB200 dose Groups (Groups 2, 3, and 5) were positive for anti-drug antibody (ADA) on Days 85 and 99 (100% incidence). Titers ranged from 25600 to 409600 on Day 85 and from 51200 to 819200 on Day 99. There was no obvious trend of titers increasing with increasing ATB200 dose level. Five of 8 animals were positive for neutralizing antibody (NAb) in Group 2 (50 mg/kg ATB200 in combination with 25 mg/kg miglustat) on Days 85 and 99.

Two of 8 were positive for NAb on Day 85 in Group 3 (100 mg/kg ATB200 in combination with 175 mg/kg miglustat) and 4 of 8 were positive on Day 99. Two of 8 were positive for NAb on Day 85 in Group 5 (100 mg/kg ATB200 monotherapy) and 3 of 8 were positive on Day 99. There was no obvious effect of ADA on ATB200 exposure or other TK parameters.

ATB200 Toxicokinetics

ATB200 toxicokinetics were measured in blood samples collected in $K_2$EDTA tubes from animals on Days 1 and 85 at the following time points:

For Groups 1, 2, 3, and 5: Predose (prior to administration of miglustat); 1 hour from initiation of infusion; 2 hours from initiation of infusion; 2.5 hours from initiation of infusion; 3 hours from initiation of infusion; 4 hours from initiation of infusion; 6 hours from initiation of infusion; 12 hours from initiation of infusion; 26 hours from initiation of infusion; 168 hours from initiation of infusion; and 336 hours from initiation of infusion (collected prior to dosing on Day 15); and For Group 4: Predose (prior to administration of miglustat); 1.5 hour post administration of miglustat; 2.5 hours post administration of miglustat; 3.5 hours post administration of miglustat; 4.5 hours post administration of miglustat; 6.5 hours post administration of miglustat; 12.5 hours post administration of miglustat; 26.5 hours post administration of miglustat; 168.5 hours post administration of miglustat; and 336.5 hours post administration of miglustat (collected prior to dosing on Day 15).

Plasma was obtained by centrifugation at 2° C. to 8° C. and aliquots (approximately 0.1 mL) were transferred to polypropylene vials, and stored frozen at −60° C. to −86° C. Analysis of ATB200 acid α-glucosidase activity and ATB200 total protein was conducted on the 2-hour postdose samples from Group 1 animals and from all samples collected from animals in Groups 2, 3, and 5. Total ATB200 protein was measured by liquid chromatography coupled to tandem mass spectrometry (LC-MS/MS). Two signature peptides (TTPTFFPK and VTSEGAGLQLQK) were used as a measure of ATB200. The results from these two peptides were consistent, indicating intact ATB200 was present in the analyzed plasma samples. Acid α-glucosidase activity was assayed using the fluorogenic substrate 4-methylumbelliferyl-α-D-glucopyranoside (4MU-Glc).

Analysis of toxicokinetic (TK) data was performed on audited/verified data sets (concentration and time) from animals in Groups 2, 3, and 5 using WinNonlin Phoenix, version 6.1 software (Pharsight Corporation). Noncompartmental analysis of individual subject plasma concentration data was used to estimate the TK parameters for acid α-glucosidase activity and ATB200 total protein (based on the two signature peptides TTPTFFPK and VTSEGAGLQLQK) following IV infusion. The dose level was entered as the actual ATB200 dose in mg, calculated based on each individual animal's dose volume, body weight, and the mean dose concentration. The start time of each dosing (initiation of infusion for ATB200) was set to zero for all profiles in the dosing regimen. Nominal sample collection times were used for all analyses. The area-under-the-plasma-concentration-time-curves ($AUC_{0-t}$) generated for ATB200 (total protein and activity assay datasets) were estimated by the log-linear trapezoidal rule. The regression used to estimate $\lambda_z$ was based on uniformly weighted concentration data.

The following parameters were calculated for each ATB200 data set (generated from the two signature peptides in the total ATB200 assay and from the ATB200 activity assay):

$R^2$—the square of the correlation coefficient for linear regression used to estimate $\lambda_{z\alpha}$. Used when a set number of points are used to define the terminal phase (or specific time range) of the concentration versus time profile;

$R^2$adj—the square of the correlation coefficient for linear regression used to estimate $\lambda_z$, adjusted for the number of points used in the estimation of $\lambda_{z\beta}$. Used when the number of points used to define the terminal phase of the concentration versus time profile may be variable;

No. points $\lambda_z$—number of points for linear regression analysis used to estimate $\lambda_z$;

$\lambda_{z\alpha}$—elimination rate constant for the first three time points after $t_{max}$;

$\lambda_{z\beta}$—terminal elimination rate constant;

$t_{1/2\alpha}$—half-life based on the first three time points after $t_{max}$;

$t_{1/2\beta}$—terminal elimination half-life based on $\lambda_z$ (0.693/$\lambda_z$);

$t_{max}$—time of maximal concentration of analyte in plasma;

$C_{max}$—maximal observed concentration of analyte in plasma;

$AUC_{0-t}$—Area-under-the-plasma-concentration-time-curve (AUC) measured from time 0 (predose) through the time point with the last measurable concentration;

$AUC_{0-\infty}$—AUC extrapolated to time infinity;

$AUC_{ext}$—portion of AUC extrapolated to time infinity presented as % of total $AUC_{0-\infty}$;

$CL_T$—total clearance (based on $\lambda_{z\beta}$); based on total dose in mg from actual body weight;

$CL_T/F$—total clearance (based on $\lambda_{z\beta}$); based on total dose in mg from actual body weight divided by the bioavailable fraction;

$V_{ss}$—apparent volume of distribution at equilibrium;

$V_z$—volume of distribution based on the terminal phase (based on $\lambda_{z\beta}$); based on total dose in mg from actual body weight;

$V_z/F$—volume of distribution based on the terminal phase (based on $\lambda_{z\beta}$); based on total dose in mg from actual body weight divided by the bioavailable fraction; and Accumulation ratios—$AR_{Cmax}$=Ratio of $C_{max}$ on Day 85 to Day 1; $AR_{AUC}$=Ratio of $AUC_{0-t}$ on Day 85 to Day 1

ATB200 concentrations and TK parameters were similar between males and females. Plasma concentrations following a 50 mg/kg 2-hour IV ATB200 infusion in combination with 25 mg/kg miglustat were measurable out to between 12 and 26 hours postdose. At the 100 mg/kg dose level (with or without 175 mg/kg miglustat), ATB200 concentrations were measurable out to 26 to 168 hours postdose. Toxicokinetic parameters for a single dose (Day 1) are shown in Table 8.

TABLE 8

| Group | Treatment | Parameter | Units | Total Protein Assay TTPTFFPK | Total Protein Assay VTSEGAGLQLQK | Activity Assay ATB200 |
|---|---|---|---|---|---|---|
| 2 | 50 mg/kg ATB200 + 25 mg/kg miglustat | $t_{max}$ | hr | 2.00 | 2.00 | 2.06 |
|  |  | $C_{max}$ | μg/mL | 890 | 900 | 495 |
|  |  | $AUC_{0-t}$ | hr · μg/mL | 3060 | 3080 | 1700 |
|  |  | $t_{1/2\alpha}$ | hr | 1.69 | 1.69 | 2.01 |
|  |  | $t_{1/2\beta}$ | hr | 1.70 | 1.71 | 1.92 |
|  |  | $CL_T$ | L/hr | 0.058 | 0.058 | 0.106 |
|  |  | $V_{ss}$ | L | 0.145 | 0.144 | 0.266 |
|  |  | $V_z$ | L | 0.144 | 0.143 | 0.296 |
| 3 | 100 mg/kg ATB200 + 175 mg/kg miglustat | $t_{max}$ | hr | 2.00 | 2.00 | 2.25 |
|  |  | $C_{max}$ | μg/mL | 1960 | 1980 | 1150 |
|  |  | $AUC_{0-t}$ | hr · μg/mL | 10400 | 10400 | 6130 |
|  |  | $t_{1/2\alpha}$ | hr | 2.77 | 2.77 | 3.07 |
|  |  | $t_{1/2\beta}$ | hr | 2.72 | 2.70 | 2.54 |
|  |  | $CL_T$ | L/hr | 0.034 | 0.034 | 0.057 |
|  |  | $V_{ss}$ | L | 0.140 | 0.140 | 0.231 |
|  |  | $V_z$ | L | 0.133 | 0.133 | 0.210 |
| 5 | 100 mg/kg ATB200 Monotherapy | $t_{max}$ | hr | 1.88 | 1.88 | 1.94 |
|  |  | $C_{max}$ | μg/mL | 1690 | 1670 | 1270 |
|  |  | $AUC_{0-t}$ | hr · μg/mL | 5490 | 5410 | 3230 |
|  |  | $t_{1/2\alpha}$ | hr | 1.56 | 1.55 | 1.28 |
|  |  | $t_{1/2\beta}$ | hr | 11.1 | 6.29 | 1.71 |
|  |  | $CL_T$ | L/hr | 0.105 | 0.105 | 0.140 |
|  |  | $V_{ss}$ | L | 0.171 | 0.149 | 0.168 |
|  |  | $V_z$ | L | 0.729 | 0.401 | 0.383 |

Toxicokinetic parameters for repeat dosing (Day 85) are shown in Table 9.

TABLE 9

| Group | Treatment | Parameter | Units | Total Protein Assay TTPTFFPK | Total Protein Assay VTSEGAGLQLQK | Activity Assay ATB200 |
|---|---|---|---|---|---|---|
| 2 | 50 mg/kg ATB200 + 25 mg/kg miglustat | $t_{max}$ | hr | 2.00 | 2.00 | 2.13 |
|  |  | $C_{max}$ | μg/mL | 927 | 921 | 586 |
|  |  | $AUC_{0-t}$ | hr · μg/mL | 3700 | 3700 | 2390 |
|  |  | $t_{1/2\alpha}$ | hr | 1.98 | 1.95 | 2.35 |
|  |  | $t_{1/2\beta}$ | hr | 2.38 | 2.40 | 2.31 |
|  |  | $CL_T$ | L/hr | 0.049 | 0.049 | 0.076 |
|  |  | $V_{ss}$ | L | 0.147 | 0.147 | 0.223 |
|  |  | $V_z$ | L | 0.168 | 0.168 | 0.254 |
| 3 | 100 mg/kg ATB200 + 175 mg/kg miglustat | $t_{max}$ | hr | 2.13 | 2.19 | 2.06 |
|  |  | $C_{max}$ | μg/mL | 2270 | 2270 | 1600 |
|  |  | $AUC_{0-t}$ | hr · μg/mL | 13900 | 13800 | 9240 |
|  |  | $t_{1/2\alpha}$ | hr | 3.62 | 3.72 | 3.34 |
|  |  | $t_{1/2\beta}$ | hr | 4.83 | 4.83 | 2.90 |
|  |  | $CL_T$ | L/hr | 0.027 | 0.027 | 0.040 |
|  |  | $V_{ss}$ | L | 0.140 | 0.140 | 0.186 |
|  |  | $V_z$ | L | 0.174 | 0.174 | 0.165 |
| 5 | 100 mg/kg ATB200 Monotherapy | $t_{max}$ | hr | 2.13 | 2.13 | 2.00 |
|  |  | $C_{max}$ | μg/mL | 2020 | 2010 | 1510 |
|  |  | $AUC_{0-t}$ | hr · μg/mL | 7830 | 7790 | 4890 |
|  |  | $t_{1/2\alpha}$ | hr | 1.93 | 1.88 | 1.44 |
|  |  | $t_{1/2\beta}$ | hr | 6.62 | 2.63 | 2.03 |
|  |  | $CL_T$ | L/hr | 0.045 | 0.045 | 0.070 |
|  |  | $V_{ss}$ | L | 0.143 | 0.127 | 0.159 |
|  |  | $V_z$ | L | 0.396 | 0.170 | 0.205 |

The time to maximal ATB200 plasma concentration ($t_{max}$) was approximately 2 hours postdose in all three dose groups. The Day 1 and Day 85 ATB200 plasma concentrations and TK parameters, as measured by the total ATB200 protein assay, were consistent between the two evaluated signature peptides, TTPTFFPK and VTSEGAGLQLQK. Exposure, as measured by $C_{max}$ and $AUC_{0-t}$, was relatively lower when measured by the acid α-glucosidase activity assay. This is to be expected, as the total protein assay measures concentration of both active and inactive enzyme while the acid α-glucosidase activity assay measures concentration of active enzyme only. ATB200 exposure increased with dose between the 50 and 100 mg/kg dose levels. The mean Day 1 initial $t_{1/2\alpha}$ (males and females combined) based on the first three time points past $t_{max}$ ranged from 1.28 to 3.07 hours. The mean Day 1 terminal half-life ($t_{1/2\beta}$) ranged from 1.70 to 11.1 hours (the longer $t_{1/2\beta}$ values were influenced by the animals that had measurable concentrations out to 168 hours postdose). A similar range of values was observed after the Day 85 dose. Little to no accumulation was observed with repeated administration, once every other week. The addition of 175 mg/kg miglustat to the 100 mg/kg ATB200 dose appeared to decrease ATB200 clearance and increase plasma exposure approximately 2-fold, relative to 100 mg/kg ATB200 monotherapy. As no adverse test article-related changes were identified, the No-Observed-Adverse-Effect-Level (NOAEL) for ATB200 in cynomolgus monkeys when given once every other week for 13 weeks by 2 hour infusion, with or without administration with miglustat, was 100 mg/kg/infusion, the highest dosage tested. At this dose level, the mean gender-averaged $AUC_{0-t}$ and $C_{max}$ (total protein) on Day 85 were 7830 (TTPTFFPK) and 7790 (VTSEGAGLQLQK) hr·µg/mL and 2020 (TTPTFFPK) or 2010 (VTSEGAGLQLQK) µg/mL, respectively, for ATB200 alone and 13900 (TTPTFFPK) or 13800 (VTSEGAGLQLQK) hr·µg/mL and 2270 (both peptides) µg/mL, respectively, in combination with 175 mg/kg Miglustat.

Miglustat Toxicokinetics

Miglustat toxicokinetics were measured in blood samples collected in $K_2EDTA$ tubes from animals on Days 1 and 85 at the following time points:

For Groups 1, 2, 3, and 5: Predose (prior to administration of miglustat); 15 minutes after administration of miglustat; 0 hour (prior to initiation of infusion); 0.5 hours from initiation of infusion; 1 hour from initiation of infusion; 2 hours from initiation of infusion; 4 hours from initiation of infusion; 6 hours from initiation of infusion; 12 hours from initiation of infusion; 26 hours from initiation of infusion; 50 hours from initiation of infusion; and 74 hours from initiation of infusion; and For Group 4: Predose (prior to administration of miglustat); 15 minutes post administration of miglustat; 30 minutes post administration of miglustat; 1 hour post administration of miglustat; 1.5 hours post administration of miglustat; 2.5 hours post administration of miglustat; 4.5 hours post administration of miglustat; 6.5 hours post administration of miglustat; 12.5 hours post administration of miglustat; 26.5 hours post administration of miglustat; 50.5 hours post administration of miglustat; and 74.5 hours post administration of miglustat.

Plasma was obtained by centrifugation at 2° C. to 8° C. and aliquots (approximately 0.2 mL) were transferred to polypropylene vials, and stored frozen at −60° C. to −86° C. Analysis of miglustat concentration was carried out using a LC-MS/MS method analogous to that described for analysis of duvoglustat concentration by Richie Khanna, Allan C. Powe Jr., Yi Lun, Rebecca Soska, Jessie Feng, Rohini Dhulipala, Michelle Frascella, Anadina Garcia, Lee J. Pellegrino, Su Xu, Nastry Brignol, Matthew J. Toth, Hung V. Do, David J. Lockhart, Brandon A. Wustman, Kenneth J. Valenzano. "The Pharmacological Chaperone AT2220 Increases the Specific Activity and Lysosomal Delivery of Mutant Acid Alpha-Glucosidase, and Promotes Glycogen Reduction in Transgenic Mouse Model of Pompe Disease." PLOS ONE (1 Jul. 2014) 9(7): e102092. Analysis of toxicokinetic (TK) data for miglustat was performed on audited/verified data sets (concentration and time) from animals in Group 2, 3, and 4 using WinNonlin Phoenix®, version 6.1 software (Pharsight Corporation). Noncompartmental analysis of individual plasma concentration data was used to estimate the TK parameters. Miglustat TK parameters were estimated by the log-linear trapezoidal rule. The regression used to estimate $\lambda_z$ was based on uniformly weighted concentration data. The following parameters were calculated:

$R^2$adj—the square of the correlation coefficient for linear regression used to estimate $\lambda_z$, adjusted for the number of points used in the estimation of $\lambda_z$. Used when the number of points used to define the terminal phase of the concentration versus time profile may be variable;

No. points $\lambda_z$—number of points for linear regression analysis used to estimate $\lambda_z$;

$\lambda_z$—the terminal elimination rate constant;

$t_{1/2}$—terminal elimination half-life based on $\lambda_z$ $(0.693/\lambda_z)$;

$t_{max}$—time of maximal concentration of analyte in plasma;

$C_{max}$—maximal observed concentration of analyte in plasma;

$AUC_{0-t}$—Area-under-the-plasma-concentration-time-curve (AUC) measured from time 0 (predose) through the time point with the last measurable concentration;

$AUC_{0-\infty}$—AUC extrapolated to time infinity;

$AUC_{ext}$—portion of AUC extrapolated to time infinity presented as % of total $AUC_{0-\infty}$;

$CL_T/F$—total clearance divided by the bioavailable fraction based on total dose in mg from actual body weight;

$V_z/F$—volume of distribution based on the terminal phase divided by the bioavailable fraction based on total dose in mg from actual body weight;

Accumulation ratios—$AR_{Cmax}$=Ratio of $C_{max}$ on Day 85 to Day 1; and $AR_{AUC}$=Ratio of $AUC_{0-t}$ on Day 85 to Day 1.

There was no consistent effect of sex on miglustat TK parameters. Miglustat plasma concentrations following either a 25 mg/kg nasogastric (NG) administration in combination with 50 mg/kg ATB200, or a 175 mg/kg NG administration (with or without 100 mg/kg ATB200), were measurable to 74.5 hours (the last measured time point). Toxicokinetic parameters for a single dose (Day 1) and for repeat dosing (Day 85) are shown in Table 10.

TABLE 10

| | | | | Miglustat Assay | |
|---|---|---|---|---|---|
| Group | Treatment | Parameter | Units | Day 1 | Day 85 |
| 2 | 50 mg/kg ATB200 + 25 mg/kg miglustat | $t_{max}$ | hr | 2.06 | 2.88 |
| | | $C_{max}$ | ng/mL | 7430 | 7510 |
| | | $AUC_{0-t}$ | hr · ng/mL | 47300 | 49100 |
| | | $t_{1/2}$ | hr | 7.44 | 8.23 |
| | | $CL_T/F$ | L/hr | 1.92 | 1.99 |
| | | $V_z/F$ | L | 20.5 | 23.3 |
| 3 | 100 mg/kg ATB200 + 175 mg/kg miglustat | $t_{max}$ | hr | 2.69 | 3.56 |
| | | $C_{max}$ | ng/mL | 20400 | 22000 |
| | | $AUC_{0-t}$ | hr · ng/mL | 182000 | 216000 |
| | | $t_{1/2}$ | hr | 6.85 | 7.86 |
| | | $CL_T/F$ | L/hr | 3.22 | 3.62 |
| | | $V_z/F$ | L | 32.3 | 39.1 |
| 4 | 175 mg/kg Miglustat Monotherapy | $t_{max}$ | hr | 3.00 | 4.13 |
| | | $C_{max}$ | ng/mL | 16400 | 14700 |
| | | $AUC_{0-t}$ | hr · ng/mL | 173000 | 204000 |
| | | $t_{1/2}$ | hr | 6.86 | 6.66 |
| | | $CL_T/F$ | L/hr | 3.67 | 3.49 |
| | | $V_z/F$ | L | 35.9 | 33.8 |

The $t_{max}$ ranged from approximately 2 to 4 hours postdose. Miglustat exposure increased with dose between the 25 and 175 mg/kg dose levels. The mean $t_{1/2}$ (males and females combined) was consistent on Days 1 and 85 and ranged from 6.66 to 8.23 hours. Little to no accumulation was observed with repeat once every other week NG administration. There was no observable effect of ATB200 co-administration on overall miglustat exposure (i.e., $AUC_{0-t}$) or TK parameters.

As no adverse test article-related changes were identified, the No-Observed-Adverse-Effect-Level (NOAEL) for miglustat in cynomolgus monkeys when given once every other week for 13 weeks nasogastrically, with or without administration with ATB200, was 175 mg/kg/dose, the highest dosage tested. At this dose level, the mean gender-averaged $AUC_{0-t}$ and $C_{max}$ on Day 85 were 204000 hr·ng/mL and 14700 ng/mL, respectively, for miglustat alone and 216000 hr·ng/mL and 22000 ng/mL, respectively, in combination with 100 mg/kg ATB200.

Example 14: Protocol for Clinical Study of Recombinant Acid α-glucosidase (ATB200) Administered Alone and Co-Administered with Miglustat Study Design:

This is an open-label, fixed-sequence, ascending-dose, first-in-human study to evaluate the safety, tolerability, and pharmacokinetics (PK) of intravenous (IV) recombinant acid α-glucosidase (ATB200, lyophilized powder reconstituted with sterile water for injection and diluted with 0.9% sodium chloride for injection) alone and when co-administered with oral miglustat (hard gelatin capsules, 65 mg). The study will be conducted in 2 stages. In Stage 1, safety, tolerability, and PK will be evaluated following sequential single ascending doses of ATB200, administered every 2 weeks as an approximately 4 hour intravenous infusion, for 3 dosing periods at 5, 10, and 20 mg/kg. In Stage 2, safety, tolerability, and PK will be evaluated following single- and multiple-ascending dose combinations: 20 mg/kg ATB200 co-administered every 2 weeks with 130 mg miglustat (two 65 mg capsules), taken orally 1 hour prior to an approximately 4 hour intravenous infusion of ATB200, for 3 doses followed by 20 mg/kg ATB200 co-administered with 260 mg miglustat (four 65 mg capsules), taken orally 1 hour prior to an approximately 4 hour intravenous infusion of ATB200, for 3 doses.

Twelve enzyme replacement therapy (ERT)-experienced subjects with Pompe disease (approximately 6 ambulatory and 6 nonambulatory) will enroll into Stage 1. Those same subjects will continue the study in Stage 2. At least 4 ambulatory subjects will be enrolled and dosed before nonambulatory subjects are enrolled. ERT-experienced (ambulatory) subjects are defined as those who have been on ERT for 2 to 6 years prior to enrollment, who are able to walk at least 200 meters in the six-minute walk test (6MWT), and have an FVC of 30-80% of predicted normal value. ERT-experienced (nonambulatory) subjects are defined as those who are completely wheelchair bound, unable to walk unassisted, and have been on ERT for ≥2 years prior to enrollment. Treatment assignment is shown in Table 11.

TABLE 11

| Number of Subjects | Population: ERT Experienced | Stage 1 | | | Stage 2 | |
|---|---|---|---|---|---|---|
| | | Period 1 Single Dose | Period 2 Single Dose | Period 3 Single Dose | Period 4 Multiple Dose Co-administration | Period 5 Multiple Dose Co-administration |
| 12 | ~6 ambulatory, ~6 nonambulatory | 5 mg/kg ATB200 | 10 mg/kg ATB200 | 20 mg/kg ATB200 | 20 mg/kg ATB200 + 130 mg miglustat | 20 mg/kg ATB200 + 260 mg miglustat |

ERT = enzyme replacement therapy.

Subjects will be required to fast at least 2 hours before and 2 hours after administration of oral miglustat. IV infusion of ATB200 should start 1 hour after oral administration of miglustat.

Study Procedures

The study consists of Screening, Baseline, Stage 1 (3-period, fixed-sequence, single-ascending-dose of ATB200 alone), and Stage 2 (2-period, fixed-sequence, multiple-dose of 20 mg/kg ATB200 co-administered with multiple-ascending-doses of miglustat).

Screening:

All subjects will provide informed consent and undergo review of eligibility criteria. Assessments for all subjects include medical history including prior infusion-associated reactions (IARs) and history of falls; review of prior and concomitant medications and nondrug therapies; vital signs (heart rate [HR], respiration rate [RR], blood pressure [BP], and temperature); height; weight; comprehensive physical examination (PE); 12-lead electrocardiogram (ECG); clinical safety laboratory assessments (serum chemistry, hematology, and urinalysis); urine pregnancy test; urine sample for hexose tetrasaccharide (Hex4); and GAA genotyping (for subjects unable to provide GAA genotyping report at screening). A blood sample will also be obtained for exploratory assessment of immunogenicity (total and neutralizing antibodies, exploratory cytokines/other biomarkers of immune system activation, cross reactivity to alglucosidase alfa, and immunoglobulin E [IgE]) if needed. A subject who meets all of the inclusion criteria and none of the exclusion criteria will be assigned to Stage 1 as described in Table 11.

Baseline:

Safety assessments for all subjects include review of eligibility criteria; medical history including infusion associated reactions (IARs) and history of falls, adverse event (AE) and serious AE (SAE) inquiry, review of prior and concomitant medications and nondrug therapies; vital signs (HR, RR, BP, and temperature); weight; brief PE; ECG; Rasch-built Pompe-specific activity (R-PAct) scale; Rotterdam Handicap Scale; and Fatigue Severity Scale; clinical safety laboratory assessments (serum chemistry, hematology, and urinalysis); urine pregnancy test; pharmacodynamic (PD) assessments (Hex4 and creatinine phosphokinase [CPK]); immunogenicity assessments (total and neutralizing antibodies, antibody cross-reactivity with alglucosidase alfa, exploratory cytokines and other biomarkers of immune system activation, cross reactivity to alglucosidase alfa, and IgE if needed); pulmonary function tests (PFTs); motor function tests; and muscle strength tests for all subjects.

Stage 1, Periods 1, 2, and 3:
This stage will include:
Safety: review of AEs, including serious adverse events (SAEs) and IARs; review of concomitant medications and nondrug therapies; vital signs (HR, RR, BP, and temperature); brief PE; ECG; clinical safety laboratory assessments (serum chemistry, hematology, and urinalysis); and urine pregnancy test
PD: urinary Hex4 and serum CPK
Immunological: blood samples for anti-recombinant acid α-glucosidase antibody titers (anti-recombinant acid α-glucosidase total and neutralizing antibody titers and antibody cross-reactivity with alglucosidase alfa) and blood samples for measurement of pro-inflammatory cytokines and other biomarkers of immune system activation. If needed, IgE measurements will also be performed.
Serial 24-hour pharmacokinetics (PK): During Period 1 (Visit 3, Day 1), Period 2 (Visit 4, Day 15), and Period 3 (Visit 5, Day 29), blood sampling for plasma acid α-glucosidase activity levels and total acid α-glucosidase protein concentrations will be taken for all subjects.

Stage 2, Periods 4 and 5:
Safety: review of AEs, including SAEs and IARs; review of concomitant medications and nondrug therapies; vital signs (HR, RR, BP, and temperature); weight; PE; ECG; clinical safety laboratory assessments (serum chemistry, hematology, and urinalysis); and urine pregnancy test
PD: urinary Hex4 and serum CPK
Immunological: blood samples for anti-recombinant acid α-glucosidase antibody titers (anti-recombinant acid α-glucosidase total and neutralizing antibody titers, and antibody cross-reactivity with alglucosidase alfa) and blood samples for measurement of pro-inflammatory cytokines and other biomarkers of immune system activation. If needed, IgE measurements will also be performed.
Serial 24-hour PK: During Period 4 (Visit 6, Day 43 and Visit 8, Day 71) and Period 5 (Visit 9, Day 85 and Visit 11, Day 113), blood sampling for plasma acid α-glucosidase activity levels, total acid α-glucosidase protein concentrations, and miglustat concentrations will be taken for all subjects.

End of Pharmacokinetic Phase:
Safety: review of AEs, including SAEs and IARs; review of concomitant medications and nondrug therapies; vital signs (HR, RR, BP, and temperature); weight; PE; ECG; clinical safety laboratory assessments (serum chemistry, hematology, and urinalysis); and urine pregnancy test
PD: urinary Hex4 and serum CPK
Immunological: blood samples for anti-recombinant acid α-glucosidase antibody titers (anti-recombinant acid α-glucosidase total and neutralizing antibody titers, and antibody cross-reactivity with alglucosidase alfa) and blood samples for measurement of pro-inflammatory cytokines and other biomarkers of immune system activation. If needed, IgE measurements will also be performed.

Subjects who prematurely withdraw from the study will come in for an Early Termination visit and will undergo all of the assessments that are to be performed at the End of PK visit. No study drug will be administered. If any of the sentinel subjects withdraw prematurely from the study, that subject will be replaced by the next ambulatory subject enrolled in the study (e.g., if Subject 1 withdraws, Subject 3 [ambulatory] will replace that subject as a sentinel subject).

Subjects who complete this study and/or other subjects who qualify will be offered the opportunity to participate in a long-term extension study and will continue to be assessed for safety and tolerability of ATB200 co-administered with miglustat. In addition, functional assessments relevant to Pompe disease will be performed in the extension study at regular intervals.

Safety Monitoring
Safety will be monitored by the Medical Monitor and the investigators on an ongoing basis, and on a regular basis by a Safety Steering Committee (SSC).

Sentinel Dosing
The first 2 ambulatory subjects in this study will be the sentinel subjects for the study and will be the first 2 subjects dosed in each period of the study (Periods 1 to 5). In the event that a sentinel subject prematurely withdraws from the study, he/she will be replaced by another ambulatory subject. Note: At least 4 ambulatory subjects will be dosed with 5 mg/kg ATB200 before any nonambulatory subjects can be dosed.

In Stage 1 (Periods 1, 2, and 3), subjects will be dosed with single ascending doses of ATB200 (5 mg/kg [Period 1], 10 mg/kg [Period 2], and 20 mg/kg [Period 3]).

Following the dosing of the 2 sentinel subjects for each study period in Stage 1, an evaluation of the available safety data (PE, vital signs, AEs, infusion reactions, ECG, and available locally performed laboratory tests) will be performed within 24 to 48 hours by the Medical Monitor and the investigators. The SSC will convene for a formal safety review when central safety laboratory data are available for both sentinel subjects at each dose level. If there SSC determines that there are no safety concerns that preclude dosing at the dose assigned for that period, 10 additional subjects will be enrolled and dosed. The SSC will also convene for a safety review when safety data (including central laboratory safety data) for all subjects at all 3 Stage-1 dose levels are available.

In Stage 2 (Periods 4 and 5), the 2 sentinel subjects will be dosed, and safety will be assessed after the first dose as for each period in Stage 1. If the SSC determines that there are no safety concerns that preclude additional dosing at 20 mg/kg ATB200 co-administered with 130 mg miglustat (Period 4) or 20 mg/kg ATB200 co-administered with 260 mg miglustat (Period 5), 10 additional subjects will receive 3 biweekly doses at the dose assigned for that period. The SSC will reconvene when all safety data (including central safety laboratory data) are available for all subjects at the end of Stage 2. The SSC will also convene ad hoc in case of an SAE or an identified safety concern.

The SSC may recommend any of the following reviews:
Continue the study without modifications
Continue the study with modifications (amendment)
Temporarily halt dosing
Permanently stop dosing If in the opinion of the SSC there are no AEs or safety concerns in the sentinel subjects that might preclude continued study dosing, dosing will continue for all remaining subjects at that dose level. Subject safety will continue to be closely monitored by the Medical Monitor and study investigators on an ongoing basis, and at regular intervals by the SSC.

Number of Subjects (Planned):

Twelve adult ERT-experienced subjects with Pompe disease (approximately 6 ambulatory and 6 nonambulatory) will enroll into Stage 1. Those same subjects will continue the study in Stage 2.

Diagnosis and Eligibility Criteria:

At the Screening Visit, adult ERT-experienced subjects with Pompe disease will be evaluated using the eligibility criteria outlined below. Each subject must meet all of the inclusion criteria and none of the exclusion criteria. Waivers of inclusion/exclusion criteria are not permitted.

Inclusion Criteria

ERT-Experienced Subjects (Ambulatory)
1. Male and female subjects between 18 and 65 years of age, inclusive;
2. Subject must provide signed informed consent prior to any study-related procedures;
3. Subjects of childbearing potential must agree to use medically accepted methods of contraception during the study and for 30 days after last co-administration of ATB200+miglustat;
4. Subject has a diagnosis of Pompe disease based on documented deficiency of acid α-glucosidase enzyme activity or by GAA genotyping;
5. Subject has received ERT with alglucosidase alfa for the previous 2-6 years;
6. Subject is currently receiving alglucosidase alfa at a frequency of once every other week;
7. Subject has received and completed the last two infusions without a drug-related adverse event resulting in dose interruption;
8. Subject must be able to walk 200-500 meters on the 6MWT; and
9. Upright forced vital capacity (FVC) must be 30% to 80% of predicted normal value.

ERT-Experienced Subjects (Nonambulatory)
10. Male and female subjects between 18 and 65 years of age, inclusive;
11. Subject must provide signed informed consent prior to any study-related procedures;
12. Subjects of childbearing potential must agree to use medically accepted methods of contraception during the study and for 30 days after last co-administration of ATB200+miglustat;
13. Subject has a diagnosis of Pompe disease based on documented deficiency of acid α-glucosidase enzyme activity or by GAA genotyping;
14. Subject has received ERT with alglucosidase alfa for ≥2 years;
15. Subject is currently receiving alglucosidase alfa at a frequency of once every other week;
16. Subject has received and completed the last two infusions without a drug-related adverse event resulting in dose interruption; and
17. Subject must be completely wheelchair-bound and unable to walk unassisted.

Exclusion Criteria

ERT-Experienced Subjects (Ambulatory)
1. Subject has received any investigational therapy for Pompe disease, other than alglucosidase alfa within 30 days prior to the Baseline Visit, or anticipates doing so during the study;
2. Subject has received treatment with prohibited medications (miglitol (eg, Glyset®); miglustat (eg, Zavesca®); acarbose (eg, Precose®, Glucobay®); voglibose (eg, Volix®, Vocarb®, and Volibo®); albuterol and clenbuterol; or any investigational/experimental drug) within 30 days of the Baseline Visit;
3. Subject, if female, is pregnant or breastfeeding at screening;
4. Subject, whether male or female, is planning to conceive a child during the study;
5. Subject requires invasive ventilatory support;
6. Subject uses noninvasive ventilatory support ≥6 hours a day while awake;
7. Subject has a medical or any other extenuating condition or circumstance that may, in the opinion of the investigator, pose an undue safety risk to the subject or compromise his/her ability to comply with protocol requirements;
8. Subject has a history of anaphylaxis to alglucosidase alfa;
9. Subject has a history of high sustained anti-recombinant acid α-glucosidase antibody titers;
10. Subject has a history of allergy or sensitivity to miglustat or other iminosugars;
11. Subject has a known history of autoimmune disease including lupus, autoimmune thyroiditis, scleroderma, or rheumatoid arthritis; and
12. Subject has a known history of bronchial asthma.

ERT-Experienced Subjects (Nonambulatory)
13. Subject has received any investigational therapy for Pompe disease, other than alglucosidase alfa within 30 days prior to the Baseline Visit, or anticipates to do so during the study;
14. Subject has received treatment with prohibited medications (miglitol (eg, Glyset®); miglustat (eg, Zavesca®); acarbose (eg, Precose®, Glucobay®); voglibose (eg, Volix®, Vocarb®, and Volibo®); albuterol and clenbuterol; or any investigational/experimental drug) within 30 days of the Baseline Visit;
15. Subject, if female, is pregnant or breastfeeding at screening;
16. Subject, whether male or female, is planning to conceive a child during the study;
17. Subject has a medical or any other extenuating condition or circumstance that may, in the opinion of the investigator, pose an undue safety risk to the subject or compromise his/her ability to comply with protocol requirements;
18. Subject has a history of anaphylaxis to alglucosidase alfa;
19. Subject has a history of high sustained anti-recombinant acid α-glucosidase antibody titers;
20. Subject has a history of allergy or sensitivity to miglustat or other iminosugars;
21. Subject has a known history of autoimmune disease including lupus, autoimmune thyroiditis, scleroderma, or rheumatoid arthritis; and
22. Subject has a known history of bronchial asthma.

Investigational Product, Dosage, and Mode of Administration:

Stage 1 (Consists of 3 Dosing Periods 2 Weeks Apart)
  Period 1: a single-dose IV infusion of 5 mg/kg ATB200;
  Period 2: a single-dose IV infusion of 10 mg/kg ATB200 to all subjects who have completed Period 1; and
  Period 3: a single-dose IV infusion of 20 mg/kg ATB200 to all subjects who have completed Period 2.

Stage 2 (Consists of 2 Dosing Periods, Each Comprising 3 Study Drug Doses, 2 Weeks Apart)
  Period 4: 130 mg of miglustat will be administered orally 1 hour before a single dose IV infusion of 20 mg/kg ATB200 to all subjects who have completed Period 3 (repeated every 2 weeks for a total of 3 administrations); and Period 5: 260 mg of miglustat will be administered orally 1 hour before a single dose IV infusion of 20 mg/kg ATB200 to all ERT-experienced subjects who have completed Period 4 (repeated every 2 weeks for a total of 3 administrations).

Note: Subjects are required to fast at least 2 hours before and 2 hours after administration of oral miglustat.

Total Duration of Study: Up to 22 weeks (up to 4 weeks screening period followed by approximately 18 weeks of study treatment [Stages 1 and 2])

Duration of single-dose PK observation (Stage 1, Periods 1, 2, and 3): 6 weeks

Duration of multiple-dose PK observation (Stage 2, Periods 4 and 5): 12 weeks

Duration of safety, tolerability, and immunogenicity observation (Periods 1, 2, 3, 4, and 5): 18 weeks Criteria for Evaluation:
Primary:
Safety Assessments:
  PEs
  Vital signs, including body temperature, RR, HR, and BP
  AEs, including IARs
  12-Lead ECG
  Clinical safety laboratory assessments: serum chemistry, hematology, and urinalysis
PK of Plasma ATB200 and Miglustat:
  Plasma acid α-glucosidase activity levels and total acid α-glucosidase protein concentrations PK parameters: maximum observed plasma concentration ($C_{max}$), time to reach the maximum observed plasma concentration ($t_{max}$), area under the plasma-drug concentration time curve from Time 0 to the time of last measurable concentration ($AUC_{0-t}$), area under the plasma-drug concentration time curve from Time 0 extrapolated to infinity ($AUC_{0-\infty}$), half-life ($t_{1/2}$), and total clearance following IV administration ($CL_T$)
  Ratios of plasma acid α-glucosidase activity and total acid α-glucosidase protein $C_{max}$ and $AUC_{0-\infty}$ for all dose regimens
  Plasma miglustat PK parameters: $C_{max}$, $t_{max}$, $AUC_{0-t}$, $AUC_{0-\infty}$, and $t_{1/2}$, apparent total clearance of drug following oral administration ($CL_T/F$), and terminal phase volume of distribution following oral administration (Vz/F) for each dose level
  Ratios of plasma miglustat $C_{max}$ and $AUC_{0-\infty}$ for each dose level
Functional Assessments (Performed at Baseline)
For Ambulatory Subjects
  Motor Function Tests
    Six minute Walk Test (6MWT)
    10-Meter Walk Test
    Gait, Stairs, Gower, and Chair score
    Timed Up and Go (TUG)
  Muscle Strength Test (medical research criteria [MRC] and hand-held dynamometer) for both upper and lower limbs
  PFTs (FVC, MIP, MEP, and SNIP)

For Nonambulatory Subjects
  Muscle Strength Test—Upper Limbs Only
    MRC and hand-held dynamometer performed for upper limbs only
  Pulmonary function tests (PFTs) (forced vital capacity [FVC], maximum inspiratory pressure [MIP], maximum expiratory pressure [MEP], and sniff nasal inspiratory pressure [SNIP])
Patient-Reported Outcomes (Performed at Baseline)
  Fatigue Severity Scale
  Rotterdam Handicap Scale
  Rasch-built Pompe-specific activity (R-PAct)
Exploratory
  Anti-ATB200 antibody titers (total and neutralizing)
  Cross-reactivity of anti-recombinant acid α-glucosidase antibodies to alglucosidase alfa
  Pro-inflammatory cytokines and other biomarkers of immune system activation
  PD markers (Hex4 and CPK)
Methods of Analysis:
Statistical Methods:
  Descriptive statistics on PK parameters will be provided. Summary statistics will be provided for all variables that are not PK parameters. Dose proportionality assessment on acid α-glucosidase activity and total acid α-glucosidase protein exposure ($C_{max}$) $AUC_{0-t}$, and $AUC_{0-\infty}$) ratios of 5, 10, and 20 mg/kg ATB200 alone. Analysis of variance (ANOVA) on acid α-glucosidase activity and total acid α-glucosidase protein exposure ($C_{max}$) $AUC_{0-t}$, and $AUC_{0-\infty}$) ratios of 20 mg/kg ATB200 alone versus 20 mg/kg ATB200+130 mg miglustat, and versus 20 mg/kg ATB200+260 mg miglustat within each population and overall. ANOVA on acid α-glucosidase activity and total acid α-glucosidase protein exposure ($C_{max}$, $AUC_{0-t}$, and $AUC_{0-\infty}$) ratios between ambulatory and nonambulatory subjects for 20 mg/kg ATB200+130 mg miglustat and 20 mg/kg ATB200+260 mg miglustat. Dose proportionality assessment for exposure ratios ($C_{max}$, $AUC_{0-t}$, and $AUC_{0-\infty}$) between 130 mg and 260 mg miglustat within each subject population and overall. The effect of immunogenicity results on PK, PD, and safety will be evaluated.

Interim Analyses:
  An interim analysis will be performed when at least 50% (n=6) of the subjects have completed Stage 2 of the study. Up to 2 additional interim analyses may be performed in the study.

Initial PK Results:
  The PK summary of GAA activity and GAA total protein for subjects is shown in Tables 12 and 13, respectively.
  In Tables 12-15 and FIGS. 24-26, the single dose (SD) measurements were taken after a single administration of miglustat and ATB200, and the multiple dose (MD) measurements were taken after the third biweekly administration of miglustat and ATB200.

TABLE 12

| Dose mg/kg ATB200 + mg miglustat | $\alpha t_{1/2}{}^a$ (hr) | $\beta t_{1/2}{}^a$ (hr) | $t_{max}{}^b$ (hr) | $C_{max}{}^c$ (ug/mL) | $AUC_{0-t}{}^c$ (hr*ug/mL) | $AUC_{0-\infty}{}^c$ (hr*ug/mL) | $AUC_{0-\infty}/D^c$ (hr*ug/mL/mg) | $CL_T{}^a$ (L/hr) | $V_{ss}{}^a$ (L) |
|---|---|---|---|---|---|---|---|---|---|
| 5 | 1.06 (9.7) | 3.15 (5.3) | 3.5 (3.5-4.0) | 53.7 (20.4) | 193 (22.5) | 193 (22.5) | 0.444 (15.4) | 2.27 (15.9) | 5.61 (21.2) |
| 10 | 1.26 (22.2) | 2.73 (18.2) | 3.75 (3.5-4.5) | 115 (28.3) | 447 (30.7) | 448 (30.6) | 0.523 (17.5) | 1.93 (15.0) | 5.39 (21.2) |
| 20 | 1.36 (25.7) | 2.16 (10.2) | 4.0 (3.5-4.0) | 256 (30.4) | 1020 (37.4) | 1021 (37.4) | 0.596 (30.1) | 1.76 (37.5) | 5.01 (28.0) |
| 20 + 130 Single Dose | 1.84 (16.0) | 2.49 (9.9) | 4.5 (4.0-5.0) | 234 (36.0) | 1209 (29.9) | 1211 (29.9) | 0.707 (23.7) | 1.45 (25.8) | 5.32 (24.8) |
| 20 + 130 Multiple Dose | 1.90 (7.5) | 2.53 (11.9) | 4.0 (3.5-5.0) | 230 (20.2) | 1180 (19.1) | 1183 (19.0) | 0.690 (15.1) | 1.46 (14.4) | 5.55 (14.2) |
| 20 + 260 Single Dose | 2.39 (11.5) | 2.70 (10.8) | 4.0 (4.0-4.5) | 228 (26.0) | 1251 (17.4) | 1256 (17.2) | 0.733 (15.8) | 1.38 (17.3) | 5.71 (20.2) |

$^a$Arithmetic mean (CV %)
$^b$Median (min-max)
$^c$Geometric mean (CV %)

TABLE 13

| Dose mg/kg ATB200 + mg miglustat | $\alpha t_{1/2}{}^a$ (hr) | $\beta t_{1/2}{}^a$ (hr) | $t_{max}{}^b$ (hr) | $C_{max}{}^c$ (ug/mL) | $AUC_{0-t}{}^c$ (hr*ug/mL) | $AUC_{0-\infty}{}^c$ (hr*ug/mL) | $AUC_{0-\infty}/D^c$ (hr*ug/mL/mg) | $CL_T{}^a$ (L/hr) | $V_{ss}{}^a$ (L) |
|---|---|---|---|---|---|---|---|---|---|
| 5 | 1.02 (3.0) | 1.83 (13.8) | 4.0 (3.5-4.0) | 61.1 (20.0) | 215 (17.1) | 218 (17.0) | 0.511 (7.3) | 1.97 (7.7) | 4.57 (6.8) |
| 10 | 1.36 (5.3) | 1.99 (56.9) | 4.0 | 143 (19.5) | 589 (16.6) | 594 (16.6) | 0.694 (12.3) | 1.45 (13.4) | 3.90 (14.5) |
| 20 | 1.65 (12.3) | 2.62 (18.5) | 4.0 | 338 (11.1) | 1547 (12.1) | 1549 (12.1) | 0.904 (12.8) | 1.11 (14.4) | 3.49 (11.6) |
| 20 + 130 Single Dose | 1.79 (10.7) | 2.63 (6.6) | 4.0 | 322 (18.2) | 1676 (14.9) | 1680 (14.8) | 0.980 (15.0) | 1.03 (17.6) | 3.78 (12.2) |
| 20 + 130 Multiple Dose | 1.99 (10.2) | 2.47 (4.2) | 4.0 (3.5-5.0) | 355 (16.5) | 1800 (12.7) | 1804 (12.7) | 1.05 (12.9) | 0.96 (13.7) | 3.70 (10.8) |
| 20 + 260 Single Dose | 2.35 (13.9) | 2.73 (10.4) | 4.0 | 350 (14.2) | 1945 (15.1) | 1953 (15.0) | 1.14 (15.8) | 0.89 (15.7) | 3.63 (16.3) |

$^a$Arithmetic mean (CV %)
$^b$Median (min-max)
$^c$Geometric mean (CV %)

Figure 24A:
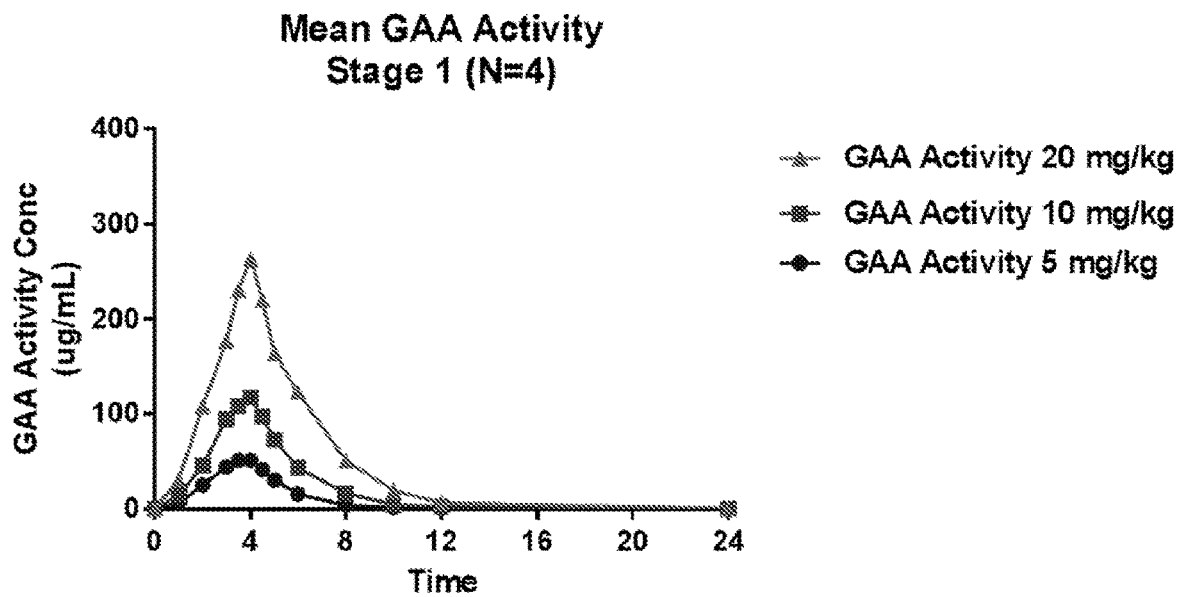
FIGS. 24A-24D are graphs showing the concentration-time profiles of GAA activity in plasma in human subjects after dosing of 5, 10 or 20 mg/kg ATB200, or 20 mg/kg ATB200 and 130 or 260 mg miglustat.
Figure 24B:
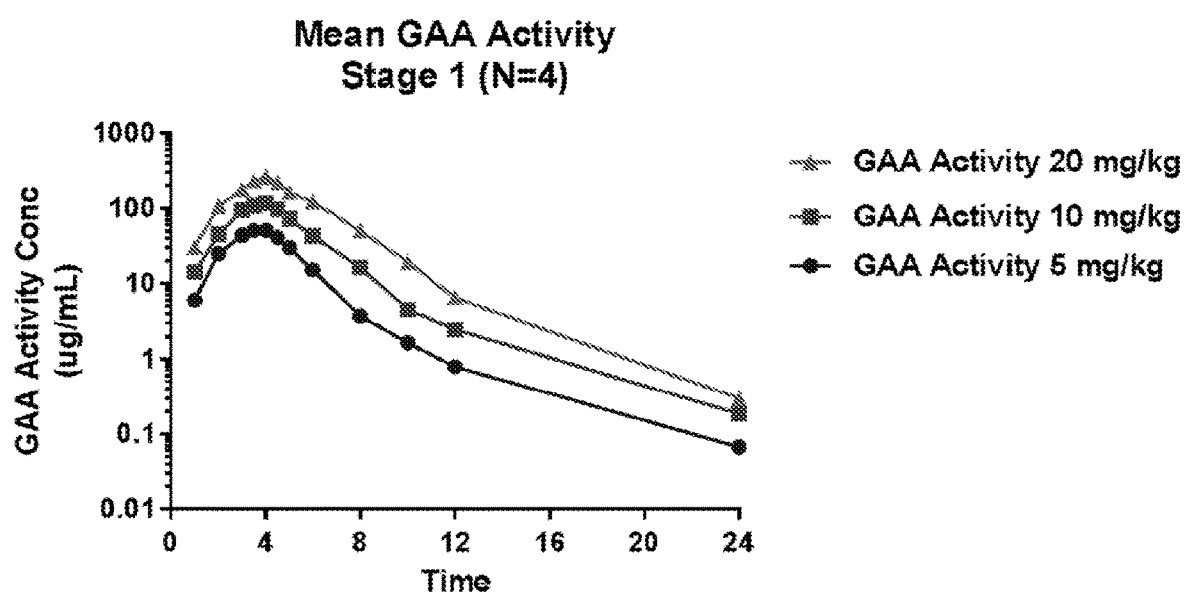

FIG. 24A shows the concentration-time profiles of mean plasma GAA activity after doses of 5 mg/kg, 10 mg/kg and 20 mg/kg ATB200. FIG. 24B also provides the concentration time-profiles profiles of mean plasma GAA activity after doses of 5 mg/kg, 10 mg/kg and 20 mg/kg ATB200, but the plasma GAA activity is displayed on a logarithmic scale. As can be seen from FIGS. 24A-24B and Table 12, ATB200 demonstrated slightly greater than dose proportional exposures for plasma GAA activity.

Figure 24C:
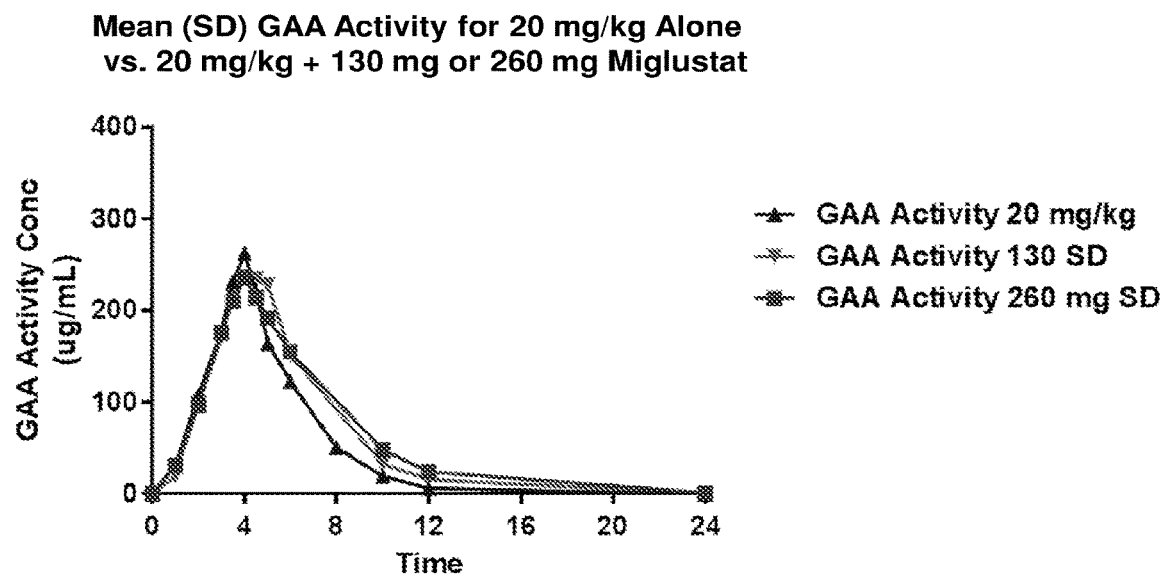
Figure 24D:
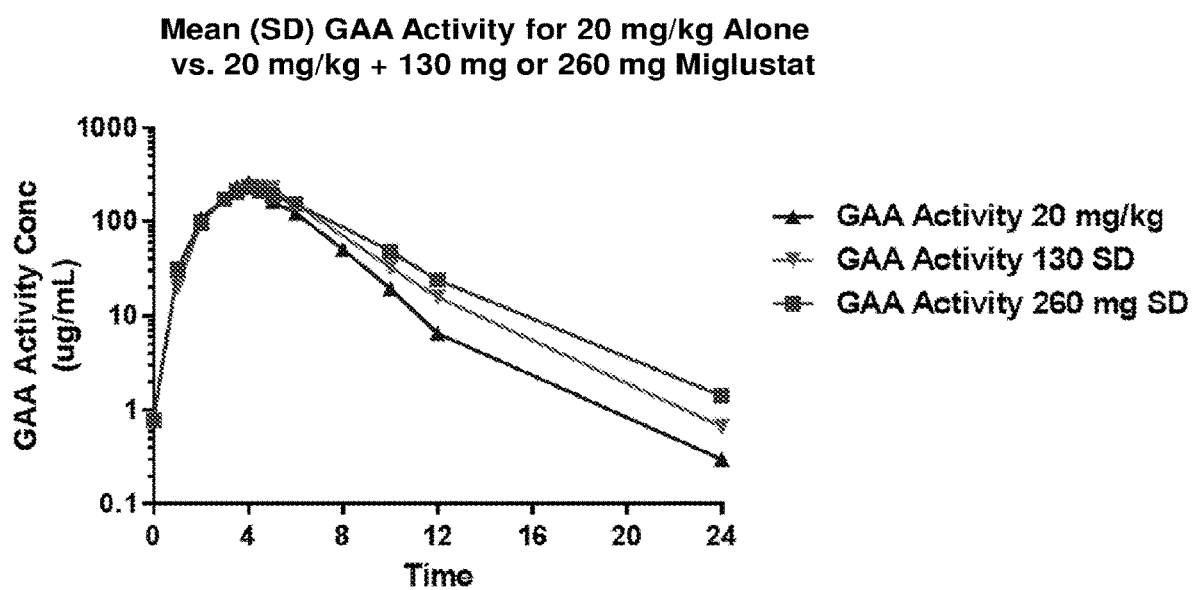

FIG. 24C shows the concentration-time profiles of mean plasma GAA activity after doses of 20 mg/kg ATB200 alone, as well as 20 mg/kg of ATB200 and 130 or 260 mg of miglustat. FIG. 24D also provides the mean plasma GAA activity after doses of 20 mg/kg ATB200 alone, with 130 mg miglustat or 260 mg miglustat, but the plasma GAA activity is displayed on a logarithmic scale.

Figure 25A:
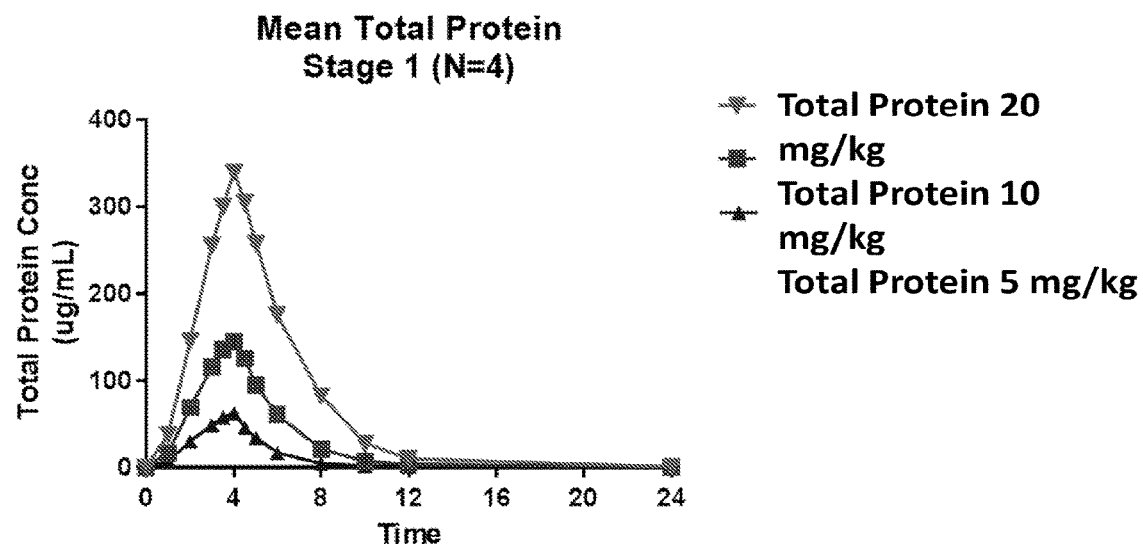
FIGS. 25A-25D are graphs showing the concentration-time profiles of GAA total protein in plasma in human subjects after dosing of 5, 10 or 20 mg/kg ATB200, 20 mg/kg ATB200 and 130 mg miglustat, or 20 mg/kg ATB200 and 260 mg miglustat.
Figure 25B:
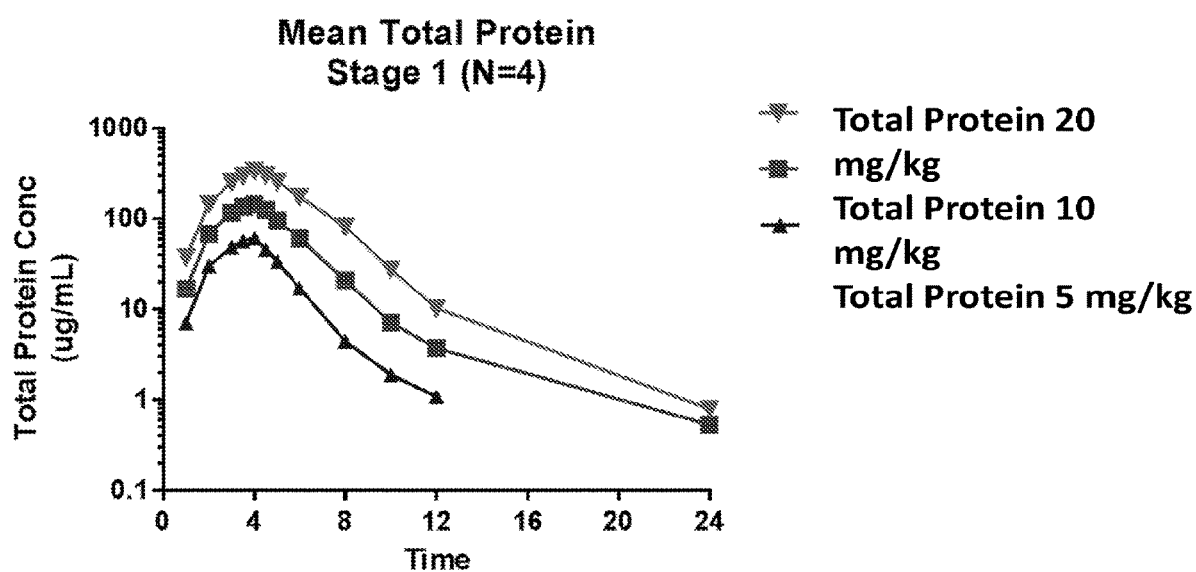

FIG. 25A shows the concentration-time profiles of mean plasma GAA total protein after doses of 5 mg/kg, 10 mg/kg and 20 mg/kg ATB200. FIG. 25B also provides the concentration time-profiles profiles of mean plasma GAA total protein after doses of 5 mg/kg, 10 mg/kg and 20 mg/kg ATB200, but the plasma GAA total protein is displayed on a logarithmic scale. As can be seen from FIGS. 25A-25B and Table 13, ATB200 demonstrated slightly greater than dose proportional exposures for plasma GAA total protein.

Figure 25C:
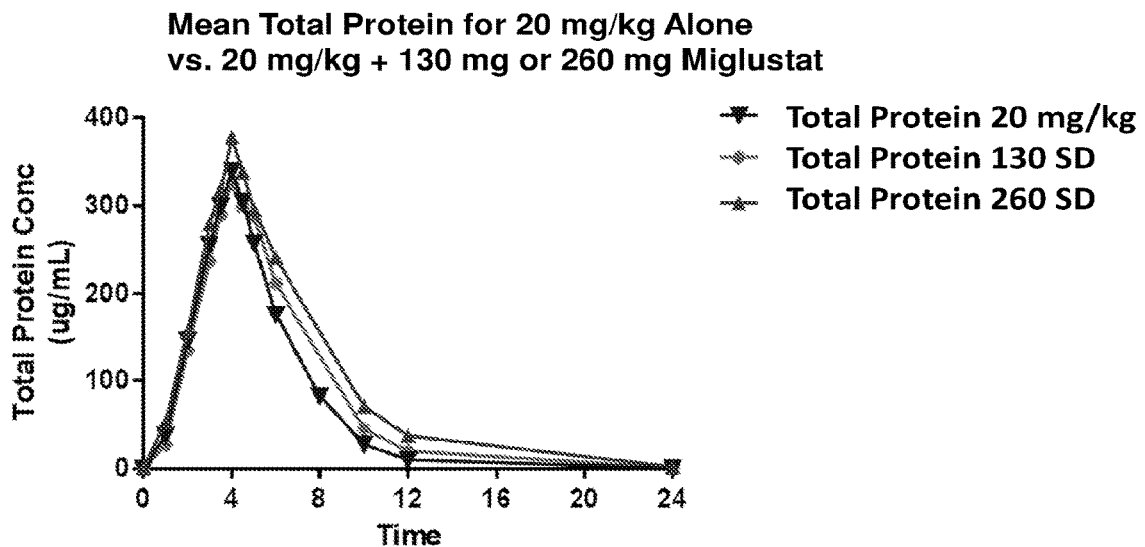
Figure 25D:
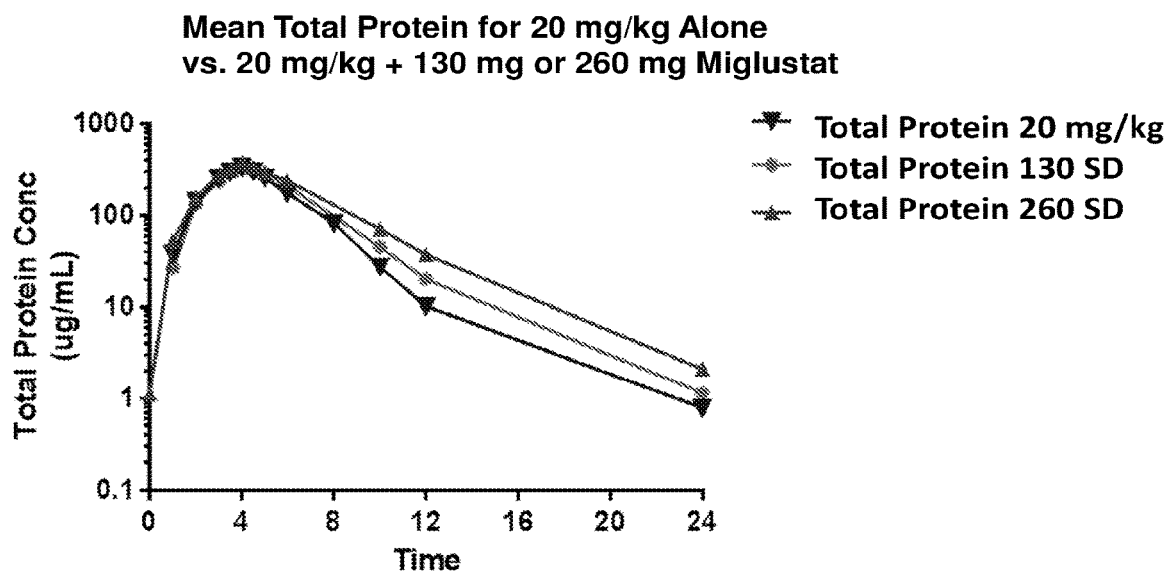

FIG. 25C shows the concentration-time profiles of mean plasma GAA total protein after doses of 20 mg/kg ATB200 alone, 20 mg/kg of ATB200 and 130 mg of miglustat, and 20 mg/kg of ATB200 and 260 mg of miglustat. FIG. 25D also provides the mean plasma GAA total protein after doses of 20 mg/kg ATB200 alone, with 130 mg miglustat or 260 mg miglustat, but the plasma GAA total protein is displayed on a logarithmic scale.

As shown in Table 13, co-administration of miglustat increased total GAA protein plasma half-life by approximately 30% relative to ATB200 administered alone. Volume of distribution ranged from 3.5 to 5.7 L for all treatments, suggesting that the glycosylation of ATB200 enables efficient distribution of ATB200 to tissues.

The PK summary for miglustat is shown in Table 14.

Thus, the partial AUC analysis demonstrates that co-administration of miglustat significantly increases the terminal phase partial AUC ($t_{max-24\ h}$) of ATB200 by approximately 15% for doses of 130 mg of miglustat and approximately 40% for 260 mg of miglustat.

TABLE 14

| Dose mg | $\beta t_{1/2}{}^a$ (hr) | $t_{max}{}^b$ (hr) | $C_{max}{}^c$ (ug/mL) | $C_{max}$/BW$^c$ (ng/mL/kg) | AUC$_{0-t}{}^c$ (hr*ug/mL) | AUC$_{O-\infty}{}^c$ (hr*ug/mL) | AUC$_{O-\infty}$/BW$^c$ (hr*ng/mL/kg) | $V_z$/F$^a$ (L) | CL/F$^a$ (L/hr) |
|---|---|---|---|---|---|---|---|---|---|
| 130 Single Dose | 4.5 (37.0) | 2.75 (1.5-3.5) | 1647 (22.1) | 19.2 (23.9) | 12620 (13.1) | 13157 (13.1) | 154 (29.7) | 65.4 (41.9) | 9.93 (13.7) |
| 130 Multiple Dose | 5.6 (12.5) | 3.0 (1.5-3.5) | 1393 (36.8) | 16.3 (36.4) | 11477 (18.0) | 12181 (16.4) | 142 (26.9) | 88.1 (26.1) | 10.8 (16.2) |
| 260 Single Dose | 5.5 (25.9) | 2.75 (1.0-5.0) | 3552 (30.2) | 41.5 (33.8) | 26631 (25.1) | 28050 (22.9) | 325 (30.8) | 79.2 (55.3) | 9.51 (27.6) |

$^a$Arithmetic mean (CV %)
$^b$Median (min-max)
$^c$Geometric mean (CV %)

Figure 26:
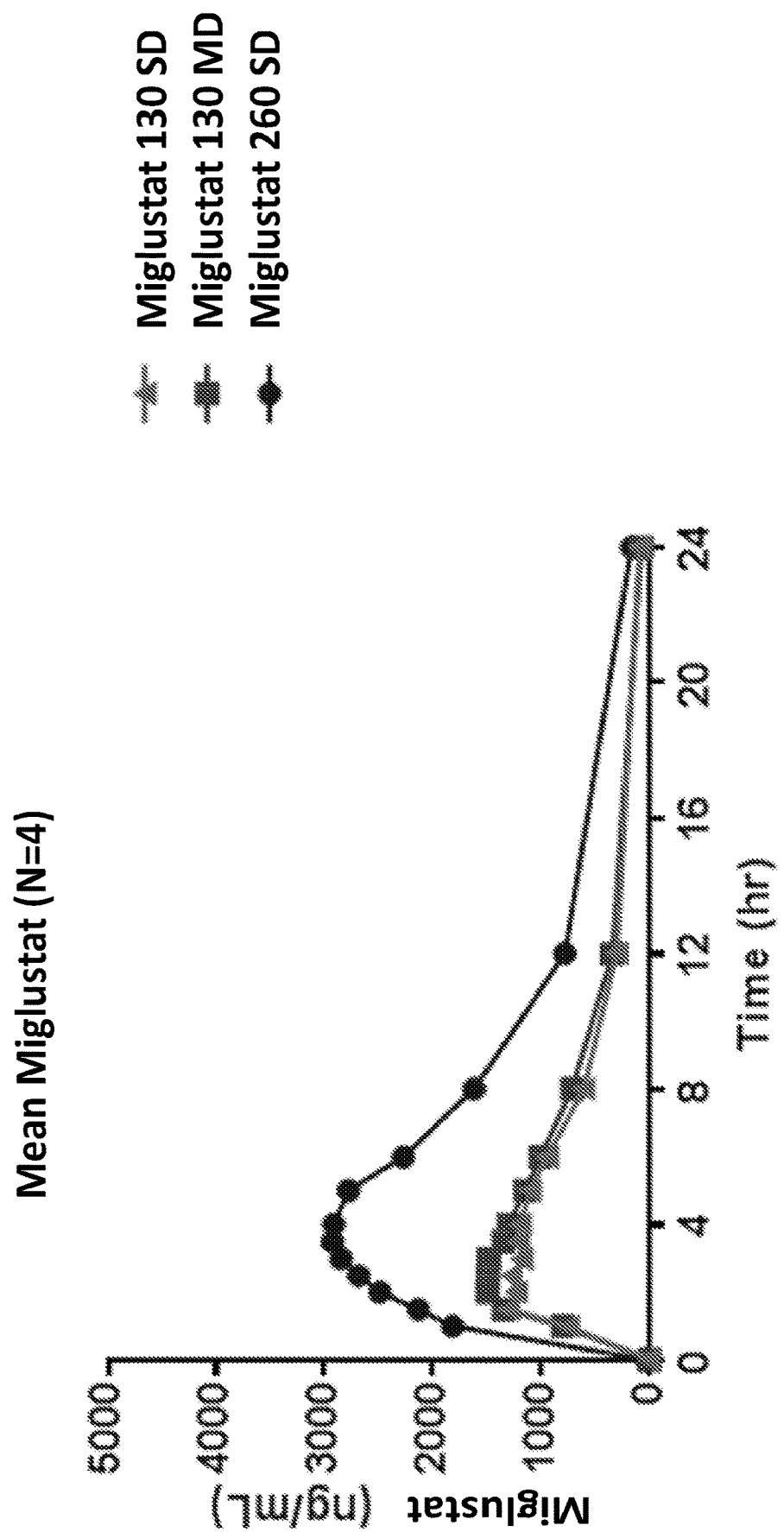
FIG. 26 is a graph showing the concentration-time profiles of miglustat in plasma in human subjects after dosing of 130 mg or 260 mg of miglustat.

FIG. 26 shows the concentration-time profile of miglustat in plasma in human subjects after dosing of 130 mg or 260 mg of miglustat.

As can be seen from Table 14 and FIG. 26, plasma miglustat, administered orally 1 hour prior to ATB200 infusion, reached peak concentrations 2 hours into the infusion and demonstrated dose-proportional kinetics.

An analysis was performed on various portions of the plasma concentration curves for GAA activity and total protein to determine partial AUCs. Table 15 provides a summary of partial AUCs from 0-$t_{max}$, $t_{max}$-6 h, $t_{max}$-10 h, $t_{max}$-12 h, and $t_{max}$-24 hr for GAA activity and total protein.

Initial Biomarker Results

Alanine aminotransferase (ALT), aspartate aminotransferase (AST) and creatine phosphokinase (CPK) levels were monitored in human patients that switched from Lumizyme® to ATB200. The patients received ascending doses of ATB200 (5, 10 and 20 mg/kg) followed by co-administration of ATB200 (20 mg/kg) and miglustat (130 and 260 mg). High levels of CPK enzyme may indicate injury or stress to muscle tissue, heart, or brain. Elevated ALT and AST are markers of liver and muscle damage from Pompe disease,

TABLE 15

| | | Arithmetic Mean pAUC (ng*hr/mL) at Time Post-Dose (N = 4) | | | | |
|---|---|---|---|---|---|---|
| Analyte | Treatment | 0-$t_{max}$ | $t_{max}$-6 h | $t_{max}$-10 h | $t_{max}$-12 h | $t_{max}$-24 h |
| GAA Activity | 20 mg/kg | 428 | 382 | 606 | 630 | 654 |
| GAA Activity | 20 mg/kg + 130 mg Single Dose | 456 | 415 | 722 | 770 | 832 |
| GAA Activity | 20 mg/kg + 130 mg Multiple Dose | 423 | 392 | 689 | 737 | 796 |
| GAA Activity | 20 mg/kg + 260 mg Single Dose | 423 | 536 | 924 | 996 | 1094 |
| Total Protein | 20 mg/kg | 621 | 603 | 943 | 981 | 1040 |
| Total Protein | 20 mg/kg + 130 mg Single Dose | 565 | 614 | 1041 | 1106 | 1189 |
| Total Protein | 20 mg/kg + 130 mg Multiple Dose | 630 | 612 | 1079 | 1154 | 1244 |
| Total Protein | 20 mg/kg + 260 mg Single Dose | 679 | 824 | 1411 | 1518 | 1665 |

As can be seen from Table 15, GAA activity percent mean increases of pAUCt$_{max-24\ h}$ for 20 mg/kg plus miglustat relative to 20 mg/kg ATB200 alone were 21.4%, 17.8%, 40.2%, for 130 mg SD, 130 mg MD, and 260 mg SD, respectively.

Similarly, GAA total protein percent mean increases of pAUC$_{tmax-24\ h}$ for 20 mg/kg plus miglustat relative to 20 mg/kg ATB200 alone were 12.5%, 16.4%, 37.5%, for 130 mg SD, 130 mg MD, and 260 mg SD, respectively.

respectively. The initial analysis of the ALT, AST and CPK levels are shown in FIGS. 38-41.

As can be seen from FIGS. 38-41, two patients showed early trend toward improvement in all three biomarkers and two patients remained stable. One patient had 44%, 28% and 34% reductions in CPK, AST and ALT respectively. Another patient had 31%, 22% and 11% reductions in CPK, AST and ALT respectively.

Thus far, there have been no serious adverse events (SAEs). AEs were generally mild and transient. There have been no infusion-associated reactions to date following 100+ infusions in all patients enrolled. All patients had anti-rhGAA antibodies at baseline which remained generally stable. Cytokines remained low and stable during infusions.

Example 15: GAA and LAMP1 Levels in Wild-Type and Pompe Fibroblasts

Figure 27:
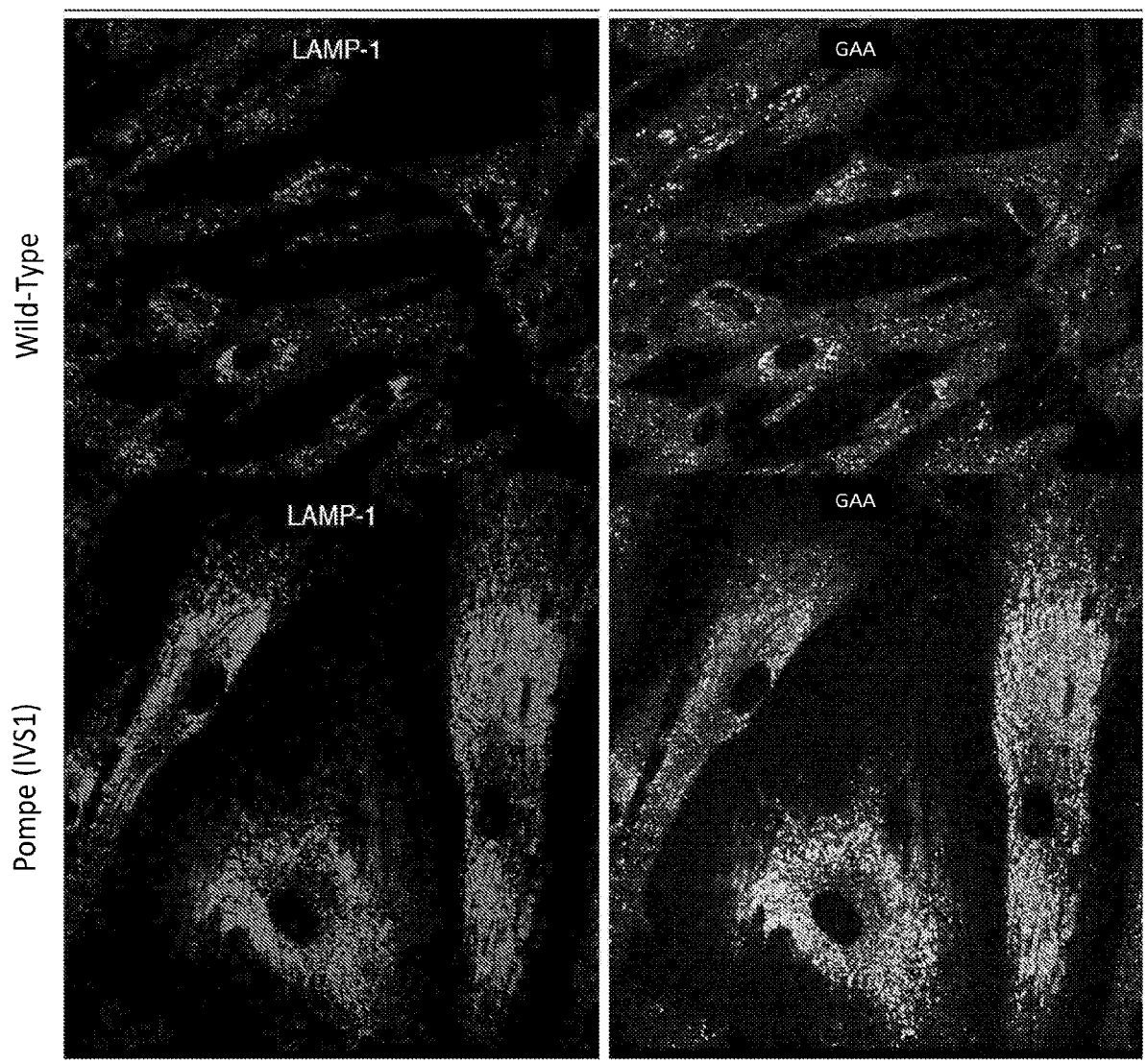
FIG. 27 is a series of immunofluorescent micrographs of GAA and LAMP1 levels in wild-type and Pompe fibroblasts.

Immunofluorescence microscopy was utilized for detecting GAA and LAMP1 levels in wild-type fibroblasts and Pompe fibroblasts with a common splicing mutation. As shown in FIG. 27, GAA is in distinct lysosomal compartments in wild-type fibroblasts. FIG. 27 also shows an abundant GAA signal in the Pompe fibroblasts, and that both the GAA and LAMP1 signals in Pompe fibroblasts appear to be localized to the ER and Golgi, rather than distal lysosomes. This is evidence of altered GAA protein trafficking in Pompe fibroblasts.

Figure 28:
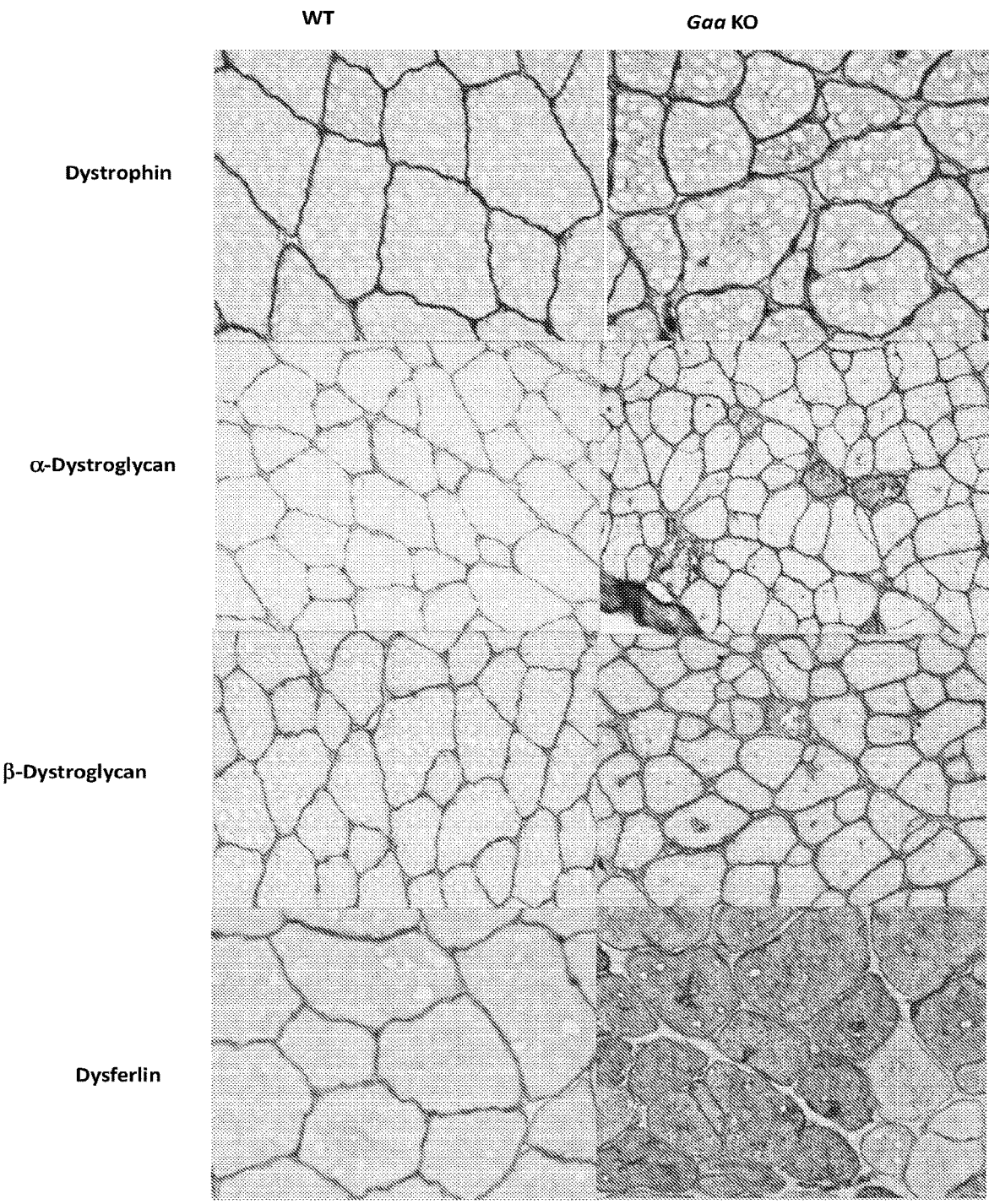
FIG. 28 is a series of photomicrographs of muscle fibers from wild-type and Gaa-knockout mice showing dystrophin, α- and β-dystroglycan, and dysferlin levels.
Figure 29A:
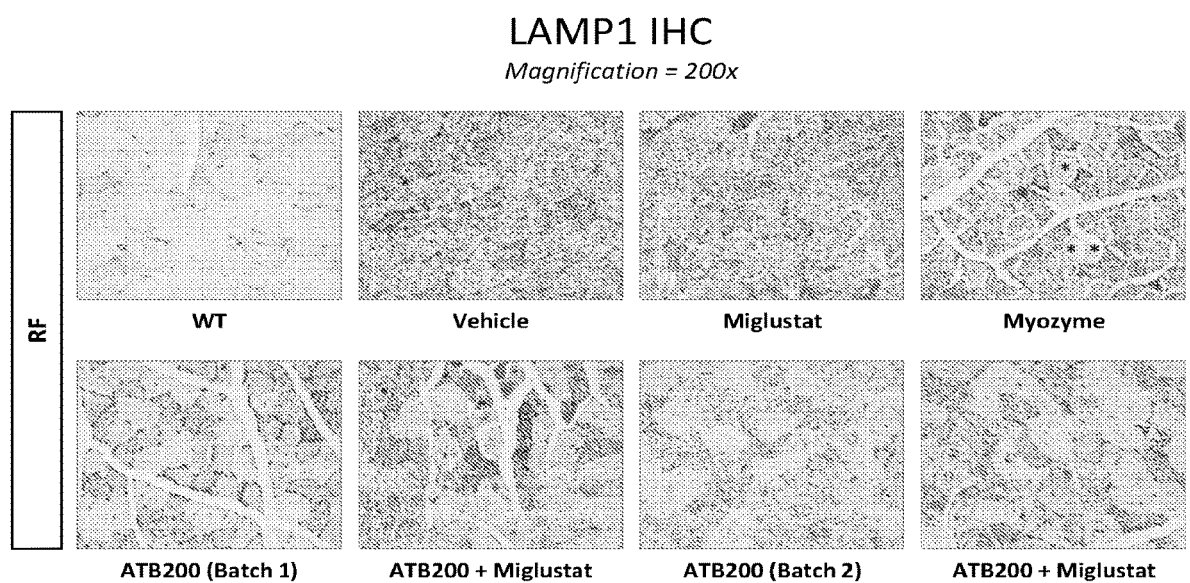
FIGS. 29A and 29B are a series of photomicrographs (200×) of muscle fibers of rectus femoris (RF) and vastus lateralis/vastus medialis (VL/VM) from wild-type and Gaa-knockout mice treated with vehicle, alglucosidase alfa and ATB200 in the presence and absence of miglustat, showing LAMP1 IHC signals.
Figure 29B:
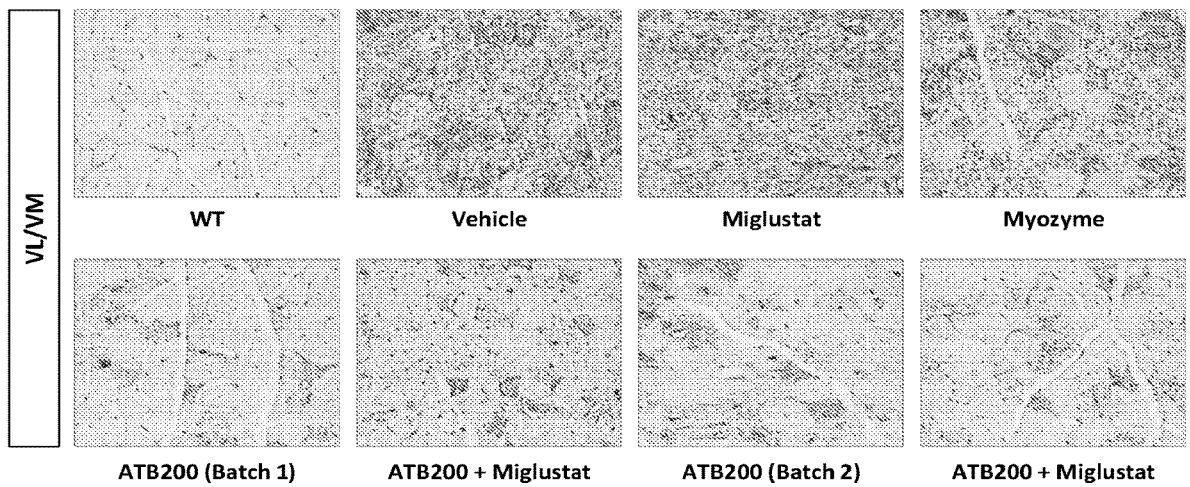
Figure 30A:
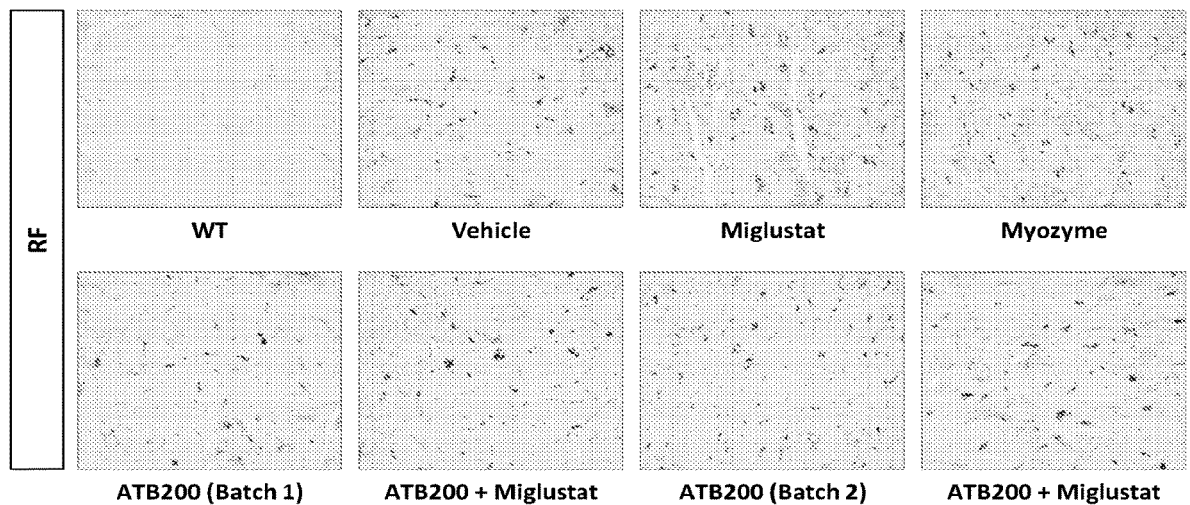
FIGS. 30A and 30B are a series of photomicrographs (200×) of muscle fibers of RF and VL/VM from wild-type and Gaa-knockout mice treated with vehicle, alglucosidase alfa and ATB200 in the presence and absence of miglustat, showing LC3 II IHC signals.
Figure 30B:
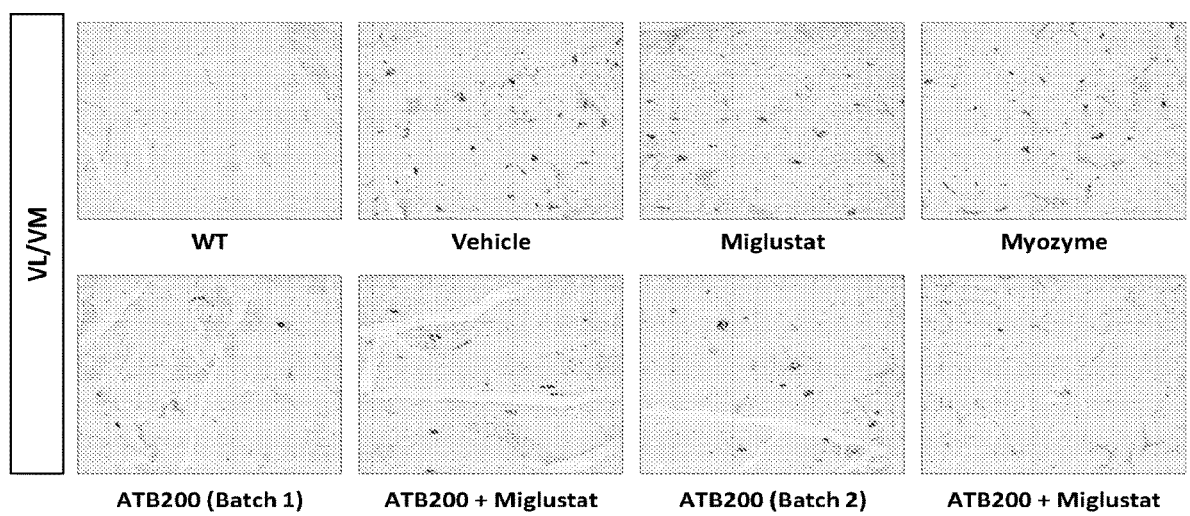
Figure 31A:
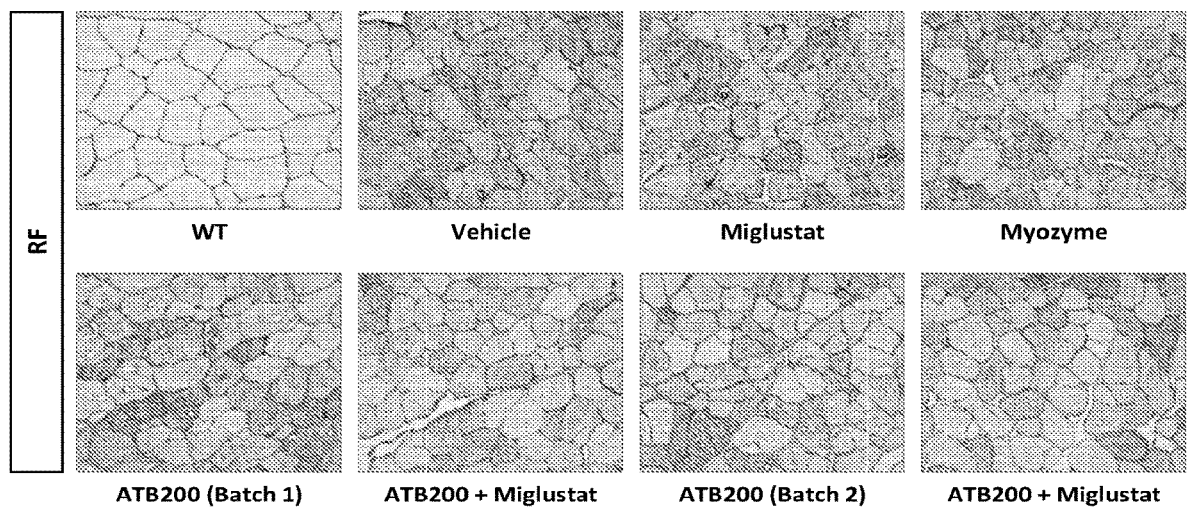
FIGS. 31A and 31B are a series of photomicrographs (200×) muscle fibers of RF and VL/VM from wild-type and Gaa-knockout mice treated with vehicle, alglucosidase alfa and ATB200 in the presence and absence of miglustat, showing dysferlin IHC signals.
Figure 31B:
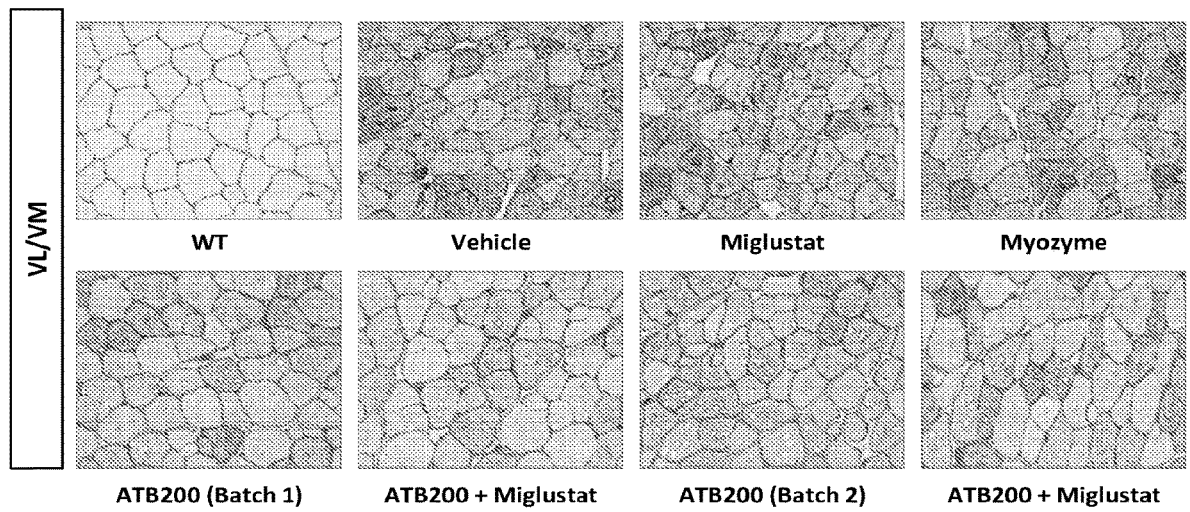
Figure 32A:
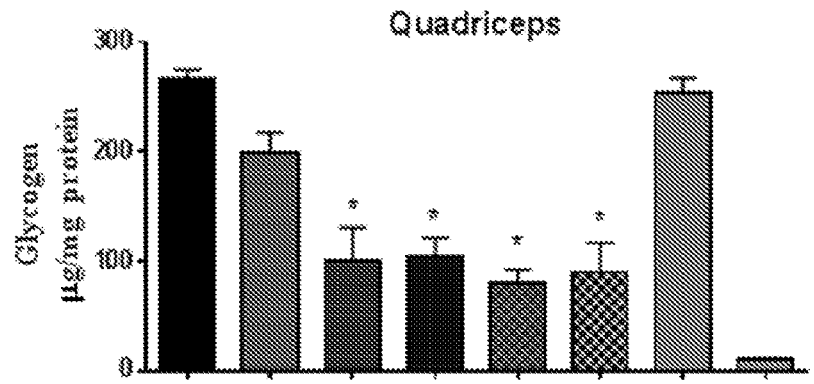
FIGS. 32A-32D are graphs showing glycogen levels in quadriceps, triceps, gastrocnemius and heart cells from wild-type and Gaa-knockout mice treated with vehicle, alglucosidase alfa and ATB200 in the presence and absence of miglustat.
Figure 32B:
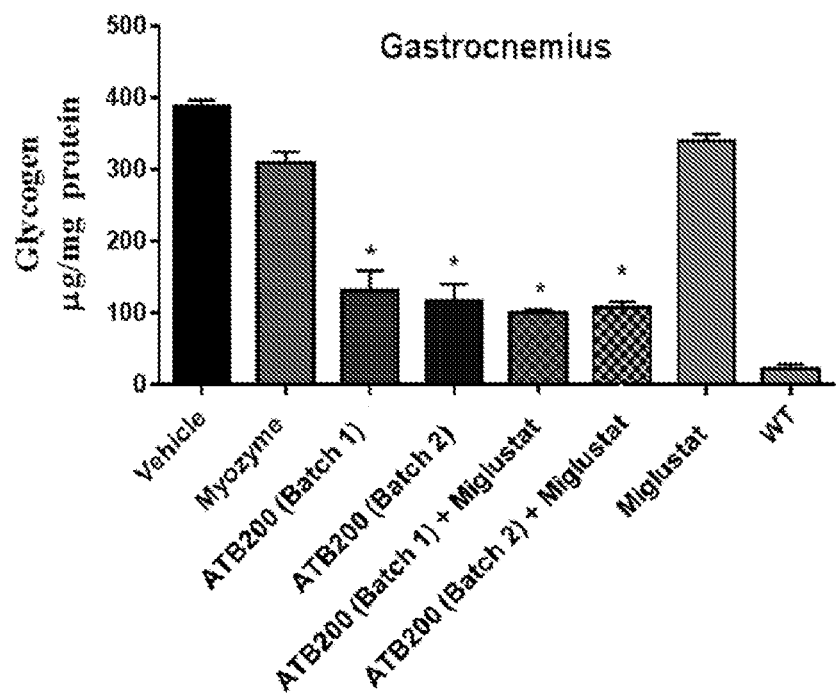
Figure 32C:
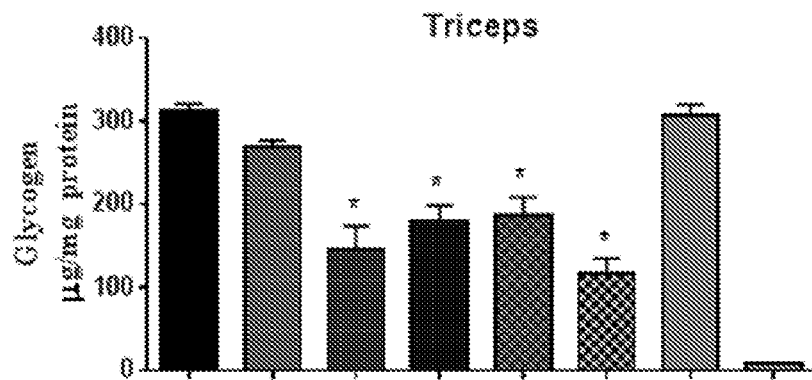
Figure 32D:
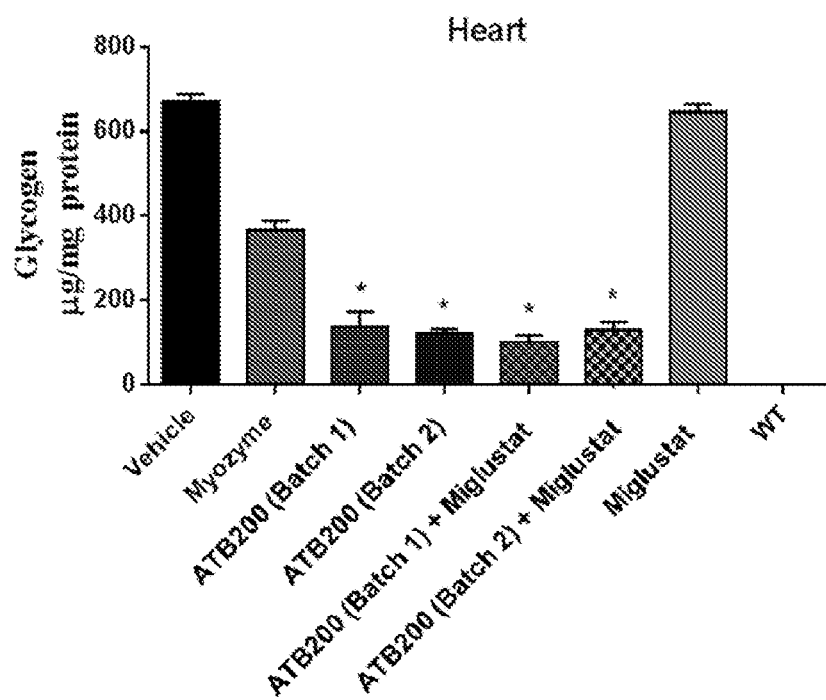

Example 16: Improvement of Cellular Dysfunction and Muscle Function in Gaa-Knockout Mice Impairment of lysosomal glycogen catabolism due to GAA deficiency has been shown to cause substantial cellular dysfunction as evidenced by pronounced, persistent autophagy and proliferation and accumulation of membrane-bound intracellular compartments filled with accumulated glycogen (N. Raben et al.). Our immunohistologic data indicate that protein trafficking is significantly altered for many proteins including several key proteins that are vital for muscle membrane stability such as dystrophin, α- and β-dystroglycan, various sarcoglycans and others that comprise the dystrophin glycoprotein complex as well as proteins involved in muscle repair such as dysferlin. These key muscle proteins require proper protein trafficking to the muscle cell membrane where they function. As shown in FIG. 28, our immunohistologic data reveal that an appreciable fraction of these key muscle proteins have an intracellular localization in muscles of Gaa knockout (KO) mouse model of Pompe disease. These data suggest that mistrafficking of these key muscle proteins may induce a pseudo-muscular dystrophy that ultimately lead to muscle weakness and disrepair. Alglucosidase alfa (Myozyme®) and ATB200 with and without 10 mg/kg miglustat were evaluated in Gaa KO mice at equivalent ERT dose (20 mg/kg) via an every other week dosing schedule. After 2 administrations, alglucosidase alfa modestly reduced accumulated lysosomal glycogen in skeletal muscles (FIGS. 32A-32C) and had negligible effects towards reducing autophagy (FIGS. 30A-30B) or lysosomal proliferation (FIGS. 29A-29B) as compared to vehicle-treated mice. In contrast, substantially better lysosomal glycogen clearance was observed with ATB200/miglustat under identical conditions (FIGS. 32A-32D). ATB200/miglustat also appeared to improve overall muscle physiology as evidenced by reduced LC3 II levels (FIGS. 30A-30B), a well-established autophagy biomarker and by clearance of accumulated intracellular vesicles stained with LAMP1 (FIGS. 29A-29B), a known resident lysosomal integral membrane protein and dysferlin (FIGS. 31A-31B), a known cell surface protein involved in muscle repair. Further, ATB200/miglustat significantly improved the muscle architecture that resembled muscle fibers of wild-type mice. Also, FIGS. 29-32 show that two different batches of ATB200 (earlier and later generation manufacturing processes) produced comparable results. In FIGS. 32A-32D, * indicates statistically significant compared to Myozyme® alone.

Example 17: Muscle Function in Gaa-Knockout Mice

Figure 33A:
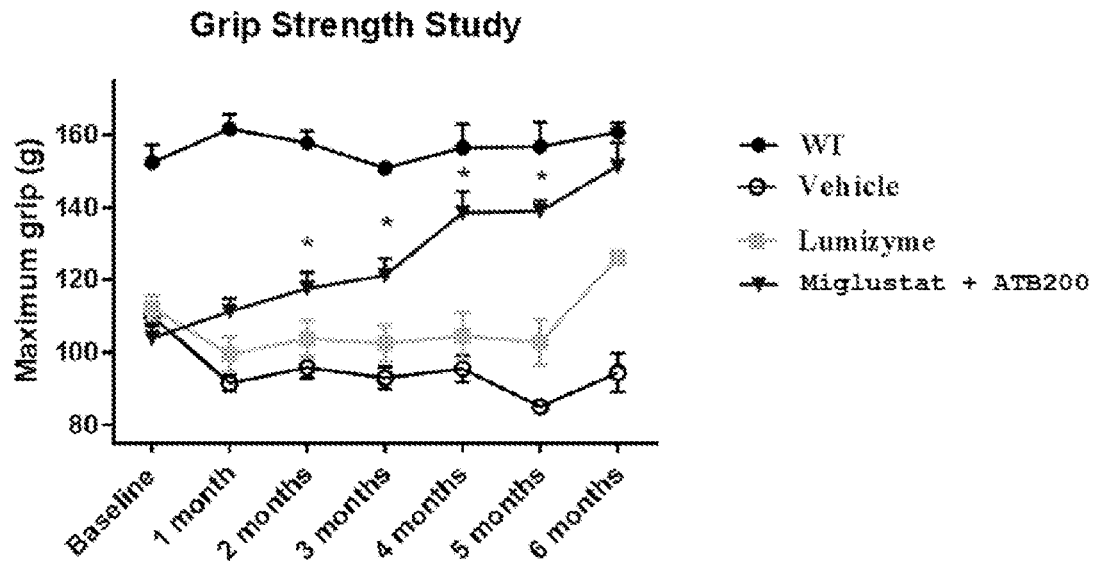
FIGS. 33A and 33B are graphs showing wire hand and grip strength muscle data for wild-type and Gaa-knockout mice treated with vehicle, alglucosidase alfa and ATB200 in the presence of miglustat.
Figure 33B:
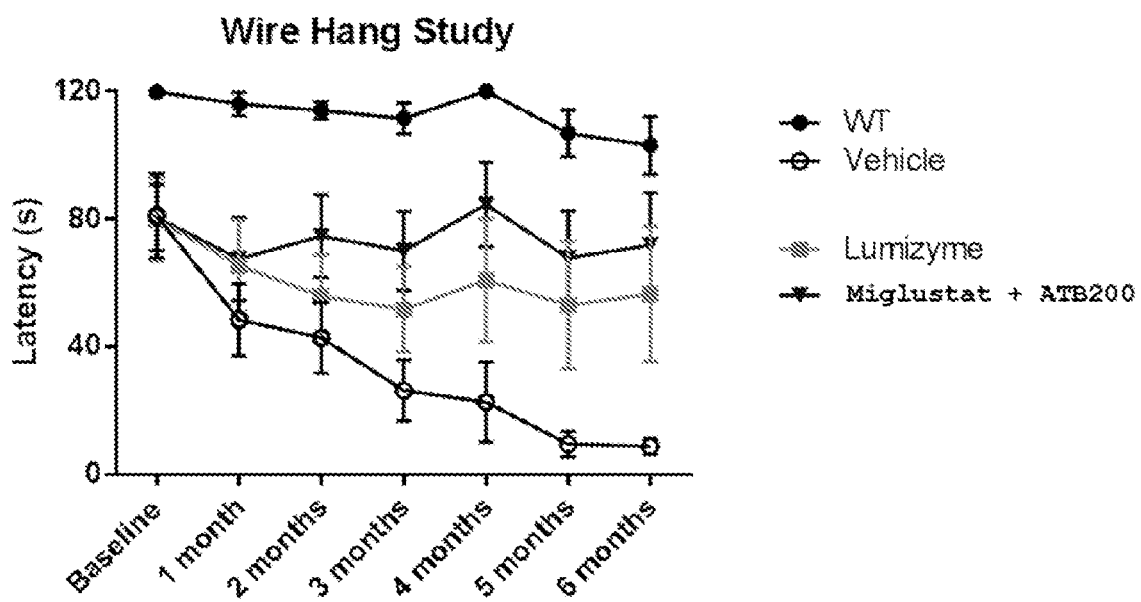
Figure 34A:
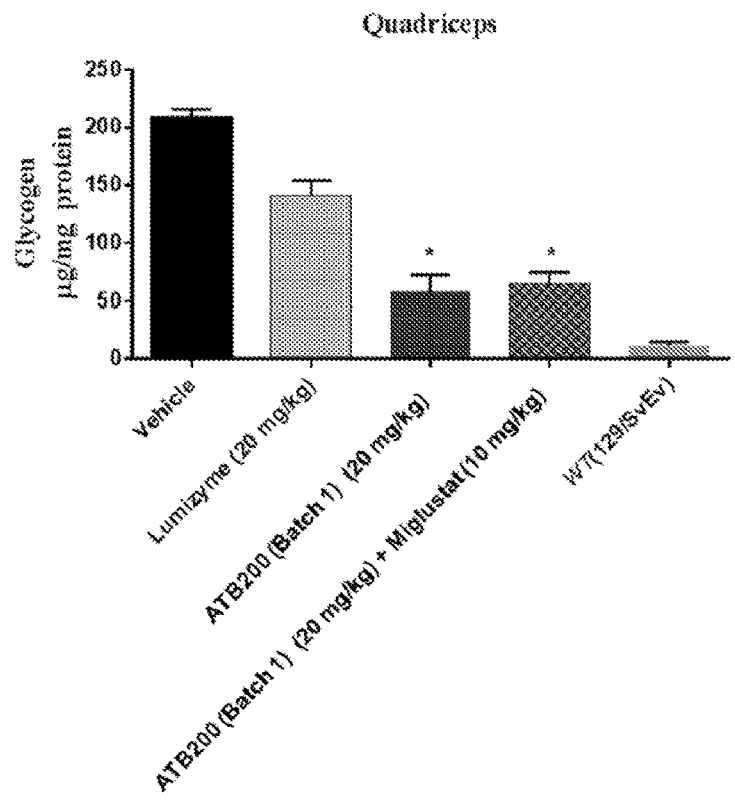
FIGS. 34A-34G are graphs showing glycogen levels in quadriceps, triceps and heart cells from wild-type and Gaa-knockout mice treated with vehicle, alglucosidase alfa and ATB200 in the presence and absence of miglustat.
Figure 34B:
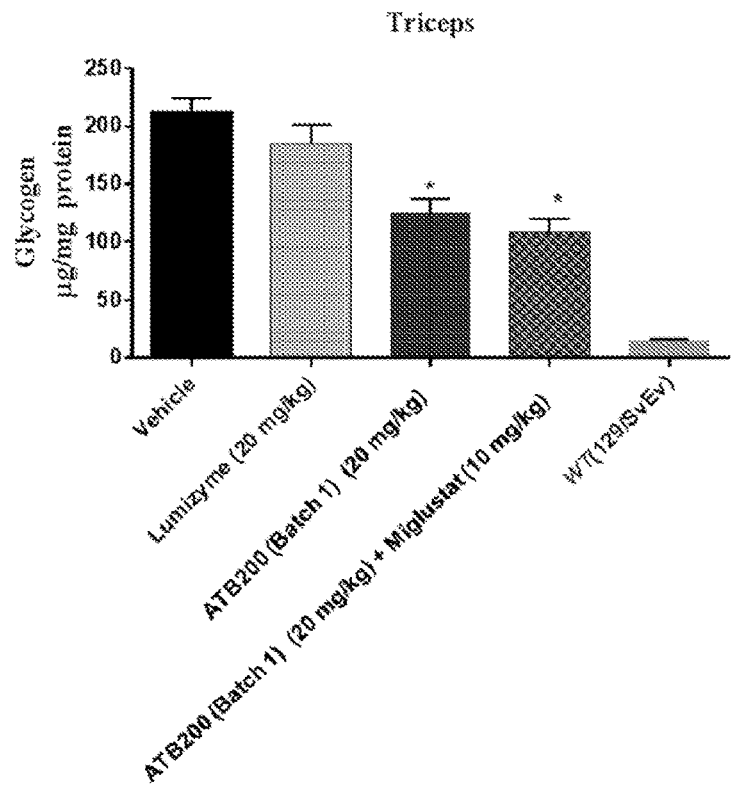
Figure 34C:
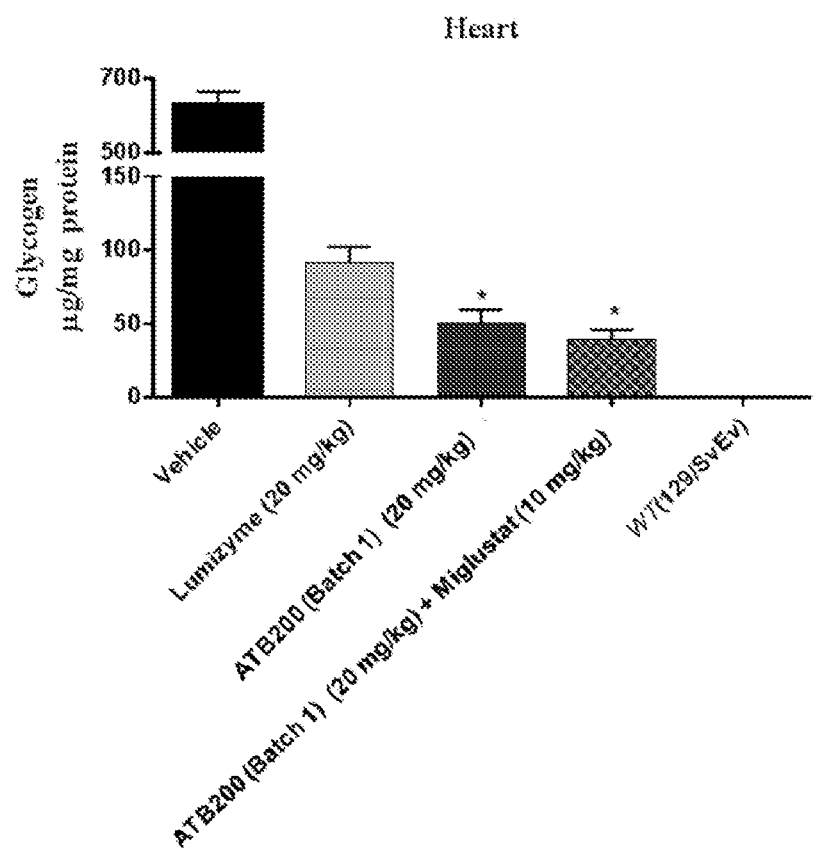
Figure 34D:
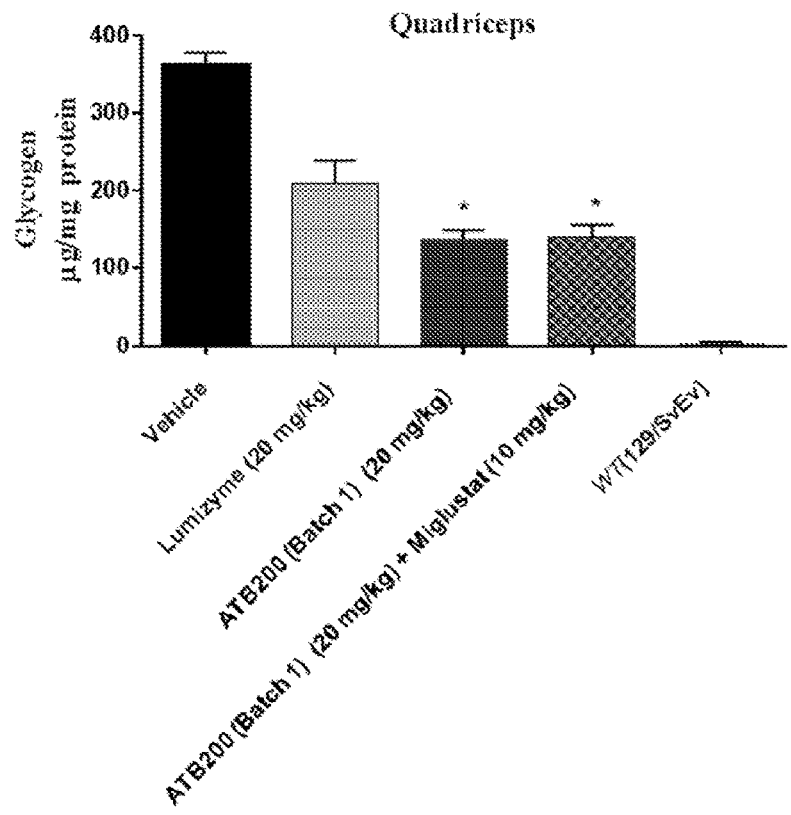
Figure 34E:
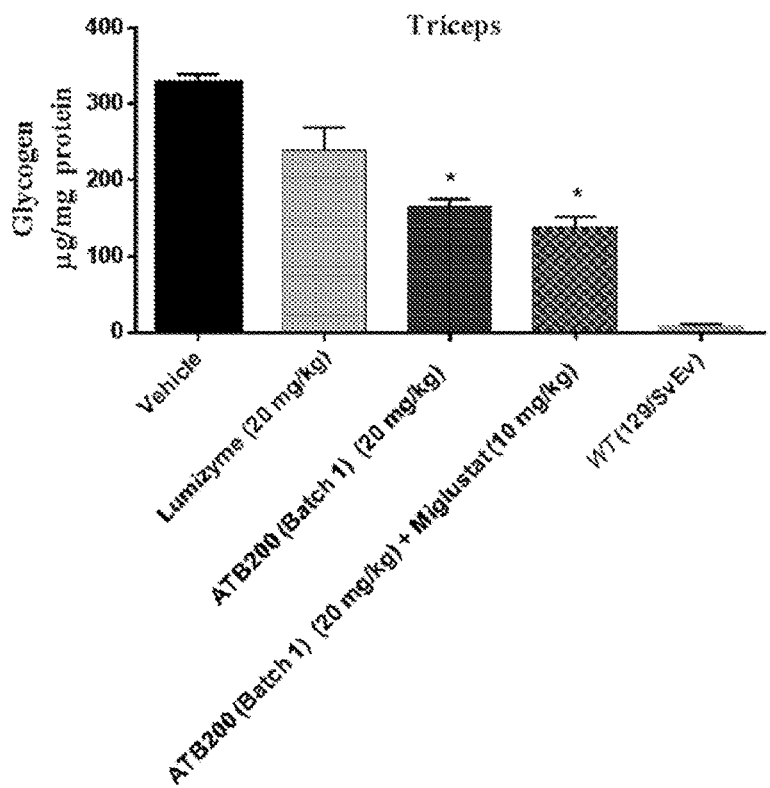
Figure 34F:
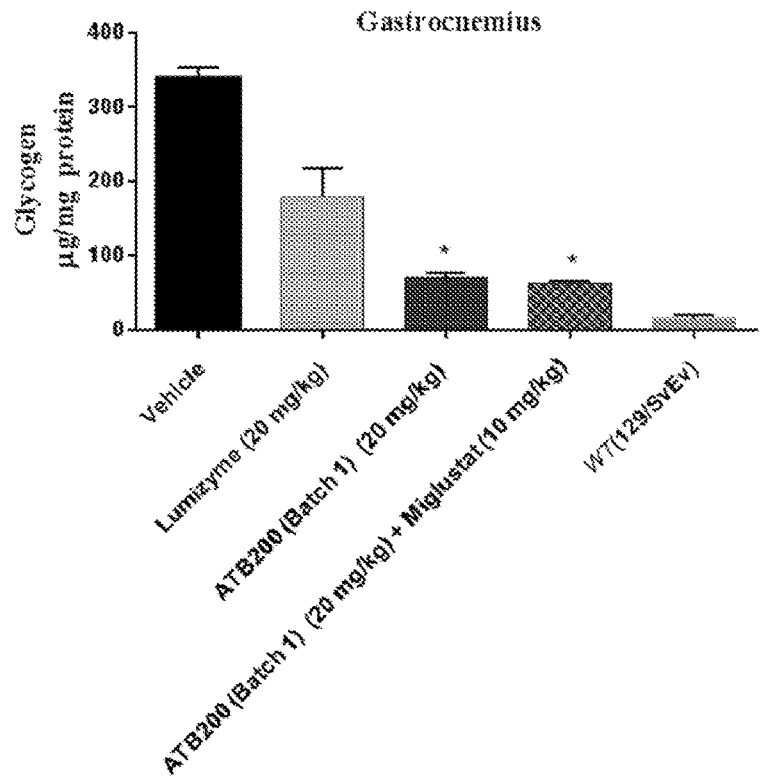
Figure 34G:
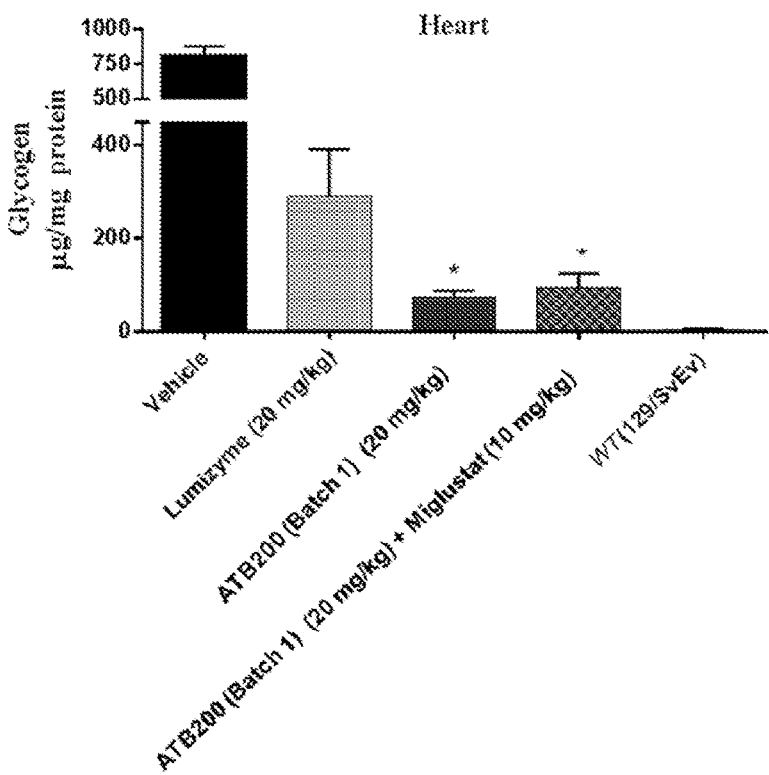

In longer-term studies of 12 biweekly administrations, 20 mg/kg ATB200 plus 10 mg/kg miglustat progressively increased functional muscle strength in Gaa KO mice from baseline as measured by both grip strength and wire hang tests (FIGS. 33A-33B).

Figure 35:
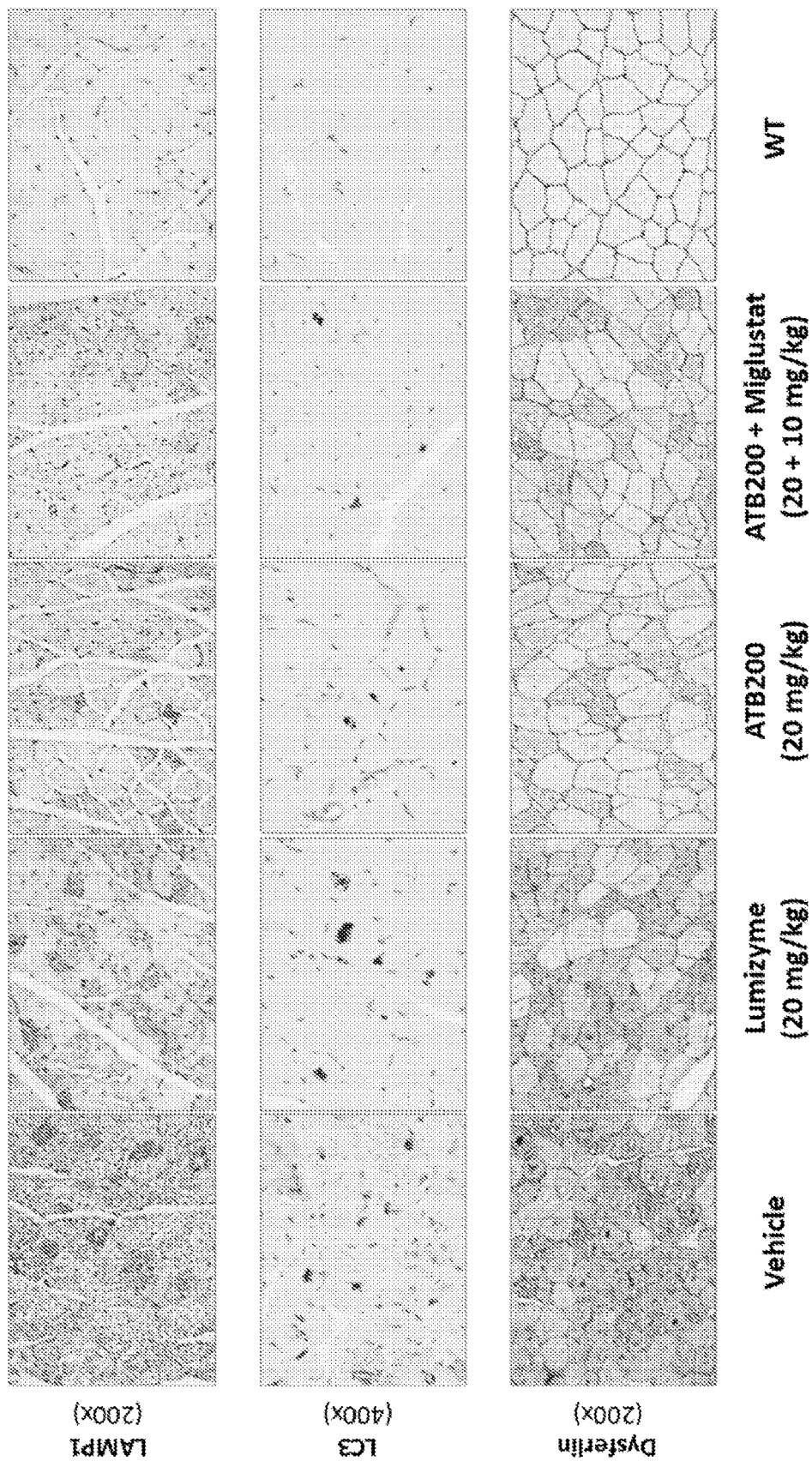
FIG. 35 is a series of photomicrographs of muscle fibers of VL/VM from wild-type and Gaa-knockout mice treated with vehicle, alglucosidase alfa and ATB200 in the presence and absence of miglustat, showing LAMP1, LC3 and dysferlin IHC signals.

Alglucosidase alfa (Lumizyme®)-treated mice receiving the same ERT dose (20 mg/kg) were observed to decline under identical conditions throughout most of the study (FIGS. 33A-33B). As with the shorter-term study, ATB200/miglustat had substantially better glycogen clearance after 3 months (FIGS. 34A-34C) and 6 months (FIGS. 34D-G) of treatment than alglucosidase alfa. ATB200/miglustat also reduced autophagy and intracellular accumulation of LAMP1 and dysferlin after 3 months of treatment (FIG. 35) compared to alglucosidase alfa. In FIG. 33A, * indicates statistically significant compared to Lumizyme® alone ($p<0.05$, 2-sided t-test). In FIGS. 34A-34G, * indicates statistically significant compared to Lumizyme® alone ($p<0.05$, multiple comparison using Dunnett's method under one-way ANOVA analysis).

Taken together, these data indicate that ATB200/miglustat was efficiently targeted to muscles to reverse cellular dysfunction and improve muscle function. Importantly, the apparent improvements in muscle architecture and reduced autophagy and intracellular accumulation of LAMP1 and dysferlin may be good surrogates for improved muscle physiology that correlate with improvements in functional muscle strength. These results suggest that monitoring autophagy and these key muscle proteins may be a rational, practical method to assess the effectiveness therapeutic treatments for Pompe disease in Gaa KO mice that may prove to be useful biomarkers from muscle biopsies in clinical studies.

Figure 40:
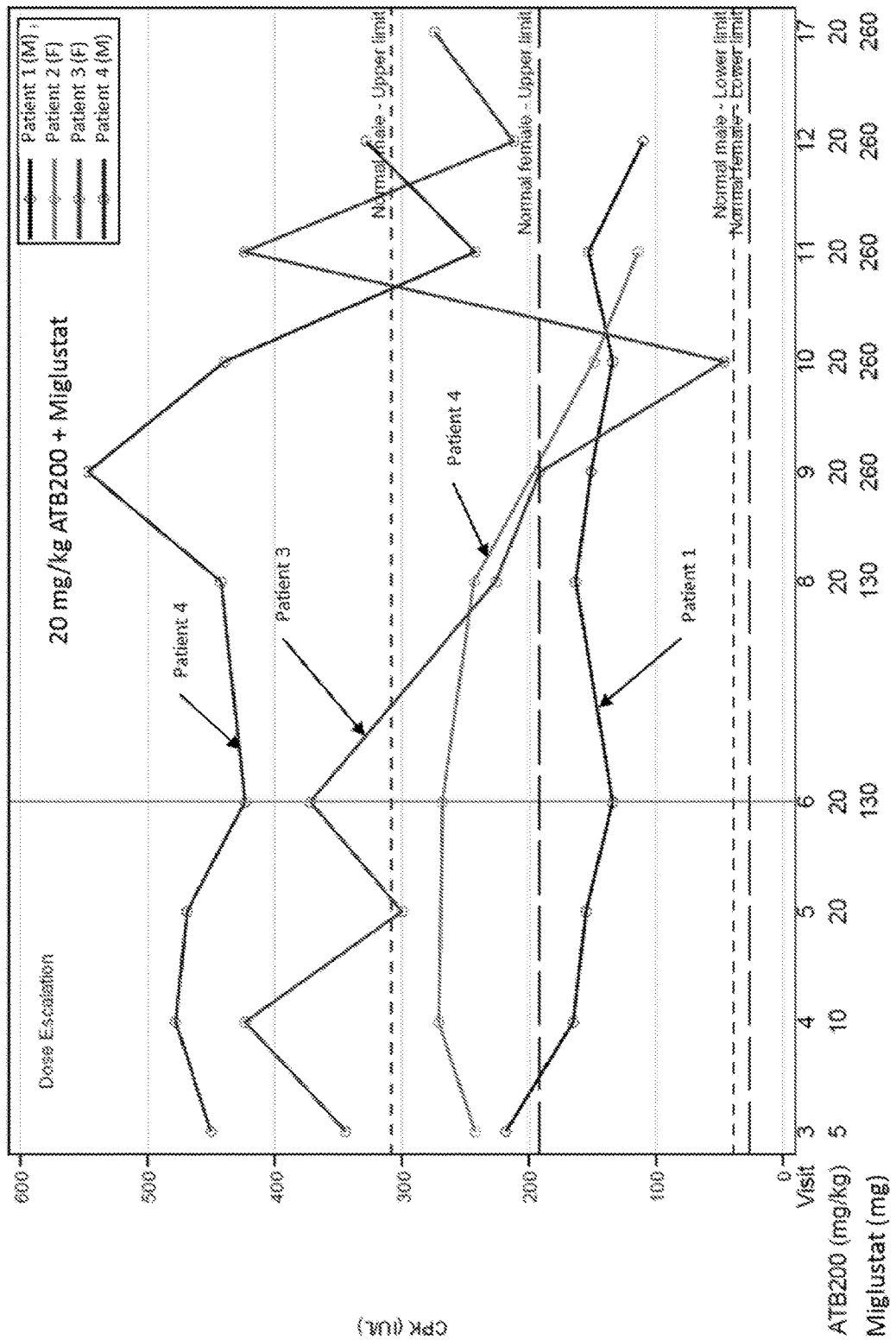
FIG. 40 is a graph showing creatine phosphokinase (CPK) levels in human patients after administration of ascending doses of ATB200 (5, 10 and 20 mg/kg) followed by co-administration of ATB200 (20 mg/kg) and miglustat (130 and 260 mg)
Figure 41:
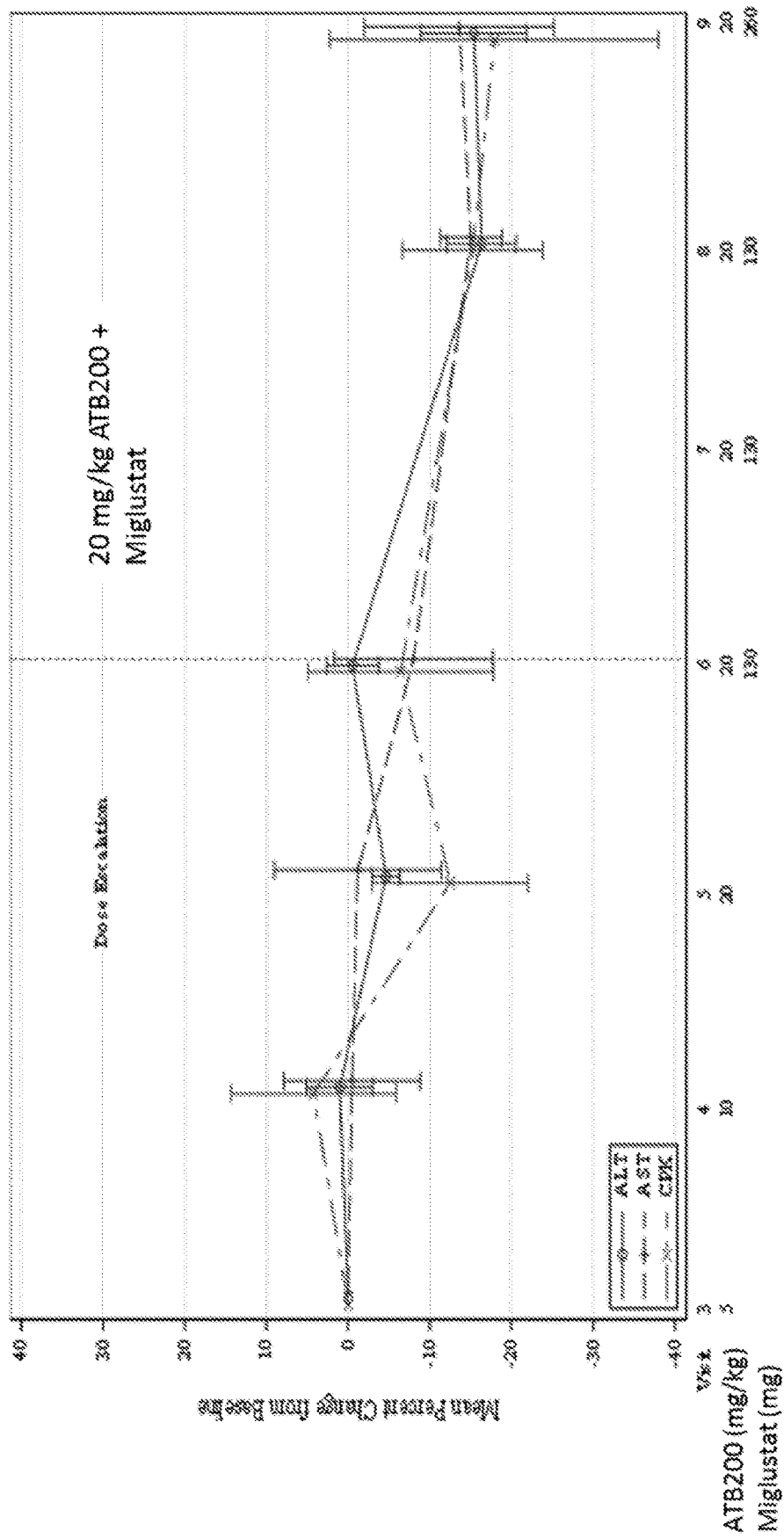
FIG. 41 is a graph showing average ALT, AST and CPK levels in human patients after administration of ascending doses of ATB200 (5, 10 and 20 mg/kg) followed by co-administration of ATB200 (20 mg/kg) and miglustat (130 and 260 mg)
Figure 42:
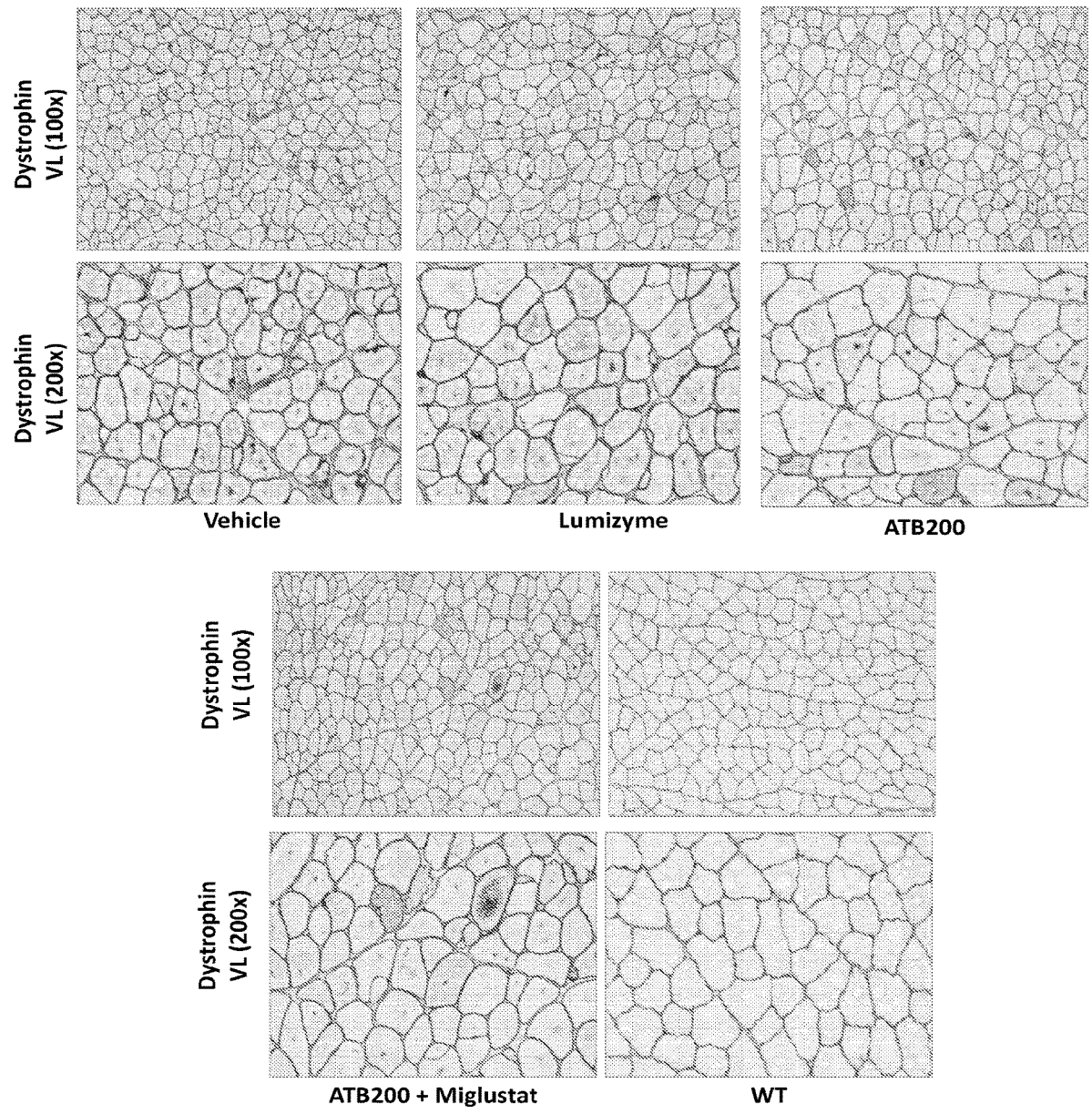
FIG. 42 is a series of photomicrographs (100× and 200×) of muscle fibers of vastus lateralis (VL) from wild-type and Gaa-knockout mice treated with vehicle, alglucosidase alfa and ATB200 in the presence and absence of miglustat, showing dystrophin signals.

FIG. 40 shows that 6 months of ATB200 administration with or without miglustat lowered intracellular accumulation of dystrophin in Gaa KO mice. There was a greater reduction for dystrophin accumulation for ATB200±miglustat than with Lumizyme®.

Example 18: Effect of Sialic Acid Content on ATB200 in Gaa-Knockout Mice

Two batches of ATB200 with different sialic acid content were evaluated for pharmacokinetics and efficacy in in Gaa KO mice. Table 16 provides a summary of the characteristics for the two batches.

TABLE 16

| Characteristic | Batch A | Batch B |
| --- | --- | --- |
| Sialic Acid | 4.0 mol/mol protein | 5.4 mol/mol protein |
| M6P content | 3.3 mol/mol protein | 2.9 mol/mol protein |
| Specific activity | 115831 (nmol 4 mu/mg protein/hr) | 120929 (nmol 4 mu/mg protein/hr) |
| CIMPR binding | $K_d$ = 2.7 nM | $K_d$ = 2.9 nM |

As can be seen from Table 16, Batch B had a higher sialic acid content than Batch A, but a slightly lower M6P content than Batch A.

Figure 36:
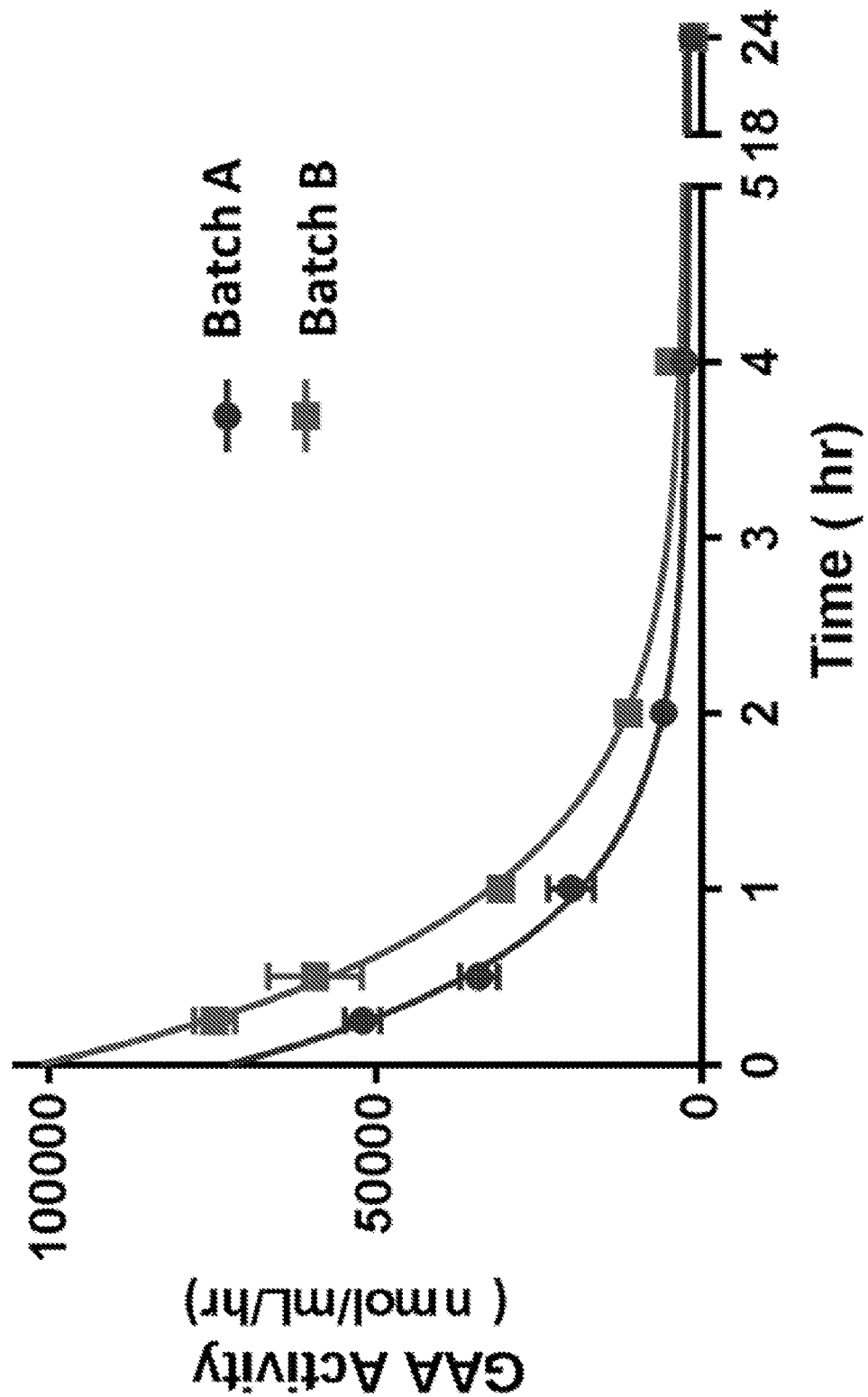
FIG. 36 is a graph showing the concentration-time profiles of GAA activity in plasma in Gaa-knockout mice after administration of two batches of ATB200 having different sialic acid content.
Figure 37A:
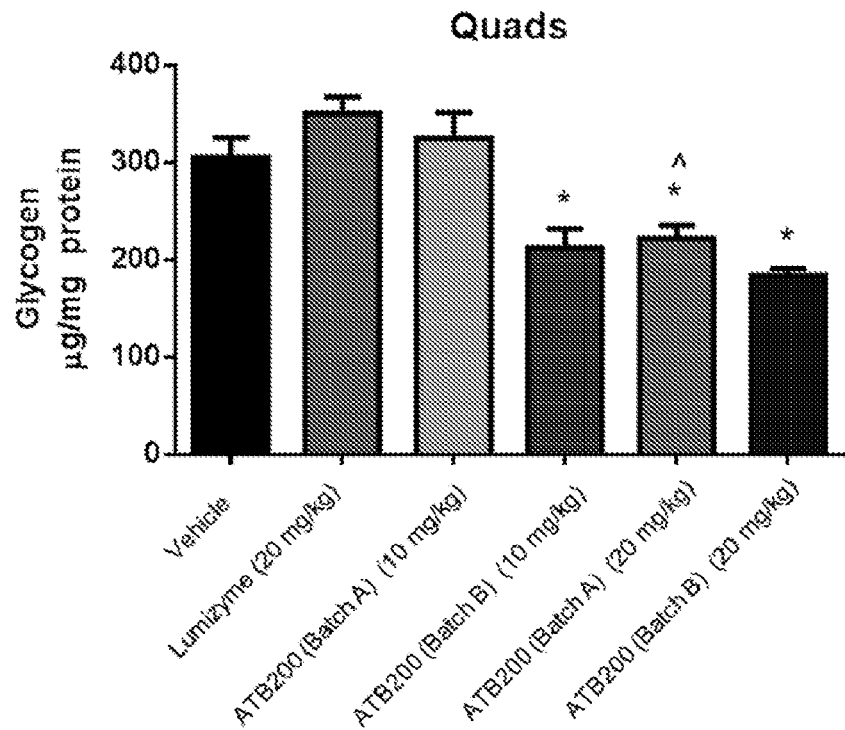
FIGS. 37A-37D are graphs showing glycogen levels in quadriceps, triceps, gastrocnemius and heart cells from wild-type and Gaa-knockout mice treated with vehicle, alglucosidase alfa and ATB200.
Figure 37B:
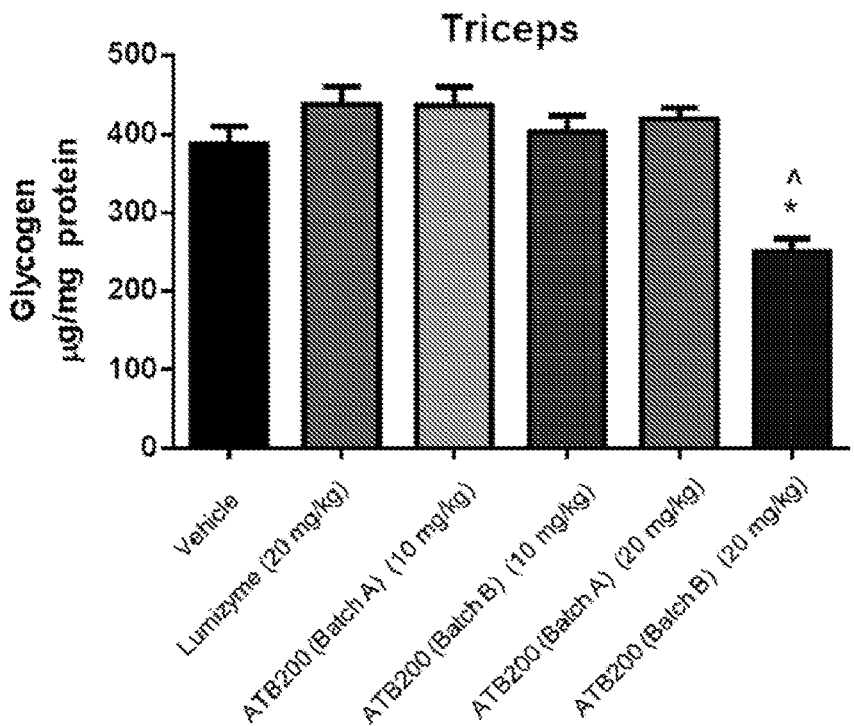
Figure 37C:
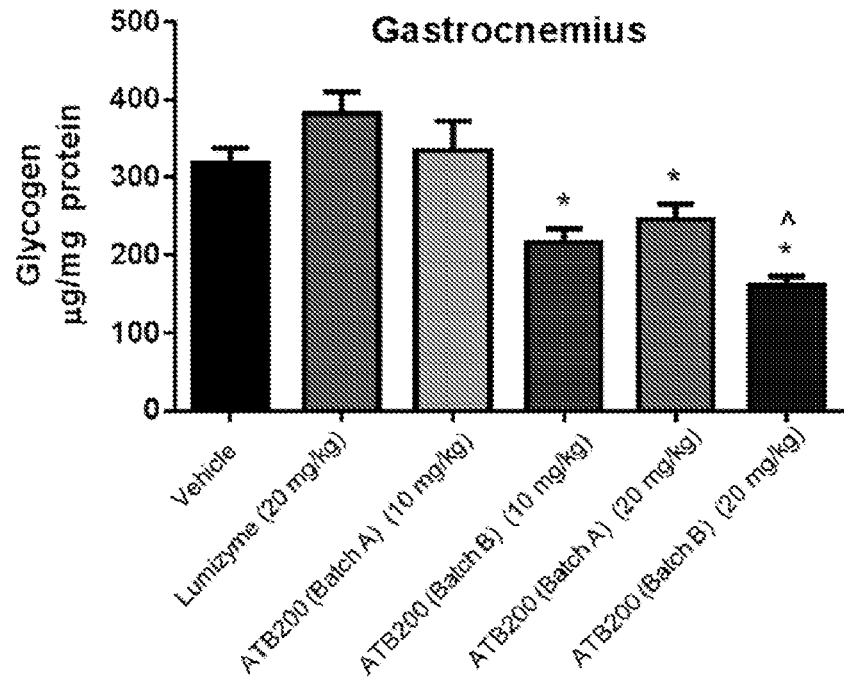
Figure 37D:
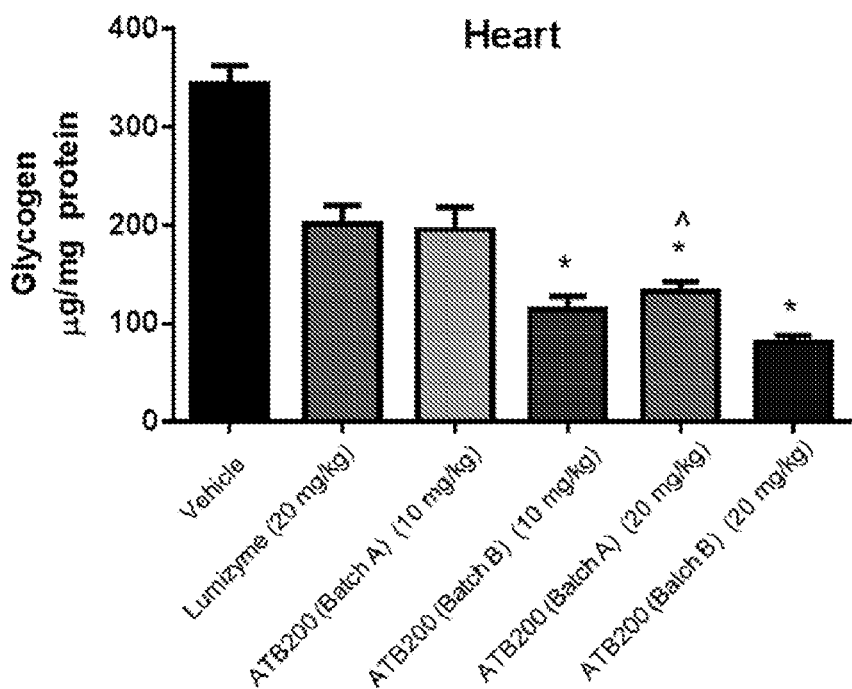
Figure 38:
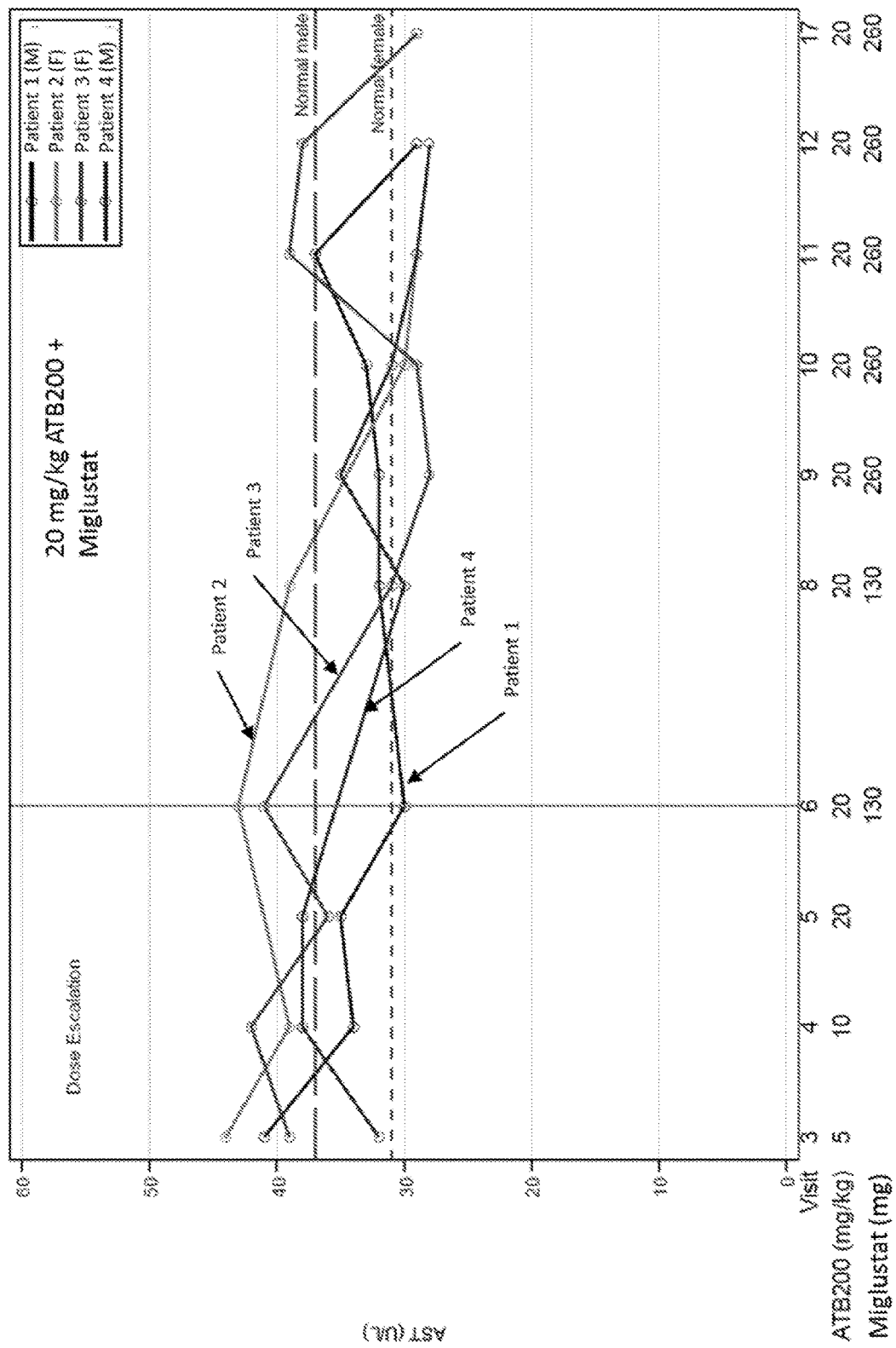
FIG. 38 is a graph showing alanine aminotransferase (ALT) levels in human patients after administration of ascending doses of ATB200 (5, 10 and 20 mg/kg) followed by co-administration of ATB200 (20 mg/kg) and miglustat (130 and 260 mg)
Figure 39:
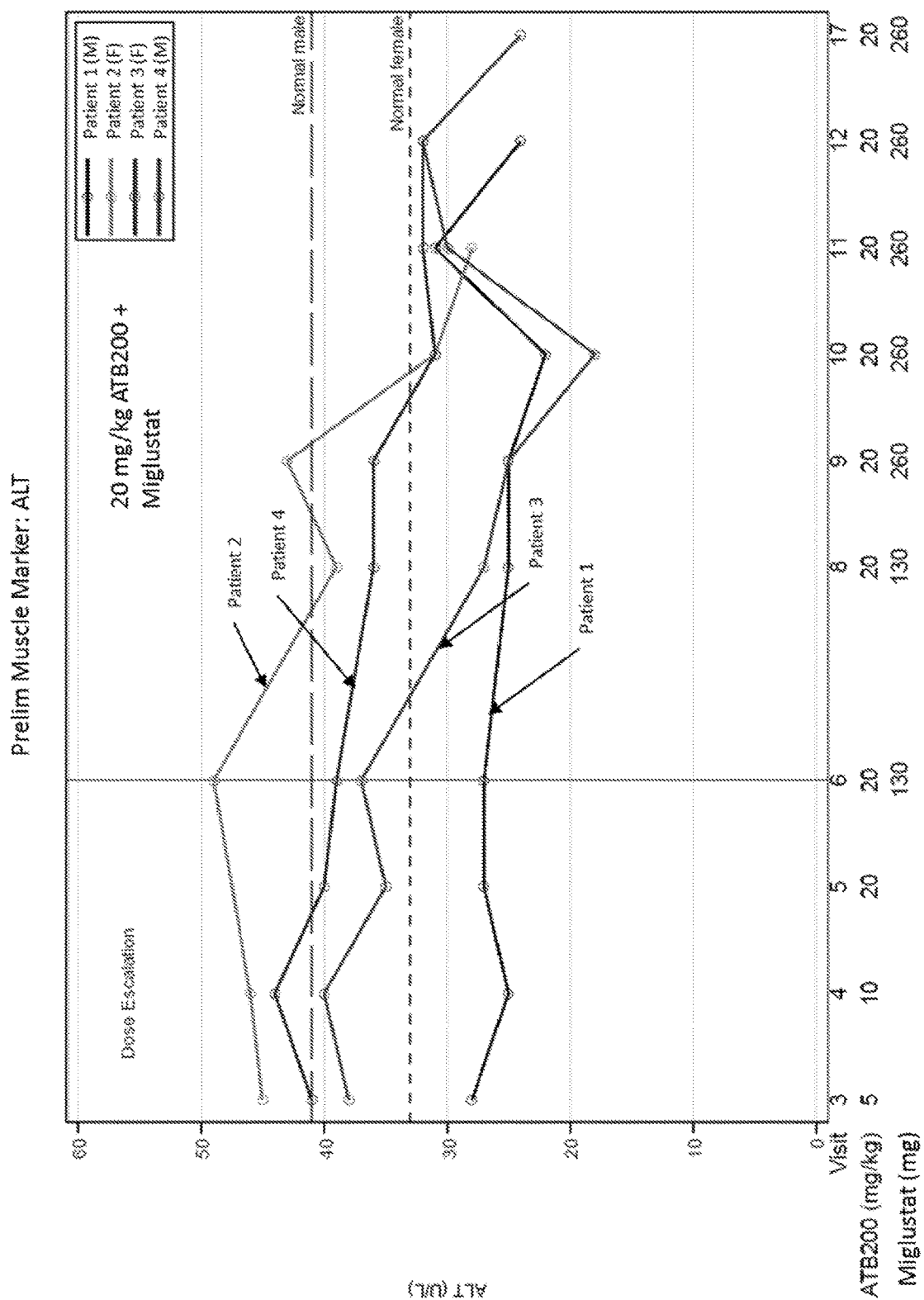
FIG. 39 is a graph showing aspartate aminotransferase (AST) levels in human patients after administration of ascending doses of ATB200 (5, 10 and 20 mg/kg) followed by co-administration of ATB200 (20 mg/kg) and miglustat (130 and 260 mg)

FIG. 36 shows the shows the concentration-time profiles of GAA activity in plasma in Gaa KO mice after a single IV bolus dosing of the ATB200. The half-life of Batches A and B are provided in Table 17 below.

TABLE 17

| Half-life (hr) | Mean ± SEM |
|---|---|
| Batch A | 0.50 ± 0.02 |
| Batch B | 0.60 ± 0.03 |

As can be seen from Table 17, Batch B had a lower half-life than Batch A. Although the decrease in half-life was modest, this decrease in half-life was statistically significant ($p<0.05$ in 2-sided t-test).

In a related study, IV bolus tail vein injections of ATB200 (Batches A and B) and Lumizyme® were given to Gaa KO mice every other week for a total of 2 injections. Glycogen levels in tissues were measured 14 days after last administration. As shown in FIGS. 37A-37D, Batch B was generally more effective in reducing glycogen than Batch A at similar doses. Both Batch A and Batch B were superior to Lumizyme® in reducing glycogen. In FIGS. 37A-37D, * indicates statistically significant compared to Lumizyme® ($p<0.05$, t-test) and ^ indicates statistically significant comparison of Batch A and Batch B at same dose ($p<0.05$, t-test).

The embodiments described herein are intended to be illustrative of the present compositions and methods and are not intended to limit the scope of the present invention. Various modifications and changes consistent with the description as a whole and which are readily apparent to the person of skill in the art are intended to be included. The appended claims should not be limited by the specific embodiments set forth in the examples, but should be given the broadest interpretation consistent with the description as a whole.

Patents, patent applications, publications, product descriptions, GenBank Accession Numbers, and protocols are cited throughout this application, the disclosures of which are incorporated herein by reference in their entireties for all purposes.

The invention claimed is:

1. A method of treating Pompe disease in a patient in need thereof, the method comprising administering miglustat to the patient in combination with a recombinant human acid α-glucosidase, wherein the recombinant human acid α-glucosidase is expressed in Chinese hamster ovary (CHO) cells and comprises an increased content of N-glycan units bearing one or two mannose-6-phosphate residues when compared to a content of N-glycan units bearing one or two mannose-6-phosphate residues of alglucosidase alfa and wherein the recombinant human acid α-alglucosidase comprises a sequence at least 95% identical to SEQ ID NO: 1 or SEQ ID NO: 5, wherein the recombinant human acid α-glucosidase is administered intravenously at a dose of about 5 mg/kg to about 20 mg/kg every week or every other week and the miglustat is administered orally at a dose of about 200 mg to about 600 mg every week or every other week.

2. The method according to claim 1 wherein at least 30% of molecules of the recombinant human acid α-glucosidase comprise one or more N-glycan units bearing one or two mannose-6-phosphate residues.

3. The method according to claim 1 wherein the recombinant human acid α-glucosidase comprises on average from 0.5 to 7.0 moles of N-glycan units bearing one or two mannose-6-phosphate residues per mole of recombinant human acid α-glucosidase.

4. The method according to claim 1 wherein the recombinant human acid α-glucosidase comprises on average at least 2.5 moles of mannose-6-phosphate residues per mole of recombinant human acid α-glucosidase and at least 4 moles of sialic acid residues per mole of recombinant human acid α-glucosidase.

5. The method according to claim 1 wherein the recombinant human acid α-glucosidase comprises seven potential N-glycosylation sites, at least 50% of molecules of the recombinant human acid α-glucosidase comprise an N-glycan unit bearing two mannose-6-phosphate residues at the first site, at least 30% of molecules of the recombinant human acid α-glucosidase comprise an N-glycan unit bearing one mannose-6-phosphate residue at the second site, at least 30% of molecules of the recombinant human acid α-glucosidase comprise an N-glycan unit bearing two mannose-6-phosphate residue at the fourth site, and at least 20% of molecules of the recombinant human acid α-glucosidase comprise an N-glycan unit bearing one mannose-6-phosphate residue at the fourth site.

6. The method according to claim 1 wherein the miglustat is administered prior to administration of the recombinant human acid α-glucosidase.

7. The method according to claim 6 wherein the miglustat is administered about one hour prior to administration of the recombinant human acid α-glucosidase.

8. The method according to claim 1 wherein the recombinant human acid α-glucosidase is administered intravenously at a dose of about 5 mg/kg to about 20 mg/kg every other week and the miglustat is administered orally at a dose of about 233 mg to about 500 mg every other week.

9. The method according to claim 1 wherein the recombinant human acid α-glucosidase is administered intravenously at a dose of about 5 mg/kg to about 20 mg/kg every other week and the miglustat is administered orally at a dose of about 50 mg to about 200 mg every other week.

10. The method according to claim 1 wherein the recombinant human acid α-glucosidase is administered intravenously at a dose of about 20 mg/kg every other week and the miglustat is administered orally at a dose of about 260 mg every other week.

11. The method according to claim 10 wherein the miglustat is administered prior to administration of the recombinant human acid α-glucosidase.

12. The method according to claim 11 wherein the miglustat is administered about one hour prior to administration of the recombinant human acid α-glucosidase.

13. The method according to claim 1 wherein the recombinant human acid α-glucosidase has a shorter half-life than alglucosidase alfa in the plasma of the patient.

14. The method according to claim 13 wherein the half-life of recombinant human acid α-glucosidase is 20-30% shorter than alglucosidase alfa in the plasma of the patient.

15. The method according to claim 13 wherein the half-life of recombinant human acid α-glucosidase is about 25% shorter than alglucosidase alfa in the plasma of the patient.

16. The method according to claim 1 wherein the recombinant human acid α-glucosidase on average has at least one more mole of N-glycan units bearing two mannose-6-phosphate residues per compared to alglucosidase alfa.

17. The method according to claim 1 wherein the recombinant human acid α-glucosidase on average has about 1.2 more moles of N-glycan units bearing two mannose-6-phosphate residues per compared to alglucosidase alfa.

18. The method according to claim 1 wherein the recombinant human acid α-glucosidase induces a lower incidence of anti-drug antibodies than alglucosidase alfa in the patient.

19. The method according to claim 1 wherein the recombinant human acid α-glucosidase reduces glycogen in muscle tissues more effectively than alglucosidase alfa.

20. The method according to claim 19 wherein the recombinant human acid α-glucosidase is administered at a dose of 10-20 mg/kg every other week.

21. The method according to claim 1 wherein the recombinant human acid α-glucosidase reduces vacuoles in muscle fibers more effectively than alglucosidase alfa.

22. The method according to claim 1 wherein the recombinant human acid α-glucosidase clears lysosomal glycogen more effectively than alglucosidase alfa in the patient.

23. The method according to claim 1 wherein the recombinant human acid α-glucosidase increases muscle function more efficiently than alglucosidase alfa.

24. The method according to claim 1 wherein the recombinant human acid α-glucosidase internalizes into muscle fibroblasts more efficiently than alglucosidase alfa.

25. The method according to claim 1 wherein the recombinant human acid α-glucosidase reduces lysosomal proliferation more efficiently than alglucosidase alfa.

26. The method according to claim 1 wherein the recombinant human acid α-glucosidase binds cation-independent mannose-6-phosphate receptor to a greater degree than alglucosidase alfa.

27. The method according to claim 26 wherein at least about 43% more of the recombinant human acid α-glucosidase binds cation-independent mannose-6-phosphate receptor than alglucosidase alfa.

28. The method according to claim 1, wherein at least 3% of the total glycans on the recombinant human acid α-glucosidase are bis-M6P glycans.

29. The method according to claim 1 wherein the recombinant human acid α-glucosidase comprises on average at least 1 mol bis-M6P per mol recombinant human acid α-glucosidase.

30. The method according to claim 1 wherein the recombinant human acid α-glucosidase comprises on average 1.3 mol bis-M6P per mol recombinant human acid α-glucosidase.

31. The method according to claim 1 wherein at least 17% of the total glycans on the recombinant human acid α-glucosidase are bis-M6P.

32. The method according to claim 1 wherein 3% to 25% of the total glycans on the recombinant human acid α-glucosidase are bis-M6P.

33. The method according to claim 1 wherein 17% to 25% of the total glycans on the recombinant human acid α-glucosidase are bis-M6P.

* * * * *

SEQUENCE LISTING

```
<160> NUMBER OF SEQ ID NOS: 6

<210> SEQ ID NO 1
<211> LENGTH: 952
<212> TYPE: PRT
<213> ORGANISM: Homo sapiens

<400> SEQUENCE: 1

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro Arg Val His Ser Arg Ala Pro Ser Pro Leu
        195                 200                 205

Tyr Ser Val Glu Phe Ser Glu Glu Pro Phe Gly Val Ile Val His Arg
    210                 215                 220
```

```
Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
            245                 250                 255

Ile Thr Gly Leu Ala Glu His Leu Ser Pro Leu Met Leu Ser Thr Ser
        260                 265                 270

Trp Thr Arg Ile Thr Leu Trp Asn Arg Asp Leu Ala Pro Thr Pro Gly
    275                 280                 285

Ala Asn Leu Tyr Gly Ser His Pro Phe Tyr Leu Ala Leu Glu Asp Gly
290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Pro Tyr Asp Glu Gly Leu Arg Arg
450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
        515                 520                 525

Ser Glu Asp Gly Cys Pro Asn Asn Glu Leu Glu Asn Pro Pro Tyr Val
530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
610                 615                 620

Ala Ser Ser Val Pro Glu Ile Leu Gln Phe Asn Leu Leu Gly Val Pro
625                 630                 635                 640
```

```
Leu Val Gly Ala Asp Val Cys Gly Phe Leu Gly Asn Thr Ser Glu
                    645                 650                 655
Leu Cys Val Arg Trp Thr Gln Leu Gly Ala Phe Tyr Pro Phe Met Arg
            660                 665                 670
Asn His Asn Ser Leu Leu Ser Leu Pro Gln Glu Pro Tyr Ser Phe Ser
            675                 680                 685
Glu Pro Ala Gln Gln Ala Met Arg Lys Ala Leu Thr Leu Arg Tyr Ala
        690                 695                 700
Leu Leu Pro His Leu Tyr Thr Leu Phe His Gln Ala His Val Ala Gly
705                 710                 715                 720
Glu Thr Val Ala Arg Pro Leu Phe Leu Glu Phe Pro Lys Asp Ser Ser
                725                 730                 735
Thr Trp Thr Val Asp His Gln Leu Leu Trp Gly Glu Ala Leu Leu Ile
                740                 745                 750
Thr Pro Val Leu Gln Ala Gly Lys Ala Glu Val Thr Gly Tyr Phe Pro
            755                 760                 765
Leu Gly Thr Trp Tyr Asp Leu Gln Thr Val Pro Ile Glu Ala Leu Gly
        770                 775                 780
Ser Leu Pro Pro Pro Ala Ala Pro Arg Glu Pro Ala Ile His Ser
785                 790                 795                 800
Glu Gly Gln Trp Val Thr Leu Pro Ala Pro Leu Asp Thr Ile Asn Val
                805                 810                 815
His Leu Arg Ala Gly Tyr Ile Ile Pro Leu Gln Gly Pro Gly Leu Thr
            820                 825                 830
Thr Thr Glu Ser Arg Gln Gln Pro Met Ala Leu Ala Val Ala Leu Thr
        835                 840                 845
Lys Gly Gly Glu Ala Arg Gly Glu Leu Phe Trp Asp Asp Gly Glu Ser
850                 855                 860
Leu Glu Val Leu Glu Arg Gly Ala Tyr Thr Gln Val Ile Phe Leu Ala
865                 870                 875                 880
Arg Asn Asn Thr Ile Val Asn Glu Leu Val Arg Val Thr Ser Glu Gly
                885                 890                 895
Ala Gly Leu Gln Leu Gln Lys Val Thr Val Leu Gly Val Ala Thr Ala
            900                 905                 910
Pro Gln Gln Val Leu Ser Asn Gly Val Pro Val Ser Asn Phe Thr Tyr
        915                 920                 925
Ser Pro Asp Thr Lys Val Leu Asp Ile Cys Val Ser Leu Leu Met Gly
        930                 935                 940
Glu Gln Phe Leu Val Ser Trp Cys
945                 950

<210> SEQ ID NO 2
<211> LENGTH: 3624
<212> TYPE: DNA
<213> ORGANISM: Homo sapiens
<220> FEATURE:
<221> NAME/KEY: CDS
<222> LOCATION: (220)..(3075)
<220> FEATURE:
<221> NAME/KEY: mRNA
<222> LOCATION: (221)..(3075)

<400> SEQUENCE: 2
cagttgggaa agctgaggtt gtcgccgggg ccgcgggtgg aggtcgggga tgaggcagca      60
ggtaggacag tgacctcggt gacgcgaagg accccggcca cctctaggtt ctcctcgtcc     120
gcccgttgtt cagcgaggga ggctctgggc ctgccgcagc tgacggggaa actgaggcac     180
```

```
ggagcgggcc tgtaggagct gtccaggcca tctccaacc atg gga gtg agg cac         234
                                           Met Gly Val Arg His
                                           1               5 ccg ccc tgc tcc cac cgg ctc ctg gcc gtc tgc gcc ctc gtg tcc ttg        282
Pro Pro Cys Ser His Arg Leu Leu Ala Val Cys Ala Leu Val Ser Leu
                10              15                  20 gca acc gct gca ctc ctg ggg cac atc cta ctc cat gat ttc ctg ctg        330
Ala Thr Ala Ala Leu Leu Gly His Ile Leu Leu His Asp Phe Leu Leu
            25              30                  35 gtt ccc cga gag ctg agt ggc tcc tcc cca gtc ctg gag gag act cac        378
Val Pro Arg Glu Leu Ser Gly Ser Ser Pro Val Leu Glu Glu Thr His
        40              45                  50 cca gct cac cag cag gga gcc agc aga cca ggg ccc cgg gat gcc cag        426
Pro Ala His Gln Gln Gly Ala Ser Arg Pro Gly Pro Arg Asp Ala Gln
    55              60                  65 gca cac ccc ggc cgt ccc aga gca gtg ccc aca cag tgc gac gtc ccc        474
Ala His Pro Gly Arg Pro Arg Ala Val Pro Thr Gln Cys Asp Val Pro
70              75                  80                  85 ccc aac agc cgc ttc gat tgc gcc cct gac aag gcc atc acc cag gaa        522
Pro Asn Ser Arg Phe Asp Cys Ala Pro Asp Lys Ala Ile Thr Gln Glu
            90                  95                  100 cag tgc gag gcc cgc ggc tgc tgc tac atc cct gca aag cag ggg ctg        570
Gln Cys Glu Ala Arg Gly Cys Cys Tyr Ile Pro Ala Lys Gln Gly Leu
        105                 110                 115 cag gga gcc cag atg ggg cag ccc tgg tgc ttc ttc cca ccc agc tac        618
Gln Gly Ala Gln Met Gly Gln Pro Trp Cys Phe Phe Pro Pro Ser Tyr
    120                 125                 130 ccc agc tac aag ctg gag aac ctg agc tcc tct gaa atg ggc tac acg        666
Pro Ser Tyr Lys Leu Glu Asn Leu Ser Ser Ser Glu Met Gly Tyr Thr
135                 140                 145 gcc acc ctg acc cgt acc acc ccc acc ttc ttc ccc aag gac atc ctg        714
Ala Thr Leu Thr Arg Thr Thr Pro Thr Phe Phe Pro Lys Asp Ile Leu
150                 155                 160                 165 acc ctg cgg ctg gac gtg atg atg gag act gag aac cgc ctc cac ttc        762
Thr Leu Arg Leu Asp Val Met Met Glu Thr Glu Asn Arg Leu His Phe
            170                 175                 180 acg atc aaa gat cca gct aac agg cgc tac gag gtg ccc ttg gag acc        810
Thr Ile Lys Asp Pro Ala Asn Arg Arg Tyr Glu Val Pro Leu Glu Thr
        185                 190                 195 ccg cgt gtc cac agc cgg gca ccg tcc cca ctc tac agc gtg gag ttc        858
Pro Arg Val His Ser Arg Ala Pro Ser Pro Leu Tyr Ser Val Glu Phe
    200                 205                 210 tcc gag gag ccc ttc ggg gtg atc gtg cac cgg cag ctg gac ggc cgc        906
Ser Glu Glu Pro Phe Gly Val Ile Val His Arg Gln Leu Asp Gly Arg
215                 220                 225 gtg ctg ctg aac acg acg gtg gcg ccc ctg ttc ttt gcg gac cag ttc        954
Val Leu Leu Asn Thr Thr Val Ala Pro Leu Phe Phe Ala Asp Gln Phe
230                 235                 240                 245 ctt cag ctg tcc acc tcg ctg ccc tcg cag tat atc aca ggc ctc gcc       1002
Leu Gln Leu Ser Thr Ser Leu Pro Ser Gln Tyr Ile Thr Gly Leu Ala
            250                 255                 260 gag cac ctc agt ccc ctg atg ctc agc acc agc tgg acc agg atc acc       1050
Glu His Leu Ser Pro Leu Met Leu Ser Thr Ser Trp Thr Arg Ile Thr
        265                 270                 275 ctg tgg aac cgg gac ctt gcg ccc acg ccc ggt gcg aac ctc tac ggg       1098
Leu Trp Asn Arg Asp Leu Ala Pro Thr Pro Gly Ala Asn Leu Tyr Gly
    280                 285                 290 tct cac cct ttc tac ctg gcg ctg gag gac ggc ggg tcg gca cac ggg       1146
Ser His Pro Phe Tyr Leu Ala Leu Glu Asp Gly Gly Ser Ala His Gly
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 295 |     |     |     |     | 300 |     |     |     |     | 305 |     |     |      |
| gtg | ttc | ctg | cta | aac | agc | aat | gcc | atg | gat | gtg | gtc | ctg | cag | ccg | agc | 1194 |
| Val | Phe | Leu | Leu | Asn | Ser | Asn | Ala | Met | Asp | Val | Val | Leu | Gln | Pro | Ser |      |
| 310 |     |     |     |     | 315 |     |     |     |     | 320 |     |     |     |     | 325 |      |
| cct | gcc | ctt | agc | tgg | agg | tcg | aca | ggt | ggg | atc | ctg | gat | gtc | tac | atc | 1242 |
| Pro | Ala | Leu | Ser | Trp | Arg | Ser | Thr | Gly | Gly | Ile | Leu | Asp | Val | Tyr | Ile |      |
|     |     |     |     |     | 330 |     |     |     |     | 335 |     |     |     |     | 340 |      |
| ttc | ctg | ggc | cca | gag | ccc | aag | agc | gtg | gtg | cag | cag | tac | ctg | gac | gtt | 1290 |
| Phe | Leu | Gly | Pro | Glu | Pro | Lys | Ser | Val | Val | Gln | Gln | Tyr | Leu | Asp | Val |      |
|     |     |     |     | 345 |     |     |     |     | 350 |     |     |     |     | 355 |     |      |
| gtg | gga | tac | ccg | ttc | atg | ccg | cca | tac | tgg | ggc | ctg | ggc | ttc | cac | ctg | 1338 |
| Val | Gly | Tyr | Pro | Phe | Met | Pro | Pro | Tyr | Trp | Gly | Leu | Gly | Phe | His | Leu |      |
|     |     |     | 360 |     |     |     |     | 365 |     |     |     |     | 370 |     |     |      |
| tgc | cgc | tgg | ggc | tac | tcc | tcc | acc | gct | atc | acc | cgc | cag | gtg | gtg | gag | 1386 |
| Cys | Arg | Trp | Gly | Tyr | Ser | Ser | Thr | Ala | Ile | Thr | Arg | Gln | Val | Val | Glu |      |
| 375 |     |     |     |     | 380 |     |     |     |     | 385 |     |     |     |     |     |      |
| aac | atg | acc | agg | gcc | cac | ttc | ccc | ctg | gac | gtc | caa | tgg | aac | gac | ctg | 1434 |
| Asn | Met | Thr | Arg | Ala | His | Phe | Pro | Leu | Asp | Val | Gln | Trp | Asn | Asp | Leu |      |
| 390 |     |     |     |     | 395 |     |     |     |     | 400 |     |     |     |     | 405 |      |
| gac | tac | atg | gac | tcc | cgg | agg | gac | ttc | acg | ttc | aac | aag | gat | ggc | ttc | 1482 |
| Asp | Tyr | Met | Asp | Ser | Arg | Arg | Asp | Phe | Thr | Phe | Asn | Lys | Asp | Gly | Phe |      |
|     |     |     |     |     |     | 410 |     |     |     |     | 415 |     |     |     | 420 |      |
| cgg | gac | ttc | ccg | gcc | atg | gtg | cag | gag | ctg | cac | cag | ggc | ggc | cgg | cgc | 1530 |
| Arg | Asp | Phe | Pro | Ala | Met | Val | Gln | Glu | Leu | His | Gln | Gly | Gly | Arg | Arg |      |
|     |     | 425 |     |     |     |     | 430 |     |     |     |     | 435 |     |     |     |      |
| tac | atg | atg | atc | gtg | gat | cct | gcc | atc | agc | agc | tcg | ggc | cct | gcc | ggg | 1578 |
| Tyr | Met | Met | Ile | Val | Asp | Pro | Ala | Ile | Ser | Ser | Ser | Gly | Pro | Ala | Gly |      |
|     |     | 440 |     |     |     |     | 445 |     |     |     |     | 450 |     |     |     |      |
| agc | tac | agg | ccc | tac | gac | gag | ggt | ctg | cgg | agg | ggg | gtt | ttc | atc | acc | 1626 |
| Ser | Tyr | Arg | Pro | Tyr | Asp | Glu | Gly | Leu | Arg | Arg | Gly | Val | Phe | Ile | Thr |      |
|     | 455 |     |     |     |     | 460 |     |     |     |     | 465 |     |     |     |     |      |
| aac | gag | acc | ggc | cag | ccg | ctg | att | ggg | aag | gta | tgg | ccc | ggg | tcc | act | 1674 |
| Asn | Glu | Thr | Gly | Gln | Pro | Leu | Ile | Gly | Lys | Val | Trp | Pro | Gly | Ser | Thr |      |
| 470 |     |     |     |     | 475 |     |     |     |     | 480 |     |     |     |     | 485 |      |
| gcc | ttc | ccc | gac | ttc | acc | aac | ccc | aca | gcc | ctg | gcc | tgg | tgg | gag | gac | 1722 |
| Ala | Phe | Pro | Asp | Phe | Thr | Asn | Pro | Thr | Ala | Leu | Ala | Trp | Trp | Glu | Asp |      |
|     |     |     |     | 490 |     |     |     |     | 495 |     |     |     |     | 500 |     |      |
| atg | gtg | gct | gag | ttc | cat | gac | cag | gtg | ccc | ttc | gac | ggc | atg | tgg | att | 1770 |
| Met | Val | Ala | Glu | Phe | His | Asp | Gln | Val | Pro | Phe | Asp | Gly | Met | Trp | Ile |      |
|     |     |     | 505 |     |     |     |     | 510 |     |     |     |     | 515 |     |     |      |
| gac | atg | aac | gag | cct | tcc | aac | ttc | atc | aga | ggc | tct | gag | gac | ggc | tgc | 1818 |
| Asp | Met | Asn | Glu | Pro | Ser | Asn | Phe | Ile | Arg | Gly | Ser | Glu | Asp | Gly | Cys |      |
|     |     | 520 |     |     |     |     | 525 |     |     |     |     | 530 |     |     |     |      |
| ccc | aac | aat | gag | ctg | gag | aac | cca | ccc | tac | gtg | cct | ggg | gtg | gtt | ggg | 1866 |
| Pro | Asn | Asn | Glu | Leu | Glu | Asn | Pro | Pro | Tyr | Val | Pro | Gly | Val | Val | Gly |      |
|     | 535 |     |     |     |     | 540 |     |     |     |     | 545 |     |     |     |     |      |
| ggg | acc | ctc | cag | gcg | gcc | acc | atc | tgt | gcc | tcc | agc | cac | cag | ttt | ctc | 1914 |
| Gly | Thr | Leu | Gln | Ala | Ala | Thr | Ile | Cys | Ala | Ser | Ser | His | Gln | Phe | Leu |      |
| 550 |     |     |     |     | 555 |     |     |     |     | 560 |     |     |     |     | 565 |      |
| tcc | aca | cac | tac | aac | ctg | cac | aac | ctc | tac | ggc | ctg | acc | gaa | gcc | atc | 1962 |
| Ser | Thr | His | Tyr | Asn | Leu | His | Asn | Leu | Tyr | Gly | Leu | Thr | Glu | Ala | Ile |      |
|     |     |     |     | 570 |     |     |     |     | 575 |     |     |     |     | 580 |     |      |
| gcc | tcc | cac | agg | gcg | ctg | gtg | aag | gct | cgg | ggg | aca | cgc | cca | ttt | gtg | 2010 |
| Ala | Ser | His | Arg | Ala | Leu | Val | Lys | Ala | Arg | Gly | Thr | Arg | Pro | Phe | Val |      |
|     |     | 585 |     |     |     |     | 590 |     |     |     |     | 595 |     |     |     |      |
| atc | tcc | cgc | tcg | acc | ttt | gct | ggc | cac | ggc | cga | tac | gcc | ggc | cac | tgg | 2058 |
| Ile | Ser | Arg | Ser | Thr | Phe | Ala | Gly | His | Gly | Arg | Tyr | Ala | Gly | His | Trp |      |
|     |     | 600 |     |     |     |     | 605 |     |     |     |     | 610 |     |     |     |      |
| acg | ggg | gac | gtg | tgg | agc | tcc | tgg | gag | cag | ctc | gcc | tcc | tcc | gtg | cca | 2106 |

```
                Thr Gly Asp Val Trp Ser Ser Trp Glu Gln Leu Ala Ser Ser Val Pro
                    615                 620                 625 gaa atc ctg cag ttt aac ctg ctg ggg gtg cct ctg gtc ggg gcc gac      2154
Glu Ile Leu Gln Phe Asn Leu Leu Gly Val Pro Leu Val Gly Ala Asp
630                 635                 640                 645 gtc tgc ggc ttc ctg ggc aac acc tca gag gag ctg tgt gtg cgc tgg      2202
Val Cys Gly Phe Leu Gly Asn Thr Ser Glu Glu Leu Cys Val Arg Trp
                650                 655                 660 acc cag ctg ggg gcc ttc tac ccc ttc atg cgg aac cac aac agc ctg      2250
Thr Gln Leu Gly Ala Phe Tyr Pro Phe Met Arg Asn His Asn Ser Leu
            665                 670                 675 ctc agt ctg ccc cag gag ccg tac agc ttc agc gag ccg gcc cag cag      2298
Leu Ser Leu Pro Gln Glu Pro Tyr Ser Phe Ser Glu Pro Ala Gln Gln
        680                 685                 690 gcc atg agg aag gcc ctc acc ctg cgc tac gca ctc ctc ccc cac ctc      2346
Ala Met Arg Lys Ala Leu Thr Leu Arg Tyr Ala Leu Leu Pro His Leu
    695                 700                 705 tac aca ctg ttc cac cag gcc cac gtc gcg ggg gag acc gtg gcc cgg      2394
Tyr Thr Leu Phe His Gln Ala His Val Ala Gly Glu Thr Val Ala Arg
710                 715                 720                 725 ccc ctc ttc ctg gag ttc ccc aag gac tct agc acc tgg act gtg gac      2442
Pro Leu Phe Leu Glu Phe Pro Lys Asp Ser Ser Thr Trp Thr Val Asp
                730                 735                 740 cac cag ctc ctg tgg ggg gag gcc ctg ctc atc acc cca gtg ctc cag      2490
His Gln Leu Leu Trp Gly Glu Ala Leu Leu Ile Thr Pro Val Leu Gln
                745                 750                 755 gcc ggg aag gcc gaa gtg act ggc tac ttc ccc ttg ggc aca tgg tac      2538
Ala Gly Lys Ala Glu Val Thr Gly Tyr Phe Pro Leu Gly Thr Trp Tyr
            760                 765                 770 gac ctg cag acg gtg cca ata gag gcc ctt ggc agc ctc cca ccc cca      2586
Asp Leu Gln Thr Val Pro Ile Glu Ala Leu Gly Ser Leu Pro Pro Pro
775                 780                 785 cct gca gct ccc cgt gag cca gcc atc cac agc gag ggg cag tgg gtg      2634
Pro Ala Ala Pro Arg Glu Pro Ala Ile His Ser Glu Gly Gln Trp Val
    790                 795                 800                 805 acg ctg ccg gcc ccc ctg gac acc atc aac gtc cac ctc cgg gct ggg      2682
Thr Leu Pro Ala Pro Leu Asp Thr Ile Asn Val His Leu Arg Ala Gly
                810                 815                 820 tac atc atc ccc ctg cag ggc cct ggc ctc aca acc aca gag tcc cgc      2730
Tyr Ile Ile Pro Leu Gln Gly Pro Gly Leu Thr Thr Thr Glu Ser Arg
            825                 830                 835 cag cag ccc atg gcc ctg gct gtg gcc ctg acc aag ggt gga gag gcc      2778
Gln Gln Pro Met Ala Leu Ala Val Ala Leu Thr Lys Gly Gly Glu Ala
        840                 845                 850 cga ggg gag ctg ttc tgg gac gat gga gag agc ctg gaa gtg ctg gag      2826
Arg Gly Glu Leu Phe Trp Asp Asp Gly Glu Ser Leu Glu Val Leu Glu
    855                 860                 865 cga ggg gcc tac aca cag gtc atc ttc ctg gcc agg aat aac acg atc      2874
Arg Gly Ala Tyr Thr Gln Val Ile Phe Leu Ala Arg Asn Asn Thr Ile
870                 875                 880                 885 gtg aat gag ctg gta cgt gtg acc agt gag gga gct ggc ctg cag ctg      2922
Val Asn Glu Leu Val Arg Val Thr Ser Glu Gly Ala Gly Leu Gln Leu
                890                 895                 900 cag aag gtg act gtc ctg ggc gtg gcc acg gcg ccc cag cag gtc ctc      2970
Gln Lys Val Thr Val Leu Gly Val Ala Thr Ala Pro Gln Gln Val Leu
            905                 910                 915 tcc aac ggt gtc cct gtc tcc aac ttc acc tac agc ccc gac acc aag      3018
Ser Asn Gly Val Pro Val Ser Asn Phe Thr Tyr Ser Pro Asp Thr Lys
        920                 925                 930
```

-continued

| | |
|---|---|
| gtc ctg gac atc tgt gtc tcg ctg ttg atg gga gag cag ttt ctc gtc<br>Val Leu Asp Ile Cys Val Ser Leu Leu Met Gly Glu Gln Phe Leu Val<br>935                    940                    945 | 3066 |
| agc tgg tgt tagccgggcg gagtgtgtta gtctctccag agggaggctg<br>Ser Trp Cys<br>950 | 3115 |
| gttccccagg aagcagagc ctgtgtgcgg gcagcagctg tgtgcgggcc tgggggttgc | 3175 |
| atgtgtcacc tggagctggg cactaaccat tccaagccgc cgcatcgctt gtttccacct | 3235 |
| cctgggccgg ggctctggcc cccaacgtgt ctaggagagc tttctcccta gatcgcactg | 3295 |
| tgggccgggg cctggagggc tgctctgtgt taataagatt gtaaggtttg ccctcctcac | 3355 |
| ctgttgccgg catgcgggta gtattagcca ccccccctcca tctgttccca gcaccggaga | 3415 |
| agggggtgct caggtggagg tgtggggtat gcacctgagc tcctgcttcg cgcctgctgc | 3475 |
| tctgccccaa cgcgaccgct tcccggctgc ccagagggct ggatgcctgc cggtccccga | 3535 |
| gcaagcctgg gaactcagga aaattcacag gacttgggag attctaaatc ttaagtgcaa | 3595 |
| ttattttaat aaaggggca tttggaatc | 3624 |

<210> SEQ ID NO 3
<211> LENGTH: 952
<212> TYPE: PRT
<213> ORGANISM: Homo sapiens

<400> SEQUENCE: 3

```
Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro Arg Val His Ser Arg Ala Pro Ser Pro Leu
        195                 200                 205

Tyr Ser Val Glu Phe Ser Glu Glu Pro Phe Gly Val Ile Val His Arg
    210                 215                 220

Gln Leu Asp Gly Arg Val Leu Leu Asn Thr Thr Val Ala Pro Leu Phe
225                 230                 235                 240
```

-continued

```
Phe Ala Asp Gln Phe Leu Gln Leu Ser Thr Ser Leu Pro Ser Gln Tyr
                245                 250                 255
Ile Thr Gly Leu Ala Glu His Leu Ser Pro Leu Met Leu Ser Thr Ser
            260                 265                 270
Trp Thr Arg Ile Thr Leu Trp Asn Arg Asp Leu Ala Pro Thr Pro Gly
        275                 280                 285
Ala Asn Leu Tyr Gly Ser His Pro Phe Tyr Leu Ala Leu Glu Asp Gly
    290                 295                 300
Gly Ser Ala His Gly Val Phe Leu Leu Asn Ser Asn Ala Met Asp Val
305                 310                 315                 320
Val Leu Gln Pro Ser Pro Ala Leu Ser Trp Arg Ser Thr Gly Gly Ile
                325                 330                 335
Leu Asp Val Tyr Ile Phe Leu Gly Pro Glu Pro Lys Ser Val Val Gln
            340                 345                 350
Gln Tyr Leu Asp Val Val Gly Tyr Pro Phe Met Pro Pro Tyr Trp Gly
        355                 360                 365
Leu Gly Phe His Leu Cys Arg Trp Gly Tyr Ser Ser Thr Ala Ile Thr
    370                 375                 380
Arg Gln Val Val Glu Asn Met Thr Arg Ala His Phe Pro Leu Asp Val
385                 390                 395                 400
Gln Trp Asn Asp Leu Asp Tyr Met Asp Ser Arg Arg Asp Phe Thr Phe
                405                 410                 415
Asn Lys Asp Gly Phe Arg Asp Phe Pro Ala Met Val Gln Glu Leu His
            420                 425                 430
Gln Gly Gly Arg Arg Tyr Met Met Ile Val Asp Pro Ala Ile Ser Ser
        435                 440                 445
Ser Gly Pro Ala Gly Ser Tyr Arg Pro Tyr Asp Glu Gly Leu Arg Arg
    450                 455                 460
Gly Val Phe Ile Thr Asn Glu Thr Gly Gln Pro Leu Ile Gly Lys Val
465                 470                 475                 480
Trp Pro Gly Ser Thr Ala Phe Pro Asp Phe Thr Asn Pro Thr Ala Leu
                485                 490                 495
Ala Trp Trp Glu Asp Met Val Ala Glu Phe His Asp Gln Val Pro Phe
            500                 505                 510
Asp Gly Met Trp Ile Asp Met Asn Glu Pro Ser Asn Phe Ile Arg Gly
        515                 520                 525
Ser Glu Asp Gly Cys Pro Asn Asn Glu Leu Glu Asn Pro Pro Tyr Val
    530                 535                 540
Pro Gly Val Val Gly Gly Thr Leu Gln Ala Ala Thr Ile Cys Ala Ser
545                 550                 555                 560
Ser His Gln Phe Leu Ser Thr His Tyr Asn Leu His Asn Leu Tyr Gly
                565                 570                 575
Leu Thr Glu Ala Ile Ala Ser His Arg Ala Leu Val Lys Ala Arg Gly
            580                 585                 590
Thr Arg Pro Phe Val Ile Ser Arg Ser Thr Phe Ala Gly His Gly Arg
        595                 600                 605
Tyr Ala Gly His Trp Thr Gly Asp Val Trp Ser Ser Trp Glu Gln Leu
    610                 615                 620
Ala Ser Ser Val Pro Glu Ile Leu Gln Phe Asn Leu Leu Gly Val Pro
625                 630                 635                 640
Leu Val Gly Ala Asp Val Cys Gly Phe Leu Gly Asn Thr Ser Glu Glu
                645                 650                 655
Leu Cys Val Arg Trp Thr Gln Leu Gly Ala Phe Tyr Pro Phe Met Arg
```

```
                    660                 665                 670
Asn His Asn Ser Leu Leu Ser Leu Pro Gln Glu Pro Tyr Ser Phe Ser
                675                 680                 685

Glu Pro Ala Gln Gln Ala Met Arg Lys Ala Leu Thr Leu Arg Tyr Ala
            690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Ile Glu Ala Leu Gly
    770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
        915                 920                 925

Ser Pro Asp Thr Lys Val Leu Asp Ile Cys Val Ser Leu Leu Met Gly
    930                 935                 940

Glu Gln Phe Leu Val Ser Trp Cys
945                 950

<210> SEQ ID NO 4
<211> LENGTH: 952
<212> TYPE: PRT
<213> ORGANISM: Homo sapiens

<400> SEQUENCE: 4

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80
```

-continued

```
Gln Cys Asp Val Pro Pro Asn Ser Arg Phe Asp Cys Ala Pro Asp Lys
                 85                  90                  95
Ala Ile Thr Gln Glu Gln Cys Glu Ala Arg Gly Cys Cys Tyr Ile Pro
            100                 105                 110
Ala Lys Gln Gly Leu Gln Gly Ala Gln Met Gly Gln Pro Trp Cys Phe
        115                 120                 125
Phe Pro Pro Ser Tyr Pro Ser Tyr Lys Leu Glu Asn Leu Ser Ser Ser
    130                 135                 140
Glu Met Gly Tyr Thr Ala Thr Leu Thr Arg Thr Thr Pro Thr Phe Phe
145                 150                 155                 160
Pro Lys Asp Ile Leu Thr Leu Arg Leu Asp Val Met Met Glu Thr Glu
                165                 170                 175
Asn Arg Leu His Phe Thr Ile Lys Asp Pro Ala Asn Arg Arg Tyr Glu
            180                 185                 190
Val Pro Leu Glu Thr Pro Arg Val His Ser Arg Ala Pro Ser Pro Leu
        195                 200                 205
Tyr Ser Val Glu Phe Ser Glu Glu Pro Phe Gly Val Ile Val His Arg
    210                 215                 220
Gln Leu Asp Gly Arg Val Leu Leu Asn Thr Thr Val Ala Pro Leu Phe
225                 230                 235                 240
Phe Ala Asp Gln Phe Leu Gln Leu Ser Thr Ser Leu Pro Ser Gln Tyr
                245                 250                 255
Ile Thr Gly Leu Ala Glu His Leu Ser Pro Leu Met Leu Ser Thr Ser
            260                 265                 270
Trp Thr Arg Ile Thr Leu Trp Asn Arg Asp Leu Ala Pro Thr Pro Gly
        275                 280                 285
Ala Asn Leu Tyr Gly Ser His Pro Phe Tyr Leu Ala Leu Glu Asp Gly
    290                 295                 300
Gly Ser Ala His Gly Val Phe Leu Leu Asn Ser Asn Ala Met Asp Val
305                 310                 315                 320
Val Leu Gln Pro Ser Pro Ala Leu Ser Trp Arg Ser Thr Gly Gly Ile
                325                 330                 335
Leu Asp Val Tyr Ile Phe Leu Gly Pro Glu Pro Lys Ser Val Val Gln
            340                 345                 350
Gln Tyr Leu Asp Val Val Gly Tyr Pro Phe Met Pro Pro Tyr Trp Gly
        355                 360                 365
Leu Gly Phe His Leu Cys Arg Trp Gly Tyr Ser Ser Thr Ala Ile Thr
    370                 375                 380
Arg Gln Val Val Glu Asn Met Thr Arg Ala His Phe Pro Leu Asp Val
385                 390                 395                 400
Gln Trp Asn Asp Leu Asp Tyr Met Asp Ser Arg Arg Asp Phe Thr Phe
                405                 410                 415
Asn Lys Asp Gly Phe Arg Asp Phe Pro Ala Met Val Gln Glu Leu His
            420                 425                 430
Gln Gly Gly Arg Arg Tyr Met Met Ile Val Asp Pro Ala Ile Ser Ser
        435                 440                 445
Ser Gly Pro Ala Gly Ser Tyr Arg Pro Tyr Asp Glu Gly Leu Arg Arg
    450                 455                 460
Gly Val Phe Ile Thr Asn Glu Thr Gly Gln Pro Leu Ile Gly Lys Val
465                 470                 475                 480
Trp Pro Gly Ser Thr Ala Phe Pro Asp Phe Thr Asn Pro Thr Ala Leu
                485                 490                 495
Ala Trp Trp Glu Asp Met Val Ala Glu Phe His Asp Gln Val Pro Phe
```

```
            500                 505                 510
Asp Gly Met Trp Ile Asp Met Asn Glu Pro Ser Asn Phe Ile Arg Gly
            515                 520                 525

Ser Glu Asp Gly Cys Pro Asn Asn Glu Leu Glu Asn Pro Pro Tyr Val
            530                 535             540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
            595                 600                 605

Tyr Ala Gly His Trp Thr Gly Asp Val Trp Ser Trp Glu Gln Leu
            610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
                660                 665                 670

Asn His Asn Ser Leu Leu Ser Leu Pro Gln Glu Pro Tyr Ser Phe Ser
                675                 680                 685

Glu Pro Ala Gln Gln Ala Met Arg Lys Ala Leu Thr Leu Arg Tyr Ala
            690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
            755                 760                 765

Leu Gly Thr Trp Tyr Asp Leu Gln Thr Val Pro Ile Glu Ala Leu Gly
            770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
                820                 825                 830

Thr Thr Glu Ser Arg Gln Gln Pro Met Ala Leu Ala Val Ala Leu Thr
            835                 840                 845

Lys Gly Gly Glu Ala Arg Gly Glu Leu Phe Trp Asp Asp Gly Glu Ser
            850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
            915                 920                 925
```

```
Ser Pro Asp Thr Lys Val Leu Asp Ile Cys Val Ser Leu Leu Met Gly
    930                 935                 940

Glu Gln Phe Leu Val Ser Trp Cys
945                 950

<210> SEQ ID NO 5
<211> LENGTH: 896
<212> TYPE: PRT
<213> ORGANISM: Homo sapiens

<400> SEQUENCE: 5

Gln Gln Gly Ala Ser Arg Pro Gly Pro Arg Asp Ala Gln Ala His Pro
1               5                   10                  15

Gly Arg Pro Arg Ala Val Pro Thr Gln Cys Asp Val Pro Pro Asn Ser
            20                  25                  30

Arg Phe Asp Cys Ala Pro Asp Lys Ala Ile Thr Gln Glu Gln Cys Glu
        35                  40                  45

Ala Arg Gly Cys Cys Tyr Ile Pro Ala Lys Gln Gly Leu Gln Gly Ala
    50                  55                  60

Gln Met Gly Gln Pro Trp Cys Phe Phe Pro Ser Tyr Pro Ser Tyr
65                  70                  75                  80

Lys Leu Glu Asn Leu Ser Ser Glu Met Gly Tyr Thr Ala Thr Leu
                85                  90                  95

Thr Arg Thr Thr Pro Thr Phe Phe Pro Lys Asp Ile Leu Thr Leu Arg
            100                 105                 110

Leu Asp Val Met Met Glu Thr Glu Asn Arg Leu His Phe Thr Ile Lys
        115                 120                 125

Asp Pro Ala Asn Arg Arg Tyr Glu Val Pro Leu Glu Thr Pro His Val
    130                 135                 140

His Ser Arg Ala Pro Ser Pro Leu Tyr Ser Val Glu Phe Ser Glu Glu
145                 150                 155                 160

Pro Phe Gly Val Ile Val Arg Arg Gln Leu Asp Gly Arg Val Leu Leu
                165                 170                 175

Asn Thr Thr Val Ala Pro Leu Phe Phe Ala Asp Gln Phe Leu Gln Leu
            180                 185                 190

Ser Thr Ser Leu Pro Ser Gln Tyr Ile Thr Gly Leu Ala Glu His Leu
        195                 200                 205

Ser Pro Leu Met Leu Ser Thr Ser Trp Thr Arg Ile Thr Leu Trp Asn
    210                 215                 220

Arg Asp Leu Ala Pro Thr Pro Gly Ala Asn Leu Tyr Gly Ser His Pro
225                 230                 235                 240

Phe Tyr Leu Ala Leu Glu Asp Gly Gly Ser Ala His Gly Val Phe Leu
                245                 250                 255

Leu Asn Ser Asn Ala Met Asp Val Val Leu Gln Pro Ser Pro Ala Leu
            260                 265                 270

Ser Trp Arg Ser Thr Gly Gly Ile Leu Asp Val Tyr Ile Phe Leu Gly
        275                 280                 285

Pro Glu Pro Lys Ser Val Val Gln Gln Tyr Leu Asp Val Val Gly Tyr
    290                 295                 300

Pro Phe Met Pro Pro Tyr Trp Gly Leu Gly Phe His Leu Cys Arg Trp
305                 310                 315                 320

Gly Tyr Ser Ser Thr Ala Ile Thr Arg Gln Val Val Glu Asn Met Thr
                325                 330                 335

Arg Ala His Phe Pro Leu Asp Val Gln Trp Asn Asp Leu Asp Tyr Met
```

```
                340                 345                 350
Asp Ser Arg Arg Asp Phe Thr Phe Asn Lys Asp Gly Phe Arg Asp Phe
            355                 360                 365

Pro Ala Met Val Gln Glu Leu His Gln Gly Gly Arg Arg Tyr Met Met
370                 375                 380

Ile Val Asp Pro Ala Ile Ser Ser Gly Pro Ala Gly Ser Tyr Arg
385                 390                 395                 400

Pro Tyr Asp Glu Gly Leu Arg Arg Gly Val Phe Ile Thr Asn Glu Thr
            405                 410                 415

Gly Gln Pro Leu Ile Gly Lys Val Trp Pro Gly Ser Thr Ala Phe Pro
            420                 425                 430

Asp Phe Thr Asn Pro Thr Ala Leu Ala Trp Trp Glu Asp Met Val Ala
            435                 440                 445

Glu Phe His Asp Gln Val Pro Phe Asp Gly Met Trp Ile Asp Met Asn
            450                 455                 460

Glu Pro Ser Asn Phe Ile Arg Gly Ser Glu Asp Gly Cys Pro Asn Asn
465                 470                 475                 480

Glu Leu Glu Asn Pro Pro Tyr Val Pro Gly Val Val Gly Gly Thr Leu
            485                 490                 495

Gln Ala Ala Thr Ile Cys Ala Ser Ser His Gln Phe Leu Ser Thr His
            500                 505                 510

Tyr Asn Leu His Asn Leu Tyr Gly Leu Thr Glu Ala Ile Ala Ser His
            515                 520                 525

Arg Ala Leu Val Lys Ala Arg Gly Thr Arg Pro Phe Val Ile Ser Arg
            530                 535                 540

Ser Thr Phe Ala Gly His Gly Arg Tyr Ala Gly His Trp Thr Gly Asp
545                 550                 555                 560

Val Trp Ser Ser Trp Glu Gln Leu Ala Ser Ser Val Pro Glu Ile Leu
            565                 570                 575

Gln Phe Asn Leu Leu Gly Val Pro Leu Val Gly Ala Asp Val Cys Gly
            580                 585                 590

Phe Leu Gly Asn Thr Ser Glu Glu Leu Cys Val Arg Trp Thr Gln Leu
            595                 600                 605

Gly Ala Phe Tyr Pro Phe Met Arg Asn His Asn Ser Leu Leu Ser Leu
            610                 615                 620

Pro Gln Glu Pro Tyr Ser Phe Ser Glu Pro Ala Gln Gln Ala Met Arg
625                 630                 635                 640

Lys Ala Leu Thr Leu Arg Tyr Ala Leu Leu Pro His Leu Tyr Thr Leu
            645                 650                 655

Phe His Gln Ala His Val Ala Gly Glu Thr Val Ala Arg Pro Leu Phe
            660                 665                 670

Leu Glu Phe Pro Lys Asp Ser Ser Thr Trp Thr Val Asp His Gln Leu
            675                 680                 685

Leu Trp Gly Glu Ala Leu Leu Ile Thr Pro Val Leu Gln Ala Gly Lys
            690                 695                 700

Ala Glu Val Thr Gly Tyr Phe Pro Leu Gly Thr Trp Tyr Asp Leu Gln
705                 710                 715                 720

Thr Val Pro Val Glu Ala Leu Gly Ser Leu Pro Pro Pro Ala Ala
            725                 730                 735

Pro Arg Glu Pro Ala Ile His Ser Glu Gly Gln Trp Val Thr Leu Pro
            740                 745                 750

Ala Pro Leu Asp Thr Ile Asn Val His Leu Arg Ala Gly Tyr Ile Ile
            755                 760                 765
```

```
Pro Leu Gln Gly Pro Gly Leu Thr Thr Thr Glu Ser Arg Gln Gln Pro
    770                 775                 780

Met Ala Leu Ala Val Ala Leu Thr Lys Gly Gly Glu Ala Arg Gly Glu
785                 790                 795                 800

Leu Phe Trp Asp Asp Gly Glu Ser Leu Glu Val Leu Glu Arg Gly Ala
                805                 810                 815

Tyr Thr Gln Val Ile Phe Leu Ala Arg Asn Asn Thr Ile Val Asn Glu
            820                 825                 830

Leu Val Arg Val Thr Ser Glu Gly Ala Gly Leu Gln Leu Gln Lys Val
            835                 840                 845

Thr Val Leu Gly Val Ala Thr Ala Pro Gln Gln Val Leu Ser Asn Gly
        850                 855                 860

Val Pro Val Ser Asn Phe Thr Tyr Ser Pro Asp Thr Lys Val Leu Asp
865                 870                 875                 880

Ile Cys Val Ser Leu Leu Met Gly Glu Gln Phe Leu Val Ser Trp Cys
                885                 890                 895
```

<210> SEQ ID NO 6
<211> LENGTH: 896
<212> TYPE: PRT
<213> ORGANISM: Homo sapiens

<400> SEQUENCE: 6

```
Gln Gln Gly Ala Ser Arg Pro Gly Pro Arg Asp Ala Gln Ala His Pro
1               5                   10                  15

Gly Arg Pro Arg Ala Val Pro Thr Gln Cys Asp Val Pro Pro Asn Ser
            20                  25                  30

Arg Phe Asp Cys Ala Pro Asp Lys Ala Ile Thr Gln Glu Gln Cys Glu
        35                  40                  45

Ala Arg Gly Cys Cys Tyr Ile Pro Ala Lys Gln Gly Leu Gln Gly Ala
    50                  55                  60

Gln Met Gly Gln Pro Trp Cys Phe Phe Pro Pro Ser Tyr Pro Ser Tyr
65                  70                  75                  80

Lys Leu Glu Asn Leu Ser Ser Ser Glu Met Gly Tyr Thr Ala Thr Leu
                85                  90                  95

Thr Arg Thr Thr Pro Thr Phe Phe Pro Lys Asp Ile Leu Thr Leu Arg
            100                 105                 110

Leu Asp Val Met Met Glu Thr Glu Asn Arg Leu His Phe Thr Ile Lys
        115                 120                 125

Asp Pro Ala Asn Arg Arg Tyr Glu Val Pro Leu Glu Thr Pro Arg Val
    130                 135                 140

His Ser Arg Ala Pro Ser Pro Leu Tyr Ser Val Glu Phe Ser Glu Glu
145                 150                 155                 160

Pro Phe Gly Val Ile Val His Arg Gln Leu Asp Gly Arg Val Leu Leu
                165                 170                 175

Asn Thr Thr Val Ala Pro Leu Phe Phe Ala Asp Gln Phe Leu Gln Leu
            180                 185                 190

Ser Thr Ser Leu Pro Ser Gln Tyr Ile Thr Gly Leu Ala Glu His Leu
        195                 200                 205

Ser Pro Leu Met Leu Ser Thr Ser Trp Thr Arg Ile Thr Leu Trp Asn
    210                 215                 220

Arg Asp Leu Ala Pro Thr Pro Gly Ala Asn Leu Tyr Gly Ser His Pro
225                 230                 235                 240

Phe Tyr Leu Ala Leu Glu Asp Gly Gly Ser Ala His Gly Val Phe Leu
```

```
                        245                 250                 255
Leu Asn Ser Asn Ala Met Asp Val Val Leu Gln Pro Ser Pro Ala Leu
                260                 265                 270

Ser Trp Arg Ser Thr Gly Gly Ile Leu Asp Val Tyr Ile Phe Leu Gly
            275                 280                 285

Pro Glu Pro Lys Ser Val Val Gln Gln Tyr Leu Asp Val Val Gly Tyr
        290                 295                 300

Pro Phe Met Pro Pro Tyr Trp Gly Leu Gly Phe His Leu Cys Arg Trp
305                 310                 315                 320

Gly Tyr Ser Ser Thr Ala Ile Thr Arg Gln Val Val Glu Asn Met Thr
                325                 330                 335

Arg Ala His Phe Pro Leu Asp Val Gln Trp Asn Asp Leu Asp Tyr Met
                340                 345                 350

Asp Ser Arg Arg Asp Phe Thr Phe Asn Lys Asp Gly Phe Arg Asp Phe
            355                 360                 365

Pro Ala Met Val Gln Glu Leu His Gln Gly Gly Arg Arg Tyr Met Met
        370                 375                 380

Ile Val Asp Pro Ala Ile Ser Ser Gly Pro Ala Gly Ser Tyr Arg
385                 390                 395                 400

Pro Tyr Asp Glu Gly Leu Arg Arg Gly Val Phe Ile Thr Asn Glu Thr
                405                 410                 415

Gly Gln Pro Leu Ile Gly Lys Val Trp Pro Gly Ser Thr Ala Phe Pro
            420                 425                 430

Asp Phe Thr Asn Pro Thr Ala Leu Ala Trp Trp Glu Asp Met Val Ala
        435                 440                 445

Glu Phe His Asp Gln Val Pro Phe Asp Gly Met Trp Ile Asp Met Asn
    450                 455                 460

Glu Pro Ser Asn Phe Ile Arg Gly Ser Glu Asp Gly Cys Pro Asn Asn
465                 470                 475                 480

Glu Leu Glu Asn Pro Pro Tyr Val Pro Gly Val Val Gly Gly Thr Leu
                485                 490                 495

Gln Ala Ala Thr Ile Cys Ala Ser Ser His Gln Phe Leu Ser Thr His
            500                 505                 510

Tyr Asn Leu His Asn Leu Tyr Gly Leu Thr Glu Ala Ile Ala Ser His
        515                 520                 525

Arg Ala Leu Val Lys Ala Arg Gly Thr Arg Pro Phe Val Ile Ser Arg
    530                 535                 540

Ser Thr Phe Ala Gly His Gly Arg Tyr Ala Gly His Trp Thr Gly Asp
545                 550                 555                 560

Val Trp Ser Ser Trp Glu Gln Leu Ala Ser Ser Val Pro Glu Ile Leu
                565                 570                 575

Gln Phe Asn Leu Leu Gly Val Pro Leu Val Gly Ala Asp Val Cys Gly
            580                 585                 590

Phe Leu Gly Asn Thr Ser Glu Glu Leu Cys Val Arg Trp Thr Gln Leu
        595                 600                 605

Gly Ala Phe Tyr Pro Phe Met Arg Asn His Asn Ser Leu Leu Ser Leu
    610                 615                 620

Pro Gln Glu Pro Tyr Ser Phe Ser Glu Pro Ala Gln Gln Ala Met Arg
625                 630                 635                 640

Lys Ala Leu Thr Leu Arg Tyr Ala Leu Leu Pro His Leu Tyr Thr Leu
                645                 650                 655

Phe His Gln Ala His Val Ala Gly Glu Thr Val Ala Arg Pro Leu Phe
            660                 665                 670
```

```
Leu Glu Phe Pro Lys Asp Ser Ser Thr Trp Thr Val Asp His Gln Leu
        675             680                 685

Leu Trp Gly Glu Ala Leu Leu Ile Thr Pro Val Leu Gln Ala Gly Lys
    690             695             700

Ala Glu Val Thr Gly Tyr Phe Pro Leu Gly Thr Trp Tyr Asp Leu Gln
705             710             715                     720

Thr Val Pro Ile Glu Ala Leu Gly Ser Leu Pro Pro Pro Ala Ala
                725             730             735

Pro Arg Glu Pro Ala Ile His Ser Glu Gly Gln Trp Val Thr Leu Pro
            740             745             750

Ala Pro Leu Asp Thr Ile Asn Val His Leu Arg Ala Gly Tyr Ile Ile
        755             760             765

Pro Leu Gln Gly Pro Gly Leu Thr Thr Thr Glu Ser Arg Gln Gln Pro
    770             775             780

Met Ala Leu Ala Val Ala Leu Thr Lys Gly Gly Glu Ala Arg Gly Glu
785             790             795             800

Leu Phe Trp Asp Asp Gly Glu Ser Leu Glu Val Leu Glu Arg Gly Ala
            805             810             815

Tyr Thr Gln Val Ile Phe Leu Ala Arg Asn Asn Thr Ile Val Asn Glu
            820             825             830

Leu Val Arg Val Thr Ser Glu Gly Ala Gly Leu Gln Leu Gln Lys Val
        835             840             845

Thr Val Leu Gly Val Ala Thr Ala Pro Gln Gln Val Leu Ser Asn Gly
    850             855             860

Val Pro Val Ser Asn Phe Thr Tyr Ser Pro Asp Thr Lys Val Leu Asp
865             870             875             880

Ile Cys Val Ser Leu Leu Met Gly Glu Gln Phe Leu Val Ser Trp Cys
            885             890             895
```